(12) United States Patent
Harmon et al.

(10) Patent No.: US 11,685,893 B2
(45) Date of Patent: Jun. 27, 2023

(54) SYSTEM AND METHOD FOR BIOMASS GROWTH AND PROCESSING

(71) Applicant: BRISA INTERNATIONAL, LLC, Duluth, GA (US)

(72) Inventors: Kevin C. Harmon, Duluth, GA (US); Shannon M. Johnson, Cumming, GA (US); Eugene T. Holmes, Cumming, GA (US)

(73) Assignee: Brisa International, LLC, Duluth, GA (US)

( * ) Notice: Subject to any disclaimer, the term of this patent is extended or adjusted under 35 U.S.C. 154(b) by 0 days.

(21) Appl. No.: 17/201,910

(22) Filed: Mar. 15, 2021

(65) Prior Publication Data

US 2021/0198615 A1 Jul. 1, 2021

Related U.S. Application Data

(63) Continuation of application No. 15/396,634, filed on Dec. 31, 2016, now Pat. No. 10,947,492, which is a
(Continued)

(51) Int. Cl.
*B01D 53/14* (2006.01)
*C02F 3/34* (2023.01)
(Continued)

(52) U.S. Cl.
CPC ......... *C12M 43/04* (2013.01); *B01D 53/1456* (2013.01); *B01D 53/1493* (2013.01); *C02F 3/34* (2013.01); *C12M 21/04* (2013.01); *C12M 23/36* (2013.01); *C12M 23/44* (2013.01); *C12M 43/02* (2013.01); *F23J 15/02* (2013.01);

*B01D 53/04* (2013.01); *B01D 53/1481* (2013.01); *B01D 53/62* (2013.01); *B01D 53/84* (2013.01);
(Continued)

(58) Field of Classification Search
CPC ...... C12M 43/04; C12M 21/04; C12M 23/36; C12M 43/02; C12M 23/44; B01D 53/1493; B01D 53/1456; B01D 2257/708; B01D 53/1481; B01D 2258/0283; B01D 53/84; B01D 2257/404; B01D 2257/302; B01D 2252/103; B01D 53/04; B01D 53/62; C02F 3/34; F23J 15/02; Y02E 20/32; Y02E 50/30; Y02E 50/10; Y02E 10/46; Y02A 50/20; Y02W 10/37; Y02P 20/59
USPC ....... 210/602, 603, 608, 609, 612, 613, 631, 210/175, 252, 259; 435/266
See application file for complete search history.

(56) References Cited

U.S. PATENT DOCUMENTS 8,887,504 B2 * 11/2014 Julian .................. F24H 4/02
60/671
2005/0120715 A1 * 6/2005 Labrador ............. F03G 7/00
60/618
(Continued)

FOREIGN PATENT DOCUMENTS

JP 3028498 B9 9/1996
WO 2013184317 A1 12/2013

*Primary Examiner* — Fred Prince
(74) *Attorney, Agent, or Firm* — Edwin A. Sisson, Attorney at Law, LLC; Edwin A. Sisson

(57) ABSTRACT

A system comprising a collocated thermal plant, water source, $CO_2$ source and biomass growth module is disclosed. A method of improving the environment by utilizing the system is disclosed.

31 Claims, 32 Drawing Sheets

Related U.S. Application Data continuation of application No. PCT/US2016/037002, filed on Jun. 10, 2016.

(60) Provisional application No. 62/255,331, filed on Nov. 13, 2015, provisional application No. 62/242,984, filed on Oct. 16, 2015, provisional application No. 62/173,905, filed on Jun. 10, 2015.

(51) Int. Cl.
| | |
|---|---|
| *F23J 15/02* | (2006.01) |
| *B01D 53/62* | (2006.01) |
| *B01D 53/84* | (2006.01) |
| *C12M 1/00* | (2006.01) |
| *C12M 1/107* | (2006.01) |
| *C12M 3/00* | (2006.01) |
| *B01D 53/04* | (2006.01) |

(52) U.S. Cl.
CPC .. *B01D 2252/103* (2013.01); *B01D 2257/302* (2013.01); *B01D 2257/404* (2013.01); *B01D 2257/708* (2013.01); *B01D 2258/0283* (2013.01); *Y02A 50/20* (2018.01); *Y02E 10/46* (2013.01); *Y02E 20/32* (2013.01); *Y02E 50/10* (2013.01); *Y02E 50/30* (2013.01); *Y02P 20/59* (2015.11); *Y02W 10/37* (2015.05)

(56) References Cited

U.S. PATENT DOCUMENTS

| | | | |
|---|---|---|---|
| 2007/0012041 A1 | 1/2007 | Goldman | |
| 2011/0092726 A1 | 4/2011 | Clarke | |
| 2012/0168373 A1* | 7/2012 | Del Porto | C02F 3/1257 |
| | | | 210/603 |
| 2012/0208254 A1* | 8/2012 | Smith | C05F 11/00 |
| | | | 435/167 |
| 2014/0030695 A1* | 1/2014 | Smith | C12M 41/48 |
| | | | 435/3 |

* cited by examiner

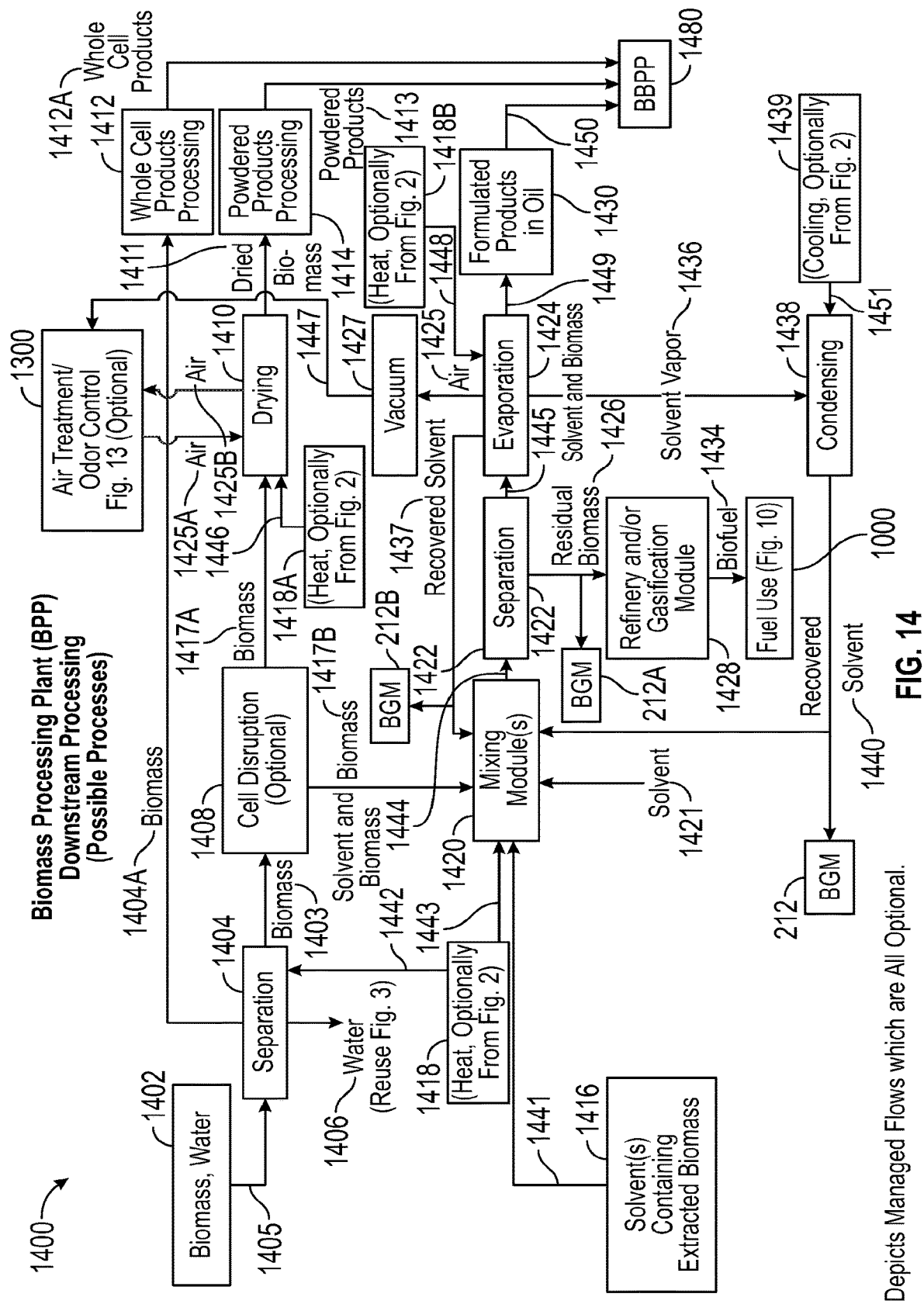

Example of Refinery and/or BPP Synergies within the Plan

24L
- Prompt Processing of Biomass Into Fuels and/or Nonfuel Products for Use Onsite, Storage, Export
- All Fuels may be Used in Plan
- Nonfuel Products Synthesized which may be Used in Plan
  - Lubricants,
  - Bioplastics
  - Paper
  - Soil Amendments/Fertilizer
  - Paints
  - Chemicals
  - Other Useful Products
- When Refinery and BPP Both Present, may Share:
  - Infrastructure in Common
  - Resources&Inputs
  - Outflows
  - May Process Outflows and/or by Products from Each Other
- Use of Power, Waste Heat, Cogenerated Cooling, $CO_2$ and/or Other Resources from Thermal Plant

Examples of BBPP Synergies within the Plan

24M
- Prompt Processing and Bottling of Desalinated Water for Freshness
- Carbonation of Water Optionally Using Purified $CO_2$ from Plan (Fig.4)
- Ability to Store and Transport Water from Source
  - Creates Versatile Water Supply
  - May Generate Water Reserve Supply to meet Varying Needs or for Emergencies
- Prompt Packaging of Biomass Products for Freshness
- Carbonation of Biomass Liquids Optionally Using Purified $CO_2$ from Plan (Fig.4)
- May Use Heat Including Waste Heat from Thermal Plant for Processing
- May Use Cogenereted Cooling from Thermal Plant for Preservation of Water and/or Biomass Products

FIG. 24C

Catalytic Hydrothermal Gasification at Subcritical Conditions

SYSTEM AND METHOD FOR BIOMASS GROWTH AND PROCESSING

This application is a continuation of, and claims priority from, allowed application Ser. No. 15/396,634 filed on Dec. 31, 2016; which is a continuation of, and claims priority from, application No. PCT/US16/37002, filed on Jun. 10, 2016; which claims priority from provisional applications No. 62/255,331 filed on Nov. 13, 2015, No. 62/242,984 filed on Oct. 16, 2015, and 62/173,905, filed on Jun. 10, 2015. This application claims priority from all these patent applications as well as incorporates by reference all their teachings into this application.

FIELD

The present disclosure relates to the field of private, public or municipal infrastructure and utility services and fields of renewable energy, biofuels, water treatment and environmental conservation and remediation.

Many different power generation and industrial systems involving the use of heat may be in use worldwide. These systems may use fuels of many types to produce power through a variety of processes. Combustion-based thermal power plants may also discharge carbon dioxide and other gases into the environment. It is generally recognized that carbon dioxide is a gas that produces an atmospheric greenhouse-effect, the excess production of which has a detrimental effect on climate worldwide. Also, power plants may discharge waste heat in ways which produce environmental damage. Other industrial systems discharge pollution in ways that may be destructive to the environment.

Thus, there may be a need to provide thermal energy production and other industrial processes that minimize the production and discharge of excess, or waste, carbon dioxide, heat, and other byproducts.

BRIEF SUMMARY

The present disclosure provides a means of abating carbon dioxide and other gases generated by thermal plants through the growth of biomass, which uses these normally harmful emissions to produce biofuels and other useful products. Biofuels and/or biomass generated may also become a source of fuel for a thermal plant where appropriate. Water treatment methods and heat, water, and other byproduct abatement and resource conservation technologies may be incorporated e.g., as described herein.

In an embodiment, the present disclosure relates to a biomass growth module optionally fuelable by an exhaust gas comprising carbon dioxide from a thermal plant; wherein the thermal plant may be optionally fuelable by a biomass and/or biofuel outflow fluid from the biomass growth module and wherein the biomass and/or biofuel outflow fluid may be optionally refined by the thermal plant and wherein the exhaust gas may provide a substantial portion of the carbon content of the biomass and/or biofuel outflow fluid.

In certain embodiments, e.g., those represented by FIG. 2, FIGS. 7A, 7B, 11, 12A, 12B, 12C, 12D, 12E, 15A, 15B, 16, 17, 18, 19, 20A, 20B, 20C, 20D and/or other figures and embodiments regarding heat capture and/or transfer, the present disclosure relates to a method of providing a cooling fluid, e.g., a necessary cooling water, to a thermal plant, while concurrently making productive use of the waste heat energy generated by the thermal plant, which waste heat may otherwise be simply discharged unproductively, and at times, destructively, into the environment. The waste heat may be used productively, e.g., to regulate bioreactor temperature and/or in a process to refine water, fuels, and/or biomass produced in a biomass growth module into useful products. In certain embodiments, e.g., those represented by FIG. 3, FIG. 4 and/or other embodiments regarding the use of water and/or carbon dioxide e.g., in the Plan, the present disclosure relates to an integrated approach to minimization of $CO_2$ emissions, power generation, biofuel production, efficient use of heat and water, as well as production of biomass-derived non-fuel products, and treatment of wastewater and waste-to-energy in some embodiments. Various embodiments provide for a wide variety of other water sources or combinations to be used to provide a medium for biomass and/or biofuel production and $CO_2$ abatement, with conservation of water and heat energy.

In an embodiment, one or more water sources may be provided for biomass growth, wherein the water may be wastewater, salt water, brackish water, purified water, potable water, non-potable water, and/or brine. The amount of carbon in the water may be from less than 0.1% to 15% by weight, or about 1, 2, 3, 4, 5, 6, 7, 8, 9, 10, 11, 12, 13, 14, or 15 percent by weight or from one integer to another in the preceding array of numbers, e.g., from about 3% to about 8%.

BRIEF DESCRIPTION OF THE FIGURES

FIG. 14 is a schematic representation of a biomass processing plant (BPP) and processing downstream from the thermal plant and biomass growth unit according to the present disclosure.

FIGS. 24A, 24B, and 24C are representations labeled 24 A-M of select infrastructure sharing and other example synergies within the Plan according to the present disclosure.

DEFINITIONS

Figure 1:
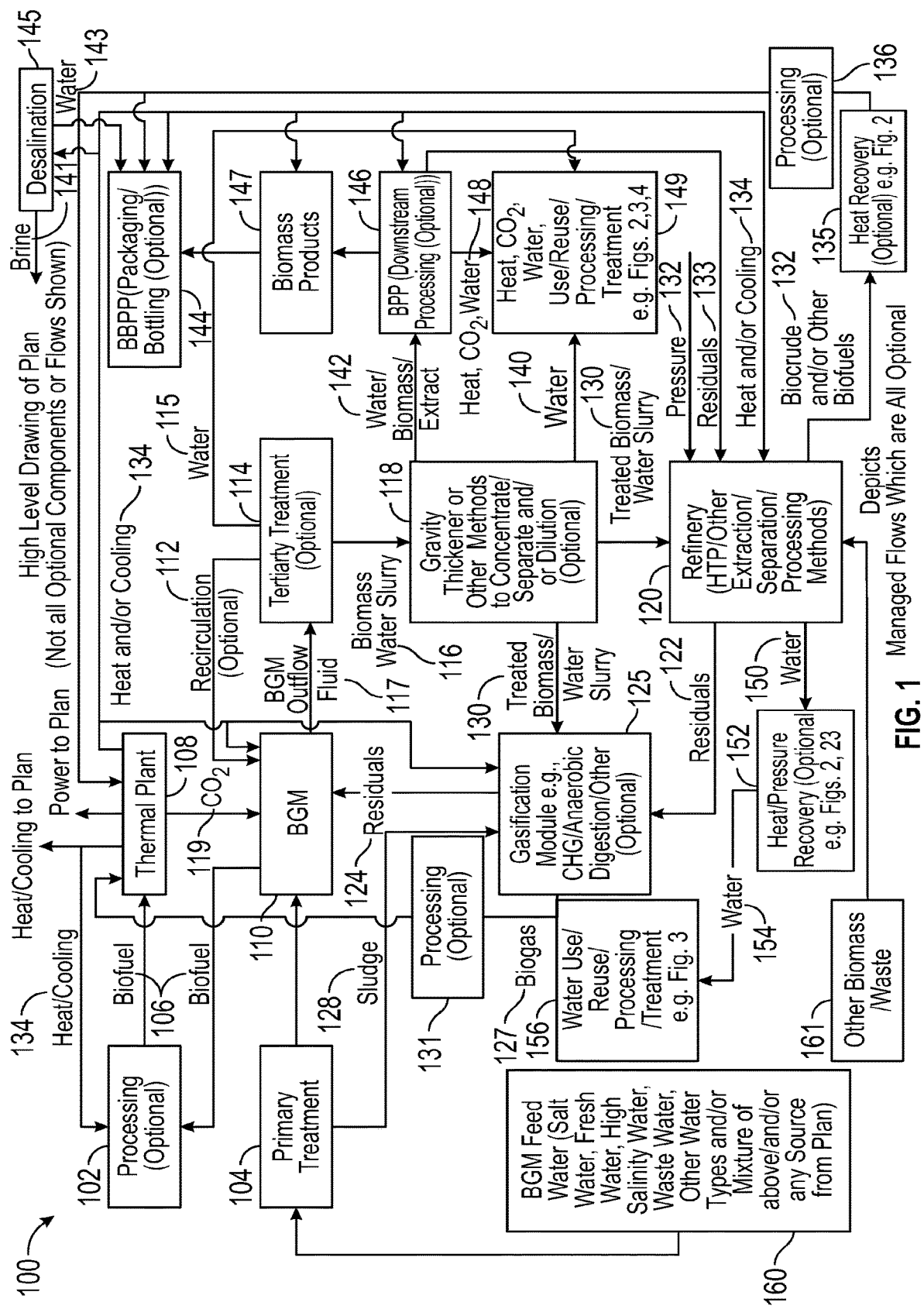
FIG. 1 is a schematic representation of a design according to the present disclosure.

Unless otherwise stated or defined in this specification and/or claims the term "carbon dioxide" means the molecule $CO_2$, which is in gas, liquid, supercritical liquid, and/or solid form or phase, optionally mixed with other gases, liquids and/or solids.

Unless otherwise stated or defined in this specification and/or claims the term "ambient carbon dioxide", or "ambient $CO_2$" may mean carbon dioxide in ambient air, captured from ambient air and/or carbon dioxide captured using capture technology, for example, the following references are incorporated herein by reference and relied upon AlgaeAirFix (http://energyenvironment.pnnl.gov/highlights/highlight.asp?id=1754) and Global Thermostat (http://globalthermostat.com/what-we-do/about-carbon-capture-and-use/).

The term "NOx" means oxides of nitrogen.

The term "SOx" means oxides of sulfur.

The term, "In an embodiment" may mean "In one or more embodiments".

Unless otherwise stated or defined in this specification and/or claims the term, "thermal plant technology", or "thermal plant system" may mean a technology type which may be comprised by a thermal plant.

Unless otherwise stated or defined in this specification and/or claims the term, "system" may mean "technology."

Unless otherwise stated or defined in this specification and/or claims the term, "fuelable" may mean "configured to receive fuel", "configured to receive fuel from", or "configured to receive fuel by".

Unless otherwise stated or defined in this specification and/or claims the term, the term "WTE system" may "WTE technology", or "WTE module".

Unless otherwise stated or defined in this specification and/or claims the term "offsite" may mean sited, or at, or in, a location away from, e.g., proximate to, or adjacent to, a located, or collocated system, module, unit, and/or subunit. Offsite may mean a distance to or from a located, or collocated system, module, unit, and/or subunit of from about 0.1 km to about 20 km, or from about 0.1 to about 0.5 km, or from about 0.1 to about 1 km, or from about 0.1 to about 2 km, from about 0.1 km to about 5 km, or from about 0.1 to about 10 km, or from about 0.1 to about 20 km or from about 0.1 to about 50 km or from about 0.1 to about 100 km, or from about 10 to about 1000 km.

Unless otherwise stated or defined in this specification and/or claims the term "offsite carbon dioxide", or "offsite $CO_2$" may mean carbon dioxide introduced to the Plan from outside the Plan, or offsite.

Unless otherwise stated or defined in this specification and/or claims the term "carbon dioxide storage", or "$CO_2$ storage" may mean a module or modules or a process(es) configured to store carbon dioxide optionally mixed with other gases and/or other materials in any phase. Carbon dioxide storage may comprise any carbon dioxide storage technique(s) or configuration known to those in the art, optionally comprising CCS, storage as a gas in a container at ambient pressure, storage in pressurized tanks, storage as a liquid, storage as a solid and/or any mixture of different phases.

Unless otherwise stated or defined in this specification and/or claims, the term "input", or "inflow", or "flow" may mean anything that may be introduced into a module, unit, or subunit, which may be denoted in the figures of this disclosure by a line or arrow connected to a box, wherein the line or arrow represents an input, and the box represents a module, unit, or subunit. In this sense, a module may be configured to communicate with and/or be joined to and/or connected to an input. Inputs or outputs (see below) may be accomplished as described herein and/or by any means known to those in the art (e.g., fluids may be piped into or out of a module motivated by a blower or pump, solids may be brought into and/or out of a module in containers, etc.).

Unless otherwise stated or defined in this specification and/or claims the term "inject" may mean to input or to create in input, or to begin an input; or a module may be configured to receive and/or to provide the injection or input.

Unless otherwise stated or defined in this specification and/or claims the term "output", or "outflow", or "flow", or "discharge", or "discharges", or "emit", or "emission", or "dump" may mean anything that exits or may be removed and/or the process of removal from a module, unit, subunit, or technology which may be denoted in the figures of this disclosure by a line or arrow connected to a box representing the module, unit, or subunit or technology. In this sense, a module may be configured to be in communication and/or connected to an output. An output may be accomplished as described herein and/or by any means known to those in the art (e.g., fluids may be piped out of a module motivated by a blower or pump, solids may be brought out of module in containers, etc.).

Unless otherwise stated or defined in this specification and/or claims the term "emitter", may mean any module, unit, subunit, technology, component or feature which emits.

Unless otherwise stated or defined in this specification and/or claims the term "flow" may mean an input, an output, or a movement of a fluid or fluids, e.g., through, or along, or within, an input or an output.

Unless otherwise stated or defined in this specification and/or claims the term "discharge" may also mean to release into the environment, and/or an output from a module. Unless otherwise stated or defined in this specification and/or claims the term "discharge", or "export", or "discharge/export", or "export/discharge" may mean to send offsite.

Unless otherwise stated or defined in this specification and/or claims the term "discharge section" may mean a portion designed to discharge (e.g., a section of an exhaust gas recovery design (e.g., FIG. 7A or 7B) designed to discharge gases into the environment).

Unless otherwise stated or defined in this specification and/or claims the term "exhaust gas recovery module" may mean a module designed to process exhaust gases through a variety of steps in order to prepare the gases, heat, pollutants, water, and/or other fluids derived from the processing as an input into a BGM, storage, and/or other use(s) in the Plan, e.g., 707.

Unless otherwise stated or defined in this specification and/or claims the term, "motive device" many mean any technology known to the person of skill in the art for moving materials, wherein the materials optionally comprise fluids.

Unless otherwise stated or defined in this specification and/or claims the term "exhaust gas" may mean an output of gaseous effluent from a thermal plant and/or other thermal process.

Unless otherwise stated or defined in this specification and/or claims the terms "purification", or "processing", or "purification/processing", or "processing/treatment" may mean removal of impurities, separation, drying, addition of chemicals, adjustment of pH, temperature change, transfer of heat and/or cooling, combination with other fluids and/or other materials and/or any other methods herein disclosed and/or those known to the person of skill in the art which may be applied to modify the characteristics of a fluid and/or other material.

Unless otherwise stated or defined in this specification and/or claims the term "water use/reuse/processing/treatment/distribution" may mean reclaiming water output(s) from modules, optional "processing/treatment" of the water, and distribution of the water to the same and/or other modules in any manner disclosed herein and/or in any means known to the person of skill in the art. Distribution may comprise piping of the water optionally with pumps. These processes may be conducted in one or more separate units and/or grids for water of different characteristics (e.g., salinity, biomass content, heat content, pH, etc.), and/or water outputs of any kind may be combined.

Unless otherwise stated or defined in this specification and/or claims the term water storage may mean any means described herein and/or known to the person of skill in the art for storing water. Water storage may comprise one or more separate modules or units which may be used to store water of different characteristics separately and/or as a mixture in any phase.

Unless otherwise stated or defined in this specification and/or claims the term "fresh water source" may mean any source of fresh water optionally comprising wastewater, optionally comprising any technique and/or equipment known to the person of skill in the art to bring the water to the Plan.

Unless otherwise stated or defined in this specification and/or claims the term "water intake (salt water)" may mean any intake or input, or technique and/or equipment to bring salt water, brackish water, and/or high salinity water into the Plan either combined and/or separately, optionally comprising a deep sea, and/or near shore intake on a salt water body.

Unless otherwise stated or defined in this specification and/or claims the term "module" may mean an optionally detachable section with one or more functions. A module may comprise one or more units, subunits and/or technologies. A module may comprise any technology, structure and/or equipment known to the person of skill in the art to enable and/or support its function individually and/or as integrated into the Plan. Where a module comprises different technologies with infrastructure in common, technologies comprised by that module may combine and share any infrastructure in common, may maintain separate infrastructure, or may combine and share some infrastructure in common. Any term depicted inside a box on a figure in the present disclosure may be a module, a unit, a subunit and/or a technology comprised by a module, unit, or subunit.

Unless otherwise stated or defined in this specification and/or claims the term "unit" may mean an optionally detachable section with one or more functions. The term "unit" may be interchangeable with the term "module". A module may comprise one or more "unit(s)". A "unit" may comprise one or more "subunit(s)" and/or "technolog(ies).

Unless otherwise stated or defined in this specification and/or claims the term "submodule" may mean "unit".

Unless otherwise stated or defined in this specification and/or claims the term "subunit" may mean an optionally detachable section with one or more functions. The term "subunit" may be interchangeable with the term "module", or the term, "unit". One or more "subunit(s)" may be comprised by a "module" and/or by a "unit".

Unless otherwise stated or defined in this specification and/or claims the term "system" may mean a whole comprising related things, or a "system" may mean an optionally integrated system or configuration comprising one or more of the following features: power generation, emissions capture, water treatment and/or fuel generation. A system may mean an optionally collocated and/or optionally integrated system or an integrated configuration of one or more modules, one or more units, and/or one or more subunits, one or more technologies, one or more components, and/or one or more features comprising one or more of the following features: power generation, emissions capture, water treatment, fuel generation, biomass production, biofuel generation, water treatment, water use, waste treatment, e.g., solid waste treatment, waste water treatment, gaseous emissions treatment, fresh water production, and/or salt water discharge mitigation. A system may comprise, or may consist essentially of, or may consist of, one or more modules, one or more units, and/or one or more subunits, and/or one or more technologies comprising one or more of the following features: power generation, emissions capture, water treatment, fuel generation, biomass production, biofuel generation, water treatment, water use, waste treatment, e.g., solid waste treatment, waste water treatment, gaseous emissions treatment, fresh water production, and/or salt water discharge mitigation. By the term "consisting essentially of" may be meant a description or recitation of one or more modules, one or more units, or one or more subunits that that do not materially affect characteristics, e.g., the basic and novel characteristics, of the described or recited system.

Unless otherwise stated or defined in this specification and/or claims the term "fermentation vessel, module or tank" may mean a container to grow biomass without light.

Unless otherwise stated or defined in this specification and/or claims the term "design" may mean a system, a configuration, a combination of systems, an association of systems, and/or modules optionally in fluid and/or electronic communication.

Unless otherwise stated or defined in this specification and/or claims the term "Plan", or "the Plan", or "design", or "the design" may mean a system of the present disclosure, the whole of the disclosure either with or without any optional modules, flows, synergies, communications and/or connections between modules. "Plan" may comprise, consist essentially of, or consist of, the sum of all systems, technologies and/or other features of the disclosure. "Plan" may comprise, consist essentially of, or consist of any embodiment of the disclosure. "Plan" comprise, consist essentially of, or consist of a system. "Plan" may comprise, consist essentially of, or consist of a design. "Plan" may comprise, consist essentially of, or consist of a grid of the disclosure. A plan may be collocated. A plan may comprise, consist essentially of, or consist of one or more systems, one or more modules, one or more units, and/or one or more subunits, all of which are in operative communication with one another.

Unless otherwise stated or defined in this specification and/or claims the term "plant", or "plant module" may mean a module of any kind which performs a technical function. It does not imply necessarily a separate building or structure, and may be connected to and/or partially integrated into other modules, technologies, or other features of the disclosure.

Unless otherwise stated or defined in this specification and/or claims the term "thermal plant", or "Thermal Plant", or "thermal plant module" may be defined as a plant or other industrial system where heat and/or carbon dioxide may be produced in any aspect of its operation, e.g., to produce power and/or work, to process materials (e.g. factories), and/or systems that in any way, support these plants and/or industrial systems. A thermal plant may mean a plant combusting fuel, biomass and/or waste to produce energy and/or other processes that involve heat and/or carbon dioxide in any phase of operation. A thermal plant may comprise any power generating plant, optionally comprising all fossil fuel-fired plants, nuclear, solar thermal, geothermal, and other power plants, and/or non-power generating plants optionally comprising a steel plant, a cement plant, a paper mill, a textile mill, a metal manufacturing plant, and another industrial plant. A thermal plant may also comprise one or more modules, technologies, or features used to generate precursor fuels for combustion, such as cellulosic ethanol, pyrolysis, HTP module(s), and/or other technologies that may generate fuels from biomass, waste, and/or by other mechanisms. A thermal plant may also comprise any additional attachment, or adjunct, or associated modules and/or technologies available for thermal plant technologies know to those of skill in the art, and/or other system(s), technologies, components, or features to support thermal plant operations, comprising those designed to treat, purify, and/or prepare fuels for use in thermal plant technologies, cool thermal plant processes, treat emissions of any outflows, to increase efficiency, such as waste heat power generation modules, to convert waste heat to cooling (e.g., cogeneration), and/or to convey inputs and/or outputs to and/or from the thermal plant, different thermal plant modules, and/or other modules in system or Plan. A thermal plant may comprise any number of the modules and/or technologies described herein as thermal plant modules and/or technologies either as separate systems and/or sharing common infrastructure and/or resources as described herein and/or as known to the person of skill in the art.

Unless otherwise stated or defined in this specification and/or claims the term "thermal power plant", or "power plant technology" may mean a thermal plant and/or individual technology partly or fully comprised by a thermal plant which produces power.

Unless otherwise stated or defined in this specification and/or claims the term "thermal plant heat and/or pressure intensive processes" may mean any process(es) in the thermal plant, a thermal plant technology and/or connected to, and/or supporting the operations of a thermal plant which may involve the use of heat and/or pressure.

Unless otherwise stated or defined in this specification and/or claims the term "combustion process" may mean any process involving combustion. It may mean a Thermal Plant technology which uses or involves combustion (e.g., of a fuel).

Unless otherwise stated or defined in this specification and/or claims the term "conduit" may mean a pipe, tube, duct, line, channel, trench, or other conveyance. It may mean a structure, system or feature to enclose, combine, protect, and/or connect one or more pipes, tubes, ducts, lines, channels, trenches, or other conveyances.

Unless otherwise stated or defined in this specification and/or claims the term "energy" may mean a force moved through a distance. The terms "work" and "energy" may be understood as interchangeable. For example, a unit of energy may be a joule, which may be energy needed to push against a force of one newton for one meter.

Unless otherwise stated or defined in this specification and/or claims the term "heat" may mean the random kinetic energy of atoms, molecules, and/or ions in a substance.

Unless otherwise stated or defined in this specification and/or claims the term "thermal energy" may mean energy in heat form. For example, a kilojoule (1000 joules) may be dissipated in 50 cc of water to raise the temperature of water by about 5° C.

Unless otherwise stated or defined in this specification and/or claims the term "cooling" may mean any means to reduce the heat of one or more substances. It may mean a system capable of cooling a material. It may mean a cool or cold material(s) optionally comprising a fluid capable of being used to produce cooling. Some examples of cooling may comprise direct interaction, mixing and/or other contact of a cooler material with a warmer one, and/or indirect interaction of a cooler material with a warmer one, such as in a heat exchange, and/or using condensation/evaporation and/or pressure, e.g., a heat pump, and/or any other means known to the person of skill in the art.

Unless otherwise stated or defined in this specification and/or claims the term "heat and/or cooling", or "heat/cooling", or "heating/cooling", or "heating and/or cooling", may mean one or more of the following features, optionally in multiples: heat, a flow of heat, cooling, a flow of cooling, and/or any combination thereof.

Unless otherwise stated or defined in this specification and/or claims the term "heat/cooling storage" may mean the storage of heat and/or cold in any means known to the person of skill in the art. Heat and/or cooling may be stored in multiple separate units within a heat/cooling storage module based on the particular temperature and/or temperature range(s) of the stored substance(s).

Unless otherwise stated or defined in this specification and/or claims the term "additional heat" may mean heat which may be added in addition to heat that has already been added to a material and/or process (optionally comprising a fluid) by another process(es). For example, waste heat may be used to provide initial heating of a material, and another heat source may be used to further elevate the temperature for a desired application (e.g., a heat exchanger, a burner).

Unless otherwise stated or defined in this specification and/or claims the term "preheating/cooling", or "pre-heating/cooling" may mean heating and/or cooling applied in preparation for a process or module.

Unless otherwise stated or defined in this specification and/or claims the term "pretreatment" may mean any means of treatment known to the person of skill in the art to prepare a material, optionally comprising a fluid and/or flow for another process. For example, pretreatment of water may comprise purification, addition of chemicals, adjustment of pH, temperature change, mixing with other water sources and/or any other means known to the person of skill in the art for preparation of water for use in a particular process.

Unless otherwise stated or defined in this specification and/or claims the term "water" may mean one or more of the following features: fresh water, wastewater, treated wastewater, salt water, brackish water, high salinity water, steam, inflow fluid, water input, outflow fluid and/or water output comprising any water in the disclosed Plan (e.g., FIG. 3), any other water source or any mixture of the foregoing, optionally mixed with biomass, biocrude, fuel and/or biofuel of any description, pollutants, minerals, and/or other materials. Water may be in any phase(s) or form, comprising liquid, supercritical liquid, gaseous, and/or solid phases. Water transfer from any module to another may comprise phase change of any kind, mixing with one or more other water source(s), and/or treatment by any means known to the person of skill in the art.

Unless otherwise stated or defined in this specification and/or claims the term "water permeable" may mean of a composition and/or structure such that water molecules can pass through, or, that water may pass through under osmotic pressure.

Unless otherwise stated or defined in this specification and/or claims the term "fluid" may mean any liquid, gas and/or other material that may be used in a process. A fluid may mean a form of matter capable of flowing under applied shear stress.

Unless otherwise stated or defined in this specification and/or claims the term "outflow fluid" or "output" may mean a fluid or fluids of any type discharged from any module and/or other component in the Plan. In this sense a module, unit, and/or subunit may be configured to communicate with and/or be joined to an outflow fluid or output.

Unless otherwise stated or defined in this specification and/or claims the term "BGM outflow fluid" may mean an outflow fluid from a BGM, comprising fluids as discharged directly from a BGM, and/or fluids discharged from a BGM and then taken through any other processing step(s) comprising concentration, thickening, de-watering, dilution, addition of chemicals, change of temperature, and/or other processing step(s) herein disclosed and/or known to those of skill in the art, and/or mixed with other sources of biomass and/or water of any description, and may comprise one or more of the following features:

a) biomass water slurry;
b) water/biomass/extract;
c) treated biomass/water slurry;
d) treated biomass water slurry;
e) TBW slurry;
f) biomass, water;
g) biocrude and/or other biofuels;
h) residuals;
i) biomass culture, water;
j) biofuel;
k) biomass;
l) biomass/sludge/residuals;
m) biomass, biofuel (gaseous), biofuel (liquid);
n) purified biofuel;
o) solvent containing extracted biomass;
p) hot biomass, biocrude and/or biofuel, water (liquid or gaseous);
q) hot biomass and/or biofuel/water slurry;
r) hot biocrude and/or biofuel (gaseous or liquid);
s) hot water and/or steam separated from biomass and/or biofuel;
t) steam & trace biomass, biocrude and/or biofuel;
u) steam/hot biomass, biocrude and/or biofuel, water;
v) biofuel/water;
w) water;
x) light oil/biomass; and/or
y) heavy oil/biomass.

Unless otherwise stated or defined in this specification and/or claims the term "growing subunit", or growing unit", or "growth stage subunit", or "growth stage unit", or "biomass growing subunit", or "biomass growth subunit" may mean a component within a biomass growth module which may use one or more photobioreactor(s), fermentation tank(s), pond(s), other reactor(s) and/or any other system(s) designed for the growth of biomass optionally comprising systems described herein and/or any other system known to the person of skill in the art.

Unless otherwise stated or defined in this specification and/or claims the term "stressing" may mean subjecting biomass to a stimulus comprising deprivation of, and/or exposure to a substance, light, certain wavelengths of light, certain temperatures, nitrogen starvation/depletion, salt and/or any other means to stimulate a particular biological response.

Unless otherwise stated or defined in this specification and/or claims the term "stressing subunit" may mean a module wherein biomass may be subjected to stressing.

Unless otherwise stated or defined in this specification and/or claims the term "milking" may mean removing a portion of a biomass using a solvent and/or by other means wherein the remaining biomass structure may be generally not destroyed.

Unless otherwise stated or defined in this specification and/or claims the term "milking subunit" may mean a module wherein biomass may be subjected to milking.

Unless otherwise stated or defined in this specification and/or claims the term "stressing and milking subunit" may mean a module wherein biomass may be subjected to stressing and/or milking.

Unless otherwise stated or defined in this specification and/or claims the term "power" may mean electricity and/or heat.

Unless otherwise stated or defined in this specification and/or claims the term "hot", or "heated" may mean heated to any temperature above ambient temperature. It may mean hotter than another material with which it exchanges heat and/or cooling. It may mean a material that has been heated by any process to any temperature higher than it was before the process was applied to the material.

Unless otherwise stated or defined in this specification and/or claims the term "refine" may mean one or more of the following features: preheating a solution containing biomass, biocrude and/or other biofuel and possibly water as a first step for other processes; separating a biomass and/or biofuel from water and/or steam and/or other liquid; purifying one or more components of the biomass and/or biofuel; converting components of biomass and/or biofuel into other compounds, comprising converting biomass into biocrude; converting biomass into biogas; separating compounds composing biocrude and/or biofuel into individual compounds or groups of compounds, such as carbon ranges; subjecting the biomass and/or biofuel to heat, pressure, hydrothermal processing and/or a similar process; addition of chemicals, blending of fuels; and/or any methods herein disclosed and/or known to the person of skill in the art for refining petroleum products and/or biofuels. Any of the above may be conducted with water and/or other fluids either present or absent.

Unless otherwise stated or defined in this specification and/or claims the term "refinery" may mean a module where refining takes place (e.g., refining of biomass, biocrude, biofuels, biogas, fuels, and/or water).

Unless otherwise stated or defined in this specification and/or claims the term "separation" may mean any means known to the person of skill in the art for separation of two or more materials, optionally comprising fluids, optionally comprising physical, chemical, thermal biological, and/or other means of separation. Separation may mean the separation of hot water and/or steam from hot biocrude and/or biofuel/water slurry and/or from a hot biocrude and/or biofuel, or both (e.g., 1510) e.g., FIG. 15, by any means known to the person of skill in the art.

Unless otherwise stated or defined in this specification and/or claims the term "biogas" may mean a gaseous fuel partially or fully derived from biomass optionally mixed with other gases, water and/or other materials.

Unless otherwise stated or defined in this specification and/or claims the term "biogas/natural gas storage" may mean a module or modules where biogas, natural gas and/or other primarily gaseous and/or liquid fuels may be either separately and/or combination stored, heated, and/or otherwise maintained in any manner known to the person of skill in the art.

Unless otherwise stated or defined in this specification and/or claims the term "biocrude", or "bio crude" may mean a primarily liquid biofuel that may be produced from biomass.

Unless otherwise stated or defined in this specification and/or claims the term "biocoal", or "bio coal" may mean a primarily solid fuel which may be produced from biomass, optionally comprising waste.

Unless otherwise stated or defined in this specification and/or claims the term "biomass" may mean material(s) derived from living or recently living organisms of any kind, e.g., algae, bacteria, fungi, yeast, and/or amoeba. Biomass may comprise: a biofuel generated the living organisms, e.g., ethanol generated by and/or from plants; biogas, biocrude, and/or other biofuels generated by plant biomass processing and/or fermentation; intact portions of biomass; portions of biological material extracted using solvents; and/or any other material that may originate as or from organisms and/or may be derived from organisms and/or the products they produce by any means herein disclosed and/or by any means known to the person of skill in the art. Biomass may mean living and/or dead organisms and/or a biofuel produced therefrom.

Unless otherwise stated or defined in this specification and/or claims the term "biomass products" may mean products made and/or derived from biomass.

Unless otherwise stated or defined in this specification and/or claims the term "Biomass Processing Plant" or "BPP" may mean a module wherein biomass optionally mixed with other materials may be processed into products in accordance with the descriptions in this specification and/or in any way known to the person of skill in the art.

Unless otherwise stated or defined in this specification and/or claims the term "refinery/BPP", or "refinery and/or BPP", or "BPP and/or refinery", or "BPP/refinery", may mean a refinery module, a BPP module or both either individually, collocated, and/or as separate modules possibly interconnected, and/or possibly sharing some infrastructure in common.

Unless otherwise stated or defined in this specification and/or claims the term "Water Bottling/Biomass Product Bottling/Packaging Plant" or "BBPP" may mean a module wherein water may be processed, e.g., purified, treated with chemicals, carbonated, and/or otherwise prepared for bottling, preserved, bottled, and/or stored in any manner herein disclosed and/or known to the person of skill in the art. In addition or alternatively, biomass products may be prepared for bottling and/or other packaging, bottled and/or otherwise packaged, preserved, cooled, heated, stored, and/or otherwise processed in any manner herein disclosed and/or known to the person of skill in the art for processing and/or packaging biomass products of any kind. The water processing and bottling may occur using a separate system optionally in a separate location from the biomass preparation and bottling and/or packaging system comprised by the BBPP.

Different biomass product preparation, packaging and/or storage may comprise one and/or more different technologies optionally conducted in separate locations comprised by the BBPP (e.g., liquid biomass processing and packaging methods may be conducted separately from those of solids, solids mixed with other materials, and/or gases.) A BBPP may also comprise any methods known to the person of skill in the art to prepare bottles and other packaging and shipping materials from recycled materials.

A BBPP may comprise any methods known to the art to prepare and sterilize bottles and/or other packaging material, to apply strapping, plastic wrap, shrink wrap, pallets and/or other bulk packaging equipment and materials (e.g., to prepare pallets of products and/or other means of mass shipment).

Unless otherwise stated or defined in this specification and/or claims the term "fuel" may mean any material which may be used to generate energy in any form. Unless otherwise stated or defined in this specification and/or claims the term "fuel" may mean a carbon-based material which may be combusted to generate energy in any form.

Energy in any form may comprise electrical energy, heat, and/or any other form(s) of energy.

Unless otherwise stated or defined in this specification and/or claims the term "offsite fuel(s)" may mean a fuel or fuels brought into and/or exported from the Plan to and/or from offsite sources.

Unless otherwise stated or defined in this specification and/or claims the term "biofuel" or "biofuels" may mean a fuel or fuels generated in whole or in part using biological materials and/or processes. A biofuel may comprise a biomass, and/or a fuel generated by biomass (e.g., ethanol generated by biomass as a byproduct in a water solution), a fuel generated from processing biomass and/or a portion of biomass by any viable process, optionally comprising a thermal, chemical, biochemical, mechanical, other biological process, and/or other methods, and/or that play a role in the production of fuels of any kind. Biofuel may comprise these fuels in gaseous, liquid, solid, supercritical fluids, and/or mixed states of matter.

Unless otherwise stated or defined in this specification and/or claims the term "hydrothermal processing" or "HTP" comprises rapid thermal processing, hydrothermal liquefaction, catalytic hydrothermal gasification, hydrothermal carbonization optionally with or without In situ transesterification (IST), and/or other biomass processing and/or refining method(s) comprising heat and/or pressure, and other processing of materials resulting from the application of heat and/or pressure. HTP may mean one or more than one HTP technique and/or technology optionally used together, optionally in series (e.g., HTL followed by CHG).

Unless otherwise stated or defined in this specification and/or claims the term "flash refining" may mean hydrothermal processing.

Unless otherwise stated or defined in this specification and/or claims the term "rapid thermal processing" or "RTP" may mean to separate and/or partially refine a BGM outflow fluid, a water and biomass mixture and/or biomass/water slurry using processes typically involving heat at ambient pressure. An example of this type of process may be the Envergent Technologies LLC Rapid Thermal Processing (RTP) technology (https://www.envergenttech.com).

Unless otherwise stated or defined in this specification and/or claims the term "hydrothermal liquefaction", or "HTL" means to separate and/or partially refine a BGM outflow fluid, water and biomass mixture and/or biomass/water slurry using processes typically involving heat and possibly pressure. HTL processes may yield biocrude.

Unless otherwise stated or defined in this specification and/or claims the term "hydrothermal carbonization", or "HTC" involves the application of mild heat and optionally pressure to biomass in an aqueous medium. At temperatures of approximately 180-250 degrees C. and pressures of approximately 10-40 bar, bio-macromolecules hydrolyze and react to yield a solid hydrochar or carbonized solid. This material may be then typically processed using "In situ transesterification" or "IST". Where referenced herein, HTC may be understood to also optionally comprise IST. Some portion of the initial biomass may be recycled to the BGM, to other HTL process(es), and/or otherwise processed in any manner as described herein, comprising processing by a refinery and/or BPP in any manner known to the person of skill in the art.

Unless otherwise stated or defined in this specification and/or claims the term "in situ transesterification" or "IST" comprises the conversion of the lipids in biochar into biodiesel without first extracting them, using alcohols such as methanol or ethanol. Subcritical IST may be done at subcritical alcohol temperatures. This generally requires the use of catalysts and high molar ratios of alcohol to oil (e.g., over 300 to 1), and may be also sensitive to water in the feedstock. Supercritical IST (SC-IST) may be done at supercritical alcohol temperatures. SC-IST does not require catalysts or high molar ratios of alcohol to oils, and may be much less sensitive to water in the feedstock. Source: Robert Levine, THE PRODUCTION OF ALGAL BIODIESEL USING HYDROTHERMAL CARBONIZATION AND IN SITU TRANSESTERIFICATION, Dissertation for PhD in Chemical Engineering, University of Michigan, 2013; incorporated herein by reference and relied upon. http://deepblue.lib.umich.edu/bitstream/handle/2027.42/99977/rblevine_1.pdf'sequence=1

Unless otherwise stated or defined in this specification and/or claims the term "catalyst" may mean a substance that increases the rate of one or more chemical reactions.

Unless otherwise stated or defined in this specification and/or claims the term "catalytic hydrothermal gasification" or "CHG" may mean a refining process that catalytically converts organic compounds to gases in water optionally comprising $CH_4$ and/or $CO_2$ using heat and/or pressure to drive the conversion while maintaining water in the liquid state. For example, the disclosure provided patent publication WO 2013/184317A1 incorporated by reference herein, may be an exemplary process. The process may also comprise catalytic and/or hydrothermally gasifying (CHG) of residual organic compounds in an aqueous fraction released from an HTL stage or process at a temperature and pressure selected to form a product gas. The product gas may contain at least one hydrocarbon or other medium BTU (British thermal unit) product gas.

Combustion of the hydrocarbon product gas may be used to provide a net positive release of energy from conversion of the biomass. An example of such process may be found at http://www.genifuel.com.

For example CHG may be effected at approximately 350 Celsius, 20-22 MPa and wherein biomass may be processed wet (approximately 80-85% water), and the emerging gas stream may be mostly steam so heat may be recovered, conversion may be high (>99%), gas output may be clean with substantially small amounts of residual tars and <1% ash; and wherein typical gas stream content may be e.g., 62% methane, 35% $CO_2$, small amounts of hydrogen gas and other fuels, e.g., ethane, propane. For example, see the website http://www.genifuel.com/gasification.html, incorporated herein by reference and relied upon.

The Genifuel gasifier may utilize instead a wet process catalyzed to yield rapid and substantially complete conversion of a biomass, producing substantially clean renewable natural gas as a product. This process may operate at much lower temperatures than other gasification methods, approximately 350° C. and 21 MPa making the construction and operation of the equipment easier. The gasifier yields both a product gas and steam, which contains the carbon dioxide produced during gasification. After condensation, the water enriched with dissolved carbon dioxide may be recycled to the BGM to accelerate growth of the next generation of biomass and/or for other use in the Plan (See FIG. 4), while reducing emissions to nearly zero.

Unless otherwise stated or defined in this specification and/or claims the term, "gasification module" may mean a module where biomass possibly mixed with water and/or other constituents, such as a BGM outflow fluid and/or a treated BGM outflow fluid, may be converted in whole or in part to one or more gases using CHG, anaerobic digestion, and/or any other means suited to the purpose to produce gases from biomass.

The gasification module may also comprise systems for processing the resulting gases to prepare them for use as fuels and/or storage, comprising drying, hydrogen sulfide removal and/or other pollutant removal, other processing, blending with other fuels, carbon capture and storage for carbon dioxide, condensation to liquids, and/or other techniques known to those of ordinary skill in the art. A gasification module may be comprised by a thermal plant and may optionally share infrastructure with other thermal plant technologies and/or processes, may be comprised by a refinery and/or BPP and may optionally share infrastructure with refinery and/or BPP technologies and/or processes, and/or may be as separate module.

Unless otherwise stated or defined in this specification and/or claims, the term "gasification equipment" may mean any equipment used in a gasification module or to support the function of a gasification module, its inputs and/or outputs or outflows.

Unless otherwise stated or defined in this specification and/or claims the term "supercritical fluids extraction" may mean an extraction process involving fluids in a supercritical state, e.g., $CO_2$, methanol, and/or ethanol.

Unless otherwise stated or defined in this specification and/or claims the term "fresh water", or "freshwater" may mean water with salinity generally below that of ocean salt water, and typically below 0.5%. For purposes of this disclosure, fresh water may refer to water of low salinity of any description, and it may comprise low salinity wastewater of any description.

Unless otherwise stated or defined in this specification and/or claims the term "wastewater" or "waste water" may mean water which may contain waste material of any type and/or the chemical byproducts associated with it. Municipal wastewater may be a common form of wastewater which may contain approximately 30 to 40 mg/L of nitrates, 5 to 10 mg/L of phosphates, varying levels of organic carbon, suspended and/or dissolved solids, and possibly other chemicals. Wastewater may also comprise farm runoff, industrial wastewater, storm water, leachate, process water from any process, and/or any other water source that contains constituents that may make it non-potable. Wastewater may be of any salinity level.

Unless otherwise stated or defined in this specification and/or claims the term "grey water", or "gray water" may mean treated wastewater or partially treated wastewater (e.g., wastewater treated using primary treatment, secondary treatment and/or tertiary treatment processes). Grey water may mean water which has been used in a process of any kind which may be non-potable after use in the process. Gray water may mean water that results from the mixing of potable and non-potable water. Gray water may mean water they may be used to dilute brine.

Unless otherwise stated or defined in this specification and/or claims the term "treated wastewater" may mean wastewater that has been treated by any physical, chemical, biological process and/or other means.

Unless otherwise stated or defined in this specification and/or claims the term "salt water" or "saltwater" may mean water with a salinity above that of fresh water and typical of ocean salinity, possibly in the range of 3% to 5% (30 g/L to 50 g/L).

Unless otherwise stated or defined in this specification and/or claims the term "brackish water" may mean any mixture of fresh water, salt water, brine water, and/or other water with a salinity typically between that of fresh water and salt water (approximately 0.5% to 3%).

Unless otherwise stated or defined in this specification and/or claims the term "high salinity water", "brine", or "brine discharge", or "brine water" may mean water with a salinity generally higher than that of ocean water (typically greater than approximately 5%, or 50 g/L).

Unless otherwise stated or defined in this specification and/or claims the term "brine electrolysis" may mean application of electrolysis to brine (e.g., brine generated as a byproduct of desalination).

Unless otherwise stated or defined in this specification and/or claims the term "desalination" may mean to process salt water in a manner that reduces its salinity, optionally comprising methods which may also generate also a high salinity water or brine.

Unless otherwise stated or defined in this specification and/or claims the term "desalination plant", or "desalination module", or "desalination plant module" may mean a module which performs desalination. A desalination plant may comprise distillation-based and/or filtration-based technologies further defined and described herein and/or other means of desalination known to the person of skill in the art.

Unless otherwise stated or defined in this specification and/or claims the term "bioreactor" may mean a fully or partially enclosed container in which biomass may be grown.

Unless otherwise stated or defined in this specification and/or claims the term "photobioreactor" may mean a fully or partially enclosed container with exposure to the sun and/or other light source in which biomass may be grown.

Unless otherwise stated or defined in this specification and/or claims the term "biomass growth module", or "BGM" may mean a module wherein biomass may be grown and processed in one or more different biomass growth units. Where flows into and/or out of the BGM may be described or implied, and/or processes may be conducted in, on or by the BGM, the BGM may mean any one or more BGUs comprised by the BGM or any subunits and/or other component(s) thereof. Unless otherwise stated or defined in this specification and/or claims the term "biomass growth unit" or "BGU" may mean a system for growing biomass and preliminary biomass processing. For purposes of this disclosure, a BGU may also comprise a wastewater treatment plant (WWTP) of any description. A BGU may comprise one or more growing subunits and other subunits that may be used to support biomass growth (e.g., FIG. 6). A BGU may also mean a system where a biological agent(s) may in any way metabolize, ferment and/or otherwise change carbon dioxide and/or other gases, such as hydrogen, nitrous oxide, carbon monoxide, and/or other gases in any manner and which may produce biomass, fuels and/or other chemical structures. Where flows into and/or out of a BGU may be described and/or implied, and/or processes may be conducted in, on and/or by a BGU, BGU may mean the whole BGU or any one or more BGU subunits and/or other components.

Unless otherwise stated or defined in this specification and/or claims the term "Autotrophic" may mean biomass which grows in the presence of light.

Unless otherwise stated or defined in this specification and/or claims the term "Heterotrophic" may mean biomass which grows in the absence of light.

Unless otherwise stated or defined in this specification and/or claims the term "Mixotrophic" may mean biomass which grows in the presence of light and in the absence of light.

Unless otherwise stated or defined in this specification and/or claims the term "BGM Feed Water" may mean a water flow comprising any water type or mixture used to supply water to a BGM, a BGU within a BGM, and/or any BGU subunit and/or other BGU component within a BGM. BGM Feed water may comprise salt water, fresh water, high salinity water, waste water, other water types, and/or mixtures of the foregoing, optionally comprising water from the Plan (e.g., FIG. 3), and in any ratio.

Unless otherwise stated or defined in this specification and/or claims the term "WWTP", or "WWTP module", or "traditional WWTP", or "traditional wastewater treatment plant", or "traditional bacteria-based wastewater treatment plant", or "traditional bacteria-based WWTP", or "conventional bacteria-based wastewater treatment plant", "conventional bacteria-based wastewater treatment plant", "WWTP using bacteria", or "WWTP using bacteria-based processes", or "WWTP using bacterial-based processes" or similar term may mean a wastewater treatment plant not using plant-based secondary treatment methods. It may mean a wastewater treatment plant using in whole or in part systems comprising bacteria-based technologies, such as activated sludge.

Unless otherwise stated or defined in this specification and/or claims the term "pollution entrainment module" may mean a module which uses any technology known to those of the art to sequester, entrain, react (e.g., reduction of NOx emissions), trap, dilute, absorb, filter, neutralize, scrub and/or otherwise treat exhaust gases with an optional flow of selected pollutants to a BGM. The module may additionally make use of treatment methods designed to prepare any liquid and/or gaseous outflow(s) from the module for introduction into a BGM, e.g., chemical treatment, pollution control, mixing with other fluids, temperature adjustment, and/or other methods known to the person of skill in the art for preparation for use of the outflow(s) for use in a BGM, for storage and later use in a BGM, and/or for discharge. The module may make use of any one or more of the following technologies/substances in any combination or sequence:
 a. Activated carbon,
 b. Hearth furnace cokes,
 c. Zeolites,
 d. Lime,
 e. Chlorine,
 f. Sprayers,
 g. Sorbents,
 h. Filtration,
 i. Catalyst(s)
 j. Photochemical methods,
 k. Selective catalytic reduction,
 l. Dry scrubber,
 m. Wet scrubber—spray tower, tray tower, packed bed tower, two pass wet scrubber, and/or other wet scrubber, and
 n. Other pollution control/entrainment techniques known to those skilled in the art.

Unless otherwise stated or defined in this specification and/or claims the term "pollution control module" may mean a module which uses any technology known to those of the art to sequester, entrain, react (e.g., reduction of NOx emissions), trap, dilute, absorb, filter, neutralize, scrub and/or otherwise treat exhaust gases for optional discharge to the environment. A pollution control module may make use of any one or more of the technologies/substances listed above for the "pollution entrainment module" and/or other technologies known to the person of skill in the art in any combination or sequence.

Unless otherwise stated or defined in this specification and/or claims the term "pollution control and/or heat recovery" may mean a pollution control module, a heat recovery module, or both.

Unless otherwise stated or defined in this specification and/or claims the term "conveyance" may mean a structure or system designed to convey materials optionally comprising fluids. A conveyance may mean a pipe for conveying fluids, (e.g., exhaust gases, water, carbon dioxide, oxygen, other gases and/or gas/liquid mixtures). A conveyance may mean a pipe to convey exhaust gases away from thermal plant or a thermal plant combustion process.

Unless otherwise stated or defined in this specification and/or claims the term "diversion" may mean a structure or system designed to divert any portion of materials and/or fluids from a conveyance. A diversion may mean a structure designed to cause the movement of materials to change direction in whole or in part.

Unless otherwise stated or defined in this specification and/or claims the term "waste heat" may mean heat that may be produced as a byproduct of a process generating primary process heat.

Unless otherwise stated or defined in this specification and/or claims the term "primary process heat" may mean heat which may be used to generate electricity or to perform any other industrial processes, such as processing steel.

Figure 2:
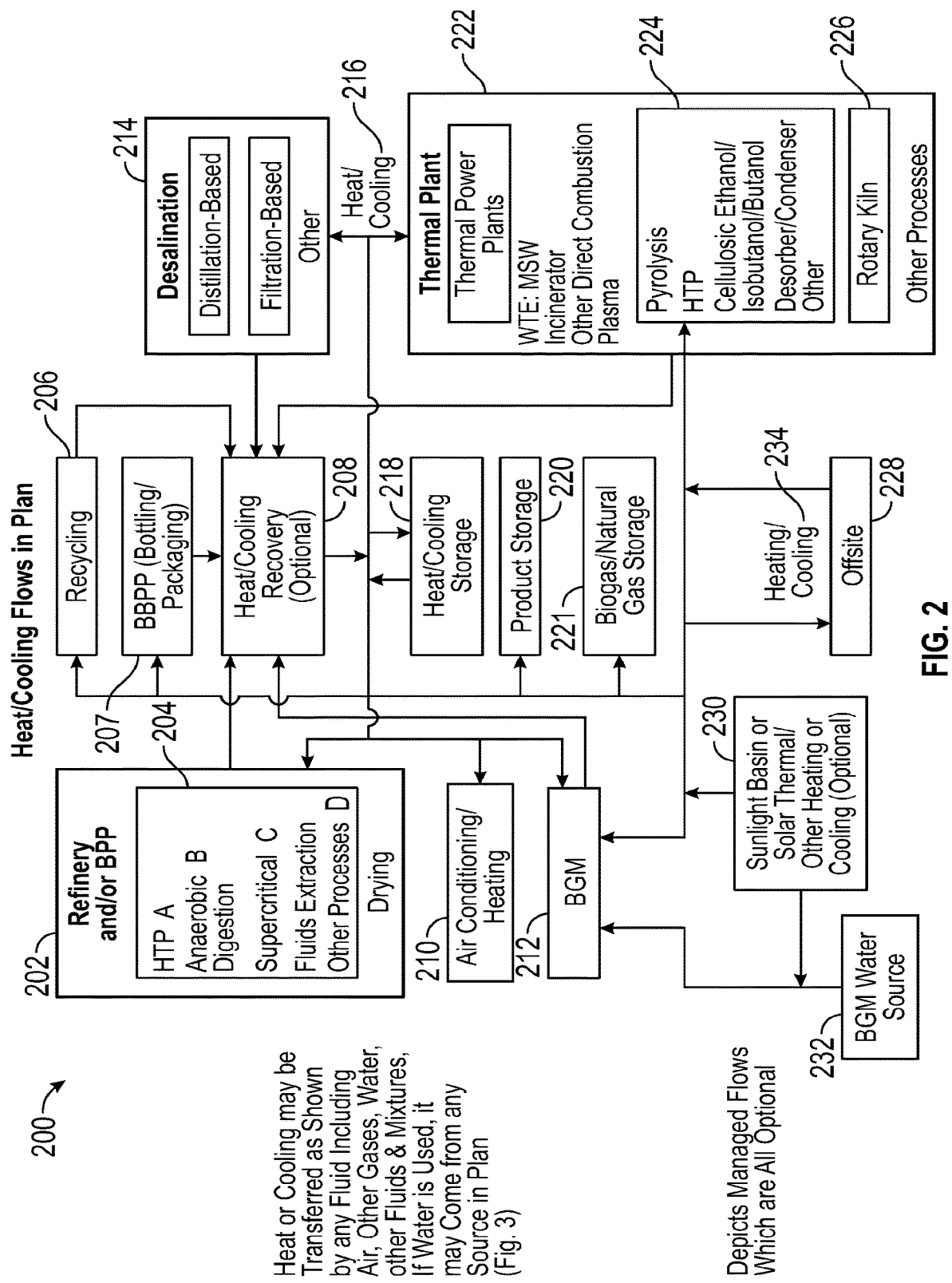
FIG. 2 is a schematic representation of heat flow within the Plan according to the present disclosure.

Unless otherwise stated or defined in this specification and/or claims the term "heat transfer" or a transfer of heat e.g., as depicted in FIG. 2 and/or other figures of this disclosure means the conveyance of heat from one portion of matter to another. Such a transfer may comprise any means known to the person of skill in the art from one material to another, comprising optionally directed contact of heated material with material to be heated, use of a heat exchanger and/or other indirect heat transfer process to transfer heat without direct contact of materials, any methods disclosed herein, and/or any other means known to the person of skill in the art. "Transfer of cooling", "cooling", or "cooling transfer" as depicted in any figure may use some of the same processes as a transfer of heat, except that the material making the transfer possesses lower thermal energy than the material it makes the transfer with, and absorbs thermal energy from the second material, thereby in essence transferring cooling. Cooling or cooling transfer may also refer to cool or cold materials optionally comprising fluids generated, such as air conditioning and/or refrigeration cogenerated by a thermal plant which may be applied to other materials and/or to materials in enclosed spaces to cool them.

Unless otherwise stated or defined in this specification and/or claims the term "heat exchange process" may mean a heat transfer wherein a heat exchanger may be used.

Unless otherwise stated or defined in this specification and/or claims the term "heat exchanger" may mean a piece of equipment used in heat transfer. A heat exchanger may be of any configuration, e.g, parallel flow, counter-flow, cross-flow, circular, or other configurations. A heat exchanger may be e.g, double pipe, shell and tube, plate, plate and shell, plate fin, adiabatic wheel, pillow plate, fluid, dynamic scraped surface, or other designs. They may comprise a phase change or direct contact heat exchangers. A heat exchanger may comprise a self-cleaning heat exchanger, waste heat recovery unit, Rankine cycle, organic Rankine Cycle, fluid heat exchanger and/or a heat recovery steam generator. Heat exchangers may be designed for any medium or combination of different media and/or fluid type(s). A heat exchanger may comprise one or more heat exchangers used together or in sequence and/or in parallel. Heat exchangers for purposes of this disclosure may also comprise any structures to transfer heat of any kind beyond the typical engineering structures referred to in the art as heat exchangers (e.g., a pool of water surrounding a BGM may be a heat exchanger, e.g., FIG. 12C). Any of these types of heat exchangers and/or others suited to the purpose may be used in any aspect of the disclosed Plan where heat exchangers may be indicated.

Unless otherwise stated or defined in this specification and/or claims the term, "heat/cooling recovery", or "heat and/or cooling recovery", or "heat recovery", or "heat recovery and reuse", or "heat recovery+reuse" may mean a recovery and/or optional distribution and/or reuse of heat and/or cooling from substances, fluids and/or flows of materials optionally from modules, systems, units, subunits, processes and/or technologies comprised by the Plan, by any means herein disclosed and/or by any means known to the person of skill in the art. Heat and/or cooling may be recovered in multiple separate units within a heat/cooling storage module based on the particular temperature and/or temperature range(s) of recovered heat and/or cooling e.g., from different modules, processes and/or technologies. Recovered heat and/or cooling may be reused in the module it was recovered from and/or in any other module(s) in the Plan (e.g., FIG. 2).

Unless otherwise stated or defined in this specification and/or claims the term, "heat/cooling recovery module", or "heat and/or cooling recovery module", or "heat recovery module", or "heat recovery and reuse module", or "heat recovery+reuse module" may mean a module where heat and/or cooling recovery take place.

Figure 23:
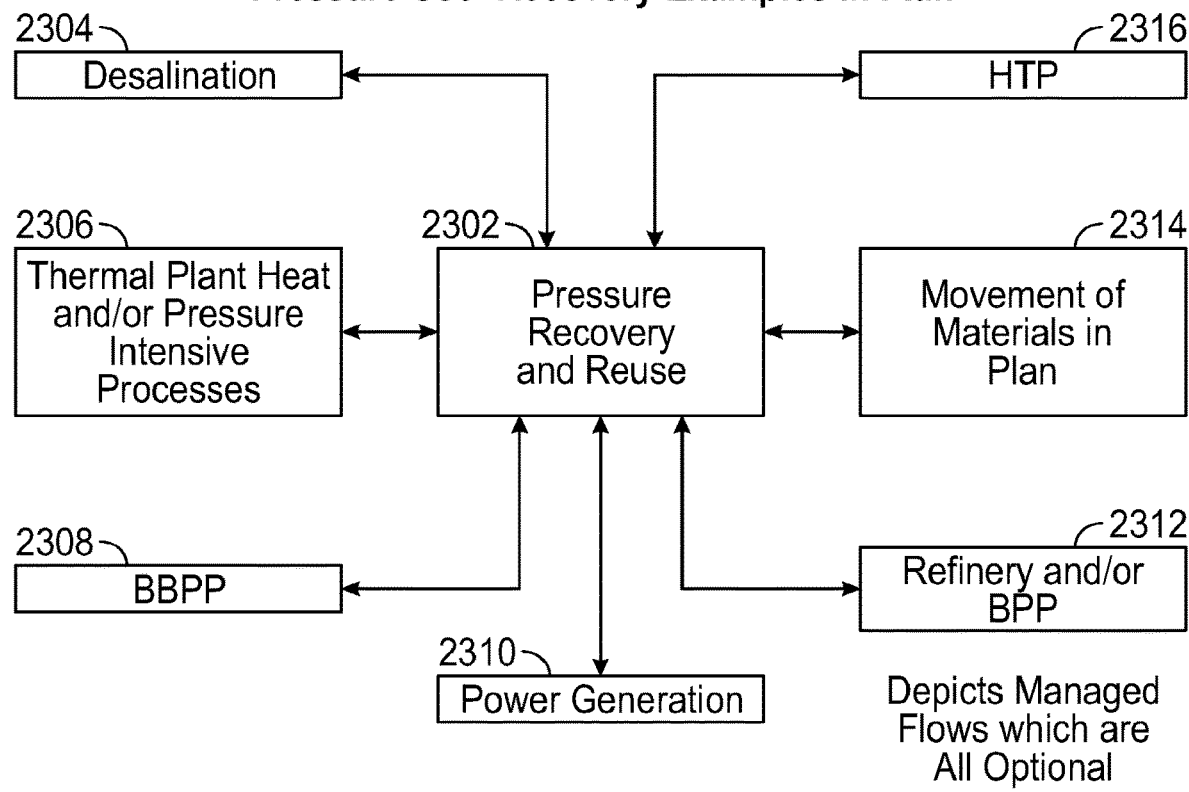
FIG. 23 is a schematic representation of pressure use, recovery and reuse within the Plan according to the present disclosure.

Unless otherwise stated or defined in this specification and/or claims the term "pressure recovery" may mean to recover pressure from one or more process(es), system(s) and/or module(s) for use in one or more of the same and/or other process(es), system(s), and/or module(s) e.g., FIG. 23. Pressure recovery may comprise any means described in this specification and/or any means known to the person of skill in the art.

Unless otherwise stated or defined in this specification and/or claims the term "pressure recovery module" may mean a module where pressure recovery occurs.

Unless otherwise stated or defined in this specification and/or claims the term "heat/pressure recovery module(s)" may mean either a heat recovery module, a pressure recovery module, or both.

Unless otherwise stated or defined in this specification and/or claims the term, "heat and/or cooling" or "heat/cooling" e.g., as represented by a line or arrow in a figure may comprise a flow of either heat, cooling, and/or a mixture thereof. The heat and/or cooling may originate in any module(s), system(s), and/or technolog(ies) in the Plan, and be transferred to any other module(s), system(s), and/or technolog(ies) in the Plan as shown in FIG. 2 and/or other FIGS. and/or description relevant to heat and/or cooling generation, capture and/or transfer.

Unless otherwise stated or defined in this specification and/or claims the term "heat storage" may mean any process, system, module and/or technology for storing heat. Heat storage technologies may comprise molten salt, heated oil, underground heat storage, storage in water and/or other liquids, and/or any other process known to those of skill in the art for storing heat. Cooling storage may be the same as heat storage, except that it stores materials of temperature low enough to provide cooling, e.g, an ice, or a fluid cooled below its freezing point, a fluid at ambient temperature used to cool a process involving high temperatures and/or hot fluids.

Unless otherwise stated or defined in this specification and/or claims the term "thermal process" may mean any process involving the use of heat whether within or outside the Plan. This may comprise any thermodynamic process and/or thermodynamic cycle.

Unless otherwise stated or defined in this specification and/or claims the term "thermodynamic process" may mean the energetic development of a thermodynamic system proceeding from an initial state to a final state. It may comprise open or closed systems, comprising systems using a thermodynamic cycle.

A "thermodynamic cycle" may mean when a thermodynamic system may be taken through a series of different states, and finally returned to its initial state. Thermodynamic cycles may comprise internal and/or external combustion modules. They may comprise, but are not limited to the following: Rankine cycle, Ericsson cycle, Brayton cycle/Joule cycle, Gas Generator cycle, Atkinson cycle, staged combustion cycle, Miller cycle, Stirling cycle, Carnot cycle, Otto cycle, diesel cycle, Kalina cycle, expander cycle, homogeneous charge compression ignition, organic Rankine cycle, supercritical Rankine cycle, regenerative Rankine Cycle, Bell Coleman cycle, hygroscopic cycle, Scuderi cycle, Stoddard cycle, Lenoir cycle, combined cycle, HEHC, mixed/dual cycle, Barton cycle, Humphrey cycle, combinations of the above, and/or other thermodynamic cycles. They may involve any or all thermodynamic process types, comprising but not limited to: isobaric, isothermal, isochloric, isoentropic, isoenthalpic, adiabatic, and/or other processes.

Unless otherwise stated or defined in this specification and/or claims the term "cogenerated cooling", or "cogeneration" may mean cooling that may be generated by a thermal plant, optionally from heat, and optionally from waste heat. It comprises any technologies known to those of skill in the art for such conversion. Cogenerated cooling may comprise air conditioning and/or refrigeration cogenerated by a thermal plant. "Cogeneration" may mean generation of other useful flows from heat (e.g., waste heat) in any manner known to a person of skill in the art.

Unless otherwise stated or defined in this specification and/or claims the term, "oxy-fuel process" may mean any process wherein oxygen may be injected into the intake of a combustion process or combustion chamber of any kind, e.g., thermal plant combustion processes, increasing the oxygen content of the gases used for combustion, and/or decreasing nitrogen content. Oxy-fuel processes may result in any proportion of oxygen in the air used for combustion above that of ambient air from less than 1% to approximately 78%. The resulting combustion discharge gases may be generally lower in NOx emissions.

Unless otherwise stated or defined in this specification and/or claims the term, "biomass/water slurry" may mean a mixture of water with biomass and/or biofuel.

A "treated biomass/water slurry", a "TBW slurry", or a "discharge of water from the biomass growth module" which may be comprised by a BGM outflow fluid, may comprise a biomass/water slurry that has been discharged from the BGM and has optionally been processed through some additional steps such as a tertiary treatment, concentration of biomass, dilution with water from another source and/or other methods of treatment disclosed herein and/or known to those of the art in preparation for use in other processes (e.g., for refining, gasification, processing into biomass products, preparation for use in a thermal plant cooling and/or heat absorption process(es), and/or for other uses as noted herein).

Unless otherwise stated or defined in this specification and/or claims the term "synergy" may mean the working together of two or more things, especially when the result may be greater than the sum of their individual effects and/or capabilities, and/or when detrimental effects may be reduced, eliminated, and/or turned into benefits in at least one thing by the use of two or more things together. Synergies may involve the use of interactions, connections, infrastructure sharing, resource sharing and/or communication (e.g., heat and/or fluid communication, etc.) between different modules of the Plan.

Unless otherwise stated or defined in this specification and/or claims the term "waste" may mean refuse, discarded materials, demolished materials, and/or byproducts of any kind. "Waste" may comprise municipal sanitary waste, demolition waste, construction waste, industrial waste, hazardous waste, biomass (e.g., wood waste generated from a lumberyard and/or other biomass waste from industry, agricultural waste material), and/or other waste materials. Waste may comprise metallic waste, glass, plastic, wood, ceramics, paper and/or any other material(s).

Unless otherwise stated or defined in this specification and/or claims the term, "waste receiving", or "waste receiving module", or "waste receiving/recycling", or "waste receiving/recycling module", or "recycling", or "recycling/waste receiving", or "recycling/waste receiving module", or "recycling module" may mean a module where waste may be transported, accumulated, stored, sorted, recycled, compacted, processed into recycled products, subjected to WTE via any number of WTE technologies, landfilled and/or otherwise treated in any means known to the person of skill in the art.

"Waste-to-energy", or "waste-to-energy module", or "WTE", or "WTE module", may mean a module which generates fuel, fuel precursors, and/or other products and/or energy in any form from waste, biomass and/or any other material. A WTE module may comprise one or more WTE systems, and may be comprised by a thermal plant.

A "WTE system", or "waste-to-energy system", or "WTE", or "waste-to-energy (WTE) system", or "waste-to-energy technology", or "WTE technology", may mean a particular system and/or technology type comprised by a WTE module and/or thermal plant which generates fuel, fuel precursors, and/or other products and/or energy in any form from waste, biomass and/or any other material. Waste-to-energy systems may comprise any technolog(ies) of this description disclosed in this specification and/or any others known to the person of skill in the art (e.g., incinerator, plasma gasification, cellulosic ethanol, pyrolysis, etc.).

Open Rankine cycle for purposes of this disclosure may mean a power generation system that mirrors a Rankine cycle in most ways, except that most notably, the water/steam mixture that may be normally condensed and returned as the working fluid may be instead replaced by a new portion of fluid. An Open Rankine cycle may involve the use of a treated biomass/water slurry.

Unless otherwise stated or defined in this specification and/or claims the term "primary treatment process", or "primary treatment" may mean the application of techniques known to the person of skill in the art for preparation of water of any kind for introduction into a BGM and/or before secondary treatment at a WWTP, possibly comprising removal of solids and/or addition of chemicals. In the case of a wastewater substrate, primary treatment may involve processes typical of primary treatment of wastewater, comprising optionally sedimentation, grit removal, screening (e.g., bar screening), and/or the use of a primary clarifier.

Unless otherwise stated or defined in this specification and/or claims the term "secondary treatment process", or "secondary treatment" may mean application of processes to further treat wastewater after primary treatment, described herein and/or known to the person of skill in the art comprising optionally biological processes to substantially remove dissolved and suspended organic compounds typically measured as BOD. Secondary wastewater treatment may be performed partially or fully in a BGM and/or in a secondary treatment system in a WWTP. Secondary treatment by a BGM may also reduce nutrient content in the water.

Unless otherwise stated or defined in this specification and/or claims the term "tertiary treatment process", or "tertiary treatment" may mean the application of techniques herein disclosed and/or known to the person of skill in the art for further treatment of a BGM outflow fluid and/or WWTP after discharge from a BGM for use of the BGM outflow fluid in a variety of applications, and/or for BGM and/or WWTP discharge, e.g., to the environment. In the case of a wastewater substrate, tertiary treatment may involve processes typical of tertiary treatment of wastewater (e.g., municipal wastewater), comprising the use of a secondary clarifier, disinfection techniques, and/or other techniques known to those in the art.

Unless otherwise stated or defined in this specification and/or claims the term "sludge processing" may mean the processing and/or treatment by any means known to those of the art of sludge of any type, comprising optionally sludge that may be generated in wastewater treatment processes. Sludge processing may be comprised by a WWTP and/or a BGM, and/or may be conducted as a separate process.

Unless otherwise stated or defined in this specification and/or claims the term "grid" or "the grid" for purposes of this disclosure may mean optional communication(s) and/or connection(s) of any description between different optional components. When discussed in connection with any figure, it may be not limited to one large interconnected system, such as an electrical grid. Rather the connections and/or communications in a "grid" as referred to herein may take the form of one or more separate subsystems of communication and/or connection between any two or more module(s)/unit(s), technology(ies) and/or other component(s) depicted by a grid, when present in certain embodiments. Any source, flow, communication and/or connection option depicted in a grid may remain in a separate subsystem e.g., a module, unit, or subunit, or may be combined with any other communication source(s) and flow(s) from the "grid" and/or other source(s) at any stage of any process depicted. For example, water flow, electrical flow, heat flow etc. may be combined, or may be separate flows within a grid, or between grids.

Unless otherwise stated or defined in this specification and/or claims the term "residuals" may mean any portion of material not used in a process when a process of any description may be conducted, such as biomass, water, sediment, sludge, solvents, chemical residues, and/or other materials.

Unless otherwise stated or defined in this specification and/or claims the term "infrastructure" may mean equipment and/or systems of any kind.

Unless otherwise stated or defined in this specification and/or claims the term "feed water" or "feedwater" may mean one or more water source(s) used to feed any module and/or process in the Plan in whole or in part. "Feed water" may mean a water source supplied to a BGM, a BGU, a growing subunit, and/or any other component of a BGU.

Unless otherwise stated or defined in this specification and/or claims the term "solar thermal" may mean a technology or module comprising one or more technologies to produce, store and/or distribute energy in any form using heat generated from sunlight (e.g., solar towers, solar troughs, etc.).

Unless otherwise stated or defined in this specification and/or claims the term "sunlight basin" may mean any structure and/or area where water may be accumulated, transported and/or circulated and exposed to sunlight, artificial light and/or ambient heat and/or cooling. A sunlight basin may comprise tank(s), pool(s), fountain(s), lake(s), stream(s), canal(s), and/or other water features of any description whereby water may absorb energy from sunlight and/or ambient heat and/or cooling.

Unless otherwise stated or defined in this specification and/or claims the term "collocated" may mean located next to or close to. Collocated may mean two things located with 0.1 km, or within 0.5 km, or within 1 km, or within 2 km, or within 5 km, or within 10 km, or within 20 km of each other, or any other distance which enables practical contribution to, benefit from, communication with, share infrastructure and/or components, and/or other interaction between different modules, systems, technologies and/or other elements of the Plan. Collocated may mean one or more systems, or one or more modules, one or more units and/or one or more subunits located, or a built or moved to or placed at a locus wherein the one or more one or more systems, or one or more modules, one or more units and/or one or more subunits may be within a circle with a radius of from about 0.01 to about 20 Km, or from about 0.01 to about 10 km, or from about 0.01 to about 8 km, or from about 0.01 to about 5 km, or from about 0.01 to about 2.5 km, or from about 0.01 to about 2 km, or from about 0.01 to 1 km, or from about 0.0.01 to about 0.2 km or from about 0.01 to 0.1 km, or from about 0.01 km to about 0.03 km, or from about 0.02 to about 0.1 km or from about 0.03 to about 0.1 km, or from about 0.04 to about 0.1 km, or any other distance which enables practical contribution to, benefit from, communication with, share infrastructure and/or components, and/or other interaction between different modules, systems, technologies and/or other elements of the Plan.

Unless otherwise stated or defined in this specification and/or claims the term "package", or, "to package", or "packaging" of or referring to water, biomass products and/or fuels (e.g., from a refinery, BPP and/or other module in a BBPP) may comprise drying, purifying, bottling, barreling, preserving, chemically treating, sterilizing, rolling, pressing, cutting, pelletizing, boxing, containerizing, compressing, pressurizing and putting into tanks, and/or other means of preparing products for storage, export and/or marketing.

Unless otherwise stated or defined in this specification and/or claims the term, "technology", or "technology type" may mean a technique, skill, method, process and/or equipment which may be used to accomplish an objective. The term "technology" may be used descriptively alone and/or as part of a compound noun to describe and/or illustrate a type of technology used in the Plan or in a specific module of the Plan. For example, a "desalination technology" or a "technology for desalination", or similar statement may mean a technology used to accomplish desalination. In Figs. of the disclosure, the word "technology" may be omitted, but the term may still be understood to describe a technology option in a figure. For example a "pyrolysis technology" may be designated simply as "pyrolysis" in a figure, and may be one technology optionally comprised by a thermal plant in certain embodiments.

Unless otherwise stated or defined in this specification and/or claims the term, "component" may mean a part or element of a larger whole. A "component" may mean a part of a module, unit, subunit, or technology. A "component" may also mean a technology.

Unless otherwise stated or defined in this specification and/or claims the term "hot mirror/other selective reflector" may mean a hot mirror and/or any other technology known to those of the art capable of selectively reflecting certain wavelengths of light, and optionally allowing others to pass through.

Unless otherwise stated or defined in this specification and/or claims the term "blue light" may mean light with wavelengths primarily in the blue range of the visible spectrum, approximately 380-500 nm.

Unless otherwise stated or defined in this specification and/or claims the term "red light" may mean light with wavelengths primarily in the red of the visible spectrum, approximately 620-750 nm.

Unless otherwise stated or defined in this specification and/or claims the term "solvent" and/or "solvents" may mean one or more substances that dissolve a solute.

Unless otherwise stated or defined in this specification and/or claims the term "ambient air" may mean air from the local environment. It may mean air from an enclosure (e.g., air inside a module or building).

Figure 13:
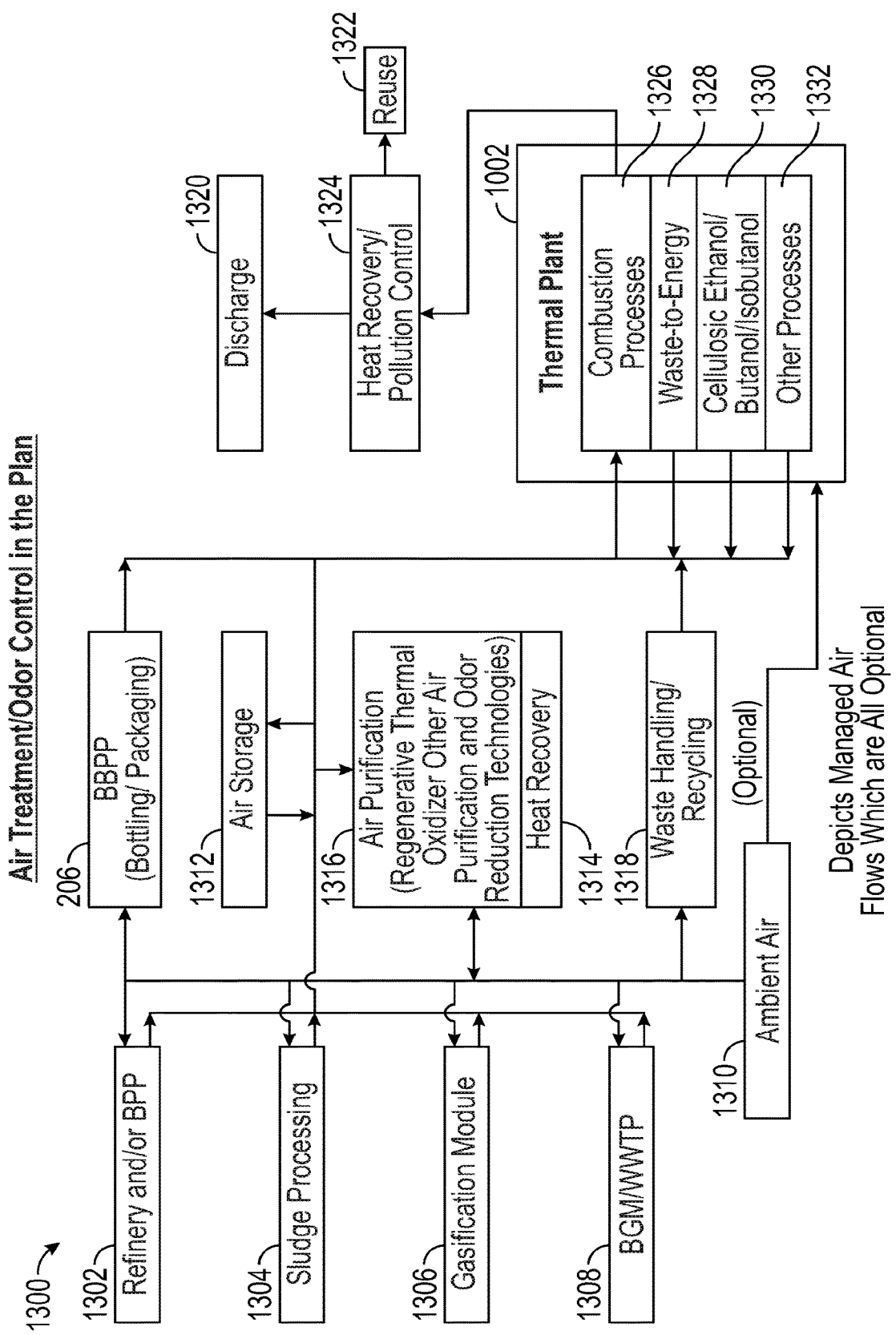
FIG. 13 is a schematic representation of air treatment and odor control according to the present disclosure.

Unless otherwise stated or defined in this specification and/or claims the term, "air treatment/odor control module", or "air plan" may mean a plan to treat, disinfect, deodorize, sanitize, circulate and otherwise control the flow and uses of air in the Plan, e.g., FIG. 13.

Unless otherwise stated or defined in this specification and/or claims the term "optional odor control air", or "optional odor control air in", may refer to air outflow that may be the product of an air treatment/odor control module prior to its introduction into thermal plant combustion process(es) 1326.

Unless otherwise stated or defined in this specification and/or claims the term "air purification", or "air purification module" may mean a module and/or technology within a module to purify air comprising any means known to those in the art to purify, deodorize, sanitize and/or otherwise improve the quality of air.

Unless otherwise stated or defined in this specification and/or claims the term "air storage" may mean any method herein disclosed or known to those in the art to store air, comprising optionally storage of air in a container at ambient pressure and/or storage in pressurized tanks.

Unless otherwise stated or defined in this specification and/or claims the term "landfill" may mean a place to dispose of waste by burying it. A landfill may comprise a municipal sanitary waste landfill, a hazardous waste landfill, a mixed waste landfill, a landfill used for waste management (e.g., temporary storage, consolidation, sorting, transfer, treatment and/or recycling), and/or other landfill type(s) known to those in the art.

Unless otherwise stated or defined in this specification and/or claims the term "landfill gases" may mean gases emitted by a landfill comprising carbon dioxide and/or combustible chemical compounds such as methane. "Landfill gases" may also be termed, "biogas", or "carbon dioxide". "Landfill gases" may also comprise equipment to capture, concentrate, purify, and/or process and deliver the landfill gases in any manner known to the person of skill in the art prepared for useful applications, such as combustion and/or use of carbon dioxide.

Unless otherwise stated or defined in this specification and/or claims the term "light oil" may mean oil which may be of lower density than water. Light oil may comprise other materials.

Unless otherwise stated or defined in this specification and/or claims the term "heavy oil" may mean oil which may be of higher density than water. Heavy oil may comprise other materials, comprising optionally solids and/or residuals of any kind.

Unless otherwise stated or defined in this specification and/or claims the term "plasma" may mean "plasma gasification" or "plasma gasification technology".

Unless otherwise stated or defined in this specification and/or claims the term, "provided", or "provides" may mean "configured to provide", or "configured to provide to", or "configured to be provided", or "configured to be provided to". The term provided may mean, in the case of a module, unit or subunit, that the module, unit or subunit may be configured to provide something and/or to receive and/or to provide what may be provided.

Unless otherwise stated or defined in this specification and/or claims the term, "directed to" may mean "configured to be directed", or "configured to be directed to". The term directed to may mean, in the case of a module, unit or subunit, that the module, unit or subunit may be configured to direct something and/or to receive and/or to provide what may be directed.

Unless otherwise stated or defined in this specification and/or claims the term, "supplied", or "supplies" may mean "configured to supply", or "configured to supply to", or "configured to be supplied", or "configured to be supplied to". The term supplied may mean, in the case of a module, unit or subunit, that the module, unit or subunit may be configured supply something and/or to receive and/or to provide what may be supplied.

Unless otherwise stated or defined in this specification and/or claims the term, "store", or "storage", or "storage unit", or "storage module" may mean a locus to keep or accumulate. The term may mean, in the case of a module, unit or subunit, that the module, unit or subunit may be configured to store what may be kept or accumulated.

Unless otherwise stated or defined in this specification and/or claims the term, "produced", or "produces" may mean "configured to produce", or "configured to be produced", or The term may mean, in the case of a module, unit or subunit, that the module, unit or subunit may be configured produce something and/or to receive and/or to provide what may be produced.

Unless otherwise stated or defined in this specification and/or claims the term, "processed", or "processes" may mean "configured to process", or "configured to be processed." The term may mean, in the case of a module, unit or subunit, that the module, unit or subunit may be configured to process something and/or to receive and/or to provide what may be processed.

Unless otherwise stated or defined in this specification and/or claims the term, "routed", or "routes" may mean "configured to route", or "configured to be routed." The term routed may mean, in the case of a module, unit or subunit, that the module, unit or subunit may be configured to route something and/or to receive and/or to provide what may be routed.

Unless otherwise stated or defined in this specification and/or claims the term, "reserved", or "reserves" may mean "configured to reserve", or "configured to be reserved." The term reserved may mean, in the case of a module, unit or subunit, that the module, unit or subunit may be configured to reserve something and/or to receive and/or to provide what may be reserved.

Unless otherwise stated or defined in this specification and/or claims the term, "fueled", or "fuels" or "fuelable" may mean "configured to fuel", or "configured to be fueled." The term may mean, in the case of a module, unit or subunit, that the module, unit or subunit may be configured to receive and/or to provide what may be fueled.

Unless otherwise stated or defined in this specification and/or claims the term, "reclaimed", or "reclaims" may mean "configured to reclaim", or "configured to be reclaimed." The term provided may mean, in the case of a module, unit or subunit, that the module, unit or subunit may be configured to reclaim something and/or to receive and/or to provide what may be reclaimed.

Unless otherwise stated or defined in this specification and/or claims the term, "sent", or "sends" may mean "configured to send", or "configured to be sent." The term may mean, in the case of a module, unit or subunit, that the module, unit or subunit may be configured to send something and/or to receive and/or to provide what may be sent.

Unless otherwise stated or defined in this specification and/or claims the term, "generated", or "generates" may mean "configured to generate", or "configured to be generated." The term generated may mean, in the case of a module, unit or subunit, that the module, unit or subunit may be configured generate something, and/or to receive and/or to provide what may be generated.

Unless otherwise stated or defined in this specification and/or claims the term, "discharged", or "discharges" may mean "configured to discharge", or "configured to be discharged." The term discharged may mean, in the case of a module, unit or subunit, that the module, unit or subunit may be configured to discharge something and/or to receive and/or to provide what may be discharged.

Unless otherwise stated or defined in this specification and/or claims the term, "delivered", or "delivers" may mean "configured to deliver", or "configured to be delivered." The term delivered may mean, in the case of a module, unit or subunit, that the module, unit or subunit may be configured to deliver and/or to receive and/or to provide what may be delivered.

Unless otherwise stated or defined in this specification and/or claims the term, "combusted", or "combusts" may mean "configured to combust", or "configured to be combusted." The term combusted may mean, in the case of a module, unit or subunit, that the module, unit or subunit may be configured to combust a fuel or substance and/or to receive and/or to provide what may be combusted.

Unless otherwise stated or defined in this specification and/or claims the term, "removed", or "removes" may mean "configured to remove", or "configured to be removed." The term removed may mean, in the case of a module, unit or subunit, that the module, unit or subunit may be configured to remove and/or to receive and/or to provide what may be removed.

Unless otherwise stated or defined in this specification and/or claims the term, "transferred", or "transfers" may mean "configured to transfer", or "configured to be transferred." The term transfers may mean, in the case of a module, unit or subunit, that the module, unit or subunit may be configured to transfer something and/or to receive and/or to provide what may be transferred.

Unless otherwise stated or defined in this specification and/or claims the term, "used", or "uses" may mean "configured to use", or "configured to be used." The term used may mean, in the case of a module, unit or subunit, that the module, unit or subunit may be configured to use something and/or to receive and/or to provide what may be used.

Unless otherwise stated or defined in this specification and/or claims the term, "blend", or "blended", or "mix", or "mixture", or "mixed", may mean to combine in any manner, or the state of being combined in any manner.

Unless otherwise stated or defined in this specification and/or claims the term, "trench" may mean a ditch comprising a long, narrow ditch, or an area excavated, prepared, maintained for the installation of piping, electrical lines, and/or other infrastructure. A "trench" may mean an area excavated and then filled in after installation of piping, electrical lines, and/or other infrastructure.

Unless otherwise stated or defined in this specification and/or claims the term, "automation", or "automation with controls", or "automation system with controls", or "automation system with flow controls" may mean an optionally computer-controlled system capable of sensing and/or regulating any condition, process, flow, input, output, in the Plan (e.g., temperature, pH, gas content, flow rate(s), density, dissolved solids, pollutant concentrations, nutrient levels, light intensity, salinity, and/or other measureable characteristics), receiving data, processing it optionally via computer, optionally using artificial intelligence or other adaptive controls to determine if adjustments to any operational parameters may be needed, sending one or more signals to one or more systems, which then makes one or more physical adjustment(s) in the operational parameters of the Plan (e.g., a change in a flow rate of fluids, a release of materials, the startup, increased rate, or decreased rate of function of a process or technology, directing materials to storage and/or other module, and/or other operational adjustments to the modules, units, subunits, technologies, and/or communications comprising the Plan).

Abbreviations:

TBW slurry—treated biomass/water slurry.
WW—Wastewater.
WWT—Wastewater Treatment.
WWTP—Wastewater Treatment Plant (Traditional, for example, using activated sludge as secondary treatment—not non-bacterial biomass-based).
"WWTP/BGM", or "BGM/WWTP" means a BGM and/or a WWTP.
"WWTP/BGU", or "BGU/WWTP" means a BGU and/or a WWTP.
TP—thermal plant.
WTE—Waste-to-Energy Technology.
HTP—Hydrothermal Processing.
CHG—Catalytic Hydrothermal Gasification.
HTL—Hydrothermal Liquefaction.
HTC—Hydrothermal Carbonization.
IST—In situ Transesterification.
RTP—Rapid Thermal Processing.
CO2—Carbon Dioxide.
DP—Desalination Plant.
BBPP—Water Bottling/Biomass Product Bottling/Packaging Plant.
BPP—Biomass Processing Plant.
"/"—Slash symbol may mean, "and/or". When separating module and/or feature names, may mean either or both of the modules and/or features before or after the slash as separate modules and/or features, and/or the modules and/or features optionally with some infrastructure and/or systems sharing.
BRC—Biofuel Research Center.
BGM—Biomass Growth Module.
BGM/WWTP or BGM and/or WWTP—A BGM, A WWTP, or both possibly interconnected, and/or possibly sharing some infrastructure in common.
BGU—Biomass Growth Unit.
WWTBGU—Wastewater Treatment BGU.
FWBGU—Fresh Water BGU.
MFWBGU—Mixed Fresh Water BGU.
SWBGU—Saltwater BGU.
BWBGU—Brackish Water BGU.
BGU/WWTP or BGU and/or WWTP—A BGU, A WWTP, or both possibly interconnected, and possibly sharing some infrastructure in common.

DETAILED DESCRIPTION

Aspects, features and advantages of several exemplary embodiments of the present disclosure will become better understood with regard to the following description in connection with the accompanying drawing(s). It should be apparent to those skilled in the art that the described embodiments of the present disclosure provided herein may be illustrative only and not limiting, having been presented by way of example only. All features disclosed in this description may be replaced by alternative features serving the same or similar purpose, unless expressly stated otherwise. Therefore, numerous other embodiments of the modifications thereof may be contemplated as falling within the scope of the present disclosure as defined herein and equivalents thereto. Hence, use of absolute terms such as, for example, "will," "will not," "shall," "shall not," "must" and "must not" are not meant to limit the scope of the present disclosure as the embodiments disclosed herein are exemplary.

The word "exemplary" is used herein to mean "serving as an example, instance, or illustration." Any aspect described herein as "exemplary" may be not necessarily to be construed as exclusive, preferred or advantageous over other aspects. Exemplary may mean, "e.g.," or "for example."

In the accompanying drawings and Figures, boxes may be understood to illustrate one or more module(s), unit(s), subunit(s), technolog(ies), component(s), process(es), input(s), output(s), feature(s) and/or other element(s) of the disclosure. Any line connecting to a box indicates an optionally managed connection or communication, e.g., electronic, fluid, gaseous, heat, energy, light and the like. Should an arrow be indicated along a line, the arrow indicates communication or optional communication in that direction along the line. Such communication in an indicated direction may include such communication in the opposite direction. If a line or arrow may be connected to or proceeds to or from a box, the communication may comprise such communication from any sub-module, sub-unit, technology, component, or other feature the box represents. If a line or arrow may be connected to or proceeds to or from a particular technology or feature listed within a box, the communication pertains to the particular technology or feature. Any connection or communication depicted may comprise any means of connection or communication known to those in the art, or any other means described herein. For example, liquids or gases may be distributed among different modules or systems using such technologies as pumps, piping, blowers, spargers, valves and/or any other technologies known to those in the art which may be suited to the purpose. Any such connection or communication may be direct or may also comprise a regulated flow, storage and/or modification of any kind to any one or more constituents comprising the communication in any manner known to those in the art as a part of such communication. For example, a communication of water may undergo treatment to remove pollutants, biomass, or other chemicals, storage, dilution, concentration, addition of chemicals, a change in temperature and/or pH, phase change and/or any other modification by means known to those of ordinary skill in the art before such communication, and/or the flow may be regulated by an automated computerized flow system using sensors, valves, storage systems and/or any other technologies known to those of the art for flow control. Sensors may measure various parameters in one module and trigger an action in another module. For example, the temperature, pH, nutrient content, turbidity, carbon dioxide content, oxygen content, and/or any other measurement in the BGM may be used to automatically trigger (e.g., using a computerized industrial control system adapted to the purpose) any input from and/or output to any other module e.g., in the Plan (e.g., heat, cooling, water, nutrients, carbon dioxide, oxygen, chemicals, and/or other inputs and/or outputs). All other modules and/or technology types e.g., in the Plan may have similar controls which may trigger inputs from other modules and/or outputs to other modules. Modules, units' subunits, technology types and other feature shown by boxes in the figures may be also optional, and all modules and/or technology types depicted may not be present in any embodiment e.g., of the Plan. Modules and/or technologies depicted and/or described herein may comprise any one or more technologies known to one of ordinary skill in the art, and/or any other variations or modifications to those technologies discussed herein. Where boxes may be drawn within other boxes, the boxes within may be understood to illustrate one or more modules, units, subunits, technologies, components, processes, inputs, outputs, features and/or other elements of the disclosure optionally comprised by the boxes which contain them. Where a specific technology, process, module or other feature may be listed within any box, it may be understood to be present only in an embodiment of the disclosed Plan, and may be illustrated in a specific figure to demonstrate communication or another relationship of the specific feature illustrated within the Plan when present in any embodiment comprising that individual feature. When more than one specific feature may be depicted in a figure, module or within a box illustrating technologies of a module, any feature depicted is generally optional, e.g., independent of another, or that two or more must be present in any embodiment; except, to the extent there is communication and/or connection between them, the two or more may be present to establish such communication and/or connection in certain embodiments. Modules shown in any drawing or Figure depicting any one or more features may be exemplary only, and any module of the disclosure may comprise any other feature fitting the definition of such module in other embodiments, and will not be limited by any exemplary technology or combination of technologies listed within a box of such module in any drawing or Figure. When discussed in connection with any figure, the term "grid" or "the grid" for purposes of this disclosure means optional communication(s) and/or connection(s) of any description between different optional components. It does not necessarily mean one large interconnected system, such as an electrical grid. Rather the connections and/or communications in a "grid" as referred to herein may mean one or more separate closed subsystems of communication and/or connection between any two or more module(s)/unit(s), technology(ies) and/or other component(s) depicted by the grid, when present in certain embodiments. Any source, flow, communication and/or connection option depicted in a grid may remain in a separate subsystem, or may be combined with any other communication source(s) and/or flow(s) from the "grid" or other source (s) at any stage of any process depicted.

Figure 28:
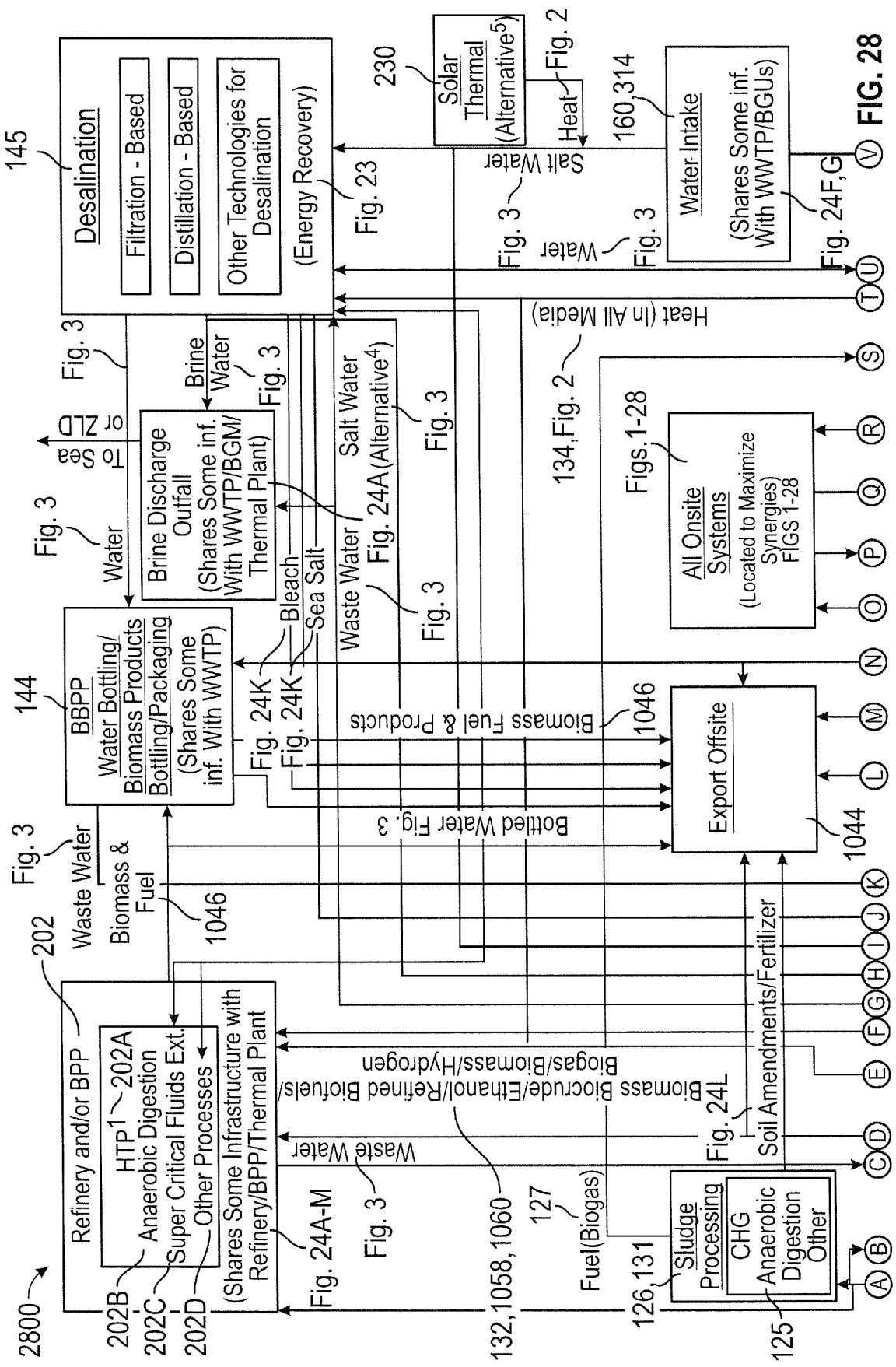
FIG. 28 is a schematic representation of a design according to the disclosure. Within this figure no line intersects, although represented in that manner.
Figure 28:
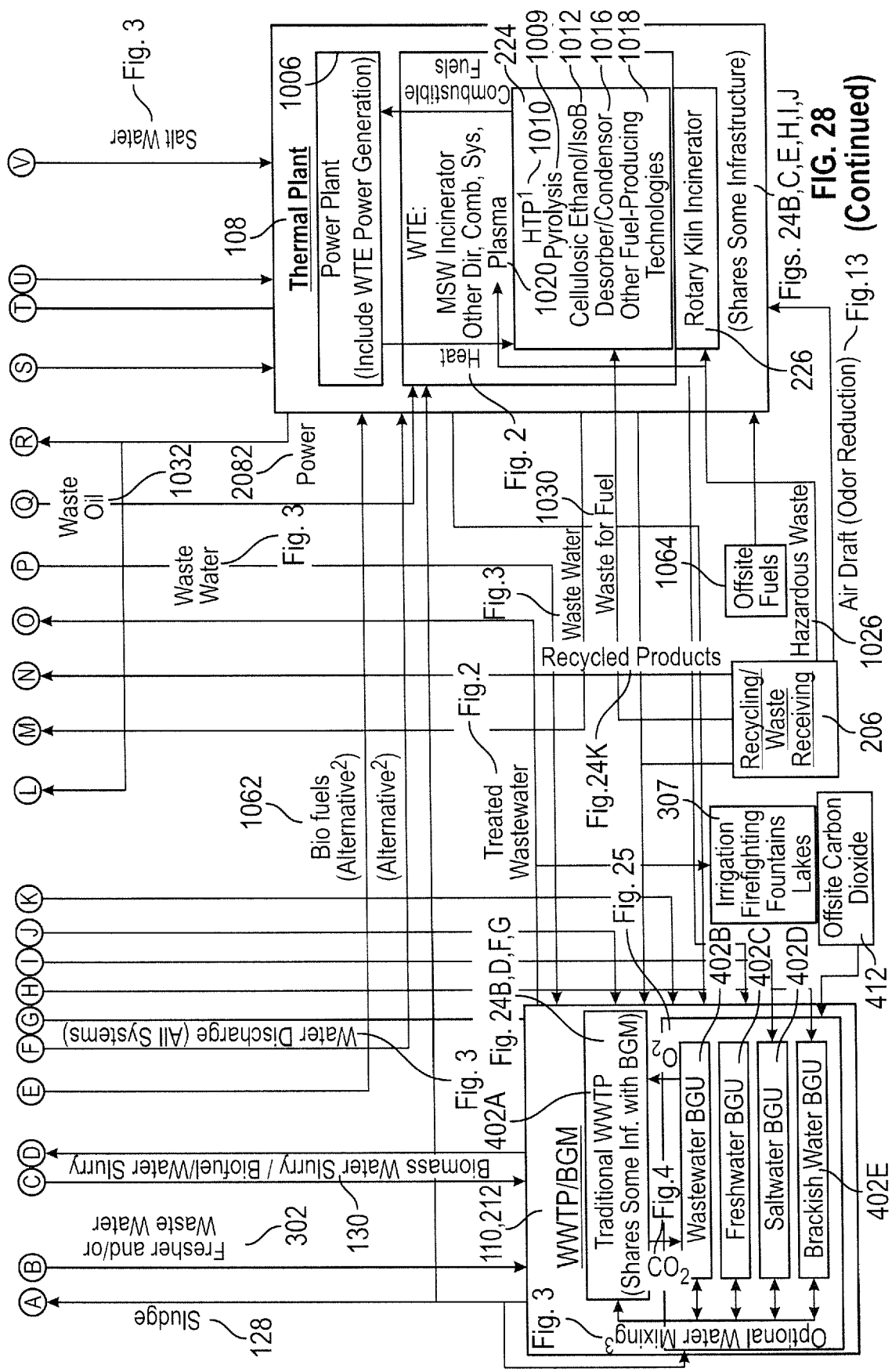

With reference to FIG. 28, the disclosure includes novel connections, communications, and/or synergies among different facility types, some of which may be generally unrelated, such as a thermal plant, a WWTP, a biomass growth module, a sludge processing plant, a refinery and/or a BPP (a downstream processing facility), a BBPP (a products packaging facility), a waste processing/recycling center, a desalination plant, solar thermal technologies, and other processes to generate electricity, fuels, products, and to productively reclaim and reuse waste heat, water, carbon dioxide, air and/or other gases, pressure, waste biomass, solvents and/or other materials. Additional optional technologies and/or modules may be added to the design e.g., Master Drawing to create additional outputs, efficiencies or synergies. Master Drawing embodies a non-limiting high-level representative embodiment of the Plan, comprising many technology options and/or connections, communications or synergies which may comprise the Plan, which may be further illustrated in subsets or subsystems of the Plan in FIGS. 1-25.

FIGS. 1-28 may depict different non-limiting designs which may include certain technologies, process flows, communications, connections, synergies, and/or other features of the Plan.

With reference to FIG. 1, a portion of the Plan may be presented in more detail. For example, design 100 includes a water feed, e.g. a salt and/or freshwater feed (which may or may not comprise wastewater) 160 that may be optionally treated in a primary treatment module, 104. Primary treatment module 104 may optionally provide sludge 128 to a gasification module, e.g., CHG module or anaerobic digester 125, and feed primary treated water to BGM 110. Residuals 124 may be optionally fed to BGM 110 after processing sludge 128 and/or other inputs in gasification module 125. Thermal plant 108, in an embodiment, burns a carbon-based fuel, e.g., a biofuel 106 provided by BGM 110 which may be optionally processed 102, Biogas 127 from the Gasification module 125 that may be optionally processed 131 and/or Biocrude and/or other biofuels 106 developed from a BGM outflow fluid 117 taken through optional processing steps such as tertiary treatment 114, a gravity thickener and/or other methods to concentrate and/or separate biomass from water, and/or dilution 118, a Refinery 120 optionally further processed (e.g., to prepare the output for use in a thermal plant and/or for export) 136 and/or optionally taken through heat recovery 135 wherein the heat recovered may be reused e.g., in the Plan e.g., in FIG. 2, and the combustion of any one or more of these fuels may provide carbon dioxide 119 to BGM 110. Thermal plant 108 may provide energy to BGM 110, Refinery 120, and/or an optional biocrude 132 processing unit 136 and/or other elements of the Plan when present, e.g., FIG. 1 and/or other figures herein. BGM 110 optionally feeds tertiary treatment module 114 that optionally provides recirculation 112 of the tertiary treated effluent back to BGM 110. A biomass and water slurry 116 may be discharged from tertiary treatment module 114 to module comprising optional gravity thickener and/or other methods, e.g, to concentrate, separate components of, and/or dilute the biomass/water slurry 118. Module 118 comprising optional gravity thickener and/or other units/methods to concentrate, separate components of, and/or dilute the biomass/water slurry 116 feeds a treated biomass/ water slurry 130 to Refinery 120 and/or to gasification module 125. Refinery 120 may also receive and/or process other biomass and/or waste from other sources 161 and/or optionally residuals 133 from optional BPP 146. Any residuals 122 from Refinery 120 processing may be fed back to gasification module 125. Any water 150 discharged from Refinery 120 may be optionally fed to heat/pressure/energy recovery unit(s) 152 with heat recovered to be used e.g., in the Plan (e.g., FIGS. 2 and 23) and the cooled water 154 sent for water reuse e.g., in the Plan 156 (e.g. FIG. 3). Module comprising optional gravity thickener and/or other methods to concentrate, separate components of, and/or dilute the biomass/water slurry 118 may optionally feed a water/biomass slurry and/or extract containing biomass 142 to an optional BPP (downstream processing facility) 146 to provide biomass products 147 (vide infra) which may be optionally packaged in an optional BBPP (a bottling and packaging plant) 144 and water, heat and/or carbon dioxide 148 suitable for reprocessing and use e.g., in the Plan (e.g. FIGS. 2, 3, and/or 4) 149. Water 115 may be also collected via water stream 115 from Tertiary Treatment module 114, and water 148 may be collected also via water stream 140 from gravity thickener and/or other methods to concentrate/separate and/or dilute biomass and water 118 for processing, treatment, and reuse e.g., in the Plan e.g. FIGS. 2, 3, 4 149. Heat and/or cooling 134 may be provided from thermal plant 108 optionally to the Biofuel processing module 102, BGM 110, Gasification Module 125, Refinery 120, optional BPP 146, Biomass Products 147 (e.g., storage), and/or optional BBPP 144, and/or for other uses e.g., in the Plan (e.g. FIG. 2). Water 143 may also be obtained from a Desalination Unit 145, which also discharges Brine 141.

In reference to FIG. 1 an embodiment of the disclosure includes a system 100 comprising: a biomass growth module (BGM) 110 and optionally: a thermal plant module 108 optionally producing an exhaust gas comprising carbon dioxide 119 optionally fueling the BGM 110; wherein the thermal plant module 108 is optionally fuelable by a BGM outflow fluid 117 from the BGM 110; wherein the BGM outflow fluid 117 is optionally refined 120 in whole or in part optionally by heat 134 from the thermal plant module 108; and/or wherein the exhaust gas 119 optionally may provide a substantial portion of the carbon content of the BGM outflow fluid 117. An embodiment includes the system wherein the BGM 110 is configured to be supplied by BGM feed water 160 which is optionally pretreated and comprising: salt water 160; fresh water 160; high salinity water 160; wastewater 160; any source of water 160 from the Plan (for example, FIG. 3); another water type(s) 160; and/or a combination thereof 160. An embodiment includes the system wherein the BGM feed water 160 is optionally processed through a primary treatment process 104, also referred to as "primary treatment", before being supplied to the BGM 110. An embodiment includes the system wherein the primary treatment process 104 comprises: screening; grit removal; sedimentation; addition of chemicals; and/or other means to prepare water for introduction into a BGM 110. An embodiment includes the system wherein sludge 128 from the primary treatment process 104 is optionally supplied to a gasification module 125. An embodiment includes the system wherein the BGM 110 is configured to produce a biofuel 106, which biofuel 106 supplies the thermal plant module 108 either directly or after additional processing 102 optionally comprising drying, separation from water such as steam stripping, for example, FIG. 21, purification, addition of chemicals, and/or blending with other fuels and/or gases and/or other processing steps known to those in the art to prepare biofuel for use as fuel in a thermal plant. An embodiment includes the system wherein the BGM outflow fluid 117 is optionally processed before optionally fueling the thermal plant module 108, and wherein the BGM outflow fluid 117 is optionally being supplied to a gasification module 125, a BPP module 146 and/or a BBPP module 144, wherein the BGM outflow fluid 117 is processed by: a tertiary treatment module 114; a gravity thickener 118 or other methods such as filtration, screening, coagulation, centrifugation, sedimentation, flocculation, bio-flocculation, flotation (including dissolved air and hydrogen), gravity settling, gravity thickener, cell disruption, bacterial extraction (e.g., a bacterial process for processing biomass, for example, see http://www.soleybio.com/extractor-bacteria.html incorporated herein by reference and relied upon); ultrasound, microwave, solvent, cold press, transesterification, evaporation, electrophoresis, electroflotation, adsorption, ultrafiltration, precipitation, chromatography, crystallization, desiccation, lyophilization, drying, sterilization, hydrothermal processing, and/or other methods suitable for processing biomass and/or biofuels known to a person of ordinary skill in the art (for example, see, Pandey, Ashok, Lee, Duu-Jong, and Chisti, Yusuf, eds. Biofuels from Algae. Amsterdam, NLD: Elsevier Science & Technology, 2013. 85-110. ProQuest ebrary. Web. 16 Sep. 2015, incorporated herein by reference and relied upon and Shelef, G., A. Sukenik, and M. Green. Microalgae harvesting and processing: a literature review. No. SERI/STR-231-2396. Technion Research and Development Foundation Ltd., Haifa (Israel), 1984, incorporated herein by reference and relied upon and/or Shelef et al., is incorporated in U.S. Provisional Application No. 62/173,905, a priority document of this specification, filed Jun. 10, 2015 as an Appendix to the Specification, also incorporated by reference in its entirety and relied upon); a dilution module 118; a refinery module 120; a heat recovery module 135, for use in the Plan, for example, FIG. 2; and/or processing 136 optionally comprising purification, addition of chemicals (e.g., to stabilize biocrude and/or biofuels), blending with other fuels, and/or any other processing steps known to those in the art to prepare the biocrude 132 and/or biofuels 132 for use in the thermal plant module 108. An embodiment includes the system wherein the tertiary treatment module 114 is configured to supply a biomass/water slurry 116 to the gravity thickener or other methods 118 known to a person of ordinary skill in the art (for example, author Shelef, et. al, 1984 and Pandey et. al, 2013 pgs. 85-110) to concentrate, separate, and/or dilute the BGM outflow fluid 117. An embodiment includes the system wherein the thermal plant module 108 is configured to optionally provide heat and/or cooling 134 to: the refinery module 120; the BPP module 146; biomass products 147; the BBPP module 144; the BGM 110; the gasification module 125; processing 102 of biofuel 106; and/or a desalination module 145. An embodiment includes the system wherein water 115 that is the result of the tertiary treatment 114 is routed for water reuse 149 in the Plan, for example, FIG. 3, and/or optional recirculation 112 to the BGM 110. An embodiment includes the system wherein the gravity thickener or other methods known to a person of ordinary skill in the art (for example, author Shelef, et. al, 1984 and Pandey et. al, 2013 pgs. 85-110) to concentrate, separate, and/or dilute 118 the BGM outflow fluid 117 comprises: a water, biomass and/or extract 142 output; a treated biomass/water slurry 130 output (also defined as a BGM outflow fluid); and/or a water output 140. An embodiment includes the system wherein any portion of the treated biomass/water slurry 130 is directed to: the refinery module 120; and/or the gasification module 125. An embodiment includes the system wherein the water, biomass, and/or an extract 142 thereof is supplied to the BPP module 146. An embodiment includes the system wherein the water 140 output from the gravity thickener or other methods known to a person of ordinary skill in the art (for example, author Shelef, et. al, 1984 and Pandey et. al, 2013 pgs. 85-110) to concentrate, separate, and/or dilute 118 the BGM outflow fluid 117 is routed for water reuse 149 in the Plan, for example, FIG. 3. An embodiment includes the system wherein the BPP module 146 comprises: biomass products 147 outputs which are optionally routed to a BBPP module 144; heat, water, and/or carbon dioxide 148 outputs which are optionally routed for reuse 149 in the Plan, for example, FIG. 2, FIG. 3 and/or FIG. 4; and/or residuals 133 optionally routed to the refinery module 120. An embodiment includes the system wherein the refinery module 120 receives optional inputs selected from: other biomass source(s) 161; other waste 161; and/or pressure 132. An embodiment includes the system wherein the refinery module 120 has optional outputs selected from: biocrude 132; biofuel 132; water 150; and/or residuals 122. An embodiment includes the system wherein the biocrude 132 and/or biofuel 132 outputs from the refinery module 120 serve in whole or in part as the BGM outflow fluid output which output optionally fuels the thermal plant module 108. An embodiment includes the system wherein the biocrude 132 and/or biofuel 132 outputs from the refinery module 120 undergo additional steps selected from the following before optionally fueling the thermal plant module 108: a heat recovery module 135, for use in the Plan, for example, FIG. 2; and/or processing 136 optionally comprising purification, addition of chemicals (e.g., to stabilize biocrude and/or biofuels), blending with other fuels, and/or any other processing steps known to those in the art to prepare the biocrude 132 and/or biofuels 132 for use in the thermal plant module 108. An embodiment includes the system wherein the refinery module 120 generates residuals 122 which are optionally sent to a gasification module 125. An embodiment includes the system wherein the gasification module 125 produces a biogas 127 output. An embodiment includes the system wherein the biogas 127 output is optionally further processed 131 optionally comprising drying, separation from water, purification, addition of chemicals, and/or blending with other fuels and/or gases and/or other processing steps known to those in the art to prepare biogas as fuel in a thermal plant." An embodiment includes the system wherein the biogas 127 output optionally partially or fully fuels the thermal plant module 108. An embodiment includes the system wherein the gasification module 125 produces a residuals 124 output. An embodiment includes the system wherein the residuals 124 output is supplied to the BGM 110. An embodiment includes the system wherein the refinery module's 120 water 150 output is directed to an optional heat 152, for example, FIG. 2 and/or pressure recovery module 152, for example, FIG. 23. An embodiment includes the system wherein the heat 152, for example, FIG. 2 and/or pressure recovery module 152, for example, FIG. 23 produces a water 154 output wherein the water is reused 156 in the Plan, for example, FIG. 3. An embodiment includes the system wherein the thermal plant module 108 optionally provides power to the Plan. An embodiment includes the system wherein the desalination module 145 generates a water 143 and/or brine 141 outputs. An embodiment includes the system wherein the water 143 output is directed to a BBPP module 144 for packaging. An embodiment includes the system wherein the brine 141 output is discharged either with or without dilution from other water sources in the Plan, for example, FIG. 3.

In reference to FIG. 1 an embodiment of the disclosure includes a system 100 comprising a BPP module 146 collocated with a BBPP module 144. An embodiment includes the system wherein the BPP module 146 provides a biomass and/or biomass product 147 output stream(s) to the BBPP module 144. An embodiment includes the system wherein the BPP module 146 receives inputs of: water 142; biomass 142; extract 142; heat 134; and/or any combination of the afore mentioned. An embodiment includes the system wherein the following are reclaimed from the BPP module 146: heat 148; carbon dioxide 148; water 148; and/or residuals 133. An embodiment includes the system wherein residuals, for example, 122, 124, 133 may comprise any portion of material not used in a process or module, including optionally: biomass; water; sediment; sludge; solvent(s); and/or chemical residues. An embodiment includes the system wherein the residuals 133 are sent to a refinery module 120. An embodiment includes the system wherein the BBPP module 144 receives an input of heat 134. An embodiment includes the system wherein the heat 134 is provided by a thermal plant module 108. An embodiment includes the system wherein the thermal plant module 108 and BBPP module 144 are collocated.

In reference to FIG. 1 an embodiment of the disclosure includes a system 100 wherein any two or more of the following are collocated: a thermal plant module 108; a BGM 110; a refinery module 120; a gasification module 125; a BPP module 146; a BBPP module 144; and/or a desalination module 145 wherein the modules are operatively in communication with one another and may exchange heat, biomass, water, carbon dioxide, residuals and/or other resources and/or byproducts as described in the Plan. An embodiment includes the system wherein any one or more of modules: a thermal plant module 108; a BGM 110; a refinery module 120; a gasification module 125; a BPP module 146; a BBPP module 144; and/or a desalination module 145 is a retrofitted module. An embodiment includes the system wherein biomass from any source(s) may be processed by: the refinery module 120; the gasification module 125; and/or the BPP module 146. An embodiment includes the system wherein residuals may be directed from any of these modules to any other(s) for processing: a thermal plant module 108; a BGM 110; a refinery module 120; a gasification module 125; a BPP module 146; a BBPP module 144; and/or a desalination module 145. An embodiment includes the system wherein fuels produced from processing may be provided as fuels to the thermal plant module 108 either directly and/or with additional treatment, processing and/or heat recovery.

In reference to FIG. 1 an embodiment of the disclosure includes a method of integrating a thermal plant 108 and a BGM 110 comprising: providing the system 100 and generating a biomass in the BGM 110. An embodiment includes the method further comprising refining the biomass to a biofuel. An embodiment includes the method further comprising delivering the biomass to the thermal plant 108. An embodiment includes the method further comprising delivering the biofuel to the thermal plant 108. An embodiment includes the method further comprising combusting the biomass in the thermal plant 108. An embodiment includes the method further comprising delivering thermal plant 108 exhaust gas 119 to the BGM 110. An embodiment includes the method further comprising processing the biomass into non-fuel products. An embodiment includes the method further comprising removing pollutants from the thermal plant 108 exhaust gas.

In reference to FIG. 1 an embodiment of the disclosure includes a method of integrating: a thermal plant module 108; a BGM 110; a refinery module 120; a gasification module 125; a BBP module 146; a BBPP module 144; and/or a desalination module 145; comprising providing the system of claim 37 wherein the one or more of: the thermal plant module 108; the BGM 110; the refinery module 120; the gasification module 125; the BBP module 146; the BBPP module 144; and/or the desalination module 145 is a retrofitted module; and integrating the one or more retrofitted module into one or more grids which grids are in operative communication with one another. An embodiment includes the method wherein operative communication comprises exchanging: heat; biomass; water; carbon dioxide; residuals; and/or other resources and/or byproducts between the one or more retrofitted module and/or the one or more grids.

In an embodiment, the disclosed design and/or methods, e.g., those of FIG. 2, may provide a highly productive, e.g., a substantially adiabatic use, of energy, e.g., waste energy, emitted from a thermal plant. For example, many thermal power plants require significant cooling while generating energy. The energy of thermal power plants or other industrial plants, e.g., steel plants, may comprise heat which may be used in a thermal process, optionally comprising a thermodynamic process or thermodynamic cycle, such as a Rankine Cycle using a working fluid to absorb and release heat to generate electricity, which may be defined herein as "primary process heat" in these systems, but another portion of the heat energy may be often wasted and dumped to the environment wherein the energy may be not used to drive other processes, for example, the heat removed in order to cool a working fluid in a thermodynamic cycle. The portion of heat generated and often discharged in this way may be termed "waste energy" or "waste heat." The amount of waste heat produced in thermal power plants typically varies between 40% and 75% of the heat content of the fuel. For example: A simple cycle power plant produces about 51-67% waste heat. A combined cycle power plant produces approximately 35-50% waste heat. Oil-fired generators and Coal-fired generators produce approximately 56-72% waste heat. Nuclear power plants produce approximately 55-70% waste heat. Most heat recovery systems may be configured to recover approximately 15-20% of the waste heat, which may be often used solely for secondary power generation, and the remaining waste heat may be simply discharged into the environment, being truly wasted, and often causing environmental damage. The disclosed integrated infrastructure Plan, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, not only has standard heat recovery technologies for power generation, but makes productive use of all waste heat, from higher temperature waste heat, to lower temperature waste heat that may be not suitable for power generation. All heat sources above ambient temperature may be put to innovative and extremely productive use e.g., in the Plan for refining biomass/biofuel, warming the BGM to optimize temperature, other low temperature power generation, recycling/packaging, desalination, and/or other uses e.g., FIG. 2. In an embodiment, the heat used in the processes and/or systems of the disclosure may be a combination of primary heat and waste heat in any proportion, e.g., from 1/50 to 1/1 or from 1/10 to 3/1, or from 1/5 to 5/1, or all waste heat, or all primary heat. In some cases, primary process heat may be substituted for, used concurrently with, and/or used to augment waste heat, e.g., for the applications in FIG. 2 and/or other figures and/or discussion relating to use of heat. Also, cooling from any source may be used in the same way, and cooling may be cogenerated from any heat source and/or reclaimed heat e.g., in the Plan by any technology know to those in the art, especially using waste and/or primary process heat from the thermal plant, and the cooling may be used e.g., in the Plan in the same manner as heat e.g., FIG. 2, and in other ways beneficial to the Plan, such as for refrigeration (e.g., of biomass products produced by the Plan), air conditioning of buildings, refining of biomass, and/or other uses e.g., FIG. 2. Thus, in an embodiment, the process and/or system of the described Plan and method may capture from approximately 10% to 90%, or from 15% to 85% or from 20% to 70% or from 30% to 60% or from 40% to 50% of the waste heat of a thermal plant and optionally heat and/or cooling generated and/or reclaimed from any of the modules e.g., FIG. 2, and uses it in the described Plan and/or method.

In an embodiment e.g., FIGS. 1 and/or 14, biomass products requiring bottling may be bottled in a collocated water bottling/biomass products bottling/packaging plant (BBPP). In an embodiment, solid biomass products and/or biomass products in oil may also be packaged in this plant.

Depending on the biomass strain used, some types of fuel may be generated directly by the biomass in the biomass growth module. In one or more embodiments, e.g., those of FIG. 1 and/or FIG. 10, these fuels may be separated from the water in the biomass growth module, either by evaporation and/or other means, and may be used directly as fuel and/or further refined and then used as fuel for the thermal plant and/or other use. These fuels may follow the process path shown in 106 and 102 of FIG. 1, FIG. 10, and/or may be routed to the Refinery and/or BPP and/or to the BBPP.

Figure 3:
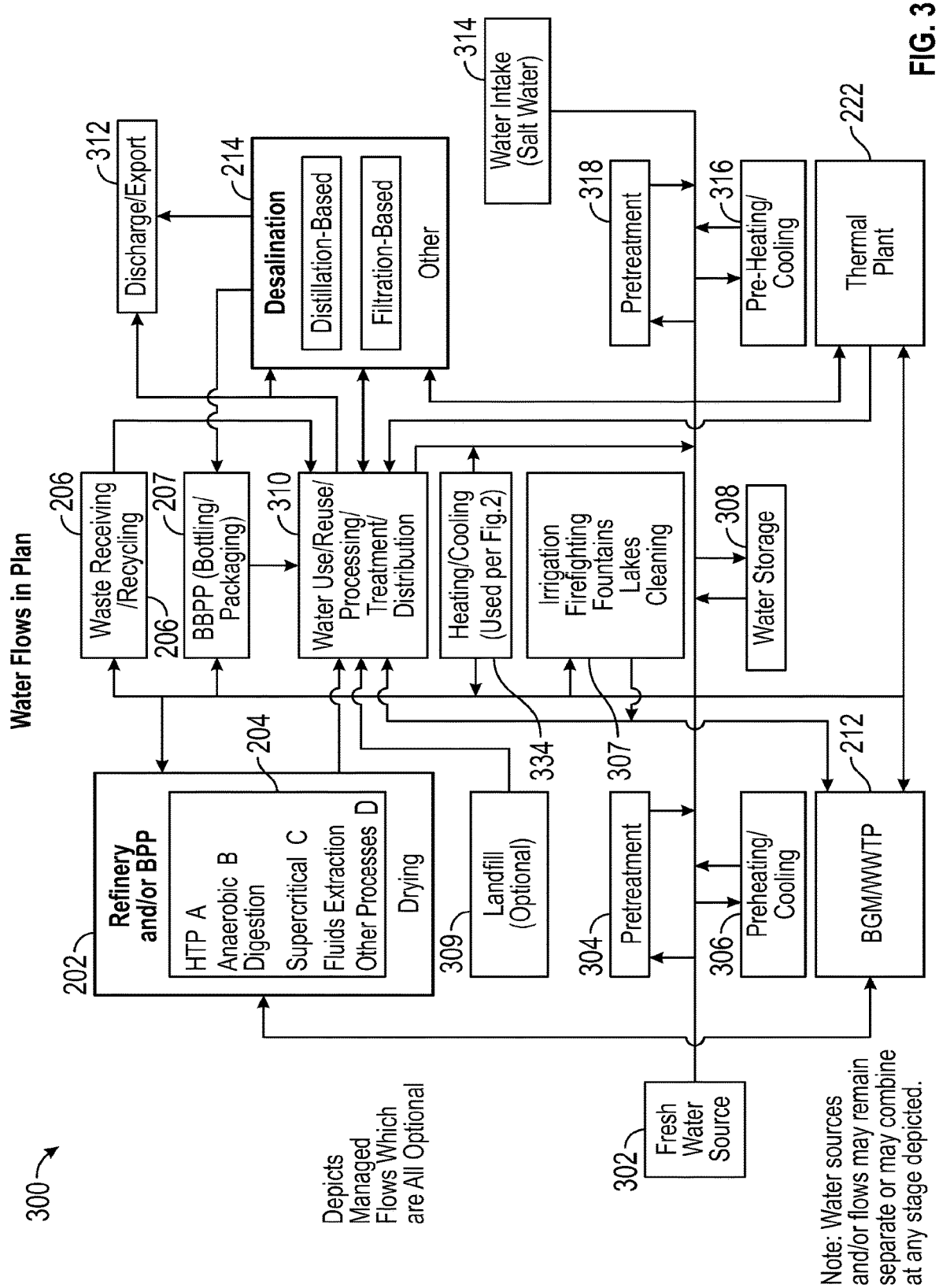
FIG. 3 is a schematic representation of a fluid/water flow within the Plan according to the present disclosure.
Figure 5:
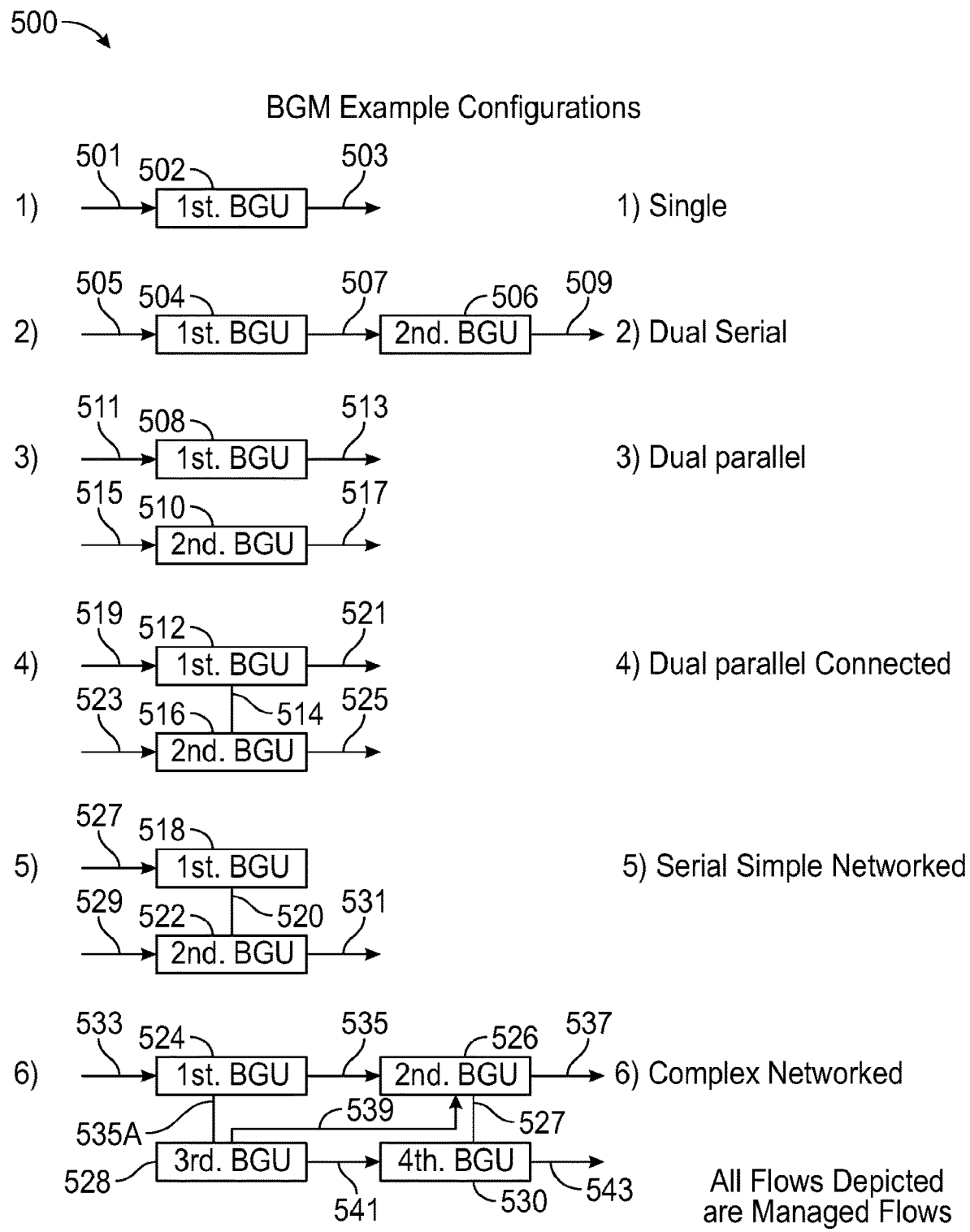
FIG. 5 is a schematic representation of a biomass growth unit design configuration according to the present disclosure.

In one or more embodiments, e.g., FIGS. 1, 3, 5, and/or 6, salt water, high salinity salt water, fresh water, wastewater (either partially treated or raw), and/or other water types may be used either in separate biomass growth units and/or combined as desired in certain BGUs and/or individual BGU subunits within the BGM, and/or several variations of BGUs may be used concurrently and/or sequentially. Further illustration of different optional BGUs and their components are given FIG. 6, and described herein.

Figure 9:
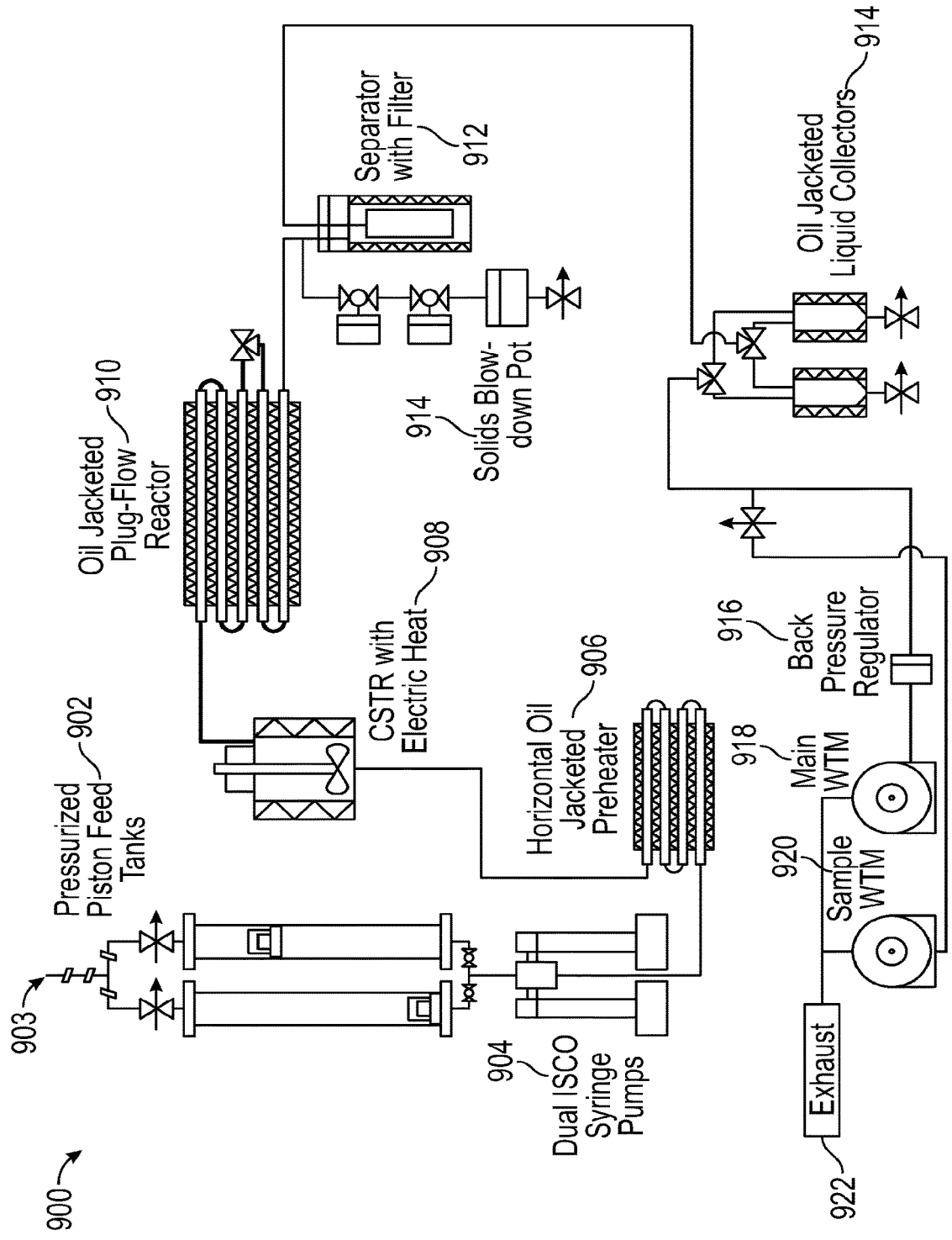
FIG. 9 is a schematic representation of a hydrothermal liquefaction system according to the present disclosure.

In one or more embodiments, e.g., FIG. 1, and/or FIG. 9, an exemplary biomass refining technique that may be used is a hydrothermal processing (HTP) method known as hydrothermal liquefaction (HTL). FIG. 9 is an exemplary process for performing HTL. Such a liquefaction process typically produces a biocrude and water. In a first step, the biomass/water slurry may be processed by a tertiary treatment, optionally concentrated by a gravity thickener 2, and/or by another concentrating technique known to a person of skill in the art, e.g., centrifugation, and/or may be diluted with water from any source. Then biomass grown in a biomass growth module containing water and/or a biomass/water slurry may be heated by the thermal plant and undergo HTP in situ, and/or the heated mixture may be sent to a refinery where it may be fed to a hydrothermal liquefaction module.

Figure 6:
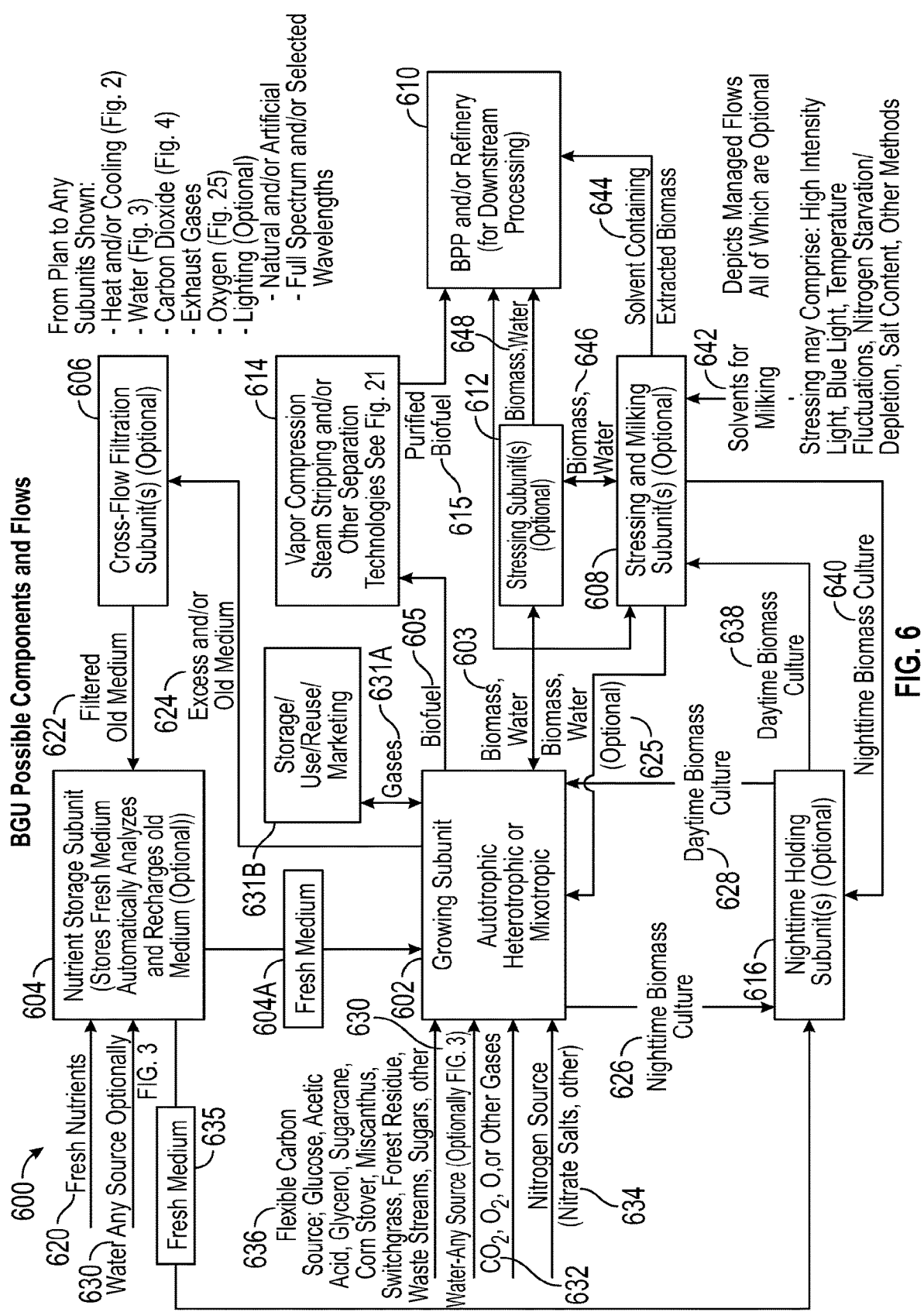
FIG. 6 is a second schematic representation of biomass growth design configuration according to the present disclosure.

In one or more embodiments, e.g., FIG. 1, and/or FIG. 6, heat and/or energy may be supplied to an HTP module by the thermal plant and/or a separate heating process optionally powered by the thermal plant. Once the hydrothermal processing is complete, the HTP module may release the products of the process, e.g., for HTL or RTP, typically mostly a biocrude and water; for CHG, biogas. The HTP module may be a static container of any design, or a moving conveyance of any description where HTP is performed, depending on design preferences. It may utilize a batch method, constant flow, intermittent flow, and/or another flow method. The biocrude may be used directly as a fuel source for the thermal plant, and/or may be further dried and/or refined, and then used as a fuel source for the thermal plant.

In one or more embodiments, e.g., FIG. 1, and/or FIG. 6, a WWTP or any of its components may be adapted for use as a BGM, or to support a BGM. WWTP ponds are generally too deep to be optimal for biomass growth, such as algae. The WWTP ponds may be filled in to provide more shallow ponds suitable to aquatic biomass, and stirring and/or a carbon dioxide source may be added, as in a raceway design. Alternatively, lighting may be added below the pond surface to light the deep WWTP ponds in order to make them suitable for biomass growth, such as algae. If beneficial, WWTP ponds and/or other structures may be used to contain water that is in contact with BGM or any of its components in order to regulate the temperature of the BGM or any of its components. For example, BGU bioreactors may be fully or partially submerged in or in another manner put in contact with (e.g. floating on) ponds currently or formerly used as part of a WWTP in order to create a more stable temperature in the bioreactor. Also, WWTP ponds and/or other structures may be heated or cooled using heat or cooling generated in the thermal plant, and/or from other sources in the Plan (e.g., FIG. 3) in order to optimize the BGM or any of its components. Any of these adaptations of a WWTP to support a BGM may be used with active WWTPs to the extent practical, or those that are converted over to BGMs, and are no longer used as WWTPs.

In one or more embodiments, e.g., FIG. 1, and/or FIG. 6, and description regarding BGU operation and design, notwithstanding the construction and/or operation of the biomass growth module(s) comprising embodiments that comprise photosynthesis, non-photosynthetic, and/or a mixture of processes for biomass growth, the design may comprise structures to partially block, redirect, filter, concentrate, and/or otherwise modify light being introduced into the biomass growth module or individual BGUs and/or BGU components. For example, in an embodiment, a photosynthetic bioreactor used to grow biomass using light is configured to grow an organism or organisms also in the dark by selectively blocking and/or filtering sunlight at predefined times and/or in response to detected conditions and selectively unblocking and/or removing such filters of the sunlight at other times and/or under other detected and/or selected conditions. Different wavelengths of light may also be filtered out where beneficial (e.g., FIG. 8) either using equipment outside of the bioreactor, and/or by modifying the bioreactor itself (e.g., the bioreactor coating is configured to selectively filter light).

In one or more embodiments, e.g., FIG. 1, FIG. 2, and/or FIG. 3, a salt water BGU discharge, or biomass/water slurry, or treated biomass/water slurry after BGM post treatment steps as noted in FIG. 1, which comprises a biomass and/or biofuel laden salt water may operate substantially free of primary and/or tertiary treatment, and/or may be used in the same methods and/or systems described for other BGU discharges in the Plan, comprising: use as cooling water in the thermal plant; to perform hydrothermal processing (HTP); to preheat for HTP, and/or other biomass processing technologies. If the BGU is heated in any manner, the heat may be reclaimed before discharge by one of the methods given herein. After biomass production and/or other uses within the Plan, the salt water used may be mixed and discharged along with the optional desalination plant brine discharge, providing some dilution effect to the brine discharge, or may be reclaimed and used as noted in the Plan (See FIG. 3).

In one or more embodiments, e.g., FIGS. 1, 3, 6, 10, 11, and/or 14, a water bottling/biomass products bottling/packaging plant (BBPP) may be added optionally as part of the Plan. In one or more embodiments, any one or more of the components within the BBPP may be used (e.g., water bottling only, biomass bottling only, and/or other biomass packaging types only.) Water bottling lines may be used to bottle treated drinking water generated from the DP.

In one or more embodiments, e.g., FIGS. 1, 3, 6, 10, 11, and/or 14, the desalinated water used for water bottling may require additional disinfection prior to bottling. Heat from the thermal plant and/or any other source(s) in the Plan (See FIG. 2) may be used for this purpose and/or for other purposes in the BBPP. The BBPP can provide drinking water for daily per capita consumption, stockpiled for emergency, and/or produced for export, if desired. The BBPP may also package liquid and/or solid biomass-derived products. It may produce carbonated water and/or biomass products using carbon dioxide from any source in the Plan, e.g., FIG. 4. It may have a separate section from the water bottling section to package biocrude and/or other biofuels. Packaging may comprise bottling, barreling, preserving, cutting, pelletizing, boxing, containerizing, compressing, pressurizing and putting into tanks, and/or other means of preparing products for storage, export and/or marketing.

In one or more embodiments, e.g., FIGS. 1, 3, 6, 10, 11, and/or 14 the BBPP may have warehouse space to store these products before shipment offsite and/or use in the Plan. In one or more embodiments, e.g., FIGS. 1, 3, 6, 10, 11, and/or 14, biomass products produced onsite, most notably liquid and/or solid biomass products, may also be bottled/packaged quickly after production and/or otherwise preserved in the BBPP. In an embodiment, the biomass products may be cooled using cogenerated cooling from the thermal plant and/or other sources before and/or after packaging to preserve freshness. The prompt packaging and/or cooling (such as refrigeration), where needed, may preserve delicate products promptly onsite and prepare them for market in the most beneficial way.

In one or more embodiments, e.g., FIG. 1, a portion or all of the BBPP equipment for disinfecting desalinated water before bottling may be shared with the WWTP and/or WWTBGU, such as disinfection treatment (e.g. UV treatment). a portion or all of the BBPP equipment for disinfecting desalinated water before bottling may be shared with the WWTP and/or WWTBGU, such as disinfection treatment (e.g. UV).

In an embodiment, e.g., FIG. 1, thermal plant technologies of any kind which may predate implementation of the Plan may be incorporated into the Plan as the thermal plant module or a component or technology of the thermal plant module (e.g., an pre-existing coal-fired plant may be retrofitted to the Plan, and become part of the thermal plant module, which connects to the rest of the Plan). In one or more embodiments, any other pre-existing component, technology, unit, subunit, feature, and/or module which may be retrofitted to become a technology, unit, subunit, feature and/or module and/or a means of connection and/or communication between modules, units, subunits, technologies and/or other features of the Plan, or to otherwise to be comprised by any feature of the Plan, may be retrofitted and included into the Plan (e.g., a waste-to-energy system, a WWTP, a BGM, a refinery, a BPP, a waste handling plant, recycling plant, a solar thermal technology, a desalination plant, a BBPP, a water intake, and/or any other module, unit, subunit technology and/or other component of the Plan).

In one more embodiments, e.g., FIGS. 1, 2, 3, 4, 7A, 7B, 10, 11, 22 and/or 25 and/or any other figures and/or description relation to resources, heat and/or cooling, and/or other aspects of a thermal plant, thermal plant technologies, fuel type and/or flow, air flow and/or content, water selection, water flow, and/or any other aspect of performance known to those in the art may be controlled with sensors and/or dynamic controls.

In an embodiment 200, with reference to FIG. 2, the thermal plant 222 provides heat energy/heat transfer and/or cogenerated cooling 216 to any one or more of the modules of grid 200. Thermal Plant (TP) 222 comprises optionally any one or more plant(s), modules, submodules, technologies, components, features, and/or supporting systems collectively fitting within the definition of a thermal plant, comprising optionally one or more of the following features: thermal power plant(s), a WTE unit, that may comprise an MSW incineration unit, other direct combustion technologies, a plasma gasification unit (plasma), and/or one or more submodules 224 comprising any biomass/WTE fuel generation technologies which may require heat and/or cooling, optionally: a pyrolysis unit, an HTP unit, a cellulosic ethanol/isobutanol/butanol unit, a desorber/condenser, and/or other technology(ies) which may generate fuel, which may require or benefit from the use of heat and/or cooling. A rotary kiln incinerator 226 may also be included in the TP 222 for rendering harmful solid wastes inert. The TP may comprise other technologies and/or features defined as thermal plant technologies. TP 222 connects optionally to any or all units of the grid through heat and/or cooling communication to desalination unit 214, a BGM 212, a refinery 202, a recycling unit 206, a BBPP (bottling/packaging plant) 207, heat/cooling recovery unit(s) 208, heat/cooling storage unit(s) 218, biogas/natural gas storage unit(s) 221, air conditioning/heating unit(s) 210, product storage unit(s) 220, and/or thermal plant technologies which may benefit from heat and/or cooling, such as pyrolysis, HTP, cellulosic ethanol/butanol/isobutanol, a desorber/condenser, and/or other thermal plant technologies using heat and/or cooling 224, and/or offsite uses 228. Refinery and/or BPP 202 comprise module(s) 204, that optionally comprise any of the following heat and/or cooling intensive processes: HTP unit (comprising technologies such as HTL, CHG, and/or RTP) 204A, anaerobic digestion unit 204B, a supercritical fluid extraction unit 204C, and/or other processes of biofuel processing known to those of skill in the art, and/or biofuel and/or biomass drying unit 202A. Heat and/or cooling may be recovered in any heat/cooling recovery processes e.g., as described herein 208 from the TP 222, desalination unit 214, BGM 212, refinery 202, recycling unit 206, BBPP (bottling/packaging plant) 207, and/or heat and/or cooling from any source interacting with the grid may be stored and later used from one or more heat/cooling storage unit(s) 218, and heat/cooling 234 from offsite sources 228, may optionally be provided back to the grid for use in any of the foregoing processes, modules, and/or units. Heat may be added to the grid by sunlight basin and/or solar/thermal plant 230 that may optionally feed a BGM water source 232, and/or the other modules shown in FIG. 3. The "sunlight basin" may comprise any method of exposing water to sunlight and/or ambient temperature. In an embodiment, in a "sunlight basin", water may be routed through decorative fountains, lakes pools and/or other features which allow for warming of certain water sources, such as deep sea intake salt water, before use in a process. All heat and/or cooling flows depicted by lines or arrows may be optional and managed. Heat and/or cooling optional managed flows (e.g., lines and/or arrows of 200), heating/cooling recovery 208, and/or heating/cooling storage 218, and/or use of heat and/or cooling and/other processes and/or configuration of modules to use heat and/or cooling as e.g., FIG. 2 may be accomplished in any manner herein disclosed and/or known to those in the art. It should be noted that while the flows, connections and/or communication of heat and/or cooling e.g., in the Plan may be presented using lines as a "grid" to illustrate any possible connection and/or communication process steps for the use of heat/cooling between different modules, units or other components, actual flows and/or sources of heat and/or cooling may or may not be mixed or combined, or used universally e.g., in the Plan. In an embodiment, higher and lower levels of heat and/or cooling may or may not be mixed, rather, actual connections and/or communication between modules and/or processes may be managed and/or limited such that flows of heat and/or cooling at different temperatures, in different media, and made available at different times may be directed to as few as one or as many as all possible uses of heat and/or cooling illustrated as the "grid". In this manner the "grid" may take the practical form of many sub-systems with separate and distinct connections/communication/flows between a smaller subset of modules/units/processes within the "grid" of FIG. 2.

The water resources needed to absorb and carry heat away from thermal plants can be very significant. When this large amount of waste heat may be discharged into the environment in the form of heated air, steam and/or water, or by other means energy may be lost, water may be used, and it can produce detrimental effects to the environment.

In an embodiment, the Plan and method relate to a method of providing a cooling fluid, e.g., an aqueous fluid, air, and/or other fluid, to a thermal plant, while concomitantly, e.g., concurrently, transferring waste heat energy generated by the thermal plant. In an embodiment, the waste heat may be used productively in a process to refine the aqueous effluent(s) or discharge(s) of a biomass growth module, e.g., water, fuels, and/or a biomass. In reference to FIG. 2 an embodiment of the disclosure includes a system 200 configured to use and reclaim heat and/or cooling from a thermal plant module and/or another module, wherein heat and/or cooling is provided to and/or reclaimed from: a BGM 212; a refinery module 202; a BPP module 202; an air conditioning/heating module 210; a recycling module 206; a BBPP module 207; a products storage module 220; a desalination module 214; a waste to energy module 222; a biogas storage module 221; a heat/cooling storage module 218; a heat/cooling recovery module 208; offsite heating/cooling 228 for use outside of the Plan; heating/cooling for discharge; and/or some systems optionally comprised by the thermal plant module 222 selected from: a pyrolysis processes module 224; a hydrothermal processing module 224; a cellulosic ethanol/butanol/isobutanol module 224; a desorber/condenser module 224; and/or other processes comprised by the thermal plant module 222 which require heat and/or cooling.

An embodiment includes the system wherein heat and/or cooling reclaimed from: a BGM 212; a refinery module 202; a BPP module 202; an air conditioning/heating module 210; a recycling module 206; a BBPP module 207; a products storage module 220; a desalination module 214; a waste to energy module 222; a biogas storage module 221; a heat/cooling storage module 218; a heat/cooling recovery module 208; offsite heating/cooling 228 for use outside of the Plan; heating/cooling for discharge; and/or some systems optionally comprised by the thermal plant module 222 selected from: a pyrolysis processes module 224; a hydrothermal processing module 224; a cellulosic ethanol/butanol/isobutanol module 224; a desorber/condenser module 224; and/or other processes comprised by the thermal plant module 222 which require heat and/or cooling is provided to: a BGM 212; a refinery module 202; a BPP module 202; an air conditioning/heating module 210; a recycling module 206; a BBPP module 207; a products storage module 220; a desalination module 214; a waste to energy module 222; a biogas storage module 221; a heat/cooling storage module 218; a heat/cooling recovery module 208; offsite heating/cooling 228 for use outside of the Plan; heating/cooling for discharge; and/or some systems optionally comprised by the thermal plant module 222 selected from: a pyrolysis processes module 224; a hydrothermal processing module 224; a cellulosic ethanol/butanol/isobutanol module 224; a desorber/condenser module 224; and/or other processes comprised by the thermal plant module 222 which require heat and/or cooling.

An embodiment includes the system wherein: a BGM 212; a refinery module 202; a BPP module 202; an air conditioning/heating module 210; a recycling module 206; a BBPP module 207; a products storage module 220; a desalination module 214; a waste to energy module 222; a biogas storage module 221; a heat/cooling storage module 218; a heat/cooling recovery module 208; offsite heating/cooling 228 for use outside of the Plan; heating/cooling for discharge; and/or some systems optionally comprised by the thermal plant module 222 selected from: a pyrolysis processes module 224; a hydrothermal processing module 224; a cellulosic ethanol/butanol/isobutanol module 224; a desorber/condenser module 224; and/or other processes comprised by the thermal plant module 222 which require heat and/or cooling are collocated.

An embodiment includes the system wherein the thermal plant module 222 is configured to supply waste heat to heat the BGM 212.

An embodiment includes the system wherein the thermal plant module 222 is configured to discharge waste heat as a heated fluid.

An embodiment includes the system wherein the heated fluid is fed directly or in part as a water source and/or gas source to the BGM 212, a BGU, and/or any subunit of a BGU.

An embodiment includes the system wherein the heated fluid is configured to provide heat transfer to the BGM 212, a BGU, and/or any subunit of a BGU without direct interaction with the BGM 212. Direct interaction may be defined as a fluid entering a module, unit and/or subunit optionally comprising mixing with its fluids and/or an incoming fluid.

An embodiment includes the system wherein offsite heating/cooling 228 comprises a fresh water source and/or salt water intake.

With reference to Table 1 a system configured to use and reclaim heat and/or cooling from a thermal plant module and/or another module, wherein heat and/or cooling is provided to and/or reclaimed from:
a) a BGM;
b) a refinery module;
c) a BPP module;
d) an air conditioning/heating module;
e) a recycling module;
f) a BBPP module;
g) a products storage module;
h) a desalination module;
i) a waste to energy module;
j) a biogas storage module;
k) a heat/cooling storage module;
l) a heat/cooling recovery module;
m) offsite heating/cooling;
n) heating/cooling for discharge; and/or
o) some systems optionally comprised by the thermal plant module selected from:
1. a pyrolysis processes module;
2. a hydrothermal processing module;
3. a cellulosic ethanol/butanol/isobutanol module; and/or
4. a desorber/condenser module.

The combinations of Table 1 provide embodiments related to this embodiment.

An embodiment includes the system wherein the fresh water source and/or salt water intake provide heat and/or cooling to any one or more of modules: a BGM 212; a refinery module 202; a BPP module 202; an air conditioning/heating module 210; a recycling module 206; a BBPP module 207; a products storage module 220; a desalination module 214; a waste to energy module 222; a biogas storage module 221; a heat/cooling storage module 218; a heat/cooling recovery module 208; and/or some systems optionally comprised by the thermal plant module 222 selected from: a pyrolysis processes module 224; a hydrothermal processing module 224; a cellulosic ethanol/butanol/isobutanol module 224; a desorber/condenser module 224; and/or other processes comprised by the thermal plant module 222 which require heat and/or cooling.

An embodiment includes the system wherein outputs of heat and/or cooling from any one of modules: a BGM 212; a refinery module 202; a BPP module 202; an air conditioning/heating module 210; a recycling module 206; a BBPP module 207; a products storage module 220; a desalination module 214; a waste to energy module 222; a biogas storage module 221; a heat/cooling storage module 218; a heat/cooling recovery module 208; offsite heating/cooling 228 for use outside of the Plan; heating/cooling for discharge; and/or some systems optionally comprised by the thermal plant module 222 selected from: a pyrolysis processes module 224; a hydrothermal processing module 224; a cellulosic ethanol/butanol/isobutanol module 224; a desorber/condenser module 224; and/or other processes comprised by the thermal plant module 222 which require heat and/or cooling share heating and/or cooling transmission modules and/or technologies, and/or heat and/or cooling storage module(s) and/or unit(s).

In reference to FIG. 2 an embodiment of the disclosure includes a method of using and reclaiming heat and/or cooling from a thermal plant module and/or another module comprising: generating heat and/or cooling at a module; transmitting heat and/or cooling to another module; using all or a portion of the heat and/or cooling in the thermal plant module and/or in the another module; and optionally transmitting unused heat and/or cooling from the thermal plant module and/or in the another module to the module, wherein heat and/or cooling is provided to and/or reclaimed from: a BGM 212; a refinery module 202; a BPP module 202; an air conditioning/heating module 210; a recycling module 206; a BBPP module 207; a products storage module 220; a desalination module 214; a waste to energy module 222; a biogas storage module 221; a heat/cooling storage module 218; a heat/cooling recovery module 208; heating/cooling external to or apart from the method for use outside 228 of the Plan; heating/cooling for discharge; and/or some systems optionally comprised by the thermal plant module 222 selected from: a pyrolysis processes module 224; a hydrothermal processing module 224; a cellulosic ethanol/butanol/isobutanol module 224; a desorber/condenser module 224; and/or other processes comprised by the thermal plant module 222 which require heat and/or cooling.

An embodiment includes the method wherein heat and/or cooling reclaimed from: a BGM 212; a refinery module 202; a BPP module 202; an air conditioning/heating module 210; a recycling module 206; a BBPP module 207; a products storage module 220; a desalination module 214; a waste to energy module 222; a biogas storage module 221; a heat/cooling storage module 218; a heat/cooling recovery module 208; heating/cooling external to or apart from the method for use outside 228 of the Plan; heating/cooling for discharge; and/or some systems optionally comprised by the thermal plant module 222 selected from: a pyrolysis processes module 224; a hydrothermal processing module 224; a cellulosic ethanol/butanol/isobutanol module 224; a desorber/condenser module 224; and/or other processes comprised by the thermal plant module 222 which require heat and/or cooling is provided to: a BGM 212; a refinery module 202; a BPP module 202; an air conditioning/heating module 210; a recycling module 206; a BBPP module 207; a products storage module 220; a desalination module 214; a waste to energy module 222; a biogas storage module 221; a heat/cooling storage module 218; a heat/cooling recovery module 208; heating/cooling external to or apart from the method for use outside 228 of the Plan; heating/cooling for discharge; and/or some systems optionally comprised by the thermal plant module 222 selected from: a pyrolysis processes module 224; a hydrothermal processing module 224; a cellulosic ethanol/butanol/isobutanol module 224; a desorber/condenser module 224; and/or other processes comprised by the thermal plant module 222 which require heat and/or cooling.

An embodiment includes the method wherein: a BGM 212; a refinery module 202; a BPP module 202; an air conditioning/heating module 210; a recycling module 206; a BBPP module 207; a products storage module 220; a desalination module 214; a waste to energy module 222; a biogas storage module 221; a heat/cooling storage module 218; a heat/cooling recovery module 208; heating/cooling external to or apart from the method for use outside 228 of the Plan; heating/cooling for discharge; and/or some systems optionally comprised by the thermal plant module 222 selected from: a pyrolysis processes module 224; a hydrothermal processing module 224; a cellulosic ethanol/butanol/isobutanol module 224; a desorber/condenser module 224; and/or other processes comprised by the thermal plant module 222 which require heat and/or cooling are collocated.

An embodiment includes the method wherein outputs of heat and/or cooling from any one of modules: a BGM 212; a refinery module 202; a BPP module 202; an air conditioning/heating module 210; a recycling module 206; a BBPP module 207; a products storage module 220; a desalination module 214; a waste to energy module 222; a biogas storage module 221; a heat/cooling storage module 218; a heat/cooling recovery module 208; offsite heating/cooling 228 for use outside of the Plan; heating/cooling for discharge; and/or some systems optionally comprised by the thermal plant module 222 selected from: a pyrolysis processes module 224; a hydrothermal processing module 224; a cellulosic ethanol/butanol/isobutanol module 224; a desorber/condenser module 224; and/or other processes comprised by the thermal plant module 222 which require heat and/or cooling share heating and/or cooling transmission modules and/or technologies, and/or heat and/or cooling storage module(s) and/or unit(s).

In certain embodiments, e.g., those represented by FIG. 2, FIGS. 7A, 7B, 11, 12A, 12B, 12C, 12D, 12E, 15A, 15B, 16, 17, 18, 19, 20A, 20B, 20C, 20D and/or other figures and embodiments regarding heat capture and/or transfer, the present disclosure relates to a method of providing a cooling fluid, e.g., a necessary cooling water, to a thermal plant, while concurrently making productive use of the waste heat energy generated by the thermal plant, which waste heat may otherwise be simply discharged unproductively, and at times, destructively, into the environment. The waste heat may be used productively, e.g., to regulate bioreactor temperature and/or in a process to refine water, fuels, and/or biomass produced in a biomass growth module into useful products.

The disclosed integrated infrastructure Plan, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, not only has standard heat recovery technologies for power generation, but makes productive use of all waste heat, from higher temperature waste heat, to lower temperature waste heat that is not suitable for power generation. All heat sources above ambient temperature may be put to innovative and extremely productive use in the Plan for refining biomass/biofuel, warming the BGM to optimize temperature, other low temperature power generation, recycling/packaging, desalination, and/or other uses as shown in FIG. 2. In one or more embodiments, the heat used in the processes and/or systems of the invention may be a combination of primary heat and waste heat in any proportion, e.g., from 1/50 to 1/1 or from 1/10 to 3/1, or from 1/5 to 5/1, or all waste heat, or all primary heat.

In one or more embodiments, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, a biomass/water slurry generated by the biomass growth module is heated by waste heat generated in the thermal plant and "flash refined" in a process referred to as hydrothermal processing, which may comprise hydrothermal liquefaction, RTP, catalytic hydrothermal gasification and/or any other hydrothermal processing method. The heated biomass/water slurry may be pressurized if necessary for the specific HTP process and/or operating conditions, and the outputs of these processes are primarily water and biocrude oil and/or methane and/or carbon dioxide.

In one or more embodiments, e.g., FIG. 2, and/or figures or description relevant to heat transfer and/or capture, the water containing biomass discharged from the biomass growth module, or "BGM outflow fluid" comprising a biomass/water slurry optionally after the processing steps shown in FIG. 1, may be sent to the thermal plant to provide cooling and/or heat capture in a variety of ways. The BGM outflow fluid containing biomass from a BGM may be used directly to cool the thermal plant, may be further processed and then used to cool the thermal plant, and/or may be used in a heat exchange system with another fluid cooling the thermal plant whereby it cools and captures heat from the thermal plant indirectly, depending on the nature of the BGM outflow fluid, and the water quality needs of the particular thermal plant technology type(s) in use, and/or other factors. Alternatively, heat from the thermal plant may be transferred by any other means to the biomass/water slurry.

In one or more embodiments, e.g., FIGS. 2, 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, heat captured from a thermal plant may be used productively to refine biofuels generated directly in the biomass growth module, and/or the biomass in a biomass/water slurry, optionally processed in any manner known to those in the art, without harvesting by the use of such methods as hydrothermal processing, and/or any other method of refining the biomass growth module output, especially those without harvesting, and/or to preheat for any of the foregoing.

Alternatively or additionally, biomass may be processed and/or harvested by any or a combination of the methods described supra and/or by any other method that produces biomass and/or biofuel that is useful for fuels and/or other products, and/or in the synthesis of fuels and/or other products.

In one or more embodiments, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, heat and/or cogenerated cooling from thermal plant combustion exhaust may be delivered via a conveyance and employed to heat and/or cool a BGM, individual BGU(s), and/or individual BGU components maintaining an optimal biological growth and/or reproduction rate in a biomass growth module. As biomass growth is typically temperature-dependent, during colder seasons, and/or with daily temperature changes, and/or other temperature fluctuations, such heat, e.g., waste heat, assists biological growth in many cases; and/or such heat may be used in other processes, optionally comprising heating water for any process or purpose in the Plan (See FIG. 2). Waste heat may also be converted to cooling (e.g., via cogeneration) in order to regulate BGM, individual BGU, or BGU component temperatures to prevent overheating, in refining/processing biomass, such as the condensing of recycled solvents, to cool/refrigerate biomass products, and/or for any other use in the Plan.

In one or more embodiments, e.g., FIGS. 2, 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer and/or FIG. 3, and/or other figures and/or description relevant to water use and/or movement, cooling water from any source may be used to cool the thermal plant, and then routed for optional primary treatment (per module 104 of FIG. 1) and then for direct use as source water in the BGM, mixed with another water source and used as source water in the BGM, or simply used to transfer heat to water used in the BGM or another process. In any of these or other manners disclosed herein, and/or by any other means known to those of skill in the art, temperature in the BGM may be regulated either directly or indirectly by water outflows from the thermal plant optionally in combination with other water sources.

Gases and/or other fluid outflows from the thermal plant, likewise may be used alone or in combination with other sources of heat to regulate the temperature of the BGM and/or other components of the Plan, (e.g., FIGS. 7A, 7B, 12A, 12B, 12C, 12D, and/or 12E). If cooling is needed, any of the aforementioned sources of heat may be used to cogenerate cooling, which may be supplied to the Plan as in FIG. 2.

In one or more embodiments, e.g., FIGS. 2, 3, 6, 7A, 7B, 11, 12A, 12B, 12C, 12D, 12E, 15A, 15B, 16, 17, 18, 19, 20A, 20B, 20C, 20D and/or other figures and/or description relevant to heat capture, and/or transfer, a BGM and/or its components, and/or water transfer, a BGM, a BGU, a BGU subunit and/or any other BGU component may be fully or partially immersed in a pool, other container, stream or water body fed by a water supply used to capture waste heat from a thermal plant, and/or supply cooling (e.g., cool water) wherein the BGM temperature is regulated by contact with heated or cool water supply.

In one or more embodiments, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, and FIG. 23, and/or other figures and/or description relevant to pressure use and/or transfer, once heat has been absorbed by the biomass/water slurry, the slurry may be optionally directed to a refinery for refinement and/or further processing, which refinery may comprise HTP module, such as the HTL module in FIG. 9, or another hydrothermal process module, where the temperature is elevated as necessary and maintained (e.g., at or above about 350 degrees Celsius (662 F) for HTL) by additional heating (from the thermal plant and/other source(s), comprising heat recovery from any aspect of the Plan, See FIG. 2), and pressure is elevated as necessary for the particular HTP method (e.g., for HTL, approximately 3000 PSI and maintained for approximately 1 hour). In an embodiment, a closed reactor may be heated from 500-1300 degrees F. with rapid heating, and the processing time may be about one minute. For example see the following references are incorporated by reference herein and relied upon: http://www.greencarcongress.com/2012/11/savage-20121108.html, http://pubs.acs.org/doi/abs/10.1021/ef301925d and/or http://www.biofuelsdigest.com/bdigest/2015/02/22/algae-liquefaction-what-is-is-and-why-it-might-be-the-key-to-affordable-drop-in-algae-biofuels/.

In one or more embodiments, e.g., FIG. 2, FIGS. 7A, 7B, 11, 12A, 12B, 12C, 12D, 12E, 15A, 15B, 16, 17, 18, 19, 20A, 20B, 20C, 20D, 23 and/or other figures and/or description relevant to heat capture and/or transfer or pressure reclamation and reuse, energy used to generate pressure and/or heat may be recovered once a hydrothermal liquefaction and/or other HTP process is completed. Such energy may then be transferred to generate supplemental power and/or increase the efficiency of the Plan and/or method as in FIG. 23.

In one or more embodiments, e.g., FIGS. 2, 15A, 15B, 16, 17, 18, 19 and/or 23, heated water and/or biocrude may be directed through other heat exchangers to reclaim heat used in processing the biomass. Pressure may be recovered or reclaimed using standard technologies such as turbine or Pelton wheel, turbocharger, pressure exchanger (such as DWEER, the rotary pressure exchanger, and Dannfoss iSave), energy recovery pump (such as the Clark pump, the Spectra Pearson pump, and/or other technologies suited to the purpose) and used to generate pressure for another portion of heated biomass/water slurry being prepared to undergo hydrothermal processing, for movement of liquids through the process, for power generation, for desalination, for other processes in the Plan, and/or other applications.

Figure 7A:
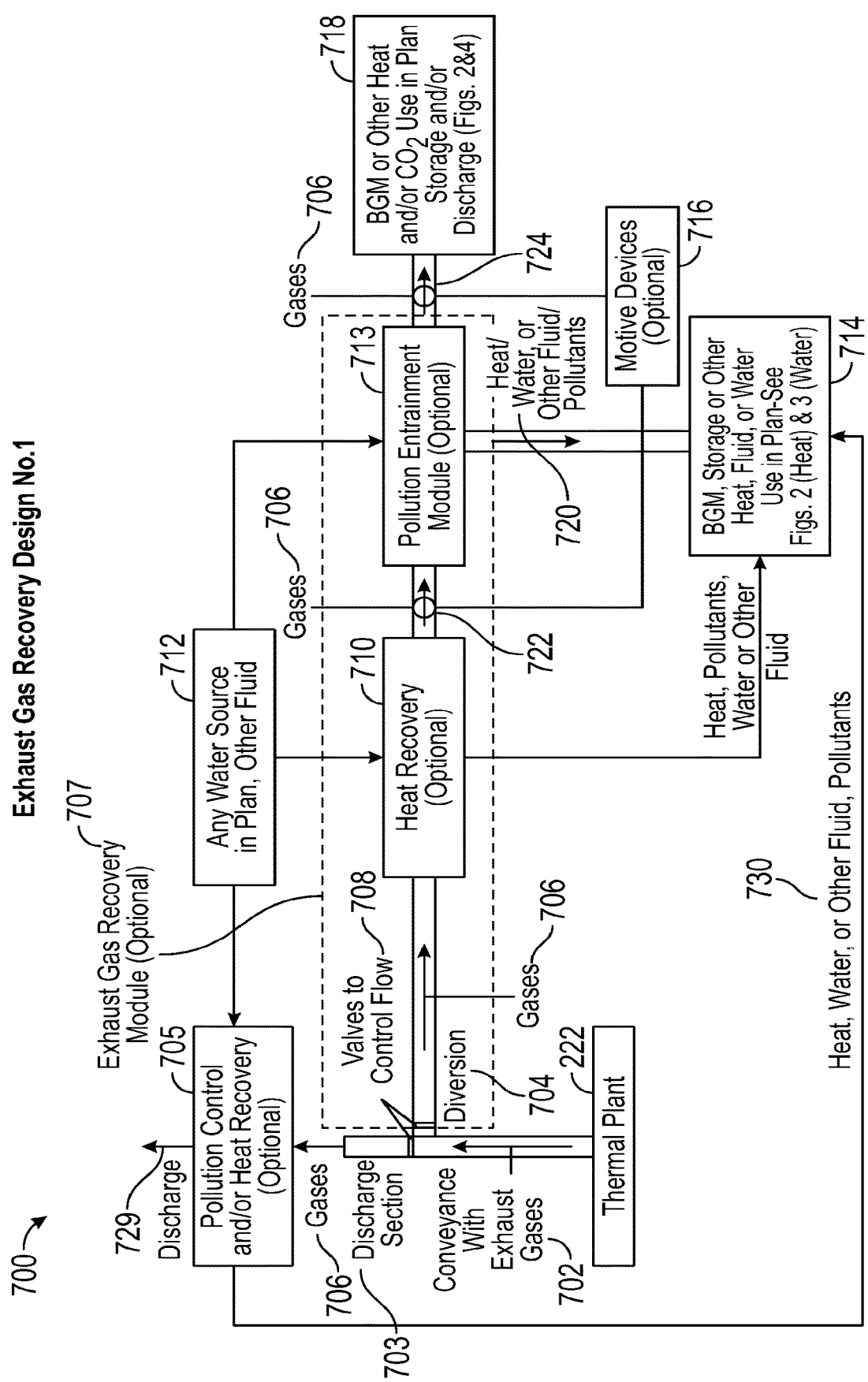
FIG. 7A is a schematic representation of a thermal plant exhaust gas recovery design according to the present disclosure.
Figure 7B:
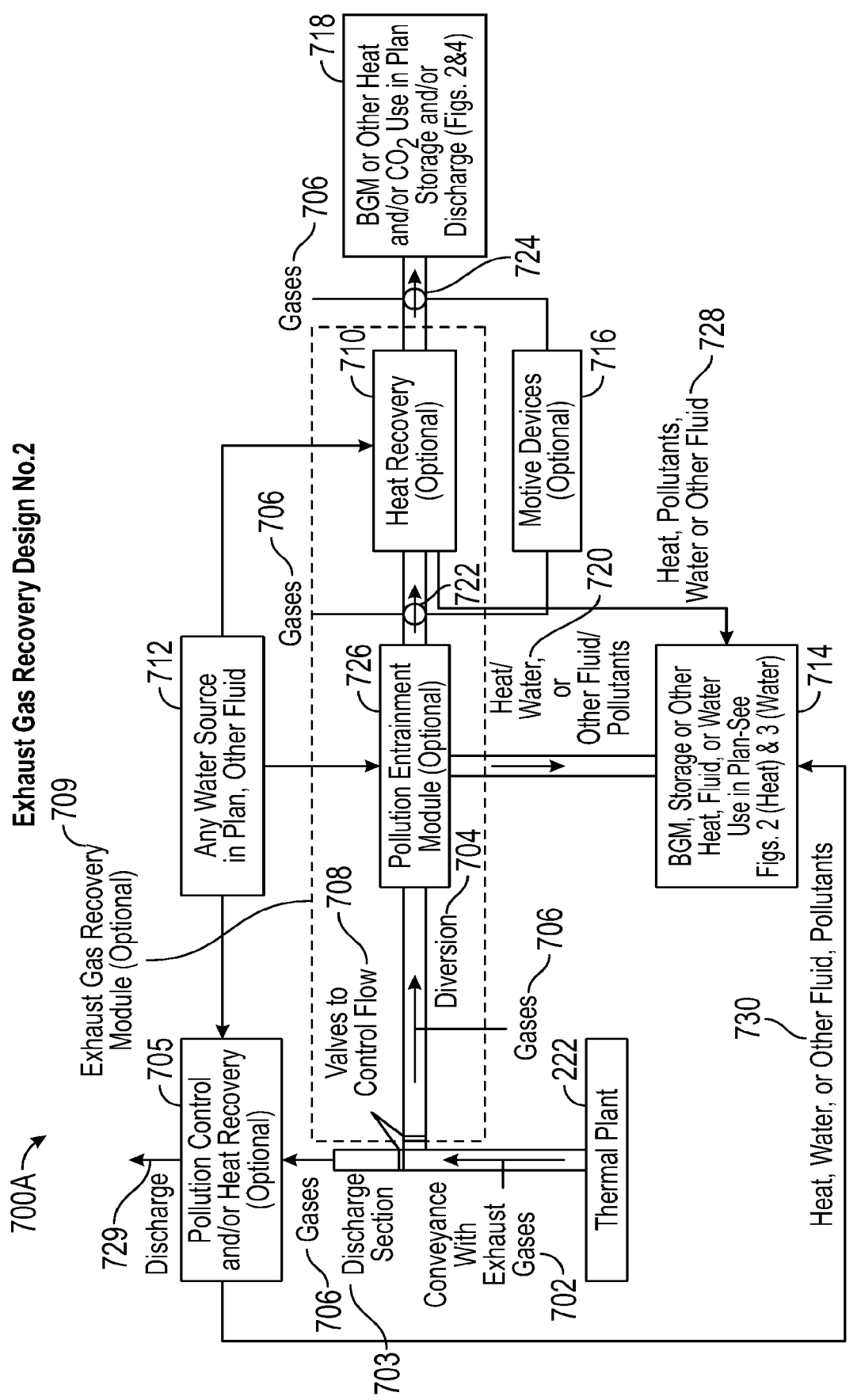
FIG. 7B is a schematic representation of a second thermal plant exhaust gas recovery design according to the present disclosure.

In one or more embodiments, e.g., FIGS. 2, 7A, 7B and/or other figures and/or description relevant to heat capture and/or transfer, recovered heat from thermal plant exhaust gases, thermal plant cooling, comprising embodiments using HTP of a biomass/water slurry, and/or any other process in the Plan may be reused for any hydrothermal processing method and/or other refining processes for water, biomass and/or biofuel, comprising distillation of fuels, drying of biomass for preheating the biomass growth module water source, for either directly and/or indirectly heating the biomass growth module, for heating anaerobic digestion (when used) to increase efficiency, biofuel, and/or waste in preparation for combustion and/or other processes, in cellulosic ethanol/butanol/isobutanol processes, in supercritical fluids extraction, for increasing the efficiency of an optional desalination unit, for HTP of any organic waste which may mixed with biomass and/or water and/or another fluid, and/or for other processes (See FIG. 2).

In one or more embodiments, e.g., FIG. 2, 7A, 7B, 12A, 12B, 12C, 12D, and/or 12E, and/or figures or description relevant to heat transfer and/or capture, heat may be generated/reclaimed for use in above applications and/or for other applications in the Plan by the following: The thermal plant's waste heat in the form of exhaust gases and that heat which is captured by thermal plant cooling water, primary process heat generated by the thermal plant (e.g., primary combustion process non-waste heat), heat generated by any other thermal plant process, heat recovered from HTP and/or other water/biofuel/biomass refining, heat that may be recovered in processes used to cool the BGM, additional solar thermal techniques of any type, comprising solar troughs and/or towers, optional desalination plant discharge, and/or any other process in the Plan where heat may be captured and/or recovered, comprising reclamation of heat resulting from any process listed in [previous section]. Heat exchangers and/or other known technologies may be used to transfer heat from one system to another and/or from one substrate to another (e.g., water, vapor, solids to another substrate) and/or different supplies of the same substrate type (e.g., wastewater to separate water supply used in different processes, gases to other gases, etc.), which may transfer heat where needed in the Plan, for example, see FIGS. 12A-12E.

In an embodiment, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, and/or FIG. 6, heat, e.g., waste heat, and/or cogenerated cooling from the thermal plant, the water discharge from HTP, and/or other heat-intensive process in the Plan (e.g., FIG. 2) may be provided to counteract temperature variations in the biomass growth module, a BGU within the BGM, and/or any component(s) of any BGU due to e.g., ambient temperature change and/or other reasons that may be detrimental to optimal biomass growth. In this manner the co-location of the thermal plant and/or other heat sources and biomass growth module may enable daily and/or year-around operation and optimization of the biomass growth module, e.g., a 24/7 operation, and use in temperate climates where biomass, such as algae cannot grow effectively at ambient temperatures for all or part of the year, or even in extremely cold climates, like arctic regions, where it is much too cold to grow biomass effectively in a normal biomass growth system. Likewise, cooling from the thermal plant may allow for biomass growth in extremely hot environments (e.g., deserts) which could normally hinder growth rates and/or limit the species available for use.

Cooling generated in this fashion may also be used to generate cooling such as air conditioning and/or refrigeration for cooling buildings, for cooling or refrigeration of biomass products, for use in biomass refining, such as condensing solvents evaporated off after extraction, for condensing and/or cooling other process gases, liquids and/or solids throughout the Plan, and/or for other uses potentially onsite and/or offsite.

In one or more embodiments, e.g., FIGS. 2, 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer and/or FIG. 6, cooling from the thermal plant may allow for biomass growth in extremely hot environments (e.g., deserts) which could normally hinder growth rates and/or limit the species available for use. Cooling generated in this fashion may also be used to generate cooling such as air conditioning and/or refrigeration for cooling buildings, for cooling or refrigeration of biomass products, for use in biomass refining, such as condensing solvents evaporated off after extraction, for condensing and/or cooling other process gases, liquids and/or solids throughout the Plan, and/or for other uses potentially onsite and/or offsite.

Figure 19:
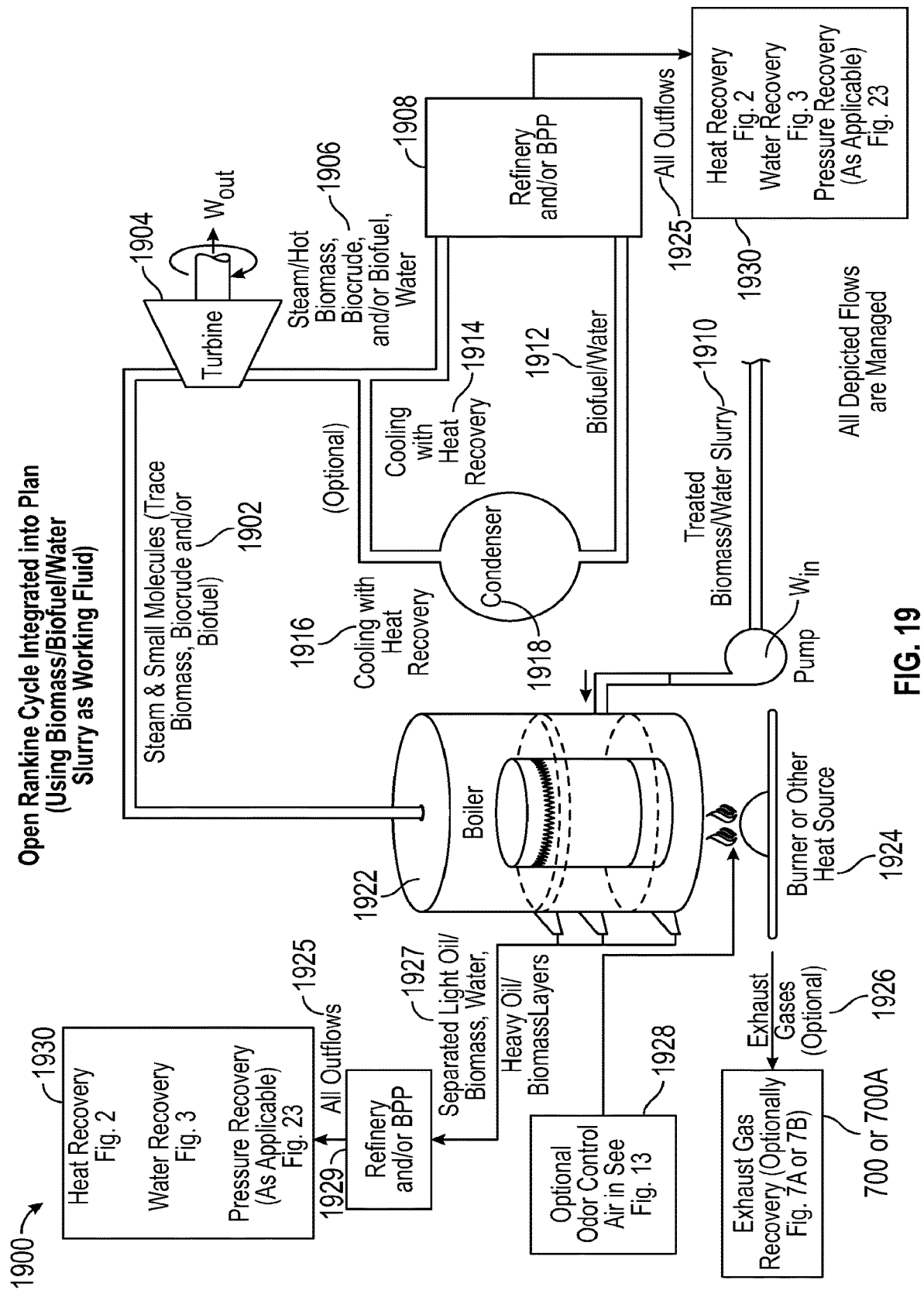
FIG. 19 is a schematic representation of an open Rankine cycle incorporated into a design according to the present disclosure.
Figure 20A:
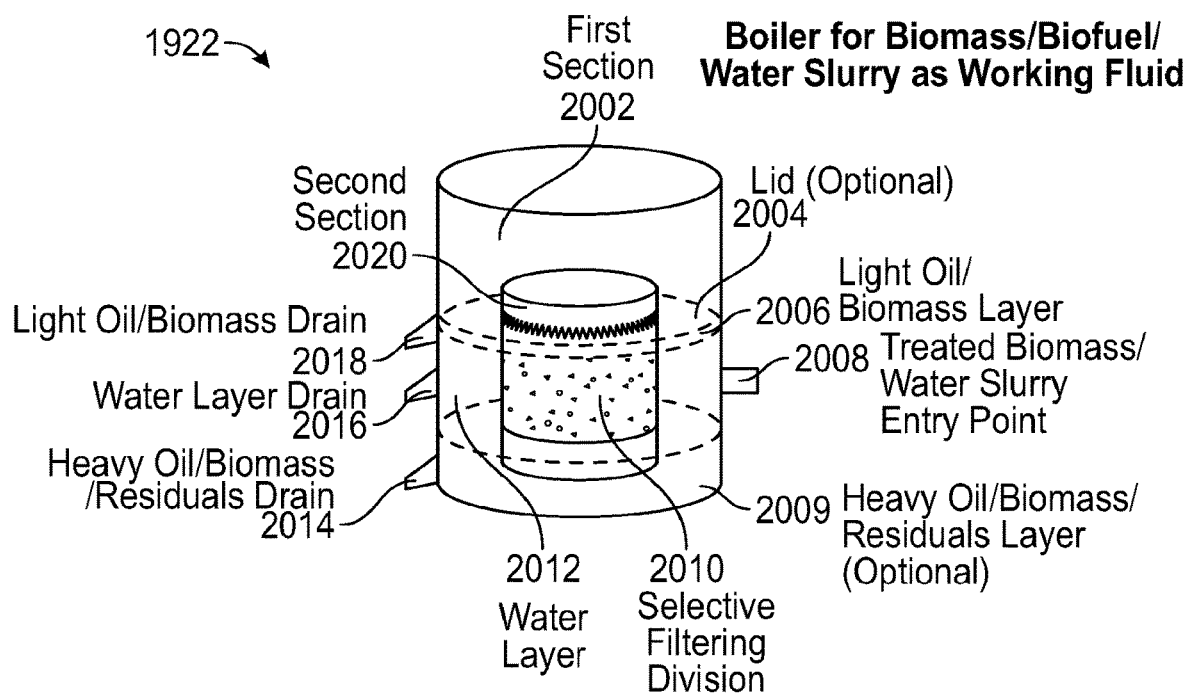
FIG. 20A is a perspective view of a boiler according to the present disclosure.
Figure 20B:
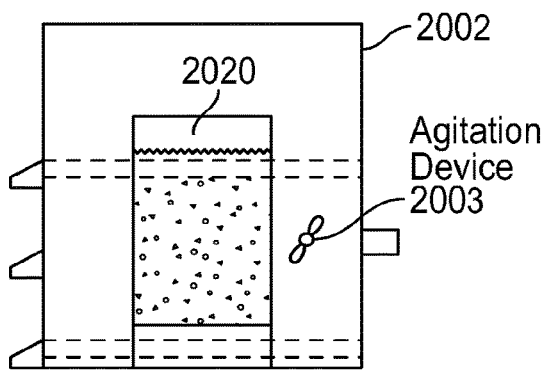
FIG. 20B is a sectional view of the boiler of FIG. 20A according to the present disclosure.
Figure 20C:
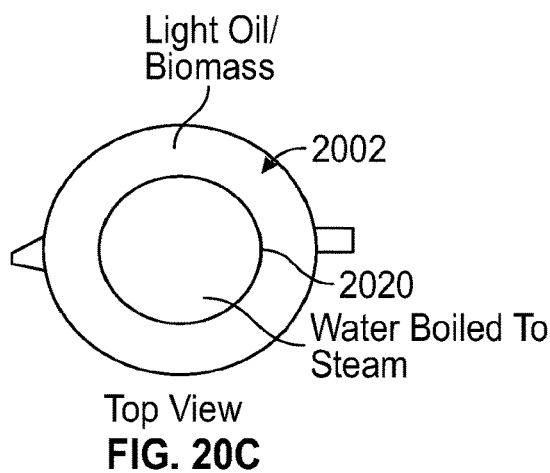
FIG. 20C is a top view of the boiler of FIG. 20A according to the present disclosure.
Figure 20D:
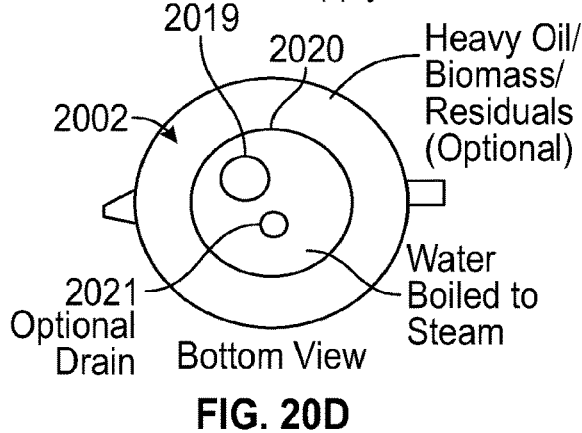
FIG. 20D is a bottom view of the boiler of FIG. 20A according to the present disclosure.
Figure 21:
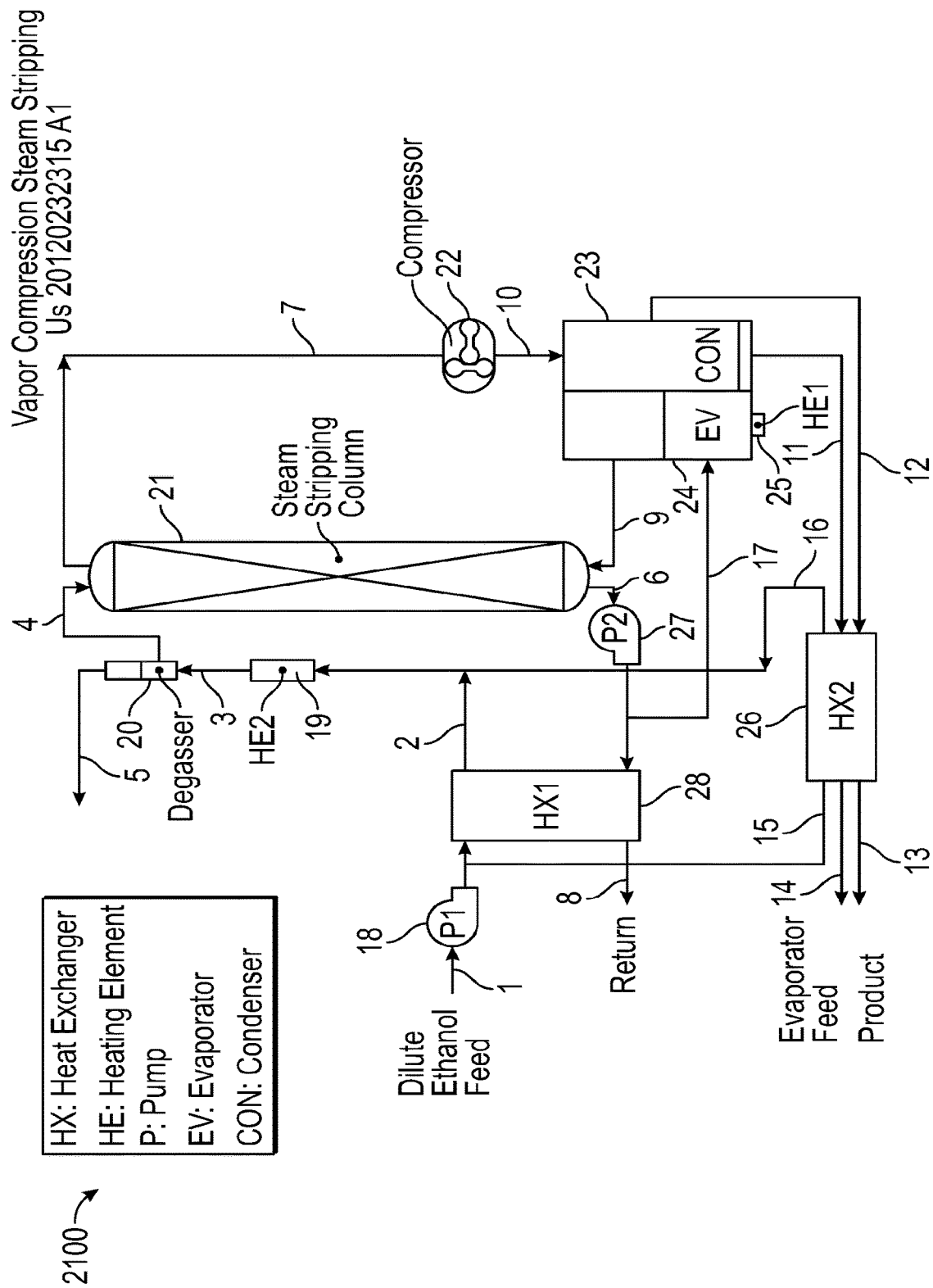
FIG. 21 is a vapor compression steam stripping system for use e.g., in the Plan of the present disclosure.

In an embodiment, e.g., those referenced in FIGS. 2, 3, 19 and/or 20 the design and/or method relate to a method of providing a working fluid, e.g., an aqueous fluid, to a thermal plant, while concomitantly, e.g., concurrently, transferring primary process heat energy generated by the thermal plant. In an embodiment, the heat is used productively in a process to refine the aqueous effluent(s) or discharge(s) of a biomass growth module, e.g., water, fuels, and/or a biomass serving as the working fluid. The use of the discharge(s) of a biomass growth module in this application may be in an open thermodynamic process, whereby fresh portions of a discharge of a biomass growth module are continually used in whole or in part as a working fluid, e.g., to generate power in the evaporation and turbine turning parts of a thermodynamic cycle, and the fully or partially refined biomass and/or biofuel resulting from such a system may be removed from the water and used a fuel in the thermal plant optionally after further refining, and/or all or a portion of the water may be reused in the thermal plant, and/or in any other process where water may be used in the Plan as shown in FIG. 3. In an embodiment, wet and/or dry biomass may be combusted to produce power in the thermal plant and/or to synthesize biomass products. Biomass may be dried using waste heat and/or airflow from the thermal plant and/or airflow to the thermal plant either in a drying module attached to the thermal plant, comprised by the Refinery and/or BPP, and/or in a separate biomass drying facility. Water captured from the drying process may be re-introduced into the biomass growth module and/or elsewhere in the Plan and/or waste heat from drying may be reclaimed and used in the Plan as in FIG. 2.

In one or more embodiments, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, a thermal plant may generate waste heat and/or primary process heat which may be exported to water desalination in the desalination plant, biomass processing, and/or for other industrial uses. Heat may be used to perform desalination or to enhance the desalination process, depending on the desalination method selected.

In one or more embodiments, e.g., FIG. 2 or other description related to heat generation and/or transfer, waste heat and/or primary process heat from Thermal Plant technologies may be used for Waste HTP and/or other biomass HTP (e.g., wood and/or agricultural waste) in the same way it is described herein for an HTP processing of a biomass/water slurry.

Figure 10:
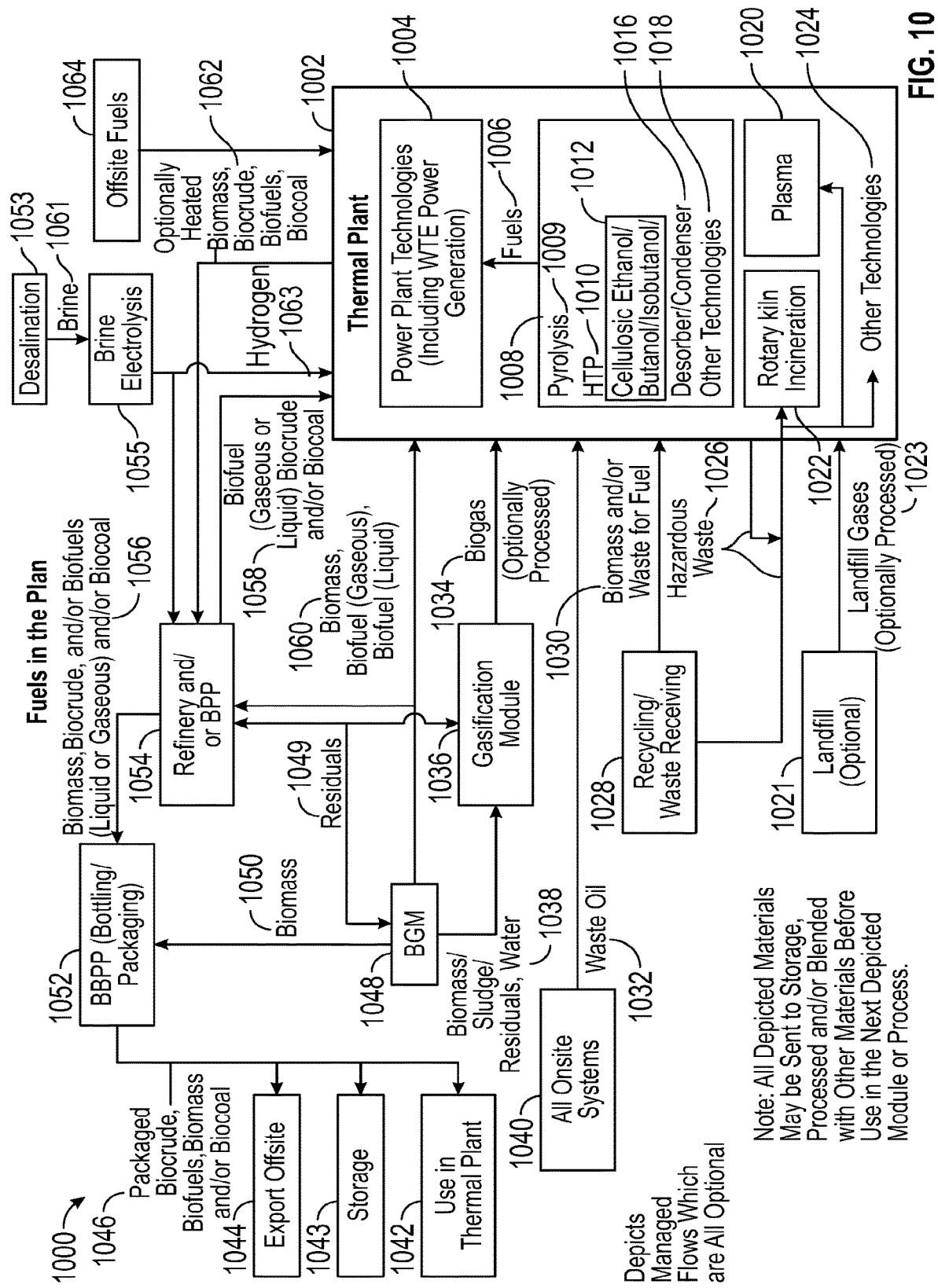
FIG. 10 is a schematic representation of biofuel and biomass and other fuel flow within the Plan according to the present disclosure.

In one or more embodiments, FIG. 2 and/or FIG. 10 and/or other description related to fuel and/or heat generation and/or transfer, the system may comprise cellulosic ethanol, butanol and/or isobutanol production. In an embodiment, these fuels may be combusted on-site to power the Plan and/or for power export offsite, and/or the fuels may be exported offsite. Cellulosic ethanol/butanol/isobutanol technologies may be used as a full or partial replacement for incineration to produce fuels for combustion, and/or to produce sugars to feed biomass (e.g., algae). Other technologies that produce compounds useful as fuels and/or as biomass feedstock from cellulose and/or other organic materials either currently or in the future may also be used in the same manner. In one or more embodiments, FIG. 2, waste heat and/or primary process heat may be utilized from the Thermal Plant in a pretreatment stage, celluoytic process, distillation process, and/or possibly other steps of these processes requiring heat.

In one or more embodiments, e.g., FIG. 2, or other description related to heat generation and/or transfer desalination plant filtration-based processes and/or distillation-based processes both may use or benefit from waste heat and/or primary process heat from the Thermal Plant. In an embodiment, filtration-based processes may utilize heat to increase the efficiency of the filtration process. In an embodiment, distillation-based processes may use heat to distill water, and/or to preheat water in order to lower the heating requirements at the distillation plant.

In one or more embodiments, e.g., FIG. 2 and/or FIG. 24K, waste heat may be used for power generation to achieve electrolysis, e.g., sodium hypochlorite (bleach) may be synthesized from DP brine discharge using brine electrolysis. The bleach may be used throughout the Plan for disinfection, cleaning, and/or other uses, and/or exported offsite. In one or more embodiments, e.g., FIG. 24K and/or FIG. 10, brine electrolysis provides hydrogen gas. The hydrogen may be used in a fuel cell to produce electricity, and/or returned to the thermal plant for combustion.

In one or more embodiments, e.g., FIG. 2, or other description related to heat generation and/or transfer heat may be transferred to the DP from the heated water, biocrude and/or biofuel that result from HTP and/or other processing methods used to process biofuel, biomass and/or a biomass/water slurry using heat exchangers and/or other technologies, and/or from any other heat source(s) in the Plan, as shown in FIG. 2. The method may beneficially raise the temperature of the feed water prior to desalination.

In one or more embodiments, e.g., FIG. 2, or other description related to heat generation and/or transfer heat may be transferred to the DP from the heated water, biocrude and/or biofuel that result from HTP and/or other processing methods used to process biofuel, biomass and/or a biomass/water slurry using heat exchangers or other technologies, and/or from any other heat source(s) in the Plan, as shown in FIG. 2. The method may beneficially raise the temperature of the feed water prior to desalination.

In one or more embodiments, e.g., FIG. 2, or other description related to heat generation and/or transfer; and/or FIG. 3, a saltwater BGU may use salt water to produce biomass initially, and subsequently, a water output may be directed in whole or in part to the DP for the desalination process after biomass separation from the water (possibly using HTP, other currently known biomass separation/refining methods, and/or methods that may be developed in the future). The biomass action on the salt water may remove organic materials, nutrients, and/or some minerals, which may result in a more efficient desalination process than regular salt water. Also the salt water after HTP or a similar process (if used) may have been heated, and that heat may increase the efficiency of the desalination process.

In one or more embodiments, e.g., FIG. 2, and/or FIG. 3 and/or other description related to heat generation and/or transfer and/or water transfer, DP brine discharge to sea and/or by other methods may be diluted with water output from the BGM and/or WWTP, as needed to mitigate salinity to reduce or eliminate environmental damage due to high-salinity and/or high temperature brine.

In one or more embodiments, e.g., FIG. 2, or other description related to heat generation and/or transfer, a BBPP may use heat from any source in the Plan for disinfection and/or any other process(es) requiring heat.

In one or more embodiments, e.g., FIG. 2, or other description related to heat generation and/or transfer, waste heat from the thermal plant and/or heat recovered from other sources in the Plan (e.g., FIG. 2) may be used to generate cooling, such as air conditioning and/or refrigeration for cooling buildings and/or for refrigeration of biomass products, for cooling the BGM where beneficial, and/or for other uses.

In one or more embodiments, e.g., FIGS. 1, 2, 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer and/or water transfer, water that has been separated from biomass in a BGM outflow fluid or biomass/water slurry after it is processed and/or refined may be used to cool the thermal plant and/or capture heat for use in the Plan.

In one or more embodiments, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, the heated biocrude that is the product of HTP processes such as HTL, may be further refined while still containing the heat from HTP. For example, HTL may typically raise the temperature of the biocrude to about 350 degrees C. or higher, which is approximately the temperature needed for additional refining to other fuels. Other HTP processes, likewise may yield heated fuels possibly mixed with water. This heated mixture may optionally be dried (chemically and/or otherwise), and/or otherwise processed to separate it from water and/or other constituents, and then sent as heated for refining to produce all other refined fuels that may be derived from the type of biomass being used. For example, most algae biomass processed through HTP may be converted to the same fuels that can be derived from petroleum, comprising LPG, gasoline, jet fuel, diesel, heating oil, fuel oil, and/or bitumen. Use of the already heated biocrude from HTP may save energy in further refining to refined fuels. Likewise, gaseous fuels that are the product of HTP processes, such as CHG, may utilize heat in the resultant gaseous biofuel possibly mixed with steam in a similar way to provide heat for separation from water and/or further refining of the biofuel. All heat used in any refining activities may be reclaimed as described herein, and/or reused in the Plan as in FIG. 2.

In an embodiment, e.g., those referenced in FIGS. 2, 3, 19 and/or 20, the design and method relate to a method of providing a working fluid, e.g., an aqueous fluid, to a thermal plant, while concomitantly, e.g., concurrently, transferring primary process heat energy and/or waste heat generated by the thermal plant. In an embodiment, the heat may be used productively in a process to refine the aqueous effluent(s) or discharge(s) of a biomass growth module, e.g., water, fuels, and/or a biomass serving as the working fluid. The use of the discharge(s) of a biomass growth module in this application may be in an open thermodynamic process, whereby fresh portions of a discharge of a biomass growth module may be continually used in whole or in part as a working fluid, e.g., to generate power in the evaporation and/or turbine turning parts of a thermodynamic cycle, and the fully or partially refined biomass and/or biofuel resulting from such a system may be removed from the water and/or used a fuel in the thermal plant optionally after further refining, heat may be reclaimed from the working fluid and used, e.g., e.g., in the Plan e.g., FIG. 2, and all or a portion of the water may be reused in the thermal plant, and/or in any other process where water may be used e.g., in the Plan e.g., FIG. 3. In an embodiment, wet and/or dry biomass may be combusted to produce power in the thermal plant and/or to synthesize biomass products. Biomass may be dried using waste heat and/or airflow from the thermal plant and/or airflow to the thermal plant either in a drying module attached to the thermal plant, comprised by the Refinery and/or BPP, and/or in a separate biomass drying facility. Water captured from the drying process may be re-introduced into the biomass growth module and/or elsewhere e.g., in the Plan and waste heat from drying may be reclaimed and used e.g., in the Plan e.g., FIG. 2.

In an embodiment, in system/grid 300, water may be used as a heat and/or cooling transfer and/or storage mechanism, a diluent, a means to transfer waste for treatment, a desalination/drinking water source, as source water for refining processes, for heat/cooling transfer, for irrigation, firefighting, cleaning, flushing, water features, a substrate for biomass growth and transport, a mode to move nutrients to the BGM, and/or other purposes e.g., as described herein. Water may be optionally in fluid communication between any or all modules, e.g., major and minor, modules, any of which may be optionally present in certain embodiments. For example, in an embodiment, refinery and/or BPP 202 may comprise modules 204, that comprise optionally any of the following: HTP 204A, anaerobic digester 204B, a supercritical fluid extraction unit 204C, and/or other processes of biomass and/or biofuel separation from water and processing known to those of skill in the art, and biofuel/biomass drying unit 202. The following modules may be optionally in fluid communication with each other: Thermal plant 222, refinery and/or BPP 202, desalination unit 214, BBPP 207 and BGM 212A fresh water source 302 and/or a salt water (e.g., sea water, brine and/or brackish water) intake 314 provide water to the grid. Downstream from source 302, pretreatment module 304 and/or Pre-heating/cooling module 306 treat water for use within the grid. Similarly, pretreatment module(s) 318 and/or Pre-heating/cooling module(s) 316 treat water for use within the grid. One or more water use/reuse/processing modules or facilities 310 may receive and/or provide water optionally treated and/or optionally combined in whole or in part with other water streams and/or otherwise processed for use or reuse to and/or from the thermal plant 222, BGM 212, Refinery and/or BPP 202, desalination plant 214, a BBPP (bottling/packaging facility) 207, waste receiving/recycling module 206, any heating and/or cooling process 334 and/or water storage facility(ies) 308, irrigation, firefighting water storage, fountains, lakes, cleaning uses 307 a landfill 309 and/or for discharge 312. Finally, in an optional embodiment, a water distribution facility 310 provides, inter alia, water for all modules, and/or for irrigation, firefighting, fountains, lakes, cleaning 307, e.g. internally to the Plan and/or externally e.g., where non-potable water may be utilized, and/or as a means to preheat or precool water for any process by exposure to ambient temperatures and/or sunlight (e.g., preheating of cold ocean water before introduction into a BGM). All water flows depicted by lines or arrows may be optional and managed. Water optional managed flows (e.g., lines and/or arrows of 300), water preheating/cooling 306, 318, pretreatment 304, 318, water use/reuse/processing/treatment/distribution 310, heating/cooling 334, water storage 308 and/or use of water in other modules e.g., FIG. 3 may be accomplished in any manner herein disclosed and/or known to those in the art. Any water source, flow/communication/connection depicted may be treated in any manner known to those in the art before use in any process/module/unit. The "grid" as referred to herein may take the form of one or more separate, water source(s)/flow(s)/communication(s)/connection(s) between one or more module(s)/unit(s), subunit(s), component(s), technolog(ies), and/or other feature (s) whereby one or more smaller, closed systems exist between any two or more components depicted in FIG. 3, or any water source/flow/communication/connection may be combined with other water source(s) and/or flow(s) at any stage of any process shown. For example: fresh water and salt water flows may be kept separate, in parts of the grid involving select modules; potable water may be kept separate from other water types; water of different temperatures may be kept separate and possibly exchange heat using a heat exchanger in order to heat or cool a process or module to a particular temperature, or may combined to reach a certain temperature required for a process; certain water flows may be kept separate for certain processes depicted, and later may be combined to reach a certain desired salinity, temperature and/or for other reasons.

Modules and specific technology types shown in the figures may be exemplary and optional, and all modules and/or technology types and/or communications with the grid depicted may be present only in certain embodiment(s) of the Plan.

A system configured to use and reclaim water used by one or more modules configured for water use wherein such water is provided to and/or reclaimed from:
    a) a fresh water source;
    b) a fresh water pretreatment module;
    c) a salt water intake;
    d) a salt water pretreatment module;
    e) a preheating/cooling module;
    f) a water storage module;
    g) irrigation;
    h) firefighting;
    i) fountains;
    j) lakes;
    k) cleaning;
    l) a BGM;
    m) a traditional WWTP module;
    n) a refinery module;
    o) a BPP module;
    p) heating and/or cooling;
    q) a recycling module;
    r) a waste receiving module;
    s) a BBPP module;
    t) a desalination module;
    u) water for discharge/export;
    v) a processing and/or treatment module; and/or
    w) a thermal plant module.

In reference to FIG. 3 an embodiment of the disclosure includes a system 300 configured to use and reclaim water used by one or more modules configured for water use wherein such water is provided to and/or reclaimed from: a fresh water source 302; a fresh water pretreatment module 304; a salt water intake 314; a salt water pretreatment module 318; a preheating/cooling module 306, 316; a water storage module 308; irrigation 307; firefighting 307; fountains 307; lakes 307; cleaning 307; a BGM 212; a traditional WWTP module 212; a refinery module 202; a BPP module 202; heating and/or cooling to the Plan 334; a recycling module 206; a waste receiving module 206; a BBPP module 207; a desalination module 214; water for discharge/export 312; a processing and/or treatment module 310; and/or a thermal plant module 222.

An embodiment includes the system wherein the water provided to and/or water reclaimed from: a fresh water source 302; a fresh water pretreatment module 304; a salt water intake 314; a salt water pretreatment module 318; a preheating/cooling module 306, 316; a water storage module 308; irrigation 307; firefighting 307; fountains 307; lakes 307; cleaning 307; a BGM 212; a traditional WWTP module 212; a refinery module 202; a BPP module 202; heating and/or cooling to the Plan 334; a recycling module 206; a waste receiving module 206; a BBPP module 207; a desalination module 214; water for discharge/export 312; a processing and/or treatment module 310; and/or a thermal plant module 222 is mixed with water from: a fresh water source 302; a fresh water pretreatment module 304; a salt water intake 314; a salt water pretreatment module 318; a preheating/cooling module 306, 316; a water storage module 308; irrigation 307; firefighting 307; fountains 307; lakes 307; cleaning 307; a BGM 212; a traditional WWTP module 212; a refinery module 202; a BPP module 202; heating and/or cooling to the Plan 334; a recycling module 206; a waste receiving module 206; a BBPP module 207; a desalination module 214; water for discharge/export 312; a processing and/or treatment module 310; and/or a thermal plant module 222 and/or with any other water source at any stage of any process depicted.

An embodiment includes the system wherein the water is provided to and/or reclaimed from modules: a fresh water source 302; a fresh water pretreatment module 304; a salt water intake 314; a salt water pretreatment module 318; a preheating/cooling module 306, 316; a water storage module 308; irrigation 307; firefighting 307; fountains 307; lakes 307; cleaning 307; a BGM 212; a traditional WWTP module 212; a refinery module 202; a BPP module 202; heating and/or cooling to the Plan 334; a recycling module 206; a waste receiving module 206; a BBPP module 207; a desalination module 214; water for discharge/export 312; a processing and/or treatment module 310; and/or a thermal plant module 222 using a conduit wherein the water conduit is shared by two or more water lines wherein the water is salt water, brine water, brackish water, fresh water, wastewater, grey water, and/or potable water.

An embodiment includes the system wherein the conduit is in operative communication with a salt water intake 314, a salt water BGU which is comprised by the BGM/WWTP module 212, a desalination module 214, a salt water cooling system(s) which is comprised by the heating/cooling module 334 for use in the Plan, e.g., FIG. 2, a discharge/export module 312, and/or another saltwater module for use in the system or Plan, e.g., FIG. 3.

An embodiment includes the system wherein the conduit has one or more separate water lines for salt water, brackish water, and/or brine water.

An embodiment includes the system wherein the conduit is in operative communication with a fresh water source 302, a fresh water BGU which is comprised by the BGM/WWTP module 212, a WWTBGU which is comprised by the BGM/WWTP module 212, a WWTP module 212, a fresh water cooling system(s) for use in the Plan, e.g., FIG. 2, a discharge/export module 312, and/or another fresh water module for use in the system or Plan, e.g., FIG. 3.

An embodiment includes the system wherein the conduit has one or more separate water lines for fresh water, potable water, wastewater, and/or brackish water.

In reference to FIG. 3 an embodiment of the disclosure includes a method of using and reclaiming water comprising: transmitting water from a module to another module; using all or a portion of the water in the another module for work; and optionally transmitting water unused for the work from the another module to the module, wherein such water is provided to and/or reclaimed from: a fresh water source 302; a fresh water pretreatment module 304; a salt water intake 314; a salt water pretreatment module 318; a preheating/cooling module 306, 316; a water storage module 308; irrigation 307; firefighting 307; fountains 307; lakes 307; cleaning 307; a BGM 212; a traditional WWTP module 212; a refinery module 202; a BPP module 202; heating and/or cooling to the Plan 334; a recycling module 206; a waste receiving module 206; a BBPP module 207; a desalination module 214; water for discharge/export 312; a processing and/or treatment module 310; and/or a thermal plant module 222.

An embodiment includes the method wherein the water provided to and/or water reclaimed from: a fresh water source 302; a fresh water pretreatment module 304; a salt water intake 314; a salt water pretreatment module 318; a preheating/cooling module 306, 316; a water storage module 308; irrigation 307; firefighting 307; fountains 307; lakes 307; cleaning 307; a BGM 212; a traditional WWTP module 212; a refinery module 202; a BPP module 202; heating and/or cooling to the Plan 334; a recycling module 206; a waste receiving module 206; a BBPP module 207; a desalination module 214; water for discharge/export 312; a processing and/or treatment module 310; and/or a thermal plant module 222 is mixed with water from: a fresh water source 302; a fresh water pretreatment module 304; a salt water intake 314; a salt water pretreatment module 318; a preheating/cooling module 306, 316; a water storage module 308; irrigation 307; firefighting 307; fountains 307; lakes 307; cleaning 307; a BGM 212; a traditional WWTP module 212; a refinery module 202; a BPP module 202; heating and/or cooling to the Plan 334; a recycling module 206; a waste receiving module 206; a BBPP module 207; a desalination module 214; water for discharge/export 312; a processing and/or treatment module 310; and/or a thermal plant module 222 and/or with any other water source at any stage of any process depicted.

An embodiment includes the method wherein the water is provided to and/or reclaimed from modules: a fresh water source 302; a fresh water pretreatment module 304; a salt water intake 314; a salt water pretreatment module 318; a preheating/cooling module 306, 316; a water storage module 308; irrigation 307; firefighting 307; fountains 307; lakes 307; cleaning 307; a BGM 212; a traditional WWTP module 212; a refinery module 202; a BPP module 202; heating and/or cooling to the Plan 334; a recycling module 206; a waste receiving module 206; a BBPP module 207; a desalination module 214; water for discharge/export 312; a processing and/or treatment module 310; and/or a thermal plant module 222 using a conduit wherein the water conduit is shared by two or more water lines wherein the water is salt water, brine water, brackish water, fresh water, wastewater, grey water, and/or potable water.

An embodiment includes the method wherein the conduit is in operative communication with a salt water intake 314, a salt water BGU which is comprised by the BGM/WWTP module 212, a desalination module 214, a salt water cooling system(s) for use in the Plan, e.g., FIG. 2, a discharge/export module 312, and/or another saltwater module for use in the system or Plan, e.g., FIG. 3.

An embodiment includes the method wherein the conduit has one or more separate water lines for salt water, brackish water, and/or brine water.

An embodiment includes the method wherein the conduit is in operative communication with a fresh water source 302, a fresh water BGU which is comprised by the BGM/WWTP module 212, a WWTBGU which is comprised by the BGM/WWTP module 212, a WWTP module 212, a fresh water cooling system(s) which is comprised by the heating/cooling module 334 for use in the Plan, e.g., FIG. 2, a discharge/export module 312, and/or another fresh water module for use in the system or Plan, e.g., FIG. 3.

An embodiment includes the method wherein the conduit has one or more separate water lines for fresh water, potable water, wastewater, and/or brackish water.

In one or more embodiments, e.g., FIG. 7A, 7B, and/or FIG. 3, water that is the substrate for any of the foregoing processes may be reused anywhere in the Plan where water is utilized, comprising as source water for the BGM, cooling the thermal plant, to dilute brine discharge of the optional desalination system, and/or for other uses (See FIG. 2). Heat exchangers and/or other known technologies may be used to transfer heat from any system in the Plan to another.

In one or more embodiments, e.g., FIGS. 2, 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer and/or FIG. 3, and/or other figures and/or description relevant to water use and/or movement, cooling water from any source may be used to cool the thermal plant, and then routed for optional primary treatment (per module 104 of FIG. 1) and then for direct use as source water in the BGM, mixed with another water source and used as source water in the BGM, or simply used to transfer heat to water used in the BGM and/or another process. In any of these or other manners disclosed herein, temperature in the BGM may be regulated either directly and/or indirectly by water outflows from the thermal plant in combination with other water sources. Gases and/or other fluid outflows from the thermal plant, likewise may be used alone or in combination with other sources of heat to regulate the temperature of the BGM and/or other components of the Plan, (e.g., FIGS. 7A, 7B, 12A, 12B, 12C, 12D, and/or 12E). If cooling is needed, any of the aforementioned sources of heat may be used to cogenerate cooling, which may be supplied to the Plan as in FIG. 2.

In one or more embodiments, e.g., FIGS. 2, 3, 6, 7A, 7B, 11, 12A, 12B, 12C, 12D, 12E, 15A, 15B, 16, 17, 18, 19, 20A, 20B, 20C, 20D and/or other figures and/or description relevant to heat capture, and/or transfer, a BGM and/or its components, and/or water transfer, a BGM, a BGU, a BGU subunit and/or any other BGU component may be fully or partially immersed in a pool, other container, water body and/or stream fed by a water supply, e.g., from onsite and/or offsite, used to provide cooling, or alternatively, to capture waste heat from a thermal plant, and/or to supply heat, wherein the BGM temperature may be regulated by contact with heated or cool water supply. Heated and/or cooled air and/or other fluid e.g., from the thermal plant and/or other modules may be used to fill containers which may be configured to come in contact with or partially or fully surround the BGM, a BGU, and/or any of its components in order to transfer heat and/or cooling. Heat and/or cooling may be supplied 234 by offsite sources 228 optionally comprising a water supply provided by offsite water source(s) comprising a fresh water source, 302, water intake for salt water 314, and/or other sources of heat and/or cooling in gaseous and/or liquid form originating offsite.

In one or more embodiments, e.g., FIG. 3, the water intake(s), shown as fresh water source 302, and/or water intake (salt water) 314, may provide a source of cooling for any process in the Plan, wherein water from an intake out to sea, especially a deep-water intake, may be significantly cooler than ambient temperature on land and may provide cooling. In an embodiment, saltwater intake water is used as source water for a SWBGU and/or BWBGU in a hot climate to regulate its temperature. In an embodiment, the salt water from the intake may be used as source water either alone or combined with other water sources to fill pools and/or other structures surrounding any BGU or BGU component in order to provide cooling and/or temperature modulation, particularly in hot environments. After use in this manner and/or in other cooling applications, decorative application, and/or in any other manner described for heat and/or cooling transfer, comprising possibly heat transfer from the thermal plant to the Plan, the water may be then routed to the DP for desalination and/or other processes where warmer water is beneficial. In this manner, water and/or cooling are provided where needed in the Plan (See FIGS. 2 and 3), and in the process, the salt water is elevated in temperature, which allows for a lower energy requirement in the desalination process and/or other processes in the Plan where warmer water is beneficial.

In an embodiment, e.g., FIG. 3, following hydrothermal processing e.g., FIG. 1, and/or other processes such as the harvesting of the biomass material from the biomass growth module discharge stream, a subsequent purifying filter, ultraviolet light, tertiary wastewater treatment (e.g., when wastewater is used in the BGM) and/or other water treatment methods known to those of ordinary skill in the art may be used to further treat the water discharge before use in other applications where necessary. Water processed through this system and/or optional subsequent refining steps can be made suitable for many uses, e.g. as a potable water stream, a non-potable stream, for discharge to the environment, for reuse in the disclosed Plan wherever water is needed (See FIG. 3).

In an embodiment, e.g., with reference to FIG. 3, an unexpected benefit may be synergies of WWTP(s) and/or WWTBGU(s) with the remainder of the Plan. Wash water and/or spilled water and/or biomass from the optional water bottling/biomass products bottling/packaging plant may be sent to the WWTP/WWTBGU for treatment, reclamation of water, or a substantial portion thereof, for example from 60 to 100% of the wash water and/or spilled water, or from 60 to 90% or from 60 to 80% or from 60 to 70% of the water. Wastewater from all other plants in the Plan may be sent directly to WWTP/WWTBGU optionally in whole or in part comprising water used to cool the thermal plant and for heat capture, if acceptable to the thermal plant cooling system(s), or may undergo treatment, and then be sent to thermal plant cooling system(s) and heat capture.

In certain embodiments, e.g., those represented by FIG. 3 and other embodiments regarding the use of water in the Plan, the present disclosure relates to an integrated approach to minimization of CO2 emissions, power generation, biofuel production, efficient use of heat and water, as well as production of biomass-derived non-fuel products, and/or treatment of wastewater and/or waste-to-energy in some embodiments. Various embodiments provide for a wide variety of other water sources or combinations to be used to provide a medium for biomass and/or biofuel production and/or CO2 abatement, with conservation of water and heat energy.

In an embodiment, one or more water sources may be provided for biomass growth, wherein the water may be wastewater, salt water, brackish water, purified water, potable water, non-potable water, and/or brine. The amount of carbon in the water may be from less than 1% to 15% by weight.

In one or more embodiments, e.g., FIG. 3 and/or FIG. 14, a SWBGU may use regular salt water, such as seawater and/or may use the brine discharge (reject high salinity water from the optional desalination plant) to grow biomass. The resultant discharge water from a brine water SWBGU may be treated the same way as brine discharge described herein, but may be lower in nutrient content, lower in some mineral content, biological materials, and/or other chemicals than seawater, after processing through a SWBGU, which may allow for the production of different biomass products, salt, and/or other products from the brine than seawater, and/or production of the same products more efficiently (e.g., more easily isolated from contaminants).

In one or more embodiments, e.g. FIG. 3, a BWBGU may be implemented by the use of a combination of any fresh and/or saltwater sources, optionally comprising wastewater of any description, salt water, brine water (e.g., from the optional desalination plant), non-waste fresh water and/or other water sources. It may have the combined synergies of a system that would normally use the water sources being combined, but the resulting brackish water discharge may be discharged as in the desalination plant, used to dilute the brine discharge, and/or may be reused in manners determined to be acceptable for cooling and/or other purposes, as in the treated wastewater system, given the resultant salinity. The resulting discharge, if not useful otherwise, may discharged to the sea and/or by other salt water disposal methods either with or without dilution.

In one or more embodiments, e.g., FIGS. 1 and/or 3, desalinated water may be produced through various processes known to the art in processing water through a BGM and/or subsequent BGM outflow fluid processing steps in the Plan.

In an embodiment, e.g., FIG. 3, certain salt water bioreactors may produce desalinated water, possibly mixed with biofuel by evaporation, and once separated from biofuel as necessary, the water is potable. In an embodiment, a SWBGU may produce desalinated drinking water either in the place of desalination technologies or to supplement desalination technologies in the Plan. Brine produced by such a system may be treated as discussed herein for other desalination technologies.

In one or more embodiments, e.g. FIG. 3, after desalination, the desalination plant brine discharge is diluted to about the salinity of seawater using wastewater, fresh water, salt water and/or other water source(s). The combined water substrate is then used in the BGM to grow biomass. This embodiment may provide a greater volume of useful water than using only wastewater and/or other fresh water in the BGM, wherein the BGM water discharge is later combined with the brine discharge to dilute it for discharge to sea. Working with water in the BGM that has a salinity comparable with ocean salinity allows for the use of biomass growth systems that have been developed on the market to operate using salt water, and in the case of a brine water combination with wastewater, the mixture may provide a better source of nutrients than are present in salt water alone, and, result in better biomass growth and production, while also treating wastewater.

In one or more embodiments, e.g. FIG. 3, a thermal plant wastewater (optionally after heat recovery) may be directed to the WWTP and/or WWTBGU.

In an embodiment, e.g., FIG. 3 and/or FIG. 1 any other wastewater source(s) in the Plan may be routed to primary treatment (per module 104 of FIG. 1) and/or then to the WWTP and/or WWTBGU.

In one or more embodiments, e.g., FIG. 3 and/or FIG. 24H, the Plan may use solar thermal technologies (e.g., solar troughs) for preheating seawater for desalination, a BGM output for HTP, for power generation, and/or for introduction of heat into the Plan wherever needed (e.g., FIG. 3). If a solar thermal technology is used, it may share steam turbines with those already in thermal plant.

In one or more embodiments, e.g. FIG. 3, demineralized water from an optional desalination plant may be utilized during firing of light oil and/or other fuels to reduce the combustion temperature and/or the generation of NOx emissions from combustion turbines (CTs) and/or other thermal plant systems. In one or more embodiments, desalinated water from the optional desalination plant may be used for relatively small volumes of water needed for CT inlet air cooling, NOx injection water, and/or potable water, and for similar uses in other thermal plant power generation systems.

In one or more embodiments, e.g. FIGS. 1 and/or 3, a portion, e.g., most, of the wastewater discharged from the thermal plant (after heat use and/or recovery), may be routed to primary treatment (per module 104 of FIG. 1) and then to the WWTP and/or WWTBGU. Some thermal plant water wastes, depending on contamination levels, may be used to dilute the desalination plant brine discharge without further treatment in order to reduce the environmental impact of the brine. Storm water runoff may be sent to a storm water retention pond or first run through an oil/water separator if it contains oil, and then sent to a storm water retention pond. This wastewater may then be routed for primary treatment (per module 104 of FIG. 1), and then to the WWTP and/or WWTBGU. Chemical cleaning wastewater and/or other chemically treated wastewater may be maintained onsite and tested and, if non-hazardous, according to a person of ordinary skill, may be routed to primary treatment (per module 104 of FIG. 1) and then to the WWTP and/or WWTBGU with the other wastewaters or directed to an evaporation pond if suitable.

In and embodiments, e.g. FIG. 3, water needed for cellulosic ethanol, butanol, and/or isobutanol processes may be taken from any source(s) in the Plan, as shown in FIG. 3.

In one or more embodiments, e.g., FIG. 3 and/or FIG. 24K, sea salt may be manufactured from the DP brine discharge and sold off-site. In one or more embodiments, e.g., FIG. 3, DP demineralized water may be supplied for use in the thermal plant where needed in any thermal plant technology or system (e.g., combustion turbines, if used, and/or other power systems). In one or more embodiments, e.g., FIG. 3, DP desalinated water (with minerals added back) may be supplied for use as appropriate in the thermal plant (e.g., combustion turbines and/or other power systems).

Figure 24A:
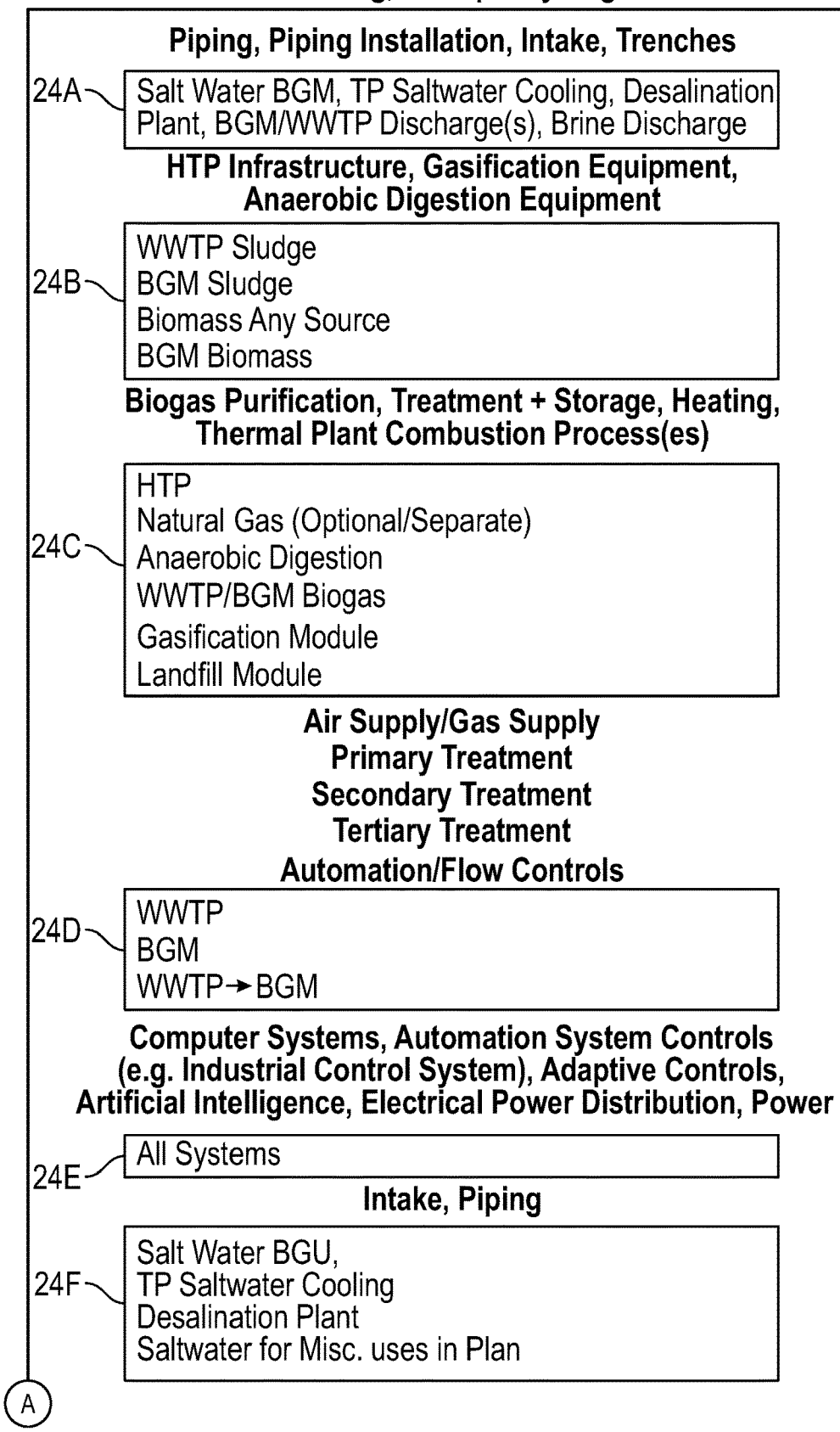

In one or more embodiments, e.g., FIG. 3 and/or FIG. 24A, the DP may share an intake with a SWBGU, a saltwater cooling source for the thermal plant (if needed), or any of these modules/uses for salt water may have separate intakes. Any of these modules/sources' intakes, if separate, or the combined intake if combined may share some piping and/or other equipment with wastewater treatment plant, BGM, and/or brine discharge outfall. In one or more embodiments the intake(s) may provide a source of cooling for any process in the Plan, wherein water from an intake out to sea, especially a deep-water intake, should be significantly cooler than ambient temperature on land and can provide cooling. In an embodiment, saltwater intake water is used as source water for a SWBGU and/or BWBGU in a hot climate to regulate its temperature.

In an embodiment, the salt water from the intake is used to fill pools and/or other structures surrounding any BGU and/or BGU component in order to provide cooling and/or temperature modulation, particularly in hot environments. After use in this manner and/or in other cooling applications, decorative application, and/or in any other manner described for heat and/or cooling transfer, comprising possibly heat transfer from the thermal plant to the Plan, the water may be then routed to the DP for desalination. In this manner, water and/or cooling are provided where needed in the Plan (See FIGS. 2 and 3), and in the process, the salt water is elevated in temperature, which allows for a lower energy requirement in the desalination process.

In one or more embodiments, e.g., FIG. 3, water reuse from the BGM and/or WWTP may be used for landscape irrigation, firefighting, water features, fountains, lakes, industrial cooling (Comprising cooling in the thermal plant), and/or cleaning processes in the Plan, as opposed to using DP desalinated water. This may greatly reduce the needed amount of desalinated water and consequently the power requirement in the Plan. It will require only additional piping. If feasible, salt water, or salt water mixed with reclaimed wastewater and/or another water source either from the BGM, WWTP and/or another source may be used for: cooling water, firewater supply, water features, fountains, lakes, and/or other uses to conserve reclaimed BGM and/or WWTP water and/or DP desalinated water in the Plan. Where usable as cooling water (e.g., in certain technologies), salt water may be used to cool the thermal plant and/or other heat sources directly and/or indirectly (via heat exchange), and may be then routed to the DP for desalination. This may save energy in the DP, as higher temperature water is easier to desalinate. Treatment of any water supply may be performed either before and/or after its use in the thermal plant and/or any other modules and/or processes in the Plan in accordance with techniques known to the art.

In an embodiment, e.g., FIG. 3, HTP discharge water may serve as feedwater for a BGU in whole or in part. This water source may contain higher levels of carbon and/or other materials left after HTP, not unlike wastewater that may require remediation and/or may facilitate biomass growth. In this case, the water source may be salt water, fresh water, and/or any other water type discussed herein as a possible water source type in a BGU which has been processed through HTP. In addition to treatment of the water by use of the residual carbon and/or possibly other material in the water, the synergies of the BGU using HTP wastewater may be the same as the type of source water used for the HTP process.

In and embodiment, e.g., FIG. 3, HTP wastewater may be processed in a manner similar to BGM outflow fluid 117. Its higher carbon content may provide a concentrated carbon stream which may be mixed with BGM outflow fluid and/or separately processed by taking it through any processing steps undertaken by the BGM outflow fluid 117.

In one or more embodiments, e.g., FIG. 3, as required, for a reverse osmosis desalination process, a Clean In Place (CIP) cycle may be used to clean a DP membrane (filtration-based processes only). In an embodiment, waste from this process may be disposed of to the WWTP and/or BGM.

In an embodiment, e.g., FIG. 3, treated wastewater from the WWTP and/or BGM may be used to dilute the DP plant brine discharge to reduce or eliminate environmental impacts. If a deep sea diffuser brine discharge outfall is used, up to 5% salinity above the naturally occurring salinity is generally acceptable. However, with freshwater dilution, the salinity could be reduced in-pipe to match the naturally occurring salinity or a salinity that is acceptable, and discharged near the shore, instead of out to sea, eliminating the significant infrastructure expense associated with a deep sea discharge. The typical salinity of ocean water is between 3% and 5%, and a typical reverse osmosis desalination plant rejection rate (rate of brine discharge as a percentage of the initial intake volume) is generally about 50%. In an embodiment the following formula may be used to calculate the amount of dilution necessary to restore the brine discharge to a target salinity:

$$S_B V_B + S_D V_D = S_T (V_B + V_D), \text{ where:}$$

$S_B$=Salinity of Brine, $V_B$=Volume of Brine,
$S_D$=Salinity of Diluent, $V_D$=Volume of Diluent, and
$S_T$=Target Salinity.

In one or more embodiments, an example of BGM and/or WWTP dilution may be utilized as follows: Assuming a WWBGU, FWBGU and/or WWTP is the source with a salinity of 0.5%, assuming ocean salinity of 4.5%, and assuming a desalination 50% rejection rate, for a near shore discharge, using the formula above, the brine would be diluted with approximately 1.125 liters of BGU and/or WWTP discharge water per liter of brine discharge water to reach background salinity. For a deep sea discharge, the brine would be diluted with approximately 1.012 liters of BGU and/or WWTP discharge water per liter of brine discharge water in order to reach 5% above background salinity, recommended discharge salinity. The brine discharge may also be diluted with salt water either from a saltwater BGU and/or a brackish water BGU, and/or another salt water source, and/or another water source in the Plan. In an embodiment, any water source(s) in the Plan in combination with or without the BGU and/or WWTP discharge (FIG. 3) may be used in order to meet desalination plant brine discharge salinity goals. In an embodiment, the water source(s) used for dilution may be strategically selected and/or combined such that water most valuable to the Plan and/or community is preserved as much as possible, and water of lesser value is used for dilution (e.g., treated wastewater, brackish water).

In one or more embodiments, in the case where there are multiple possible dilution sources, the above formula may be modified as follows calculate the volumes of each diluent water source that may be combined to achieve a target salinity:

$$S_B V_B + (S_{D1} V_{D1} + S_{D2} V_{D2} + S_{D3} V_{D3} \ldots) = S_T(V_B + V_{D1} + V_{D2} + V_{D3} \ldots), \text{ where:}$$

The numbers represent different diluent water sources.

As many diluent sources as are available may be added in the same way (denoted by " . . . " above). In one or more embodiments, the disclosed Plan provides a novel means and method of planning and/or combining water resources strategically by use of this formula and strategic selection of water sources to generate salinity targets as mentioned above. This process and method may be used to dilute the brine to the same or similar salinity as naturally occurring salinity for near shore discharge, or an acceptable salinity for deep sea discharge, or possibly some salinity between the two for a sea discharge between the two distances. In an embodiment, if the brine is heated due to processing through desalination and/or another reason, after optional heat recovery to the Plan, if the brine temperature may be impacting on the local environment, or regulated by law, dilution strategies may also incorporate calculations and diluent source water selections to adjust the heat of the brine discharge to appropriate levels. As is known to the person of ordinary skill in the art, mathematical and/or physical modeling and/or other studies may be needed to determine actual numbers, based on discharge design, local features and/or other considerations.

In one or more embodiments, e.g., FIG. 3, wastewater may be directed to a WWTP and/or WWTBGU.

In one or more embodiments, e.g., FIG. 3, wastewater from all onsite modules and/or from offsite sources may be directed to a WWTP and/or WWTBGU.

In one or more embodiments, e.g., FIGS. 3, a water bottling/biomass products bottling/packaging plant (BBPP) may be added optionally as part of the Plan. In one or more embodiments, any one or more of the components within the BBPP may be used (e.g., water bottling only, biomass bottling only, and/or other biomass packaging types only.) Water bottling lines may be used to bottle treated drinking water generated from the DP.

DP Brine Disposal Technologies: Brine Disposal to Sea—Discharge to Sea or another water body: In an embodiment, e.g., FIG. 3 and/or FIG. 24A a DP brine discharge outfall may share some piping and/or other equipment with the WWTP/BGM outfall, and/or may utilize the same piping and/or outfall. In an embodiment, brine may be discharged to land using zero liquid discharge. In an embodiment, brine may be discharged underground and/or by another means known to the person of ordinary skill in the art.

In one or more embodiments, e.g., FIG. 3 and/or FIG. 24A, a SWBGU may share infrastructure with the optional desalination plant, comprising, for example, the water intake from the sea, pumps, pipes, heat use, water use and/or an outfall. In an embodiment, a SWBGU may use salt water separately from the desalination plant, it may receive brine as source water from the desalination plant, and/or its output may be directed to the desalination plant (see description in desalination section).

In one or more embodiments, e.g., FIG. 3 and/or FIG. 24A, the DP may share an intake and/or piping throughout the Plan with a SWBGU, a saltwater cooling source for the thermal plant (if needed), or any of these modules/uses for salt water may have separate intakes. Any of these modules/sources' intakes, if separate, or the combined intake if combined may share some piping and/or other equipment with wastewater treatment plant, BGM, and/or brine discharge outfall. In one or more embodiments the intake(s) may provide a source of cooling for any process in the Plan, wherein water from an intake out to sea, especially a deep-water intake, may be significantly cooler than ambient temperature on land and may provide cooling. In an embodiment, saltwater intake water may be used as source water for a SWBGU and/or BWBGU in a hot climate to regulate its temperature. In an embodiment, the salt water from the intake is used to fill pools and/or other structures surrounding any BGU and/or BGU component in order to provide cooling and/or temperature modulation, particularly in hot environments. After use in this manner and/or in other cooling application(s), decorative application(s), and/or in any other manner described for heat and/or cooling transfer, comprising possibly heat transfer from the thermal plant to the Plan, the water may be then routed to the DP for desalination. In this manner, water and/or cooling are provided where needed in the Plan (See FIGS. 2 and 3), and in the process, the salt water is elevated in temperature, which allows for a lower energy requirement in the desalination process.

Figure 24B:
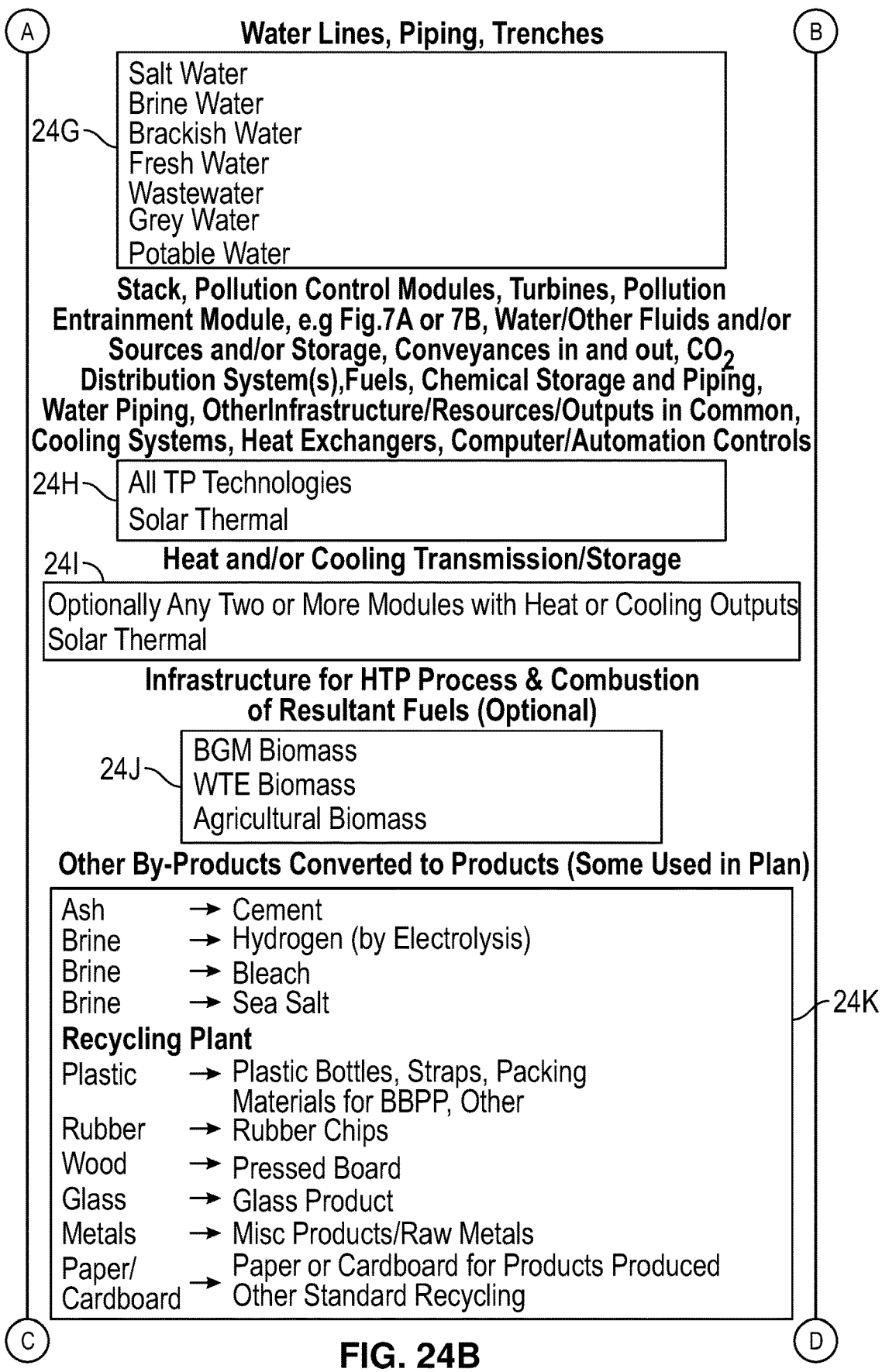

In an embodiment, e.g., FIG. 3 and/or FIG. 24B, an HTP module or unit, which may be used as described herein to process biomass, and/or similar methods, may also be used as a means of converting waste into energy. HTP and/or equivalent technologies to a person of ordinary skill may be used to convert a wide variety of organic materials to produce biocrude. An HTP module, unit or equivalent processing system(s) set up for biomass may be shared with those being used to process solid waste. HTL may be conducted in accordance with the PNNL process patent WO 2013/184317A1 as shown in FIG. 9. Other variations of HTP or similar processes suited to the purpose may also be used.

With Reference to FIG. 1, The disclosure incorporates the use of different facility types, some of which may be typically unrelated, not in operative communication with each other, and/or not collocated, such as a thermal plant, a biomass growth module, a refinery, a downstream processing facility (BPP), products packaging facility (BBPP), and processes to generate electricity, fuels, products, and to productively reclaim and reuse waste heat, water, carbon dioxide, air and other gases, pressure, waste biomass, solvents and other materials. Additional optional technologies may be added to the design in FIG. 1 to create additional outputs, efficiencies and/or synergies. These technologies may be discussed herein.

Figure 4:
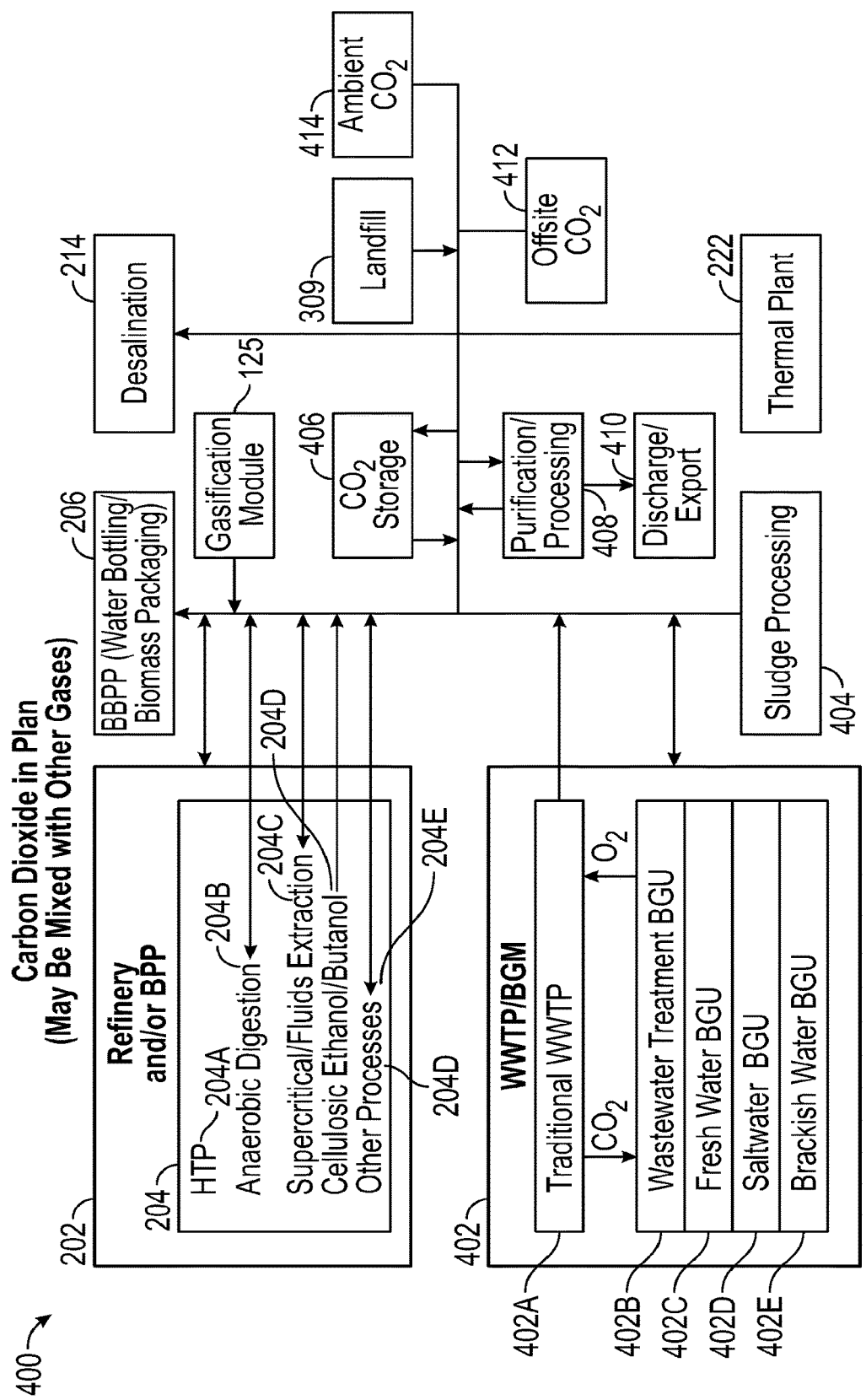
FIG. 4 is a schematic representation of carbon dioxide flow within the Plan according to the present disclosure.

In an embodiment, and with reference to FIG. 4, the present disclosure may be directed to a novel method and design for the production of fuel and/or other products, reduction of $CO_2$ and other emissions, and innovative methods of conservation of water and energy in performing these vital processes. The method and Plan may be adapted to the geography, available resources, and needs of a particular location.

In an embodiment 400, the Plan and method relate to the minimization of $CO_2$ emitted by a major $CO_2$ emission source or sources represented in FIG. 4 as the thermal plant 222, e.g., a hydrocarbon-burning thermal power plant, waste-to-energy plant and/or other thermal plant technology(ies) generating $CO_2$ comprising optionally industrial plants such as cement factories, and/or other $CO_2$ emitters not comprised by the thermal plant optionally e.g., in the Plan, such as the Refinery and/or BPP 202, sludge processing module 404 which may be optionally conducted in primary treatment module 104 in FIG. 1, desalination module 214, optional landfill 309, WWTP 402, and/or other optional $CO_2$ sources and shown in FIG. 4. In an embodiment, the percentage of carbon removed from the waste stream of the thermal plant and/or other $CO_2$ emitters and optionally incorporated as biomass growth into the aqueous effluent(s) or discharge(s) of the biomass growth module and/or used in other processes which require carbon dioxide e.g., FIG. 4 may be approximately from about 30% to about 80% of the waste stream carbon, or from about 50% to about 100%, or from about 75% to about 100% or from about 80% to about 100% or from about 80% to about 95%.

In an embodiment, a thermal plant 222 and biomass growth module 402 and/or other optional $CO_2$ producers and/or users may be preferably located at a common locus, e.g., in close proximity, and may be arranged for convenient transfer of the $CO_2$ to the biomass growth module 402. $CO_2$ may be captured from a thermal plant 222 by pre-combustion capture, post-combustion, oxy-fuel process combustion capture and or any other means known to the person of skill in the art. Carbon dioxide may also be generated by the following optional systems: a WWTP 402A, WWTP sludge processing 404, biomass, certain types of BGUs, biomass refining, cellulosic ethanol/butanol/isobutanol, WWTP sludge, other organic source, anaerobic digestion 204B, an optional landfill 309, other processes (e.g., FIG. 4) and/or offsite sources.

Carbon dioxide and/or the accompanying gases from any source optionally may be purified and/or otherwise processed by any means known to those of ordinary skill in the art before and/or after any process in FIG. 4. In some embodiments, e.g., those of FIG. 4, the carbon dioxide may be directly or indirectly transferred e.g., piped, to: a biomass growth module, and/or to a biomass growth module, to the biofuel refining/separation plant for use in biomass refining and/or separations techniques, comprising supercritical fluids extraction 204C, and/or sent to the water bottling/biomass packaging plant 206 for use in carbonation of liquids, and/or other uses, and/or stored either as a gas, compressed gas, liquid and/or solid (dry ice), and/or may be marketed offsite. Carbon dioxide may be captured using Carbon Capture and Storage (CCS) and/or any other technique known to the art where beneficial, comprising optionally in the purification/processing module of FIG. 4. Using such different sources and/or destinations for $CO_2$ together in one site allows more synergies between different systems. Carbon dioxide may be distributed among these systems using such technologies as blowers, piping, spargers, and/or any other technologies known to the person of skill in the art which may be suited to the purpose.

With reference to Table 3, a system configured to use and reclaim carbon dioxide wherein the carbon dioxide is provided by:
 a) a thermal plant module;
 b) a sludge processing module;
 c) a traditional WWTP module;
 d) a carbon dioxide storage module;
 e) an ambient carbon dioxide source(s);
 f) a purification module;
 g) a refinery module;
 h) a BPP module;
 i) a supercritical fluids extraction module;
 j) a gasification module;
 k) a BGM;
 l) a cellulosic ethanol/butanol/isobutanol module;
 m) a landfill module; and/or
 n) a source outside the system (offsite).

Thus, a combination recited in Table 3 may provide an embodiment of the system so described.

Thus, with respect to design 400, in an embodiment, for example, refinery and/or BPP 202 optionally comprise module 204, which may comprise any of the following: HTP 204A, anaerobic digester 204B, a supercritical fluid extraction unit 204C, Cellulosic ethanol/butanol/isobutanol 204D, and/or other processes of biomass and/or biofuel processing known to those of skill in the art 204E. The following modules and/or technologies optionally present may generate carbon dioxide, and/or may release it after performing functions for reuse in the grid: Thermal Plant 222, WWTP 402A, WWTP sludge processing 404, certain types of BGUs comprised by the WWTP/BGM module 402, the refinery and/or BPP 202 (e.g., optional technologies such as cellulosic ethanol/butanol/isobutanol 204D, anaerobic digestion 204B, supercritical fluids extraction 204C and/or other technologies 204E), a gasification module 125, an optional landfill 309, carbon dioxide storage 406, ambient carbon dioxide 414 and/or offsite sources 412. Any or all of these sources may be optionally in fluid communication with carbon dioxide-using modules and/or certain technologies optionally present within modules e.g., in the Plan, comprising: the refinery and/or BPP 202, Desalination unit 214, WWTP/BGM 402, BBPP 206, carbon dioxide storage 406.

WWTP/BGM 402 comprises optionally a WWTP 402A and/or wastewater treatment BGU 402B, and/or a freshwater BGU 402C, and/or a saltwater BGU (optionally comprising brine water) 402D and/or a brackish water BGU 402E. Any flow of carbon dioxide (which may be optionally combined with other gases, particulates, and/or other matter in any process depicted) may be purified and/or otherwise processed at any stage of any process depicted in FIG. 4 as shown in module 408. In an embodiment any portion of the flows of carbon dioxide, after optional purification/processing 408, may be released either back to the grid and/or into the environment 410. Oxygen from photosynthetic embodiments of any BGU may be transferred to a WWTP and/or a non-photosynthetic BGU. Within the WWTP/BGM 402. In an embodiment, carbon dioxide generated by thermal plant 222 and/or any other module(s) may be transferred to any module(s) as needed within grid 400. For example in an embodiment, carbon dioxide may be transferred to on-grid storage facility 406, with or without purification/processing at module 408 and then sent to a carbon dioxide discharge and/or export facility 410. Sludge processing unit 404 may supply carbon dioxide to the grid. BBPP (Water bottling unit) 206 may use the carbon dioxide to prepare pressurized sparkling water for drinking. Photosynthetic and/or mixotrophic BGUs of any water type listed (402B, 402, 402D, and/or 402E), or other water types may use carbon dioxide from any source(s) shown to grow biomass. In an embodiment, where a WWTP 402A may be used concurrently with a BGM 402B, carbon dioxide from the WWTP 402A may be transferred to any one or more BGUs 402B, 402C, 402D, 402E to facilitate biomass growth, and/or oxygen from any one or more BGUs 402B, 402C, 402D, 402E may be transferred to the WWTP 402A to facilitate the bacterial breakdown of waste. Other biomass processes whereby biomass may metabolize or ferment carbon dioxide and/or other gases, such as hydrogen, nitrous oxide, carbon monoxide, and/or other gases, and change them into other chemical structures may be used as a BGU. These systems may also receive carbon dioxide as a BGU.

With reference to FIG. 4, carbon dioxide flows depicted by lines or arrows may be optional and managed. Carbon dioxide optional managed flows (e.g., lines and/or arrows of 300), carbon dioxide storage 406 and generation, collection, transportation, treatment and/or management of carbon dioxide in modules and/or flows of FIG. 4 may be accomplished in any manner herein disclosed and/or known to the person of skill in the art. The "grid" as described in connection with FIG. 4 may not necessarily mean one large interconnected system. It may comprise any combination of individual systems of communication of carbon dioxide between any two or more modules. Thus a grid may comprise any one or more separate, distinct systems to transfer carbon dioxide between a subset of modules depicted in FIG. 4. These systems may combine or partially combine flows of carbon dioxide at any point in any process depicted.

In an embodiment, water, an aqueous solution, steam, air and/or other gases may be used for the capture and/or distribution of heat, pressure and/or other energy from the thermal plant 222 to the biomass growth module 402 and/or other facilities to assist refining, processing and return of biomass and/or biofuels from the BGM 402 as fuel to the thermal plant 222, for the production of other products, and/or for other processes e.g., as described herein.

In reference to FIG. 4 an embodiment of the disclosure includes a system 400 configured to use and reclaim carbon dioxide wherein the carbon dioxide is provided by: a thermal plant module 222; a sludge processing module 404; a traditional WWTP module 402A; a carbon dioxide storage module 406; an ambient carbon dioxide source(s) 414; a purification module 408; a refinery module 202; a BPP module 202; a supercritical fluids extraction module 204C; a gasification module 125; a BGM 402; a cellulosic ethanol/butanol/isobutanol module 204D; a landfill module 309; and/or offsite sources 412. An embodiment includes the system wherein carbon dioxide from: a thermal plant module 222; a sludge processing module 404; a traditional WWTP module 402A; a carbon dioxide storage module 406; an ambient carbon dioxide source(s) 414; a purification module 408; a refinery module 202; a BPP module 202; a supercritical fluids extraction module 204C; a gasification module 125; a BGM 402; a cellulosic ethanol/butanol/isobutanol module 204D; a landfill module 309; and/or offsite source(s) 412 is optionally provided to: a BGM 402; a refinery module 202; a BPP module 202; a purification/processing module 408; a carbon dioxide storage module 406; a BBPP module 206; a desalination module 214; and/or a discharge and/or export module 410. An embodiment includes the system wherein oxygen generated in the BGM 402 is directed to the traditional WWTP module 402A.

In reference to FIG. 4 an embodiment of the disclosure includes a method of using and reclaiming carbon dioxide comprising generating carbon dioxide at a thermal plant module 222; a sludge processing module 404; a traditional WWTP module 402A; a carbon dioxide storage module 406; an ambient carbon dioxide source(s) 414; a purification module 408; a refinery module 202; a BPP module 202; a supercritical fluids extraction module 204C; a gasification module 125; a BGM 402; a cellulosic ethanol/butanol/isobutanol module 204D; a landfill module 309; and/or offsite sources 412, using the carbon dioxide in the generating module, and reclaiming any unused carbon dioxide for further use or discharge, wherein the carbon dioxide is generated or provided by: a thermal plant module 222; a sludge processing module 404; a traditional WWTP module 402A; a carbon dioxide storage module 406; an ambient carbon dioxide source(s) 414; a purification module 408; a refinery module 202; a BPP module 202; a supercritical fluids extraction module 204C; a gasification module 125; a BGM 402; a cellulosic ethanol/butanol/isobutanol module 204D; a landfill module 309; and/or offsite sources 412. An embodiment includes the method wherein carbon dioxide from: a thermal plant module 222; a sludge processing module 404; a traditional WWTP module 402A; a carbon dioxide storage module 406; an ambient carbon dioxide source(s) 414; a purification module 408; a refinery module 202; a BPP module 202; a supercritical fluids extraction module 204C; a gasification module 125; a BGM 402; a cellulosic ethanol/butanol/isobutanol module 204D; a landfill module 309; and/or offsite source(s) 412 is optionally provided to: a BGM 402; a refinery module 202; a BPP module 202; a purification/processing module 408; a carbon dioxide storage module 406; a BBPP module 206; a desalination module 214; and/or a discharge and/or export module 410. An embodiment includes the method comprising directing oxygen generated in the BGM 402 to the traditional WWTP module 402A.

In some embodiments, e.g., those of FIG. 4, the carbon dioxide may be directly or indirectly transferred e.g., piped, to: a biomass growth module, and/or to a biomass growth module, to the biofuel refining/separation plant for use in biomass refining and/or separations techniques, comprising supercritical fluids extraction, and/or sent to the water bottling/biomass packaging plant for use in carbonation of liquids, and/or other uses, and/or stored either as a gas, compressed gas, liquid and/or solid (dry ice), and/or may be marketed offsite.

In one or more embodiments, e.g. FIG. 4 and/or FIG. 2 or other description related to heat generation and/or transfer, the Plan can mitigate a carbon dioxide release (e.g., of a conventional fuel-burning thermal plant) and/or use the CO2 to generate additional power from any source with the BGM. This presents a very attractive synergy with offsite carbon dioxide producers. In an embodiment, e.g., a local (possibly offsite) thermal plant (e.g., a coal-burning power plant or industrial plant) sends exhaust gases (e.g., stack gases), optionally pretreated to the BGM, which may provide power with substantially complete carbon capture (e.g., zero or low carbon emissions), mitigation of other emissions, such as SOx, NOx, particulates, and/or metals, and BGM generation of biofuel from the emissions for additional power and/or for export. In one or more embodiments, examples of additional and/or alternate sources of power generation which may be used as thermal plant technologies in the Plan, as offsite thermal plants, and/or as additional non-thermal power sources comprise plants using coal, petroleum fuels, nuclear, solid fuels (such as petroleum coke, biomass and/or others), wind, solar thermal and/or photovoltaic, geothermal, hydroelectric, micro-hydro generation, combined heat and power, and/or other systems suited to the purpose. These additional systems may be connected to the Plan to provide any combination of the following benefits, and/or other benefits, as identified herein for thermal plants and on a project-by-project basis may comprise: augmentation of power production; carbon dioxide and/or other emissions mitigation of exhaust from these plants in the BGM; provision of cooling water source from the WWTBGU and/or WWTP; capture of heat for use in HTP, desalination, heating the BGM, BGU(s), and/or their components, and/or for other uses of heat onsite as shown in FIG. 2; and/or for reduction of reserve plant margins.

In one or more embodiments, e.g., FIG. 4, carbon dioxide may be released in the cellulosic ethanol/butanol/isobutanol production phase and/or as part of the thermal plant activities combusting the resultant fuels. Thus, carbon dioxide may be captured and/or used in other aspects of the Plan. This and other optional sources and uses of carbon dioxide in the Plan are given in FIG. 4, and discussed herein.

In one or more embodiments, e.g. FIG. 4 and/or other figures and/or description relating to flows of other gases, heat, cooling, water, fuels, and/or materials of any kind, sensors and/or flow controls of any description may be used to control these carbon dioxide flows and/or any other flows in the Plan. These flows may be stored in whole or in part before use as described (e.g., these flows may be stored overnight, and directed to a photosynthetic BGM.

In a non-limiting set of embodiments 500, with respect to FIG. 5, a biomass growth module (BGM) may contain one or more biomass growth units (BGUs). The BGUs may be used separately, or in combination with each other, possibly sharing and/or exchanging resources and/or flows, to form the BGM. For example, in a first embodiment of this aspect, fluid intake 501, single BGU 502 and fluid outflow 503 may be a first combination. In a second embodiment, fluid intake 505 to first BGU 504, outflow/inflow 507, second BGU 506 and outflow 509, in series, may be a second combination. In a third embodiment, a system may comprise n BGU's in parallel, wherein n may be from 2 to 30, or 2 to 10 or 2 to 5. For example fluid intake 511, first BGU 508, and outflow 513 may be in a first series. Parallel to the first series, fluid intake 515, second BGU 510, and outflow 517 may be in a second series. In a fourth embodiment, two parallel BGU's may be connected in fluid communication, e.g., to manage inflows and outflows and/or to provide other benefits to either BGU, such as sharing of certain components, controlled mixing of different water types at certain stages, sharing of certain infrastructure, and/or for other purposes. Such benefits may apply to all BGU configurations where there may be fluid communication. Fluid intake 519, first BGU 512, and outflow 521 form a first series. Fluid intake 523, second BGU 516, and outflow 525 form a second series. Bridging element 514 allows movement of fluid between BGU's 512 and 516. In a fifth embodiment, inflow 527 provides fluid to first BGU 518. Outflow 520 provides fluid to second BGU 522, which also optionally receives fluid inflow 529. Outflow 531 may be the single outflow from both BGU's therefore. In a sixth embodiment, an exemplary networked configuration may be provided. Intake 533 provides fluid to first BGU 524. First BGU provides fluid outflows 535, 535A, and to second and third BGU's 526 and 528 respectively. Third BGU 528 provides fluid outflow 539 to second BGU 526 and fluid outflow 541 to fourth BGU 530. Second and fourth BGU's 526 and 530 exchange fluids via bridging element 527. Second BGU discharges via an outflow 537. Fourth BGU discharges via outflow 543. The configurations depicted may be exemplary of possible configurations of different BGUs within a BGM. A BGM may comprise any configuration and/or networking of BGUs and the inputs and/or outputs of any BGU subunits or other components beneficial to the intended purpose of growing, supporting, separating, and/or preliminarily processing biomass.

In reference to FIG. 5, an embodiment of the disclosure includes a system 500 configured for biomass growth comprising a biomass growth module (BGM) wherein the BGM comprises one or more biomass growth units selected from the following configurations: single 502; dual serial 504, 506; dual parallel 508, 510; dual parallel connected 512, 514, 516; serial simple networked 518, 520, 522; and/or complex networked 524, 526, 528, 530. An embodiment includes the system wherein any one or more of the BGUs is: an autotrophic BGU; a heterotrophic BGU; and/or a mixotrophic BGU. An embodiment includes the system wherein any of the BGUs may share and/or exchange inputs and/or outputs optionally comprising: carbon dioxide; oxygen; water; nutrients; biomass; growth medium; solvent; carbon source; nitrogen or other gases; and/or light source(s) 501, 503, 505, 507, 509, 511, 513, 515, 517, 519, 521, 523, 525, 520, 527, 529, 531, 533, 535, 537, 535A, 539, 527, 541, 543.

In reference to FIG. 5, an embodiment of the disclosure includes a method for growing biomass comprising networking a set of biomass growth units in a biomass growth module (BGM) wherein the set comprises a biomass growth unit which is: a single biomass growth unit 502; a dual serial biomass growth unit 504, 506; a dual parallel biomass growth unit 508, 510; a dual parallel connected biomass growth unit 512, 514, 516; a serial simple networked biomass growth unit 518, 520, 522; and/or a complex networked biomass growth unit 524, 526, 528, 530. An embodiment includes the method wherein any one or more of the BGUs is operating: autotrophically; heterotrophically; and/or mixotrophically. An embodiment includes the method wherein any of the BGUs is sharing and/or exchanging inputs and/or outputs optionally comprising: carbon dioxide; oxygen; water; nutrients; biomass; growth medium; solvent; carbon source; nitrogen or other gases; and/or light source(s) 501, 503, 505, 507, 509, 511, 513, 515, 517, 519, 521, 523, 525, 520, 527, 529, 531, 533, 535, 537, 535A, 539, 527, 541, 543.

In one or more embodiments, e.g., FIG. 5, a biomass growth module may comprise several biomass growth units in any configuration, comprising any number of the same and/or different BGUs used and/or connected in parallel with fully separate components, any number of BGUs used and/or connected in series, any number of BGUs connected at any stage of their processes, and/or BGUs sharing different components and/or equipment, such as a nutrient source, stressing unit, filtration unit, milking unit, holding tank, piping, heat transfer equipment, carbon dioxide source, extraction unit, and/or any other component, resource, and/or byproduct of the Plan, such as carbon dioxide, heat, water, oxygen, growth medium, carbon source, solvent, and/or other light organic material, (e.g., volatile organic compounds, such as a C1-C10 hydrocarbon, alcohol, ether, ester, acid and the like, wherein the volatile compound is combustible), and/or biomass. (See some example configurations in FIG. 5).

In one or more embodiments, e.g., FIGS. 5 and/or 6, different BGUs comprised by the BGM operate autotrophically, heterotrophically, and/or mixotrophically during the same time of day (e.g., an autotrophic BGU exposed to the sun and a heterotrophic BGU in a closed reactor), and/or at different times of the day, and/or may exchange carbon dioxide and/or oxygen and/or other resources in regulated flows.

In one or more embodiments, e.g., FIG. 6, BGUs comprised by the BGM which may be used in one or more embodiments comprise open ponds, closed ponds, channels, high rate ponds, waste stabilization ponds, other ponds of any description and/or other water bodies and/or portions thereof, whether covered and/or open to the environment, and other open and/or closed systems of any kind adapted for biomass growth. BGUs may comprise nutrient streams, water streams, external and/or internal lighting, water jets, paddle wheels and/or other liquid movement and/or agitation technologies, gas delivery technologies for the delivery of CO2 and/or other gases, and/or any of the wide variety of technologies employed to enhance biomass growth and/or processing.

In one or more embodiments related to biomass growth methods and systems and/or plans therefor, e.g., FIG. 6, the biomass growth module, certain BGUs comprising it, and/or certain components comprising a BGU may be installed in contact with the ground, partially and/or fully underground, in contact with water, or partially or fully submerged in water as is most beneficial to the location with consideration of temperature stability and/or optimization. For example, in Artic/Antarctic cold climates, the biomass growth module or any of its components may be preferably fully or partially underground, and/or in a container (e.g., a bioreactor) filled with water, air and/or other fluid. Either the ground, the water, the surrounding air, and/or any other material in contact with, and/or flowing into the BGU (e.g., source water) may be heated by the thermal plant (e.g., using waste heat and/or primary process heat as described herein) to maintain a beneficial temperature for biomass growth. In an embodiment, discharges from the BGM, piping, and/or other components in the Plan, likewise may be installed partially or wholly underground. The ground which contacts the BGM, BGM component(s) and/or other components in the Plan may be heated and/or cooled using heat and/or cogenerated cooling from the thermal plant and/or heat from other sources in the Plan and/or other sources (e.g., geothermal heat, if locally available, and/or other sources). In an embodiment, the BGM and/or any of its components may be designed to float on the top of water, where the water helps to regulate the temperature, and/or the movement of water in contact with the BGM component (e.g., waves or currents) may be utilized in mixing the biomass and/or other elements contained in the BGM. In an embodiment, if the BGM is in contact with or partially or fully submerged in water, a water tank, pool, and/or other water structure may be used to contain the water, heat and/or cooling generated by the thermal plant, its output and/or other heat source(s) in the Plan (e.g. FIG. 2) may be used to regulate the temperature in the water structure in order to maintain optimal temperature in the biomass growth module or any of its component(s). In an embodiment, the biomass growth module may alternatively or additionally comprise devices and/or structures to contain and/or control the flow of air around the biomass growth module or any of its components and to the heat and/or cool the air in order to regulate the biomass growth module or its components' temperature using air, other gas, and/or vapor. Heated air, other gas and/or vapor and/or cogenerated cooling air may be generated from the thermal plant and/or other sources in the Plan, and/or other sources may be used for this purpose (e.g., waste heat and/or cooling in air may be directed to a greenhouse and/or other structure containing the BGM). In an embodiment, heat exchangers, repositioning, restructuring, covers, evaporative techniques and/or any other means and/or structure suitable to transferring heat to and/or from the biomass growth module or any of its components, conserving heat and/or releasing or otherwise mitigating excess heat may be used to regulate the BGM or any of its components' temperature, preferably using electricity, heat and/or cooling generated by the thermal plant and/or other sources in the Plan where feasible in the implementation and/or operation of these techniques.

In one or more embodiments, e.g., FIG. 6, a WWTBGU may be used alongside a WWTP, whereby it may be used to mitigate the CO2 from the WWTP, and/or provide O2 to the WWTP to achieve near zero carbon dioxide release in wastewater treatment.

Figure 25:
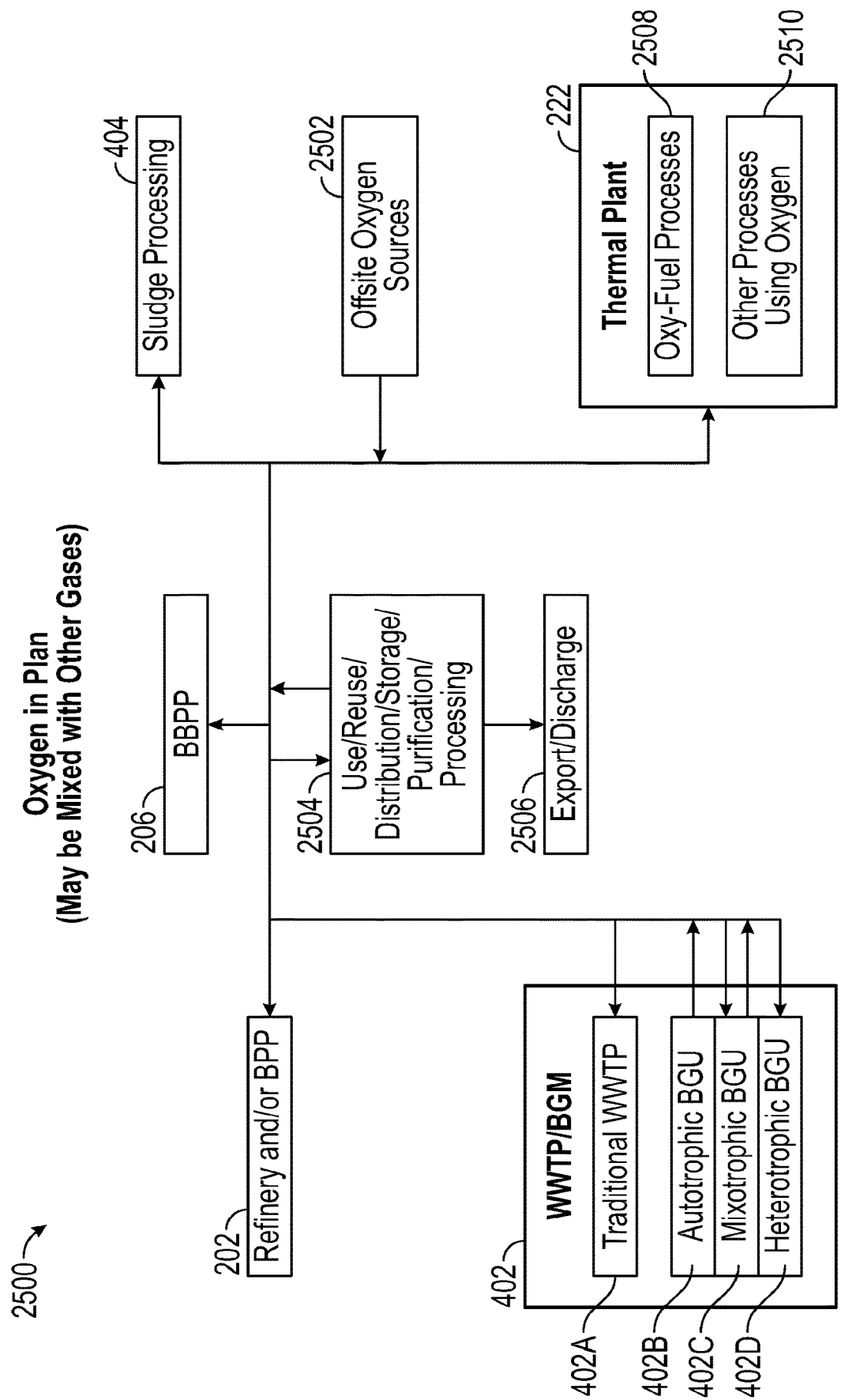
FIG. 25 is a schematic representation of oxygen flow within the Plan according to the present disclosure.

The oxygen generated by a WWTBGU and/or other BGU may also be captured, exported and marketed, injected into thermal plant combustion processes for reduction of NOx emissions and/or for other uses as in FIG. 25.

With reference to FIG. 6, unlike past technologies which rely on one very particular biomass cultivation system, such as an array of tubes or a strictly photosynthetic algae pond system, or separating the biomass with only one method, such as screening of algae, or processing of biomass with only one method, such as chemical extraction of oils, or other particular approaches to the growth and/or processing of biomass, the present disclosure embodies a wide array of different technologies, options and/or configurations in order to enable a flexible biomass growth and/or processing platform capable of adapting from one site to another based on any given constraints of a particular site.

In an embodiment, e.g. FIG. 6, oxygen from daylight photosynthesis in the BGM is stored and directed back into the BGM at night for a heterotrophic and/or mixotrophic growth process(es). Likewise carbon dioxide generated in heterotrophic growth processes may be stored at night, and directed back to the BGM during the day for autotrophic biomass growth process(es).

In an embodiment, e.g., FIG. 6, in an embodiment, a supplemental nutrient supply line(s) 620 may optionally deliver a controlled amount of nutrients (such as nitrogen or phosphorus) from nutrient supply controlled by a motive device such as a variable speed pump, which receives an input signal from a water and/or biomass measurement and/or other parameter measurement device such that a control signal is sent to the motive device to regulate the inflow of nutrients into the BGM or any component thereof. The measurement device may be set to measure water content of essential nutrients in the system, biomass density, pH, temperature and/or any number of other factors. All systems in the Plan may have sensors and/or automated and/or manual valves and/or other flow rate controls to dispense materials, apply heat and/or cooling, add or reduce carbon dioxide and/or other gases, add or reduce additional water of any type, and/or to meet any other needs of all systems in the BGM.

In one or more embodiments, e.g., FIG. 6, the biomass growth module may comprise adequate structures, and/or control modules, hardware and/or software, such as valves to inject or release gases, liquids, and/or solids as necessary to maintain optimal biomass growth. Sensors may be used to detect any condition in the BGM and/or any of its components, atmosphere, and/or surrounding systems, to send a signal to a control system, which may then trigger an automatic response to make an adjustment to BGM and/or the supporting systems. For example, a sensor may monitor BGM component temperature, and trigger an automated response to release additional heated water into a pool, heating a BGM component to optimize its temperature. This automated system may be controlled by computer. The computer software may employ intelligent adaptive controls.

In one or more embodiments, e.g., FIG. 6, Oxygen and/or other gases released from a BGU may be collected and/or stored and/or rerouted for use in heterotrophic biomass growth processes, in other processes beneficial to the Plan, and/or may be marketed. In an embodiment, oxygen collected from a BGU may be injected in whole and/or in part into thermal plant combustion processes to reduce NOx emissions.

In an embodiment, e.g., FIG. 6 the BGM may comprise not only one technology design, but possibly an array of different BGUs which use an array of bioreactors, tanks, ponds, with any necessary supporting subunits as in FIG. 6, other designs suited to the purpose and/or any combination of technologies designed to grow and/or process biomass.

In one or more embodiments, e.g., FIG. 6 or other figures and/or description regarding BGUs, either a conventional bacteria-based wastewater treatment plant (WWTP), and/or one or more WWTBGUs, may be located proximate to where wastewater treatment is implemented in any embodiment. In this sense, the WWTP, and/or the WWTBGU a locus of wastewater treatment are collocated. These systems may also be operably connected to share infrastructure in common, and/or may exchange gases (e.g., a photosynthetic WWTBGU may supply oxygen to a WWTP, and/or a WWTP may supply CO2 to a photosynthetic WWTBGU, as described herein, e.g., FIGS. 4 and 25). One of these WWTPs or BGUs may be built first, followed later by the other, wherein the original system may continue to operate, or may be later partially or fully converted to the other system type for treating wastewater (e.g., a WWTP may be built first, and a WWTBGU may be added later to operate concurrently or to replace a WWTP in whole or in part). Consequently, the Plan may have either system, or both. Synergies exist between the two systems when collocated, and also in the case where a WWTP exists first, and it is then converted to a WWTBGU, as described below.

In an embodiment, e.g., FIG. 6 and/or any figure or description relevant to a WWTBGU, a WWTBGU may effectively perform minimally what is commonly referred to in the wastewater treatment industry as "secondary treatment" of wastewater to a degree that is superior to that of a traditional WWTP. Primary and possibly tertiary treatment may be needed to complete the process to typical municipal wastewater treatment standards. If a standard WWTP is in operation, and is later adapted into a WWTBGU as understood by a person of ordinary skill in the art, and/or in accordance with description and/or embodiments in this disclosure, or if operating alongside the WWTBGU, the primary and/or tertiary treatment infrastructure initially developed for the WWTP may also be adapted for use in the WWTBGU or shared with the WWTBGU, and/or if a WWTP is adapted to a WWTBGU, possibly parts or all of the secondary treatment infrastructure may be adapted for use in the WWTBGU. If only a WWTBGU is built, and some aspects of primary and/or tertiary treatment are not needed, those steps may be eliminated, reducing infrastructure and/or operation and maintenance costs.

Biomass Growth Units Combined to Meet Different Project Goals: In one or more embodiments, e.g., FIGS. 1, 4, 5, 6, 11, and/or other figures and/or description relevant to integration of Plan components with BGUs, all BGUs described herein may be implemented in different combinations, in multiples, in connection and/or communication (e.g., FIG. 5, connected systems depicted), and/or different orders of priority to achieve particular project goals. For example, in order to mitigate all carbon dioxide and to treat all wastewater available to the Plan, in an embodiment, a WWTBGU may be built first to treat all of the wastewater available, and a SWBGU may be designed and implemented to mitigate any remaining CO2 in the event a WWTBGU's use of CO2 is maximized given the wastewater supply, and additional CO2 from the thermal plant still remains to be used. In this embodiment, the SWBGU may be scaled according to the remaining CO2 supply to achieve zero net carbon dioxide production onsite. Any other BGU type(s) may also be used instead of the WWTBGU or SWBGU in this example if considered more advantageous. For example, a FWBGU may be used instead of a WWTBGU where wastewater treatment is not feasible or desirable as a component of a particular project.

In one or more embodiments, e.g., FIGS. 2, 3, 6, 7A, 7B, 11, 12A, 12B, 12C, 12D, 12E, 15A, 15B, 16, 17, 18, 19, 20A, 20B, 20C, 20D and/or other figures and/or description relevant to heat capture, and/or transfer, a BGM and/or its components, and/or water transfer, a BGM, a BGU, a BGU subunit and/or any other BGU component may be fully or partially immersed in a pool, other container, water body and/or stream fed by a water supply used to capture waste heat from a thermal plant, wherein the BGM temperature is regulated by contact with heated water supply.

In an embodiment, e.g. FIG. 6, carbon dioxide generated in heterotrophic growth processes may be stored at night, and directed back to the BGM during the day for autotrophic biomass growth process(es). In an embodiment, e.g. FIG. 6, and/or other figures and/or description relating to transfer of gases, any gases that may be generated in any process or stage likewise may be stored and reused at any other process/stage of biomass growth as is beneficial (See FIG. 6) and/or elsewhere in the Plan. In an embodiment, e.g., FIG. 6, a biomass growth module and/or BGUs it comprises may operate heterotrophically exclusively, and an organic (biologically based) carbon and an oxygen stream may be added to facilitate growth. In one or more embodiments, e.g., FIGS. 5 and/or 6, different BGUs comprised by the BGM operate autotrophically, heterotrophically, and/or mixotrophically during the same time of day (e.g., an autotrophic BGU exposed to the sun and a heterotrophic BGU in a closed reactor), and/or at different times of the day, and may exchange carbon dioxide and/or oxygen and/or other resources in regulated flows.

With reference to FIG. 6, in an embodiment 600, a biomass growth module comprises a BGU with a growing subunit which optionally receives the exhaust gases, and/or the treated exhaust gases and/or liquids from a pollution entrainment module of an exhaust gas recovery module (e.g., FIG. 7, 707, 709, 713, 724, 726, 718) and/or other treatment technolog(ies) 636, wherein they may be combined with a water source 630, optional nutrient stream and/or other elements to promote growth 634 and/or 636 for the particular biomass species being cultivated. A biomass "seed" source, may be added to start and/or support or enable biomass growth. In photosynthetic or mixotrophic embodiments, carbon dioxide and/or other gases, e.g., harmful gases, may be used to produce biomass, and oxygen may be released. The oxygen may be stored and/or transferred; the oxygen may be used in other processes e.g., in the Plan; and/or marketed e.g., FIG. 25. In non-photosynthetic or mixed embodiments (e.g., heterotrophic and mixotrophic), oxygen may be used, and carbon dioxide may be released. The carbon dioxide from these processes may be captured and/or marketed, and/or used as otherwise indicated e.g., in the Plan (See FIG. 4).

With reference to FIG. 6, unlike past technologies which rely on one very particular biomass cultivation system, such as an array of tubes, or a strictly photosynthetic algae pond system, or separating the biomass with only one method, such as screening of algae, or processing of biomass with only one method, such as chemical extraction of oils, or other particular approaches to the growth and/or processing of biomass, the present disclosure embodies a wide array of different technologies, options and/or configurations in order to enable a flexible biomass growth and/or processing platform capable of adapting from one site to another based on any given constraints of a particular site.

With reference to FIG. 6, the growing subunit 602 combined with any subset of the submodules within FIG. 6 may form a viable BGU design which may replace in whole or in part the BGM's of FIG. 2, FIG. 3, FIG. 4, and/or FIG. 5, e.g., BGM 110, and/or 212 and/or WWTP/BGM 402.

The biomass growth unit(s) within a biomass growth module may comprise a "growing subunit" 602 which may use one or more bioreactor(s), pond(s), and/or any other system known to those of skill in the art designed for growth of biomass. For example, one or more flat panel photobioreactors may be employed. $CO_2$ 632 may be used in certain growing subunits from the exhaust of the thermal plant 222, either by use of the thermal plant exhaust gases directly, and/or after passing through a pollution entrainment module e.g., FIGS. 7A and 7B, and/or other processing technology adapted for the purpose. Liquids carrying entrained pollutants from an exhaust gas stream may be also provided to the growing subunit, for example those entrained using a pollution control module 705 or pollution entrainment module e.g., FIGS. 7A and 7B, 713, 726 and/or other technologies suited to the purpose. A medium, for example fresh medium 604A, in FIG. 6 may be a liquid designed to support the growth and reproduction of biomass. After use by the biomass, the excess and/or old medium 624 can be optionally filtered (e.g., by a cross-flow filtration and/or other filtration methods know to those of skill in the art) 606 and/or optionally stored 604 for later use. The optional nutrient storage subunit 604 stores fresh medium 604A and may be configured to automatically analyze and recharge old medium 624 and/or 622 to provide a medium suitable for biomass growth. The optional cross-flow filtration subunit 606 takes excess and/or old medium 624 and filters out impurities to provide a medium suitable for biomass growth. The optional nighttime holding subunit 616 functions as a storage vessel for biomass culture during the night. The optional stressing subunit 612 takes biomass and subjects it to stressing (for example high intensity light, blue light, temperature fluctuations, nitrogen starvation/depletion, salt content and/or other methods known to those of skill in the art) in order to produce a desired product. The optional stressing and milking subunit 608 takes biomass and subjects it to stressing in addition to milking which uses solvents 642 and/or other means known to those in the art to continually extract desired products from the biomass usually without destruction of the cells. Separation technologies, such as vapor compression steam stripping 614 (see FIG. 21) may be used to separate and purify biofuel 615 which some biomass excrete while growing.

In an embodiment showing some possible process paths for many different growth methods, growing subunit 602 grows biomass selected from among autotrophic, heterotrophic, and/or mixotrophic biomass varieties. The growing subunit optionally receives fresh medium 604A from nutrient storage subunit 604. Nutrient storage subunit 604 receives inputs of fresh nutrients 620 and water from any source 630 (e.g., see FIG. 3). After processing, excess and/or old medium 624 may be optionally returned to a cross-flow filtration subunit 606 and filtered old medium 622 may be returned to nutrient storage subunit 604. Growing subunit 602 may also receive inputs of daytime biomass culture 628 from optional nighttime holding subunit 616, biomass and water from optional stressing subunit 612, biomass and water 625 from optional stressing and milking subunit 608, water from any source 630 (e.g., see FIG. 3), carbon dioxide ($CO_2$), oxygen, and/or other feed gases 632, flexible carbon source 636 (e.g., glucose, acetic acid, glycerol, and/or other sources), and/or nitrogen source 634 (e.g., a nitrate ion feed). Growing subunit 602 may receive inputs and/or supply outputs of gases 631A for storage/use/reuse and/or gases generated in the growing subunit may be marketed 631B. Optional nighttime holding subunit 616 receives inputs of nighttime biomass culture 626 from growing subunit 602, nighttime biomass culture 640 from optional stressing and milking subunit 608 and fresh medium 604A from optional nutrient storage subunit 604.

Optional Stressing subunit 612 receives inputs of biomass and water 603 from growing subunit 602 and biomass and water 646 from optional stressing and milking subunit 608. The resulting stressed biomass and water 648 may be transferred to BPP and/or refinery 610 (for downstream processing). Optional stressing and milking subunit 608 receives optional inputs of biomass and water 625 from growing subunit 602, biomass and water 646 from optional stressing subunit 612 and/or daytime biomass culture 638 from optional nighttime holding subunit 616 for processing and extraction with solvents for milking 642. Stressing in subunits 608 or 612 may include high intensity light, blue light, temperature fluctuations, nitrogen starvation/depletion, salt content, and/or other methods know to the person of skill in the art. Solvent containing extracted biomass 644 from the stressing and milking subunit 608 may be transferred to BPP and/or refinery 610 (for downstream processing) to obtain useful products such as astaxanthin, arachidonic acid, beta-carotene and/or other products. Vapor compression steam stripping and/or other separation technologies 614 (e.g., FIG. 21), receives biofuel (e.g., ethanol and/or butanol) from growing subunit 602. The resulting purified biofuel may be transferred to BPP and/or refinery 610 (for downstream processing). Biomass and water from growing subunit 602 may be directly transferred to BPP and/or refinery 610 (for downstream processing) optionally after being treated by any means herein disclosed and/or known to the person of skill in the art, comprising optionally any or all of the processing steps shown for the BGM outflow fluid 117 downstream from the BGM 110 in FIG. 1, 100 to obtain fuels and/or useful products from biomass (e.g., algae) such as *chlorella* and *spirulina*.

In an embodiment, any module or subunit within the BGU may receive any of the following inputs delivered to the module or subunit by any means herein disclosed and/or in any manner known to the person of skill in the art: heat and/or cooling, water, carbon dioxide, exhaust gases, oxygen, light (natural and/or artificial, full spectrum and/or selected wavelengths), and/or other inputs as necessary to support biomass growth and processing.

FIG. 6 and the foregoing description demonstrate many optional process paths for growth and/or processing of biomass. In practice, likely only a subset of the inputs and/or modules in FIG. 6 may be used in any BGU, depending on the type of Growing Subunit used, the type of biomass used, and the product type or types being developed in the BGU.

In an embodiment, an Autotrophic Growing Subunit may grow biomass (e.g., algae) autotrophically utilizing light and carbon dioxide. The growing subunit 602 will start with an initial biomass culture of the autotrophic variety, and may receive inputs of light, carbon dioxide 632, water from any source 630, fresh medium 604A, an optional nitrogen source 634 and biomass and water 603, 625, 628 from optional stressing subunit 612, optional stressing and milking subunit 608, and/or optional nighttime holding subunit 616. The outputs of an autotrophic growing subunit may comprise 1) oxygen which may be routed for storage/use/reuse and/or marketing, 2) biofuel which may be purified through separation technologies 614 and transferred to BPP and/or refinery 610 for downstream processing, 3) biomass and water which may be directly transferred to BPP and/or refinery 610 for downstream processing, 4) biomass and water 603 which may be transferred to the optional stressing subunit 612 which may also receive biomass and water 646 from optional stressing and milking subunit 608 and the resulting biomass and water 648 may be transferred to BPP and/or refinery 610 for downstream processing, 5) biomass and water 625 which may be transferred to optional stressing and milking subunit 608 which may also receive biomass and water 646 from optional stressing subunit 612. At night the nighttime biomass culture 640 may be transferred to the optional nighttime holding subunit 616 and during the day the daytime biomass culture 638 may be transferred back to the stressing and milking subunit 608. Solvents for milking 642 may be added to the stressing and milking subunit 608 and the resulting solvent containing extracted biomass 644 may be transferred to BPP and/or refinery 610 for downstream processing.

In an embodiment, a Heterotrophic Growing Subunit will grow biomass (e.g., algae) heterotrophically in the dark utilizing typically organic carbon and oxygen. The growing subunit 602 may receive inputs of oxygen 632, a flexible carbon source 636 (such as glucose, acetic acid, glycerol and/or other sources) water from any source 630, fresh medium 604A, and/or biomass and water 603, 625, 628 from optional stressing subunit 612, optional stressing and milking subunit 608 and/or optional nighttime holding subunit 616. The outputs of a heterotrophic growing subunit may comprise 1) carbon dioxide which may be routed for storage/use/reuse/marketing, 2) biofuel which may be purified through separation technologies 614 and transferred to BPP and/or refinery 610 for downstream processing, 3) biomass and water which may be directly transferred to BPP and/or refinery 610 for downstream processing, 4) biomass and water 603 which may be transferred to the optional stressing subunit 612 which may also receive biomass and water 646 from optional stressing and milking subunit 608 and the resulting biomass and water 648 may be transferred to BPP and/or refinery 610 for downstream processing, 5) biomass and water 625 which may be transferred to the optional stressing and milking subunit 608 which may also receive biomass and water 646 from optional stressing subunit 612. At night the nighttime biomass culture 640 may be transferred to the optional nighttime holding subunit 616 and during the day the daytime biomass culture 638 may be transferred back to the stressing and milking subunit 608. Solvents for milking 642 may be added to the stressing and milking subunit 608 and the resulting solvent containing extracted biomass 644 may be transferred to BPP and/or refinery 610 for downstream processing.

In an embodiment, a Mixotrophic Growing Subunit may grow algae mixotrophically utilizing organic carbon, oxygen, light and carbon dioxide simultaneously. The growing subunit 602 may receive inputs of oxygen 632, carbon dioxide 632, flexible carbon source 636 (such as glucose, acetic acid, glycerol and/or other carbon sources) water from any source 630, fresh medium 604A, a nitrogen source 634 and biomass and water 603, 625, 628 from optional stressing subunit 612, optional stressing and milking subunit 608 and/or optional nighttime holding subunit 616. The outputs of a mixotrophic growing subunit may comprise 1) carbon dioxide and oxygen which may be routed for storage/use/reuse/marketing, 2) biofuel which may be purified through separation technologies 614 and transferred to BPP and/or refinery 610 for downstream processing, 3) biomass and water which may be directly transferred to BPP and/or refinery 610 for downstream processing, 4) biomass and water 603 which may be transferred to the optional stressing subunit 612 which may also receive biomass and water 646 from optional stressing and milking subunit 608 and the resulting biomass and water 648 may be transferred to BPP and/or refinery 610 for downstream processing, 5) biomass and water 625 which may be transferred to the optional stressing and milking subunit 608 which may also receive biomass and water 646 from optional stressing subunit 612. At night the nighttime biomass culture 640 may be transferred to the optional nighttime holding subunit 616 and during the day the daytime biomass culture 638 may be transferred back to the stressing and milking subunit 608. Solvents for milking 642 may be added to the stressing and milking subunit 608 and the resulting solvent containing extracted biomass 644 may be transferred to BPP and/or refinery 610 for downstream processing.

In reference to FIG. 6 an embodiment of the disclosure includes a system 600 configured to grow and process biomass comprising a biomass growing subunit 602 selected from: an autotrophic growing subunit 602; a heterotrophic subunit 602; and/or a mixotrophic subunit 602. An embodiment includes the system wherein the growing subunit 602 is configured to receive inputs selected from: water from any source 630 selected from: salt water 630; fresh water 630; high salinity salt water 630; wastewater 630; and/or mixtures of the afore mentioned 630; carbon dioxide 632; oxygen in any form 632; other gases, for example, NOx and/or SOx 632; a nitrogen source 634; a carbon source 636 selected from: glucose 636; acetic acid 636; glycerol 636; sugarcane 636; corn stover 636; miscanthus 636; switchgrass 636; forest residue 636; waste streams 636; and/or sugars 636; biomass and water 603, 625; fresh medium 604A; and/or a daytime biomass culture 628. A daytime biomass culture is defined as a biomass culture grown during the daytime. An embodiment includes the system wherein the growing subunit 602 is configured to optionally discharge: biomass and water 603; a biofuel 605; gases 631A; a nighttime biomass culture 626; and/or an excess and/or old medium 624. A nighttime biomass culture is defined as a biomass culture grown during the nighttime. An embodiment includes the system wherein the fresh medium 604A is supplied to the growing subunit 602 by an optional nutrient storage subunit 604. An embodiment includes the system wherein the nutrient storage subunit 604 is configured to receive optional inputs selected from: fresh nutrients 620; feed water 630; and/or filtered old medium 622. An embodiment includes the system wherein the daytime biomass culture 628 is supplied by an optional nighttime holding subunit(s) 616. An embodiment includes the system wherein the nighttime holding subunit(s) 616 is optionally configured to receive inputs selected from: fresh medium 635; and/or a nighttime biomass culture 626, 640 from one or more different inputs. An embodiment includes the system wherein the nutrient storage subunit 604 is configured to provide a fresh medium 635 to the nighttime holding subunit(s) 616. An embodiment includes the system wherein a nighttime biomass culture 626, 640 is provided to the nighttime holding subunit(s) 616 by: the growing subunit 602; and/or a stressing and milking subunit(s) 608. An embodiment includes the system wherein the growing subunit 602 is configured to provide and optionally receive biomass and water 603, 625 to and/or from: a BPP module 610; a refinery module 610; a stressing subunit(s) 612; and/or the stressing and milking subunit(s) 608. An embodiment includes the system wherein the stressing subunit(s) 612 is optionally configured to provide and receive biomass and water 646 to and/or from the stressing and milking subunit(s) 608. An embodiment includes the system wherein the stressing subunit(s) 612 is configured to provide biomass and water 648 to the BPP module 610 and/or the refinery module 610. An embodiment includes the system wherein the stressing and milking subunit(s) 608 is configured to receive a daytime biomass culture 638 from an optional nighttime holding subunit(s) 616. An embodiment includes the system wherein the stressing and milking subunit(s) 608 is optionally configured to provide biomass and water 625 to the growing subunit 602. An embodiment includes the system wherein the stressing and milking subunit(s) 608 is configured to receive an input of solvent(s) 642 for milking biomass. An embodiment includes the system wherein the stressing and milking subunit(s) 608 is configured to supply solvent containing extracted biomass 644 to the BPP module 610 and/or the refinery module 610. An embodiment includes the system wherein any portion of the biofuel 605 is supplied to a vapor compression steam stripping and/or other separation technologies subunit 614, for example, FIG. 21. An embodiment includes the system wherein the vapor compression steam stripping and/or other separation technologies subunit 614 is configured to supply a purified biofuel 615 stream to the BPP module 610 and/or the refinery module 610. An embodiment includes the system wherein the growing subunit 602 is configured to supply gases 631A to a subunit for storage/use/reuse/marketing 631B, wherein the gases 631A are optionally: stored; reused in the growing subunit; reused in a different growing subunit; reused for other purposes in the Plan; and/or marketed. An embodiment includes the system wherein the excess and/or old medium 624 is provided to an optional cross-flow filtration subunit 606. An embodiment includes the system wherein filtered old medium 622 from the cross-flow filtration subunit 606 is provided to the nutrient storage subunit 604. An embodiment includes the system wherein any subunit is configured to receive a stream of resources optionally selected from: heat and/or cooling optionally from the Plan, for example, FIG. 2; water from any source optionally from the Plan, for example, FIG. 3; carbon dioxide optionally from the Plan, for example, FIG. 4; exhaust gases optionally from the Plan; oxygen optionally from the Plan, for example, FIG. 25; other gases, for example, NOx and/or SOx; and/or lighting —natural and/or artificial, full spectrum and/or selected wavelengths. An embodiment includes the system wherein the stressing subunit(s) 612 and/or the stressing and milking subunit(s) 608 are configured to receive inputs optionally selected from: high intensity light; blue light; temperature fluctuations; nitrogen starvation/depletion; salt content; and/or other methods known to a person of ordinary skill in the art.

In reference to FIG. 6 an embodiment of the disclosure includes a method of producing biomass comprising growing a biomass in a system 600.

In an embodiment, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, heat and/or cogenerated cooling from thermal plant combustion exhaust can be delivered via one or more conveyance(s) and employed to heat and/or cool a BGM, individual BGU(s), and/or individual BGU subunits, or components maintaining an optimal biological growth and/or reproduction rate in a biomass growth module. As biomass growth may be typically temperature-dependent, during colder seasons, and/or with daily temperature changes, and/or other temperature fluctuations, such heat, e.g., waste heat, assists biological growth in many cases; and/or may be used in other processes, comprising heating water for any process or purpose e.g., in the Plan (See FIG. 2). Waste heat may also be converted to cooling (e.g., via cogeneration) in order to regulate BGM, individual BGU, and/or BGU component temperatures to prevent overheating, in refining/processing biomass, such as the condensing of recycled solvents, to cool/refrigerate biomass products, and/or for any other use e.g., in the Plan.

With respect to FIG. 7A, in certain embodiments of an exhaust gas recovery module 700, the thermal plant 222 feeds exhaust (or stack gases) 706 into a conveyance 702 discharging 703 the products of combustion. A gas diversion 704 may be taken off the conveyance 702. Optional valves, e.g., a control valve 708, control the flow of gases either through the stack/conveyance 702 and/or the diversion 704. Gases 706 not routed to the diversion 704 may be optionally treated with standard pollution control technologies and/or heat recovery technologies 705 known to those of ordinary skill in the art. Gases passed through diversion 704 may be routed through an optional exhaust gas recovery module 707, wherein they may be passed through an optional heat recovery unit 710 and then through an optional pollution entrainment module 713, e.g., another embodiment of a pollution control module 705, which may use any technolog(ies) known to those of skill in the art (e.g., for treating exhaust gases), but which may focus more on technologies known to entrain pollutants for use in a BGM 714, such as a wet scrubber. Any water and/or other fluid source 712 may provide fluid as needed to heat recovery unit 710, making use of technologies such as a heat exchanger 710 and to a pollution control/heat recovery unit 705, and pollution entrainment module 713. Pollution control/heat recovery 705, optional pollution entrainment module 713, and heat recovery module 710 all may supply heat and/or nutrients and/or water and/or other fluids and/or pollutants 720, 730, 731 to a BGM, to be stored and/or routed for other heat and/or water and/or other fluid use e.g., in the Plan 714. Motive Devices 716, 722 and 724 facilitate movement of gases through this exhaust gas recovery module 707. Exhaust gases from this process may be directed to the BGM 714 to provide carbon dioxide and/or other gases, for other carbon dioxide use e.g., in the Plan (FIG. 4) and/or to any use for heat e.g., in the Plan (FIG. 2) and/or to storage and/or for discharge 729. The diversion 704 may carry anywhere from zero to 100 percent of the exhaust effluents. In an embodiment, the diversion 704 may carry any selected portion of effluents, e.g., $CO_2$, that may be routed directly to the biomass growth module 714 and/or treated using other apparatus and/or methods that may be suited to purpose of preparation of the exhaust or stack gas effluent 706 for biomass production, and/or optionally treated and routed for other uses of carbon dioxide and/or heat e.g., in the Plan and/or for storage and/or discharge 700. The pollution control measures used to treat any exhaust or stack gases before release into the environment may comprise technologies such as a wet or dry scrubber, a lime slurry spray drier to remove sulfur and/or chlorine compounds, and/or a baghouse to remove particulates. Activated carbon may be injected into the baghouse to remove mercury and/or dioxins. Other technologies and/or methods known to those of ordinary skill in the art may be used to treat exhaust gases prior to discharge. Heat recovery may be performed at any stage before discharge into the environment by standard technologies, such as heat exchangers, and the heat and any water, or other fluids, and/or pollutants may be provided to the BGM and/or to the Plan 730.

In an alternative embodiment, heat recovery may occur in a process step after the use of a pollution entrainment module, e.g., FIG. 7B. Aside from the change in sequence of the pollution entrainment module and heat recovery unit, the rest of the design remains substantially the same as FIG. 7A. With respect to FIG. 7B, in certain embodiments of an exhaust gas recovery module 700A, the thermal plant 222 feeds exhaust into an optional conveyance 702 discharging the products of combustion. A diversion of gases 704 may be taken off the conveyance 702. Optional valves, e.g., a control valve 708, control the flow of gases either through the conveyance 702 and/or the diversion 704. Gases 706 not routed to the diversion 704 may be optionally treated with standard pollution control technologies and/or heat recovery technologies 705 known to those of ordinary skill in the art. Gases passed through diversion 704 may be routed through an optional exhaust gas recovery module 709 wherein they may be passed through optional pollution entrainment module 726, e.g., another embodiment of a pollution control module 705, which may use any technologies known to the art, but which may focus more on technologies known to entrain pollutants for use in a BGM, such as a wet scrubber, and then to a heat recovery unit 710. Any water and/or other fluid source 712 may provide fluid as needed to heat recovery unit 710, making use of technologies such as a heat exchanger 710 and to a pollution control/heat recovery unit 705, and pollution entrainment module 726. Pollution control/heat recovery 705, optional pollution entrainment module 726, and heat recovery module 710 all supply heat and/or nutrients and/or water and/or other fluids and/or pollutants 728 o a BGM, to be stored and/or routed for other heat and/or water and/or other fluid use e.g., in the Plan 714. Optional motive devices 716, 722 and 724 facilitate movement of gases through this exhaust gas recovery module 700. Exhaust gases 706 from this process may be directed to the BGM to provide carbon dioxide and/or other gases, for other carbon dioxide use e.g., in the Plan (FIG. 4) and/or to any use for heat e.g., in the Plan (FIG. 2) and/or to storage and/or discharged 718. The diversion 704 may carry anywhere from zero to 100 percent of the exhaust or stack effluents.

Reversing the pollution entrainment module 726 and heat recovery module 710 in FIG. 7A and FIG. 7B in some embodiments may provide beneficial uses of the high heat content in the exhaust gas using the pollution entrainment module 726 before it may be directed to heat recovery 710. In addition to constraining contaminants as described above, the pollution entrainment module 726, when used, may also act as a heat exchanger to a degree, and additional heat recovery may occur with the other optional heat recovery technologies such as heat exchangers.

In an embodiment, the pollution control measures 705 used to treat any exhaust gases before release into the environment may comprise technologies such as a wet and/or dry scrubber, a lime slurry spray drier to remove sulfur and/or chlorine compounds, and/or a baghouse to remove particulates. Activated carbon may be injected into the baghouse to remove mercury and/or dioxins. Other technologies known to those of ordinary skill in the art may be used to treat exhaust gases prior to discharge. Heat recovery may be performed optionally at any stage before discharge into the environment by standard technologies, such as heat exchangers, and the heat and any water, or other fluids, and/or pollutants may be provided to the BGM and/or to the Plan 730.

In this manner (e.g., as described in 700 or 700A) and/or in another manner known to the person of ordinary skill in the art, the exhaust gas effluent 706 may be treated (e.g., to remove pollutants) and heat captured before either transfer 730 to the biomass growth module 714, or release into the environment, or both. In an embodiment, controlled amounts of exhaust gases 706 from this process may be directed to the BGM 714 in order to provide carbon dioxide, and/or anywhere else e.g., in the Plan carbon dioxide may be used, e.g., FIG. 4. This carbon dioxide stream may be optionally further treated before such use. In an embodiment, the pollution entrainment module 726 and/or pollution control module 705 may scrub volatile organic compounds out of the water, react out NOx compounds, condense certain compounds, capture oxides of sulfur, rendering a useful, weak, sulfurous acid, capture particulate matter, capture metals, dioxins/furans and/or otherwise clean the exhaust effluents. In an embodiment, the CO2 and NOx content of these flows to the BGM 714 may vigorously promote photosynthesis in the biomass growth module in photosynthetic embodiments. In an embodiment, nitrogen-enriched water from these processes may be routed to assist in growth of crops other than those in the biomass growth module. In water, such as that used in the pollution entrainment module 726 and/or in the BGM 714, sulfur dioxide forms sulfurous acid ($H_2SO_3$), a weak acid. One valuable use of sulfurous acid may be to remediate alkaline and salty soils and/or water. In an embodiment, it may be used in this manner wherever it may be advantageous e.g., in the Plan and/or offsite.

With respect to designs 700 or 700A, in an embodiment, given the content of pollutants in the exhaust gas and/or any liquid discharge from the pollution entrainment module and/or liquid discharge from the pollution control module to be directed to the BGM, the liquid discharge and/or exhaust gases directed to the BGM (whether processed through exhaust gas recovery module 700, 700A or another means) may be treated in any manner known to those in the art to allow for biomass growth. For example if the gases contain high levels of sulfur oxides (SOx), or the liquid discharge has entrained a high content of SOx emissions, reducing the pH of the discharge to levels lower than the biomass can tolerate in the BGM, either liquid discharge and/or the BGM may be treated with sodium hydroxide and/or another chemical to elevate the pH to levels acceptable to the biomass. Any other treatment method(s) known to the person of skill in the art may be used to prepare either exhaust gases and/or liquids of any kind for introduction into the BGM, or particular BGUs within a BGM.

In reference to FIGS. 7A and 7B, an embodiment of the disclosure includes a system comprising: A thermal plant module 222 comprising a source of exhaust gases 706; wherein the exhaust gases comprise carbon dioxide; and wherein a conveyance 702 carries the exhaust gases away from the source; wherein a diversion 704 therefrom carries any portion of the exhaust gases from the conveyance into an exhaust gas recovery module comprising: one or more valves 708; one or more motive devices 716; a heat recovery module 710; and/or a pollution entrainment module 713, 726.

An embodiment includes the system wherein a discharge section 703 of the conveyance 702 is configured to convey any portion of the exhaust gases 706 for discharge 729.

An embodiment includes the system wherein one or more valves 708 are positioned on the conveyance 702 to control the flow of exhaust gases 706 through the discharge section 703.

An embodiment includes the system wherein a pollution control module 705, pollution entrainment module 713, 726, and/or heat recovery module 705 are provided on the discharge section 703.

An embodiment includes the system wherein the pollution control module 705, pollution entrainment module 713, 726, and/or either or both of the heat recovery modules 705, 710 are configured to optionally provide heat, water, gases, carbon dioxide, or other fluid(s), and/or pollutants 720, 730, 731 to a BGM 714, either directly from the thermal plant 222, or optionally after pollution control treatment 705, chemical treatment, and/or combination with water 712, 728 from other sources, optionally from the Plan, for example, FIG. 3.

An embodiment includes the system wherein the pollution control module 705, pollution entrainment module 713, 726, and/or either or both of the heat recovery modules 705, 710 are configured to store or hold 718 the heat, water, gases, carbon dioxide, or other fluid(s), and/or pollutants 720, 730 before providing the heat, water, gases, carbon dioxide, or other fluid(s), and/or pollutants 720,730,731 to a BGM 714 optionally after pollution control treatment, chemical treatment, and/or combination with water 728 from other sources.

An embodiment includes the system wherein the pollution control module 705, pollution entrainment module 713, 726, and/or heat recovery module 705, 710 utilize(s) a heat exchanger 710.

An embodiment includes the system wherein the pollution control module 705, pollution entrainment module 713, 726 and/or heat recovery module 705, 710 utilize: activated carbon, hearth furnace cokes, zeolites, lime, chlorine, sprayers, sorbents, filtration, photochemical methods, selective catalytic reduction, dry scrubber, wet scrubber, e.g., spray tower, tray tower, packed bed tower, two-pass wet scrubber, and/or other wet scrubber; and/or any of the above in any sequence or combination.

An embodiment includes the system wherein the discharge section 703 is configured to optionally discharge 729 any portion of the exhaust gases 706.

An embodiment includes the system wherein an optional valve 708 at or near the beginning of the diversion 704 is configured to control the flow of exhaust gases 706 from the conveyance 702 through the exhaust gas recovery module 707, 709.

An embodiment includes the system optionally comprising one or more motive devices 716 to control flow of the exhaust gases 706 from the conveyance 702, through discharge section 703, through the diversion 704, and through the exhaust gas recovery module 707, 709.

An embodiment includes the system wherein an optional heat recovery module 710 is provided either upstream (e.g., FIG. 7A) or downstream (e.g., FIG. 7B) from the pollution entrainment module 713, 726.

An embodiment includes the system wherein water from any source in the Plan 712 optionally pretreated may be used in the pollution entrainment module 713,726, the pollution control module 705, and/or either of the heat recovery modules 705, 710.

An embodiment includes the system wherein water from any source in the Plan or other fluids optionally pretreated 712 may be used in the heat recovery modules 705, 710.

An embodiment includes the system wherein the gases comprising carbon dioxide and/or remaining heat 724 after the above process as in the exhaust gas recovery module 707, 709 are provided to a BGM and/or other heat and/or carbon dioxide use either directly or after mixing with other gases 718, and/or are stored for later use in the BGM and/or for discharge 718.

An embodiment includes the system wherein the motive device(s) 716 are selected from a damper, a blower, and a combination thereof.

An embodiment includes the system comprising controlling pressure at the diversion 704, the outlet of the discharge section 703, and/or or the conveyance 702 by controlling the valves 708 and/or operation of the motive device(s) 716.

An embodiment includes the system wherein the pollution entrainment module 713, 726, exhaust gas recovery module 707, 709, pollution control and/or heat recovery module(s) 705, 710 are configured to remove pollutants from the exhaust gases 706 into water 712 and transfer the pollutants to the BGM 714 via the water; and wherein the BGM 714 is configured to remove and/or utilize in the pollutants: any portion of organic compounds contained therein; any portion of the sulfur compounds contained therein; any portion of the particulates contained therein; any portion of the metals contained therein; any portion of the heat contained therein with respect to ambient temperature; any portion of the oxides of sulfur are converted into sulfurous acid; any portion of sulfur oxide(s) wherein optionally salts are removed from the water by using sulfurous acid resulting from exhaust gas sulfur oxide(s) removal and conversion to sulfurous acid in the water; and/or any portion of exhaust gas NOx emissions are retrieved from the exhaust gases into the water which may become biomass-available nitrogen compounds.

An embodiment includes the system configured such that a growth rate of the biomass in the BGM 718 is regulated by: exposing the biomass to heat removed from the exhaust gases 706 into the water used in the pollution entrainment module 713, 726 and/or other heat recovery modules 705, 710 and/or heat remaining in the exhaust gases 724; distributing thereto at least a portion of carbon dioxide from the exhaust gases 706; distributing compounds of nitrogen derived from the NOx in the exhaust gases 706 and the water 712 sprayed into the pollution entrainment module 713, 726 and/or the pollution control module 705; distributing other organic compounds from the exhaust gases 706 which may be utilized by the biomass; distributing other inorganic compounds from the exhaust gases 706 which may be utilized by the biomass; and/or exposing a greater surface area of the biomass to the exhaust gases 706 and optionally to light, heat and/or nutrients by churning the water in which the biomass is growing by pulsing the flow of exhaust gases 706 into the BGM 718 and/or varying exhaust gas flow rates across a planar cross-section in a BGM's growing subunit to create a stirring action.

An embodiment includes a system for biomass growth resource management comprising a pollution control module 705, a pollution entrainment module 713, 726, and/or one or more heat recovery modules 705, 710 configured to optionally provide heat, water, gases, carbon dioxide, other fluid(s), and/or pollutants 720 to a BGM 714 and/or other heat or water use module 718 or process in the system.

An embodiment includes the system wherein the pollution control module 705, a pollution entrainment module 713, 726, and/or one or more heat recovery modules 705, 710 are optionally configured to provide heat, water, gases, carbon dioxide, other fluid(s), and/or pollutants 720 to a another module, design, component, and the like, either directly, after treatment, and/or after mixing with other fluids and/or for storage for later use in the BGM 714, 718 and/or for discharge 700, 700A.

An embodiment includes the system wherein the pollution control module 705, pollution entrainment module 713, 726, and/or heat recovery module(s) 705, 710 utilize a heat exchanger 710.

An embodiment includes the system wherein the pollution control module 705, pollution entrainment module 713, 726 and/or heat recovery module(s) 705, 710 utilize: activated carbon; hearth furnace cokes; zeolites; lime; chlorine; sprayers; sorbents; filtration; photochemical methods; selective catalytic reduction; dry scrubber; wet scrubber, e.g., spray tower, tray tower, packed bed tower, two-pass wet scrubber, and/or other wet scrubber; other pollution control or entrainment techniques known to those skilled in the art; and/or any of the above in any sequence or combination.

An embodiment includes the system wherein an optional heat recovery module 710 is provided either upstream (e.g., FIG. 7A) or downstream (e.g., FIG. 7B) from the pollution entrainment module 713, 726.

An embodiment includes the system wherein water from any source in the Plan 712 optionally pretreated may be used in: the pollution entrainment module 713, 726; the pollution control module 705; and/or either of the heat recovery modules 705, 710.

In further reference to FIGS. 7A and 7B, an embodiment of the disclosure includes a method of trapping exhaust gases (within an integrated power generation, fuel generation, and waste treatment integrated system) comprising: capturing exhaust gas 706 from a system thermal plant 222, conveying the exhaust gas 706 to a diversion 704 operatively connected to the thermal plant 222; and diverting a portion of the exhaust gas 706 to a gas recovery module 707, 709.

An embodiment includes the method comprising discharging a portion of the exhaust gas 706 to a discharge section 703, a pollution control module 705, a pollution entrainment module 713, 726, and/or heat recovery module 705, 710 are provided on the discharge section 703 and extracting from the portion of exhaust gas 706 heat, water, gases, carbon dioxide, or other fluid(s), and/or pollutants 720.

An embodiment includes the method comprising storing and/or delivering the heat, water, gases, carbon dioxide, or other fluid(s), and/or pollutants 720 to a BGM 714 or other system module.

An embodiment includes the method of managing a biomass growth resource comprising providing the system including a pollution control module 705, a pollution entrainment module 713, 726, and/or one or more heat recovery modules 705, 710, configured to optionally provide heat, water, gases, carbon dioxide, other fluid(s), and/or pollutants 720 to a BGM 714 and/or other heat or water use module or process in the system.

Figure 22:
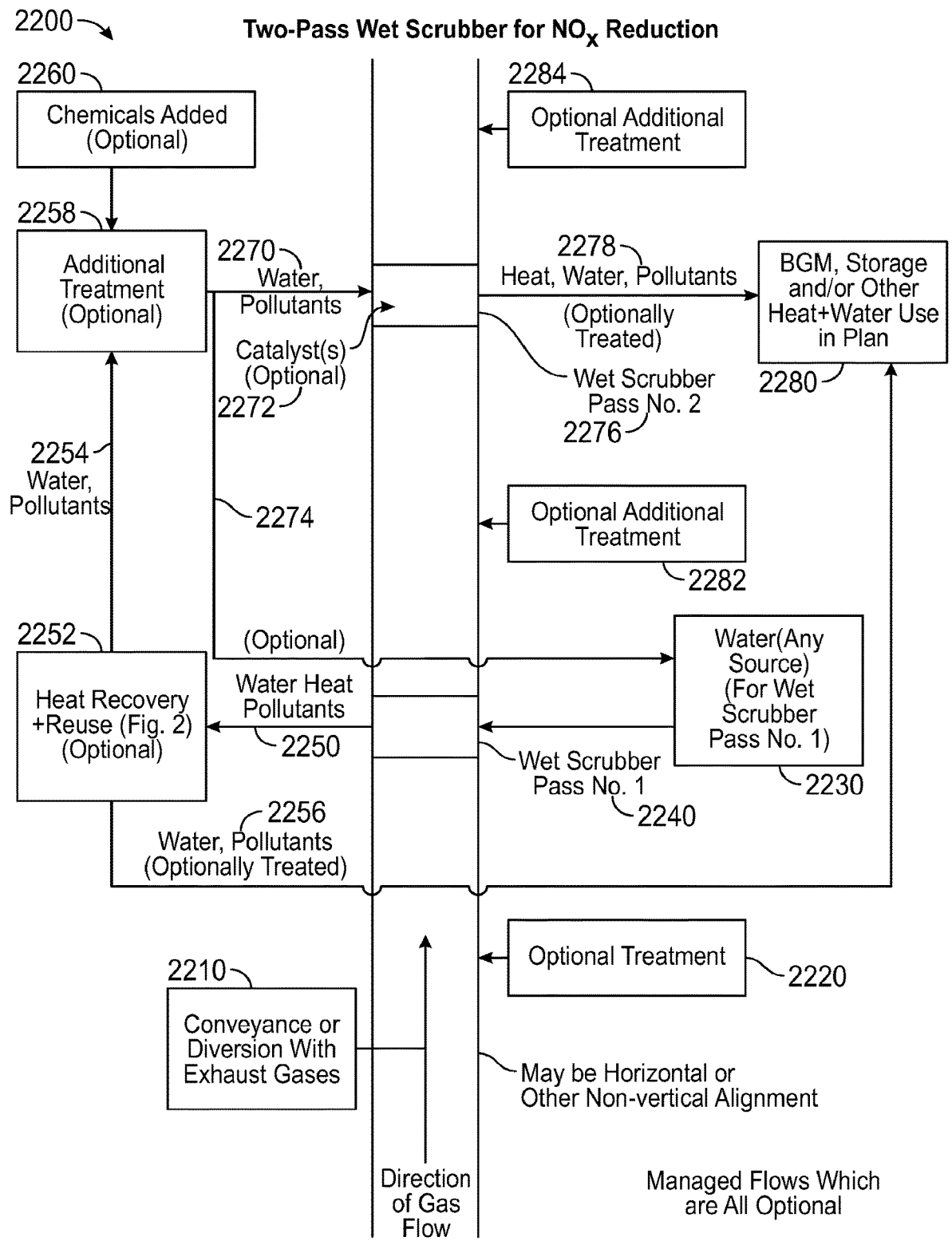
FIG. 22 is a Two-Pass Wet Scrubber for NOx Reduction according to the present disclosure.

In further reference to FIGS. 7A and 7B, an embodiment of the disclosure includes a method of remediating an exhaust gas comprising further treating exhaust gas with the water and pollutants 720 removed from exhaust gases 706, e.g., in a second scrubber process, e.g., FIG. 22 a two pass wet scrubber for NOx reduction, and/or other process.

In further reference to FIGS. 7A and 7B, an embodiment of the disclosure includes a method of remediating alkaline water and/or salty water and/or soil comprising treating the alkaline water and/or the salty water and/or the soil with the water and pollutants 720 removed from exhaust gases 706, e.g., using any means known to those in the art.

With respect to capture of carbon dioxide, e.g., reference to FIG. 7A and/or 7B, power plant exhaust may be composed of between 3-15% carbon dioxide. If an oxy-fuel process may be used, the carbon dioxide percentage may be significantly higher. In an embodiment, it may be anticipated that nearly 100 percent of the carbon dioxide introduced into the biomass growth module may be converted to biomass when utilizing photobioreactor(s) and photosynthetic algae in the BGM, and a significant portion, which may be from 50%-85%, may be utilized in embodiments using pond-based or other open systems. In an embodiment, the percentage of carbon emitted from the exhaust gases and converted to biomass in the biomass growth module may be from 30% to 80% of the carbon, or from 50% to 100%, or from 70% to 100%, or from 75% to 100% or from 80% to 100% or from 80% to 95% of the carbon.

In an embodiment, e.g. FIG. 4 and/or other figures and/or description relating to flows of other gases, heat, cooling, water, fuels, and/or materials of any kind, sensors and/or flow controls of any description may be used to control these carbon dioxide flows and/or any other flows e.g., in the Plan. Flows may be stored in whole or in part before use as described (e.g., these flows may be stored overnight, and directed to a photosynthetic BGM during the day).

Nitrogen oxides (NOx) emissions, especially NO for example, in exhaust gases, may be often not effectively removed by wet scrubbers due to low solubility in water. However, acidic water may be more effective at removing NOx. Also, lower temperature water may be more effective at removing NOx.

With reference to FIG. 22, a Two-Pass Wet Scrubber for NOx Reduction 2200 provides a means to purify polluted gases in a more effective manner than a common single-pass wet scrubber. A conveyance or diversion 2210, e.g., such as those used to convey gases from a Thermal Plant 222 to a pollution control module 705 or pollution entrainment module 713 e.g., FIG. 7A or 7B carries exhaust gases to a wet scrubber's first pass 2240 which uses water from any source 2230 in a scrubber in any manner known to those skilled in the art. The outflow of water from this process carries heat and/or pollutants 2250 to an optional heat recovery and reuse module 2252. This outflow water 2250 may have substantially removed the SOx content of the exhaust gases, which may be converted in the water to sulfurous acid, reducing the pH of the water, possibly to a pH of between 4 and 6. The lower pH water may be more effective at reducing NOx emissions in the exhaust gases if used in a second pass than water of neutral pH, or may be more easily treated to optimize pH for the wet scrubber. After optional heat recovery which may reduce the temperature of the water, further increasing its effectiveness in reducing NOx as scrubber source water, while providing heat to the Plan 2252, any portion of the water with pollutants 2256 may be optionally treated in any manner known to those in the art and sent for use in the BGM, to storage, or other heat and/or water use e.g., in the Plan 2280. Any other portion of the water and pollutants 2254 may undergo optional additional treatment in any manner known to those of skill in the art 2258, comprising the optional addition of chemicals (e.g., ammonia, urea, other chemicals) 2260 in preparation for use in a scrubber. The resulting water mixture may then be used in one or two different ways: in the first wet scrubber pass 2274, 2230, 2240; and/or in a second wet scrubber pass 2270, 2276. Any portion of the water carrying pollutants 2274 may be returned to provide any portion of the source water 2230 for use in the first wet scrubber pass action on the exhaust gases (the wet scrubber's "first pass") 2240, reducing the source water's pH and increasing its effectiveness at NOx removal, and/or to a flow of the exhaust gases downstream from the first scrubber pass 2250, to be used in whole or in part as the water source 2270 for a second wet scrubber section (i.e., a "second pass") 2276. The second pass may thereby be conducted with water of lower pH, and, may provide a better reduction of NOx gases from the exhaust gas stream. This scrubber process may be conducted in the presence of one or more catalysts 2272, and/or in any other means known to those in the art to effectively mitigate NOx emissions (e.g., catalysts fixed to ceramics used to facilitate the reduction of NOx). The outflow from the second pass 2278 may be then sent either directly to the BGM 2280 or treated in any way known to those in the art and then sent for use in the BGM, to storage, and/or other heat and/or water use e.g., in the Plan 2280. The Two-Pass Wet Scrubber for NOx Reduction may be used in conjunction with any other pollution control, entrainment, and/or mitigation means known to those of skill in the art (e.g., in a pollution control module 705 or pollution entrainment module 713 e.g., FIG. 7A or 7B). Additional treatment of any kind as known to the person of skill in the art may be used at any stage, e.g., before the first pass of the scrubber, between the first and second passes, and/or after the second pass 2220, 2282, 2284.

In reference to FIG. 22, an embodiment of the disclosure includes a system 2200 configured to reduce NOx and SOx gaseous emissions of an exhaust gas, wherein said exhaust gas is optionally delivered to a BGM 2280, the system comprising: a conveyance or diversion 2210 configured to direct the exhaust gas to a wet scrubber 2240; a wet scrubber 2240 configured to utilize water from any source 2230 in the system, configured to capture SOx in the exhaust gas (a first pass 2240); and wherein the scrubber 2240 defines outflows of water, heat, and/or other pollutants 2250 and wherein the outflow water, heat, and/or other pollutants 2250 is or are used for subsequent scrubbing (the second pass 2276), wherein the subsequent scrubbing is effective to remove NOx. An embodiment includes the system wherein the outflow of water, heat, and/or pollutants 2250 from the first pass 2240, optionally treated 2256, is provided in whole or in part to: a heat recovery and reuse module 2252; a BGM 2280; a storage module(s) 2280; a module for other heat recovery and use in Plan 2280, for example, FIG. 2; and/or a module for water recovery and use in Plan 2280, for example, FIG. 3. An embodiment includes the system, wherein any portion of the outflow of water and/or pollutants 2254 is chemically treated 2258, 2260 for use in a scrubber. An embodiment includes the system, wherein optionally, any portion 2274 of the resulting optionally treated outflow of water and/or pollutants 2270 from the first pass 2240 is used in the scrubber's first pass 2240 after optionally mixing with a water source 2230.

An embodiment includes the system, wherein any portion of the optionally treated outflow of water and/or pollutants 2270 optionally mixed with another water source is directed for use in the second scrubber pass 2276. An embodiment includes the system, wherein one or more catalysts 2272 are used in a scrubber 2276. Catalyst is defined as a chemical which facilitates a beneficial chemical reaction comprising a reducing agent of any kind optionally comprising anhydrous ammonia, aqueous ammonia and/or urea.

An embodiment includes the system, wherein the outflow of water, heat and/or pollutants 2278 from the second scrubber pass 2276, optionally treated, is directed for use in: a BGM 2280; a storage module(s) 2280; a module for heat recovery and use in Plan 2280, for example, FIG. 2; and/or a module for water recovery and use in Plan 2280, for example, FIG. 3. An embodiment includes the system, wherein optional treatment of the exhaust gas is performed: before use in the first scrubber pass 2220; between the first scrubber pass and the second scrubber pass 2282; and/or after the second scrubber pass 2284. Optional treatment is defined as optionally pollution reduction, temperature change, reduction of the volume of gases, addition of other gases, and/or any other means known to those of the art for preparing gases for optimal use in one or more of the scrubber passes, or for additional treatment (e.g., in preparation for discharge to the environment) after one or more scrubber passes have been completed. In reference to FIG. 22 an embodiment of the disclosure includes a system 2200 for managing and treating pollutants wherein water and/or pollutants from any source 2278 optionally treated are provided to: a BGM 2280; a storage module(s) 2280; a module for heat recovery and use in Plan 2280, for example, FIG. 2; and/or a module for water recovery and use in Plan 2280, for example, FIG. 3. An embodiment includes the system, wherein the water and/or pollutants are heated before being provided to any one or more of modules: a BGM 2280; a storage module(s) 2280; a module for heat recovery and use in Plan 2280, for example, FIG. 2; and/or a module for water recovery and use in Plan 2280, for example, FIG. 3. An embodiment includes the system, wherein the heat, water, and/or pollutants 2278, are provided by the outflow of a wet scrubber 2276.

In reference to FIG. 22 an embodiment of the disclosure includes a method of scrubbing a SOx and NOx pollutants from a stack gas comprising: directing an exhaust gas through a conveyance or diversion 2210 to a scrubber 2240, scrubbing the exhaust in the scrubber with a fluid configured to remove SOx pollutants from the exhaust gas, and scrubbing the exhaust in a second scrubber 2276 with the fluid. An embodiment includes the method, wherein the second scrubber 2276 is the scrubber. An embodiment includes the method, wherein the fluid is chemically treated 2258, 2260 before the exhaust is scrubbed in the scrubber and/or the second scrubber 2276.

Thus, with reference to FIG. 9, a hydrothermal liquefaction process 900 includes pressurized feed tanks 902, capable of receiving biomass and/or biocrude 903, may be fed by pumps, e.g., syringe pumps 904, to a preheating unit, e.g., a horizontal oil jacketed preheater 906. Continuous stirred tank reactor (CSTR) 908 receives and heats preheated biomass and/or biocrude. A downstream reactor, e.g., oil-jacketed plug-flow reactor 910 destroys the cellular structure of any remaining biomass and sent to a filtration/purification process, e.g., separator with filter 912. Liquid product, e.g., an oil or oil-water mixture, may be sent to a collection vessel or process, e.g., oil-jacketed liquid collectors 914. Biocrude or refined biofuel exits the process through a Back Pressure Regulator 916, main WTM 918 and sample WTM 920, with an Exhaust 922.

The water resources needed to absorb and carry heat (e.g., waste heat) away from thermal plants can be very significant. When this large amount of waste heat may be discharged into the environment in the form of heated air, steam and/or water, and/or by other means, energy may be lost, water may be used, and it can produce detrimental effects to the environment. The systems within this disclosure effectively make use of heat, comprising waste heat, for a variety of processes e.g., as described herein.

Figures 15A, 15B:
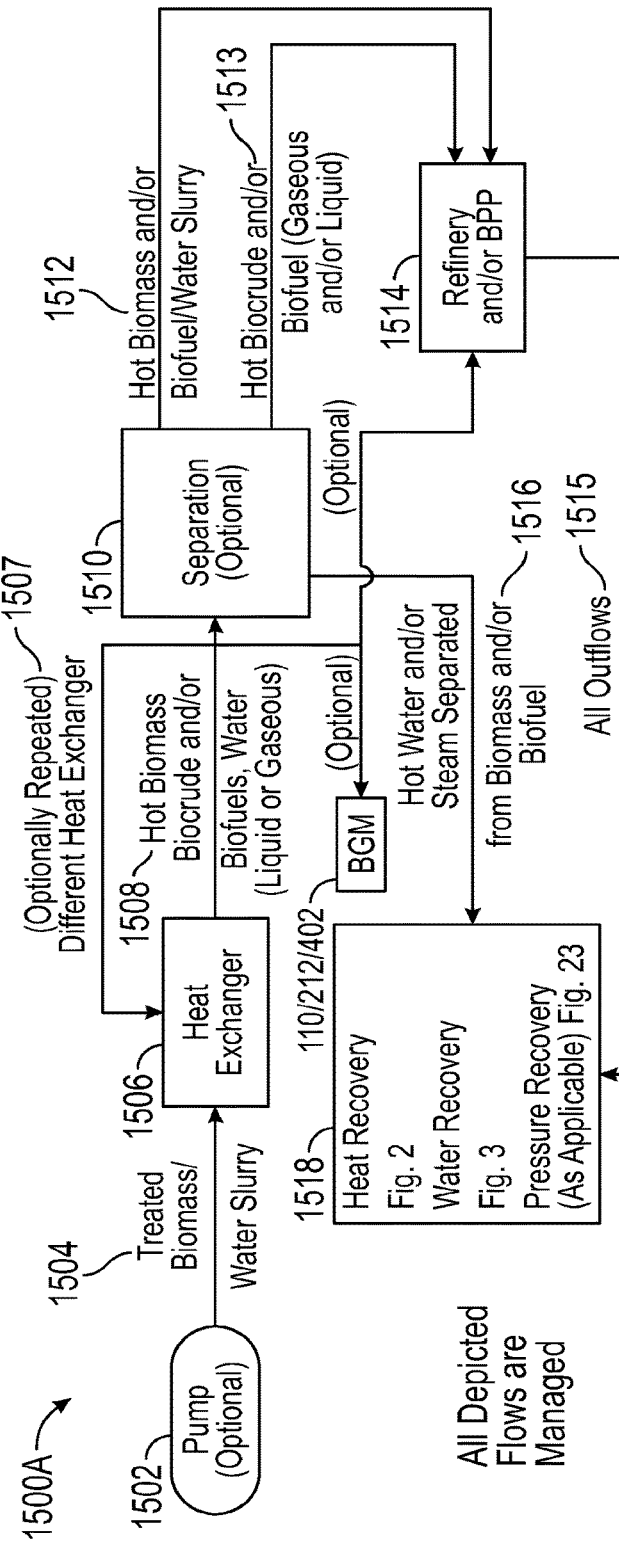
FIG. 15A is a schematic representation of a first heat transfer module according to the present disclosure.
FIG. 15B is a schematic representation of a second heat transfer module according to the present disclosure.

With reference to FIG. 15A, notwithstanding the concentration of biofuel in the biomass, a biomass/water slurry e.g., a treated biomass/water slurry (TBW slurry) 1504 may be transferred to a thermal process, such as the thermal plant 222 to be used as a cooling fluid. In embodiment 1500A (Module #1), optional pump 1502 sends treated biomass 1504 in a water slurry through heat exchanger 1506 to provide cooling for a thermal process, e.g., the cooling/condensation stage of a thermodynamic cycle, e.g., a Rankine cycle, and/or other process steps where cooling water may be needed in any thermal process, e.g., thermal plant 222. Thus, the resulting hot biomass and/or biocrude and/or biofuel water mixture 1508 may be optionally sent to a Refinery and/or BPP 1514, and/or the BGM 110, 212, 402, and/or transferred to a separation module 1510. Depending on the separation technology employed, and whether or not sufficient temperature may be attained to achieve in situ conversion of biomass to biocrude and/or biofuels by HTP and/or another process, hot biomass and/or biofuel water slurry 1512 and/or hot biocrude and/or biofuel (gaseous or liquid) 1513 may be transferred to refinery and/or BPP 1514. Afterward, heat may be captured from the thermal processes of module #1 at module 1518, a heat recovery module. Recovery of water, pressure, gases (such as carbon dioxide) and/or other byproducts may also be performed at this stage in module 1518. In this embodiment hot water/steam 1516 may be separated and sent to module 1518 from separation module 1510. In an embodiment, outflows from the refinery and/or BPP may be sent to module 1518 for recovery of heat, water, pressure, gases (such as carbon dioxide). Alternatively, in an embodiment, the hot biomass and/or biocrude and/or biofuel water mixture 1508 instead may be rerouted through another pass in any heat exchanger in the system or Plan 1507 before being sent to a separation module 1510 and/or the refinery and/or BPP 1514, with the heated mixture being pumped 1507 through another heat exchanger 1506, then proceeding through all of the steps listed above. In an embodiment, this process may be repeated any number of times to achieve a desired temperature. In this manner, the TBW slurry 1504 may be gradually heated through a variety of heat exchange processes. This may help mitigate biofouling, and/or other problems associated with rapid heating to high temperature. The heat exchanger(s) 1506, 1507 in this process or other processes in the disclosed Plan may use technologies which prevent or inhibit fouling, comprising selection of advantageous heat exchanger designs, the use of special materials to protect the heat exchangers, like titanium, a magnetite layer, other coatings and/or materials, pretreatment of the cooling fluid, additives to the cooling fluid, such as additives to change the pH, temperature and flow controls, and other measures known to those of the art to prevent biofouling due to the biomass content of the TBW slurry 1504 and/or other types of fouling, or may comprise other technologies not strictly termed or considered heat exchangers, which may be suited to the purpose of transferring either heat and/or cooling.

In an embodiment, the heated solution that may be the product of an initial heat exchange process or other process steps may be treated in any manner known to the art and/or may be combined with other fluid source(s) before further steps depicted in FIG. 15A. In an embodiment e.g., FIGS. 2, 15A and/or 15B, additional heat, optionally thermal plant primary process heat and/or heat from a different source (e.g., a dedicated burner) may be applied at any stage of the process depicted in FIG. 15A where it may be beneficial. The refinery and/or BPP 1514 may further refine the materials directed to them e.g., as described herein. In an embodiment, the biocrude and/or biofuel(s) resulting from this process may be directed to the thermal plant 222 to provide power and/or may be exported offsite. In an embodiment, the heat exchange process 1506 may be used to heat the TBW slurry 1504 for optimization of temperature in the BGM 110/212/402, rather than for refining or preheating for refining. In this embodiment, the TBW slurry downstream from the heat exchanger 1508 may be routed in whole or in part to the BGM 110/212/402. In an embodiment, any one or more of the process paths downstream from the heat exchanger 1506 may be followed using separate modules 1500A. For example, one version of 1500A may use a heat exchanger 1507 which generates high heat to separate and refine biomass e.g., 1510 or 1514, and another separate module 1500A may be used in another heat exchanger 1507 to provide lower temperature heated fluid to a BGM e.g., 1500A.

In an embodiment, and with reference to FIG. 15B and with reference, optionally to FIG. 3, embodiment 1500B may be described. Optional pump 1502 transfers a fluid, e.g., a cooling fluid 1521 to a heat exchanger 1520 to provide heated fluid 1522 that may be then transferred for direct use e.g., in the Plan and/or to heat recovery unit, and/or a fluid recovery unit, and/or optionally pressure recovery unit 1524. Also, in an embodiment, any fluid source 1521 may be routed through two or more heat exchange processes 1520 e.g., anywhere in the Plan 1524 before being used e.g., in the Plan 1524 to heat other processes, and/or for other uses where heated fluid 1522 may be beneficial. Heated fluid 1522 is optionally used a source of feed water 1522 for BGM 110/212/402 either directly or mixed with other source(s) (e.g., to optimize BGU temperature and/or other aspects important to biomass growth), and/or optionally in an embodiment, heated fluid 1522 may be sent to heat recovery unit, and/or a fluid recovery unit, and/or pressure recovery unit 1524 to recover heat, fluid and/or pressure in whole or in part and then fluid 1523 may be transferred and used either directly or in combination with other fluid(s) for use as feed water for BGM 110/212/402 and/or any BGU, and/or any BGU subunit comprised by the BGM. In an embodiment, heated fluid 1522 may be sent to heat recovery unit, and/or a fluid recovery unit, and/or pressure recovery unit 1524 to recover heat, fluid and/or pressure in whole or in part and then fluid 1525 may be transferred and used either directly or in combination with other fluid(s) to feed container 1220, which keeps fluid 1525 separate from BGM 1218/110/212/402, but allows transfer of heat to BGM 1218/110/212/402 and/or any BGU, and/or any BGU subunit comprised by the BGM. In this manner, heat or heated fluid 1522, 1524 may be used e.g., in the Plan directly and/or recovered for any use e.g., in the Plan (See FIG. 2). Where water may be used, the water may be also reclaimed and used e.g., FIG. 3. Other fluids used in this process may also be reclaimed. Where possible, pressure may be also reclaimed and used wherever beneficial e.g., in the Plan (e.g., FIG. 23, 2300). In an embodiment, in this fashion, optionally, thermal process (e.g., thermal plant 222) waste heat and/or heat from any other fluid, source or process in the Plan, system or design may be transferred to the biomass/water slurry 1504 and/or BGM 110, 212, 402, 1218 either as heated in the heat exchanger 1522, and/or after optional recovery in whole or in part of heat, fluid, and/or pressure 1524, 1523 to be used in whole or in part as feed water to the BGM 101, and/or any individual BGU 600 comprised by the BGM, and/or any individual growing subunit comprised by the BGU 630, 602 and/or any other subunit comprised by a BGU e.g., FIG. 6, 600, and/or to heat the BGM indirectly using fluid 1525 after optional recovery in whole or in part of heat, fluid, and/or pressure 1524, wherein fluid 1525, optionally combined with other fluids, by use of use of a container 1220 which keeps the heated fluid separate from the BGM 1218, 110, 212, 402. These systems and/or methods of transferring heat may be used in the BGM 1218, 110, 212, 402, and/or any individual BGU 600 comprised by the BGM, and/or any individual growing subunit 630, 602, and/or any other subunit comprised by a BGU e.g., FIG. 6, 600, and or to recover heat for use in the Plan 1524, FIG. 2, in order to use heat where it may be most effective in the Plan. In an embodiment, using a different configuration of water sources and/or heat exchangers, e.g., any water and/or other fluid source 1521 may be used to cool a thermal process or fluid, and/or to capture heat from any fluid, source and/or process, and then to transfer heat to the biomass/water slurry 1504, and/or BGM 1218, 110, 212, 402 via heat exchange or any other method known to those of skill in the art, and/or the recovered heat may be used in any other process where heat may be beneficial e.g., in the Plan (FIG. 2), comprising in an embodiment, cogeneration to produce cooling, also to be used in the Plan, system, or design e.g., FIG. 2. In thermal plant thermal processes where air may be used in firing a boiler or to cool the working fluid, heat recovery module #1 (FIG. 15A) and/or heat recovery module #2 (FIG. 15B) using a heat exchanger (e.g. 1506 and/or 1520) may be used to transfer heat from the air to the biomass/water slurry, e.g., FIG. 7A and/or FIG. 7B. In an embodiment, any number or sequence of either of the heat transfer modules #1 or #2 shown in FIG. 15A or 15B (1500A or 1500B) or any other heat transfer process may be used in any thermal process to transfer heat in specific manners beneficial to the Plan. For example, a heat exchanger of either type in FIG. 15A or 15B 1506, 1520 may be used as a first step in cooling a working fluid at high heat to transfer heat in a heat exchange for high heat uses, such as biomass refining, and/or any number of subsequent uses of either heat transfer module 15A or 15B or another method may be used subsequently e.g., to further cool the working fluid, and to transfer, for example, lower levels of heat to the Plan for lower heat applications, such as heating the BGM 110/212/402 or any of its components to an optimal temperature, to a storage module for later use of heat e.g., in the Plan and/or for other uses e.g., FIG. 2.

In reference to FIGS. 15A and 15B, and FIGS. 16-18, an embodiment of the disclosure includes a system for heat transfer comprising a heat transfer module 1500A, 1500B configured to transfer heat from a thermal process to a system module and/or a treated biomass/water slurry 1504, for example, FIG. 15A.

In reference to FIGS. 15A and 15B, and FIGS. 16-18, an embodiment of the disclosure includes a system for heat transfer comprising a heat transfer module 1500A, 1500B configured to transfer heat from a thermal process to a system module by a heat exchanger 1506, 1520 in the Plan, for example FIG. 15A or 15B.

An embodiment includes the system wherein the heat transfer module 1500A, 1500B configuration comprises the biomass/water slurry, e.g., the treated biomass/water slurry, 1504 in operative communication with the heat exchanger 1506, for example FIG. 15A.

An embodiment includes the system wherein the biomass/water slurry, e.g., the treated biomass/water slurry 1504, is converted in whole or in part into a biocrude 1508 and/or a biofuel 1508 in the heat transfer module 1500A.

An embodiment includes the system wherein the heat exchanger 1506 comprises an outflow comprising in liquid and/or gaseous state: hot biomass 1508; hot biocrude 1508; hot biofuels 1508; and/or water 1508/steam 1508.

An embodiment includes the system wherein additional heat is provided to the heat transfer module 1500A by a separate heat source.

An embodiment includes the system wherein the separate heat source is a burner.

An embodiment includes the system wherein the outflow 1508 is directed to another one or more heat exchange processes 1507.

An embodiment includes the system wherein the outflow 1508 is directed to: a refinery module 1514; a BPP module 1514; a BGM 110/212/402; and/or a separation module 1510.

An embodiment includes the system wherein the separation module 1510 comprises outputs optionally comprising: a hot biomass and/or biofuel and water slurry 1512; a hot biocrude and/or biofuel (gaseous and/or liquid) 1513; and/or hot water and/or steam separated from biomass and/or biofuel 1516.

An embodiment includes the system wherein the hot biomass and/or biofuel and water slurry 1512 and/or the hot biocrude and/or biofuel (gaseous and/or liquid) 1513 are directed to a refinery module 1514 and/or a BPP module 1514.

An embodiment includes the system wherein an outflow 1515 from the refinery module 1514 and/or the BPP module 1514 are optionally directed to modules for the recovery and reuse of heat 1518, for example FIG. 2, water 1518, for example FIG. 3, and/or pressure 1518, for example FIG. 23.

An embodiment includes the system wherein the hot water and/or steam separated from biomass and/or biofuel 1516 is optionally directed to modules for the recovery and reuse of heat 1518, for example FIG. 2, water 1518, for example FIG. 3, and/or pressure 1518, for example FIG. 23.

An embodiment includes the system wherein the outflow 1508 comprising hot biomass, biocrude, biofuels, and/or water (liquid or gaseous) is directed to a BGM 110/212/402.

An embodiment includes the system configured such that a fluid 1521 optionally comprising any fluid source, if water, for example, FIG. 3 is delivered to the heat exchanger 1520 via an optional pump 1502, for example, FIG. 15B.

An embodiment includes the system wherein water 1521 in the Plan for example FIG. 3, is used as a fluid for heat transfer, for example FIG. 15B.

An embodiment includes the system wherein the heat exchanger 1520 has an outflow of heated fluid 1522.

An embodiment includes the system wherein the heated fluid 1522 is directed for use in the Plan or to modules for the optional recovery and reuse in the Plan of heat 1524, for example FIG. 2, water 1524, for example FIG. 3, fluid 1524 and/or pressure 1524, for example FIG. 23.

An embodiment includes the system wherein any portion of the heated fluid 1522 is directed to the BGM 110/212/402 for use in whole or in part as the BGM feedwater.

An embodiment includes the system wherein the modules 1524 are configured to produce a reclaimed fluid output 1523, 1525.

An embodiment includes the system wherein any portion of the reclaimed fluid 1523 is directed to the BGM 110/212/402 for use in whole or in part as the BGM feedwater.

Figure 12A:
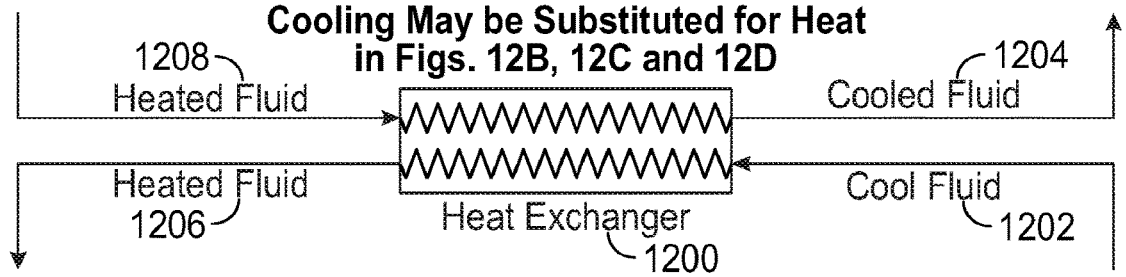
FIG. 12A is a schematic representation of heated or cooled fluid flow according to the present disclosure.
Figure 12B:
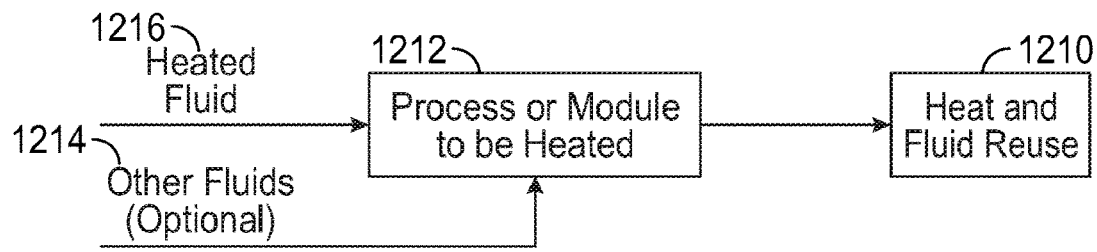
FIG. 12B is a second schematic representation of heated or cooled fluid flow according to the present disclosure.
Figure 12C:
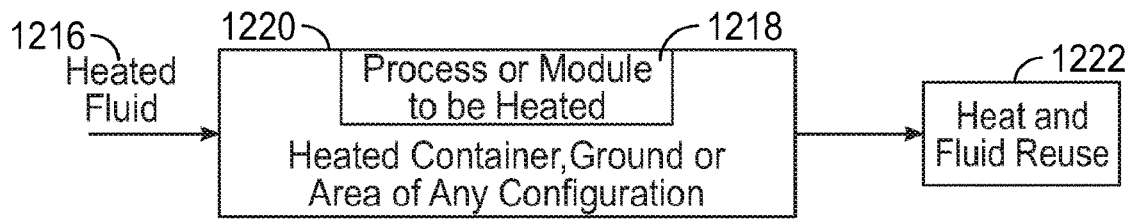
FIG. 12C is a third schematic representation of heated or cooled fluid flow according to the present disclosure.

An embodiment includes the system wherein any portion of the reclaimed fluid 1525 is directed to a container 1220 for transferring heat in the Plan, for example, FIG. 12*c*, FIG. 2.

An embodiment includes the system wherein the container 1220 for transferring heat in the Plan, for example, FIG. 12*c*, FIG. 2 is configured to be in contact with a BGM 1218, 110/212/402.

An embodiment includes the system wherein any of the heat exchangers 1506, 1507, 1520 in any one or more of these systems is configured to cool one or more thermal processes and receives heat therefrom.

An embodiment includes the system wherein a thermal process is a thermodynamic process.

An embodiment includes the system wherein a thermodynamic process is a thermodynamic cycle.

Figure 16:
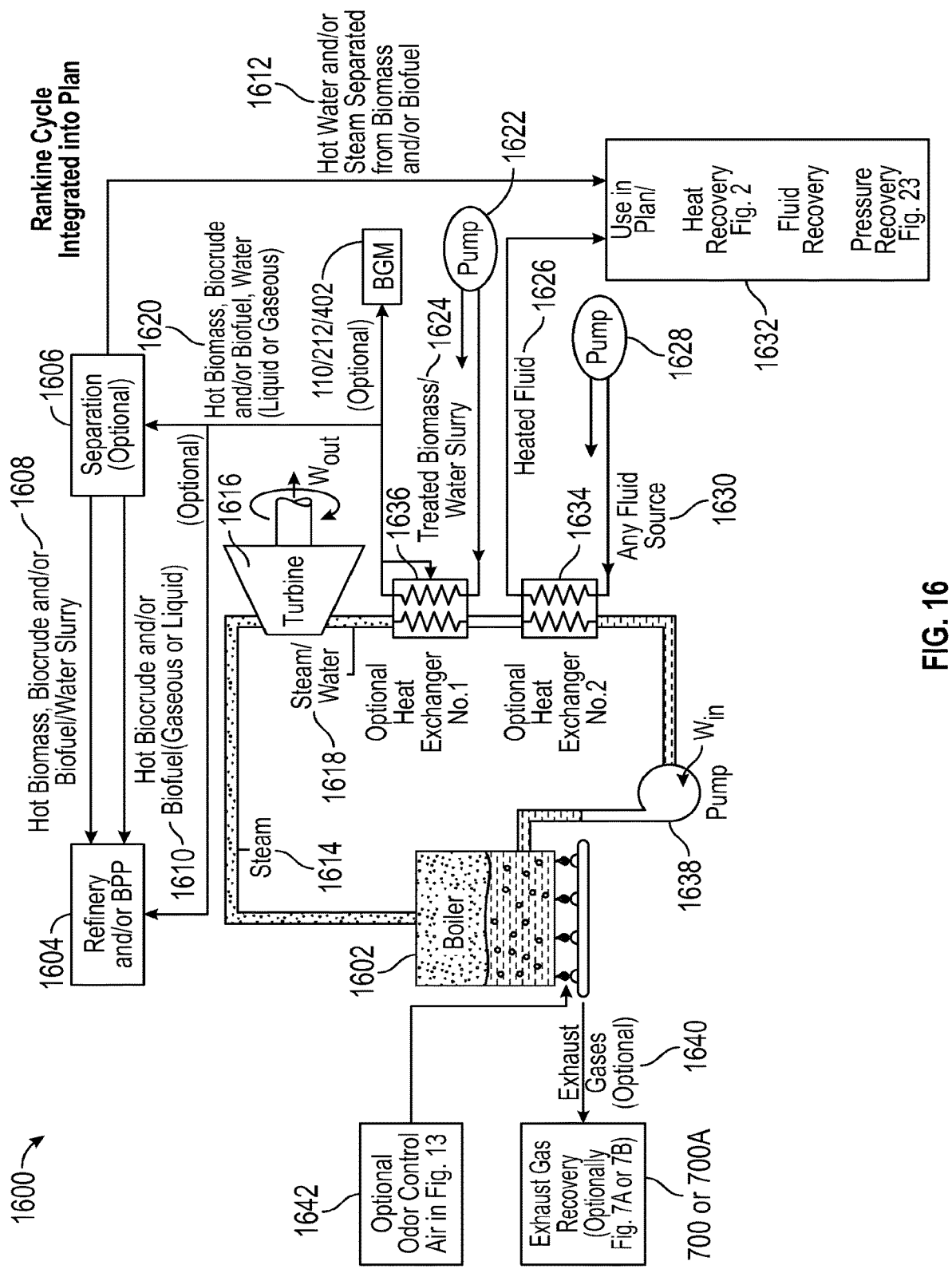
FIG. 16 is a schematic representation of a Rankine cycle incorporated into a design according to the present disclosure.

An embodiment includes the system wherein a thermodynamic cycle is a Rankine Cycle 1600, for example, FIG. 16.

Figure 17:
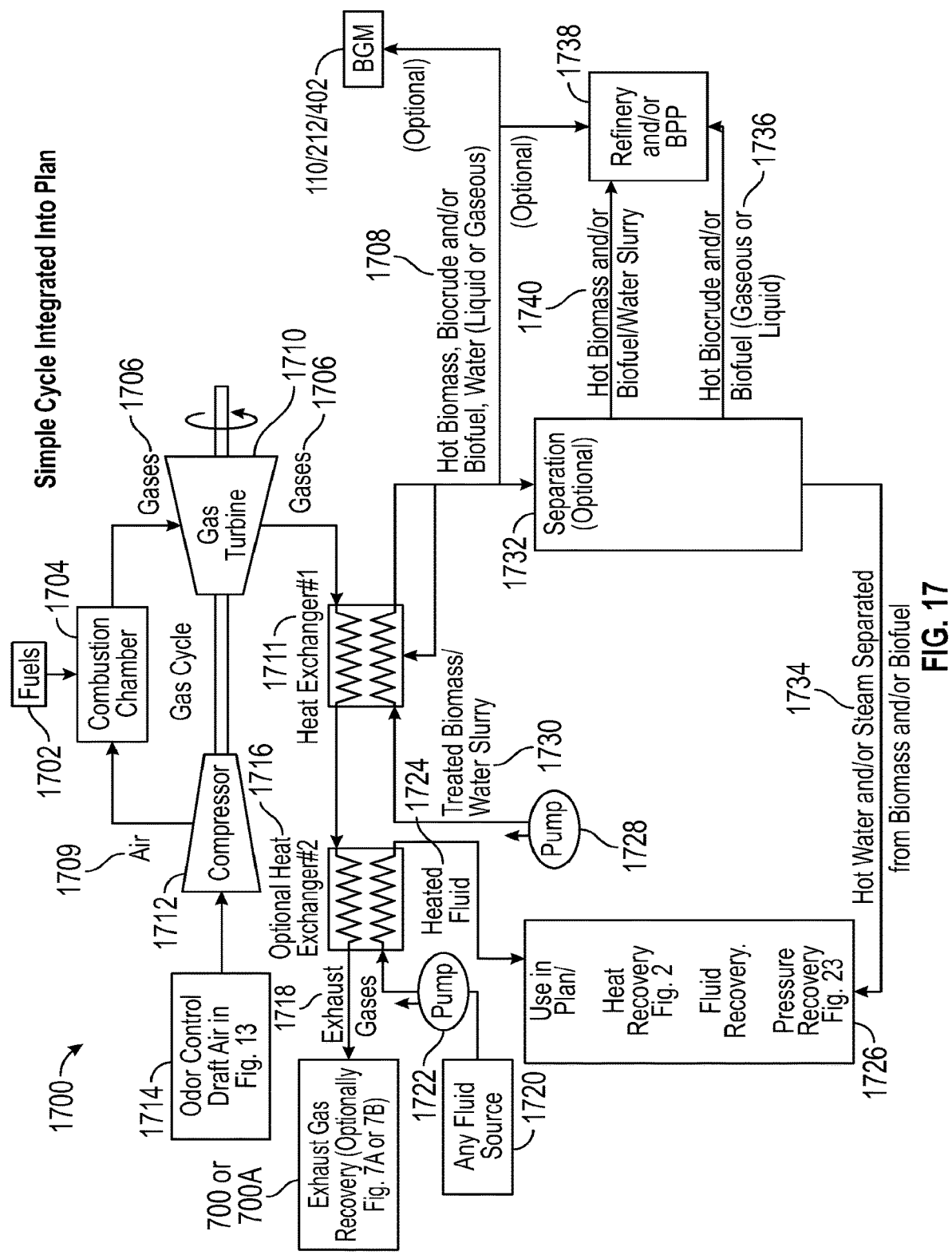
FIG. 17 is a schematic representation of a simple cycle system integrated into a design according to the present disclosure.

An embodiment includes the system wherein the thermodynamic cycle is a Simple Cycle 1700, for example, FIG. 17.

Figure 18:
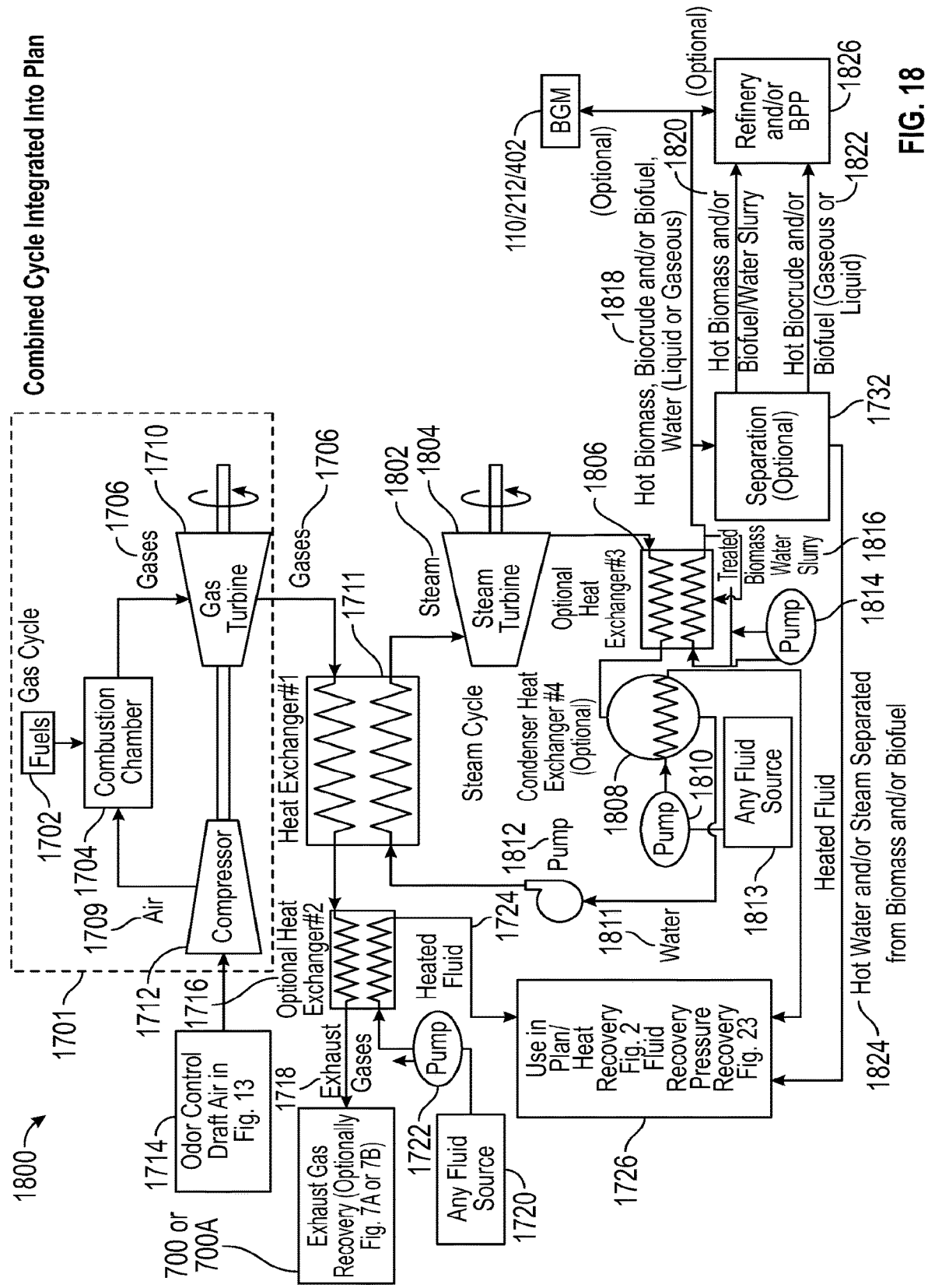
FIG. 18 is a schematic representation of a combined cycle system integrated into a design according to the present disclosure.

An embodiment includes the system wherein the thermodynamic cycle is a Combined Cycle 1800, for example, FIG. 18.

In reference to FIGS. 15A and 15B, and FIGS. 16-18, an embodiment of the disclosure includes a method of transferring heat to a component or module comprising providing the system 1500A, 1500B, 1600, 1700, 1800 and generating heat, transferring the heat to a heat transfer module 1500A, 1500B, 1600, 1700, 1800 and transferring the heat to a system module and/or a treated biomass/water slurry 1504.

An embodiment includes the method wherein the heat transfer module 1500A, 1600, 1700, 1800 comprises an outflow comprising in liquid and/or gaseous state: hot biomass 1508 1512; hot biocrude 1508, 1513; hot biofuels 1508, 1512, 1513, 1516; and/or water 1508, 1512, 1516/ steam 1508, 1512, 1516.

In reference to FIGS. 15A and 15B, and FIGS. 16-18, an embodiment of the disclosure includes a method of transferring heat to a component or module comprising providing the system 1500A, 1500B, 1600, 1700, 1800 and generating heat in a thermal process transferring the heat to a heat exchanger 1506, 1507, 1520 and transferring the heat to the system component or module, e.g., a BGM 110/212/402, 1218.

Processes described in FIG. 15A and/or FIG. 15B may be utilized at one or more points in a Rankine Cycle. In a specific embodiment 1600 and with respect to FIG. 16, the system of 1500A and/or 1500B may be integrated into a Rankine Cycle. Optional pump 1622 sends a biomass water slurry, e.g., a treated biomass/water slurry 1624 through heat exchanger 1636 wherein the now hot biomass water mixture 1620 may be submitted to another heat exchange process 1636 (not necessarily the same one), and/or a BGM 110, 212, 402 and/or to an optional separation module 1606, and/or directly to a refinery and/or BPP 1604. Hot water and/or steam from separation module 1612 may be returned for direct use e.g., in the Plan or for indirect use in Plan through heat recovery, fluid recovery and/or pressure recovery unit 1632. In a second process, pump 1628 pumps any fluid source 1630 used through heat exchanger 1634 and heated fluid 1626 returned for direct use e.g., in the Plan and/or for indirect use in Plan through heat recovery, fluid recovery and/or pressure recovery unit 1632. Heat exchangers 1634 and 1636 may be interfaced with a boiler/pump/turbine system. For example, boiler 1602 heats water to steam 1614 that drives turbine 1616. The output water/steam 1618 downstream from turbine 1616 may be processed through heat exchangers 1634 and 1636. Recovery pump 1638 transfers recovered water to boiler 1602. Odor control module 1642 (e.g., 1300) optionally feeds air to the boiler burners and exhaust gases 1640 may be fed to exhaust gas recovery modules, e.g., 700 and/or 700A in FIGS. 7A and 7B. Separation module 1606 sends hot biomass, biocrude, and/or biofuel and water 1608 and/or hot biocrude and/or biofuel in gaseous and/or liquid form 1610 to refinery and/or BPP 1604. In an embodiment, the process described above e.g., 1600 and any number or combination of the modules 1500A and/or 1500B may be used in the standard Rankine Cycle or in any variation of the Rankine Cycle, comprising the Rankine Cycle with Reheat, the Regeneration Rankine Cycle (with either open or closed feedwater heater), the Supercritical Fluid Rankine Cycle, the Organic Rankine Cycle, and any other variation of the Rankine Cycle, where cooling may be needed anywhere in the cycle, with one likely use of the process being the condensing stage of the cycle.

In an embodiment 1700, and with respect to FIG. 17, the system of 1500A and/or 1500B may be integrated into a Simple Cycle. In this embodiment, pump 1728 supplies treated biomass water slurry 1730 to heat exchanger 1711. Hot biomass, biocrude and/or biofuel and water mixture 1708 may be then sent to another heat exchange process 1711 (not necessarily the same one), and/or either directly to a refinery 1738, and/or a BPP 1738, and/or to a BGM 110, 212, 402 and/or to an optional separation module 1732. Separation module 1732 provides a hot biomass, biocrude and/or biofuel and water mixture 1740 and/or a hot biocrude and/or biofuel mixture 1736 to refinery and/or BPP 1738 for further processing. Hot water and/or steam 1734 may be transferred from separation module 1732 for direct use e.g., in the Plan and/or for indirect use in Plan through heat recovery, fluid recovery and/or pressure recovery 1726. Fuel 1702, e.g., a biofuel prepared and/or separated from a biomass growth module 212, may be burned in combustion chamber 1704 with compressed air 1709 emerging from compressor 1712. Exhaust gases 1706 drive gas turbine 1710 and then 1706 may be fed to heat exchanger 1711 and then optionally to heat exchanger 1716.

Cooled exhaust gases 1718 may be then recovered and/or processed by a recovery module, e.g., 700 or 700A. Heat exchanger 1716 may be supplied any fluid 1720 optionally by pump 1722 and heated fluid 1724 returned to recovery unit 1726. Air supplied to compressor 1712 may be optionally supplied from odor control module 1714, e.g. 1300. In an embodiment, following these heat exchange processes, the exhaust gases from the simple cycle, combined cycle (See below, 1800), and/or other thermal processes producing exhaust gases may be sent to the exhaust gas recovery module (FIG. 7A or 7B) for recovery of additional heat, treatment to remove pollutants, and use of carbon dioxide and the other processes in this system, and/or other treatment/pollution control method(s).

In one or more embodiments, e.g., those embodiments of FIGS. 15A, 15B, 16, 17, and/or 18, notwithstanding the concentration of biofuel in the biomass, a biomass/water slurry is transferred, to thermal plant to be used as a cooling fluid. A biomass/water slurry may pass through a heat exchanger to provide cooling for a thermal power plant, e.g., the cooling/condensation stage of a thermodynamic cycle (e.g., Rankine cycle, other), and/or other process steps where cooling water is needed in any thermal plant.

Optionally, thermal plant waste heat may be transferred to the biomass/water slurry using a different configuration of water sources and/or heat exchangers, e.g., any water and/or other fluid source may be used to cool the thermal plant, and/or to transfer heat to the biomass/water slurry via heat exchange and/or any other method.

In one or more embodiments, e.g., FIGS. 2, 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, thermal plant waste heat is used to refine the TBW slurry, and/or to elevate its temperature to reduce the amount of heat needed for HTP and/or other refining processes. Depending on the operating temperature and/or pressure reached in the heat exchanger, some or all of the biomass contained in the heated TBW slurry may be converted to biocrude and possibly other biofuels in situ (that is, while being conveyed through this process) via HTP and/or another mechanism.

In one or more embodiments, e.g., FIGS. 2, 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, depending on the amount of heat needed for HTP or HTP preheating, if used, and/or other processes and/or project parameters, such as the type, size, and/or operating temperature of thermal plant working fluid in use, the volume of water available from the TBW slurry and/or other sources in the Plan, and/or the amount of cooling needed in the thermal plant to achieve a complete condensation step in any thermodynamic cycle, only one or more than one heat exchange process using either the TBW slurry and/or any other fluid source may be used cool the thermal plant and/or to transfer thermal plant waste heat to the Plan, and in any sequence. For example, a heat exchanger containing the TBW slurry may be used first in the condensation step of a thermodynamic cycle, and/or another heat exchanger containing another fluid source may be used second, and another heat exchanger using a third fluid source may be used as a third step in cooling the working fluid and/or transferring heat to the Plan.

In one or more embodiments, an initial heat exchange process, due to the higher temperatures attainable, may be used to provide heat for high temperature HTP of the TBW slurry, where a second or third heat exchange process may be needed to further reduce the temperature of the working fluid to complete the condensation stage of a thermodynamic cycle. In an embodiment, the waste heat from a second or third heat exchange process may be directed to lower heat applications in the Plan, such as heating the BGM, cellulosic ethanol, and/or to processes where any amount of heating/ preheating is desirable, such as desalination. In an embodiment, any residual heat after other processes in the Plan requiring heat have been supplied, may be directed toward desalination. Alternately, only one or more than two different heat exchange processes using either type of cooling fluid may be used, depending on design considerations, e.g., whether it is preferable to perform HTP or another process in situ, or at the refinery. In an embodiment, the TBW Slurry and/or any other fluid source may be heated progressively also in two or more heat exchangers also where beneficial, for example, where it may be beneficial to more gradually heat the TBW slurry to avoid problems in the system such as biofouling. In this embodiment, for example, the TBW slurry at ambient temperature may be directed to one heat exchange process which raises its temperature to a certain point (e.g., 120 degrees C.), and then may be directed to another heat exchange process to further elevate its temperature to 350 degrees C., for example, or another temperature beneficial to the preheating for or performance of HTP. Likewise, any other fluid source in the Plan (e.g., FIG. 15B) may also be routed through two or more heat exchangers in the design (comprising step 1520) before use in the Plan/Recovery 1524 in order to optimize engineering considerations, and/or to provide the optimal quantity and/or temperature of heated fluid for any application in the Plan. These heat exchange processes may occur in the same thermal process, thermodynamic cycle, in different thermal plant technologies, and/or in any other process where heat maybe either generated and/or reclaimed. In an embodiment, all needs for heat and/or cogenerated cooling (which is generated by heat) in the Plan may be considered, and heat/waste heat of different temperatures may be prioritized and budgeted for all needs for heat and/or cooling within the Plan, with some or all of the heat being supplied by any heat exchange process in the condensation stage of a thermodynamic cycle, by any other any thermal process in the thermal plant, comprising possibly primary process heat, and/or by heat and/or reclaimed heat from any heat source(s) in the Plan (See FIG. 2). In an embodiment, the need for heat in all processes may also be planned in accordance with the need for cooling of all thermal plant technologies, such that adequate cooling is provided, and any leftover heat after all other processes requiring heat have been heated, may be directed to the desalination plant, if present in the Plan, and/or possibly to discharge.

In an embodiment e.g., FIGS. 2, 15A and/or 15B, additional heat, optionally thermal plant primary process heat and/or heat from a different source (e.g., a dedicated burner) may be applied at any stage of the process depicted in FIG. 15A where it is beneficial.

With reference to FIG. 18, and in embodiment 1800, the system of 1500A and and/or 1500B may be integrated into a Combined Cycle. In Gas Cycle 1701, fuel 1702, e.g., a biofuel prepared and/or separated from a biomass growth module 212, may be burned in combustion chamber 1704 with compressed air 1709 emerging from compressor 1712. Exhaust gases 1706 drive gas turbine 1710 and then 1706 may be fed to heat exchanger 1711 and then optionally to heat exchanger #2 1716. Air supplied to compressor 1712 may be optionally supplied from odor control module 1714 e.g., 1300. Gases emerging from heat exchanger 1711 may be fed to optional heat exchanger 1716. Cooled exhaust gases 1718 may be then recovered and/or processed by a recovery module, e.g., 700 or 700A. In a Steam Cycle 1801, pump 1812 drives water through heat exchanger 1711 and resulting steam 1802 drives turbine 1804.

Recovered steam and water may be optionally processed through heat exchanger #3 1806 then condenser heat exchanger #4 1808, and water 1811 returned to pump 1812.

Pump 1814 supplies heat exchanger 1806 with a treated biomass/water slurry 1816 and hot biomass, biocrude and/or biofuel and water mixture 1818 that emerges from exchanger 1806 as may be then sent either to another heat exchange process 1806 (not necessarily the same one), and/or directly to a refinery and/or BPP 1826, and/or to a BGM 110, 212, 402 and/or to an optional separation module 1732. Hot biomass and/or biofuel and water mixture 1820 and/or a hot biocrude and/or biofuel mixture 1822 may be sent to refinery and/or BPP 1826. Hot water and/or steam 1824 may be sent from separation module 1732 for direct use e.g., in the Plan and/or for indirect use in Plan through heat recovery, fluid recovery and/or pressure recovery unit 1726. Optional heat exchanger 1716 may be supplied any fluid 1720 by pump 1722 and heated fluid returned to recovery unit 1726. Optional heat exchanger 1808 may be supplied any fluid 1813 by pump 1810 and heated fluid returned to recovery unit 1726.

Heat or cooling either generated or recovered from any process, as described in the present disclosure may be transferred within the Plan in any manner known to those in the art. FIGS. 12A-12E illustrate some non-limiting embodiments.

In an embodiment, with respect to FIG. 12A, heated fluid 1208, e.g., which may be heated water source from a thermal plant and/or other heat-intensive technology, may be routed to heat exchanger 1200. Cool fluid, e.g., water and a biomass 1202, may be separately transferred to heat exchanger 1200. Heat from heated fluid 1208 may be transferred to cool fluid 1202, such that after heat exchange cooled fluid 1204 and heated fluid 1206 emerge from the heat exchanger 1200.

With respect to FIG. 12B, heated fluid 1216, may be transferred to unit 1212, e.g., a BGM, and processed, whereupon the heat may be transferred to module 1210, whereupon the heat and fluid may be recovered 1210. Another fluid, e.g., a heated fluid from a thermal plant 1214, may supply heat, cooling, nutrients, acidity, alkalinity, and/ or any other element to module 1212. For example, if heated fluid 1216 may be too hot for process 1212, other fluid may be used to regulate temperature. If other elements may be involved in this process (e.g., biomass), those elements may be provided and/or processed e.g., as described herein.

With respect to FIG. 12C, heated fluid (e.g., water) 1216 may be transferred to module 1220. Module 1220 may comprise another module 1218 that requires heat input for functioning. After heat transfer, fluid may be transferred to module 1222 whereupon the heat and fluid from the heated fluid 1216 may be recovered.

In an embodiment, e.g., FIGS. 2, 3, 6, 7A, 7B, 11, 12A, 12B, 12C, 12D, 12E, 15A, 15B, 16, 17, 18, 19, 20A, 20B, 20C, 20D and/or other figures and/or description relevant to heat capture, and/or transfer, a BGM and/or its components, and/or water transfer, a BGM, a BGU, a BGU subunit and/or any other BGU component may be fully or partially immersed in a pool, other container, water body (e.g., a pond, lake or stream) fed by a water supply, e.g., from onsite and/or offsite, used to provide cooling, or alternatively, to capture waste heat from a thermal plant, and to supply heat, wherein the BGM temperature may be regulated by contact with heated and/or cool water supply. Heated and/or cooled air or other fluid e.g., from the thermal plant and/or other modules may be used to fill containers which may be configured to come in contact with or partially or fully surround the BGM, a BGU, or any of its components in order to transfer heat and/or cooling. Heat and/or cooling may be supplied 234 by offsite sources 228 optionally comprising a water supply provided by offsite water source(s) comprising a fresh water source, 302, water intake for salt water 314, and/or other sources of heat and/or cooling e.g., in gaseous and/or liquid form originating offsite.

Figure 12D:
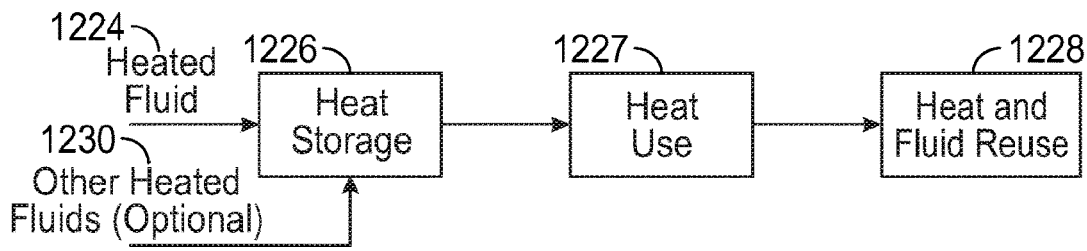
FIG. 12D is a fourth schematic representation of heated or cooled fluid flow according to the present disclosure.

With respect to FIG. 12D, a heated fluid, e.g., water 1224, may be transferred to a heat storage unit 1226. Heat storage unit 1226 optionally receives another heated fluid.

Upon receiving the need, heat storage unit 1226 transfers heat to another module 1227 and any excess heat and/or fluid may be transferred to module 1228. The same process may be used where cooling takes the place of heat in the process in order to store and/or transfer cooling. This process may be used anywhere e.g., in the Plan where heat and/or cooling may be present, e.g., to manage and/or regulate the flow of heat cooling and/or fluids to any process.

Figure 12E:
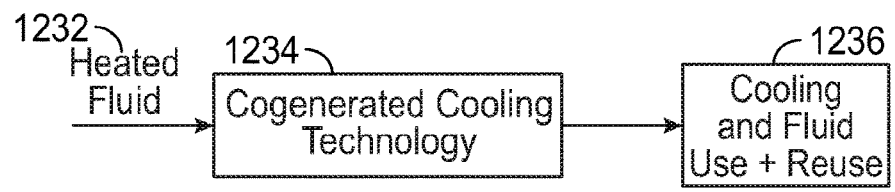
FIG. 12E is a fifth schematic representation of heated or cooled fluid flow according to the present disclosure.

With respect to FIG. 12E, heated fluid 1232, e.g., water used to cool a thermal plant, may be transferred to a cogenerated cooling technology module 1234. The cooled fluid may be used and/or reused in module 1236.

In an embodiment, with respect to FIGS. 12B, 12C, and 12D, cooling may be substituted for heat wherever heat or "heated" may be noted, and cooling may take the place of heating to reverse the processes depicted.

With respect to FIG. 19, in an embodiment, a treated biomass/water slurry 1910 may be pumped to a first section of a boiler designed with two sections 1922. Application of heat 1924 causes partial or full in-situ HTP and/or other refining and/or separation into 3 layers: 1.) light oil possibly mixed with biomass; 2.) water; and optionally 3.) heavy oil possibly mixed with biomass and residuals. Drains remove materials from each of the three layers 1927 at controlled rates, which may be then sent to a refinery and/or BPP 1929. All outflows from the refinery and/or BPP 1925 may be routed for heat recovery, water recovery, and/or pressure recovery 1930. The boiler 1922, has a selective filtering division 2010 which allows water and possibly other small molecules, such as ethanol, to pass through from the first section to the second section (represented here as an inner section). An optional stirring/agitation device may be provided in the first section to unclog the selectively permeable layer 2003. Water and possibly other small molecules which pass from the first section to the second section, possibly combined with another water source pumped to second section, may be converted to steam and trace biomass, biocrude and/or biocrude 1902, and the resulting pressure drives turbine 1904. Resulting mixture comprising optionally steam, hot biomass, biocrude, biofuel, and/or water or a portion thereof (e.g. vapor) 1906 may be optionally then cooled with heat being recovered and used in Plan 1916 in condenser 1918. A cooled biofuel and water mixture 1912 may be then sent to refinery 1908. Alternatively, or together, mixture 1906 may be sent directly to refinery 1908 upon departure from turbine 1904. All outflows 1925 from the refinery and/or BPP 1908 may be routed for heat recovery, water recovery, and/or pressure recovery 1930. Air may be optionally fed to burner 1924 from odor control air module 1928 (e.g., 1300). Exhaust gas 1926 may be optionally captured in an exhaust gas recovery module 700 or 700A (e.g., with reference to FIG. 7 or 7A). Boiler 1922 may comprise one or more embodiments or designs to accommodate processing a water/biomass/biofuel slurry. For example, with respect to FIG. 20A, boiler 1922 comprises a first section wall 2002 and a second section wall 2020. The annular space between first section wall 2002 and second section wall 2002 may be configured to contain a multi-layer composition, e.g., a light oil biomass layer 2006 with a density less than the density of water, a water layer 2012, and a heavy-oil biomass and residuals layer 2009 with a density greater than the density of water. A selective filtering division allows water and possibly other small molecules to pass from first section to second section 2010. An optional stirring/agitation device may be provided in the first section to unclog the selectively permeable layer 2003. An optional stationary or movable lid may be provided to prevent evaporation of biofuels from the first section and splashing from first section to second section 2004. An entry port 2008 feeds a treated biomass/water slurry (TBW slurry) to the annular space. An optional drain may be provided to drain the second section 2021. The flow rate of the TBW slurry may be managed using flow controls.

As the TBW slurry may be provided, drains 2018, 2016 and 2014, may be configured to provide a managed feed of the three layers out of the annular space. An additional optional inlet may be provided to provide additional flow of water to second boiler section as necessary 2019. The configuration of the boiler, comprising the first and/or second section shapes, may be modified in order to optimize any or all of the processes conducted in the boiler, comprising HTP of the biomass contained in the TBW slurry, vaporization of water, and/or the rates at which these processes occur.

In reference to FIGS. 19-20, an embodiment of the disclosure includes a system 1900 configured to use a treated biomass/water slurry 1910 as a thermodynamic process working fluid.

An embodiment includes the system further comprising a boiler 1922 comprising a first 2002 and second 2020 section wherein the first and second regions are adapted to process the slurry 1910.

An embodiment includes the system wherein the first section of the boiler 2002 is configured to receive the slurry 1910.

An embodiment includes the system further comprising a selective filtering division 2010 positioned between the first 2002 and second 2020 sections.

An embodiment includes the system wherein the filtering division 2010 is configured to permit water to pass from the first section 2002 to the second section 2020.

An embodiment includes the system wherein the filtering division 2010 is configured to permit small molecules to pass from the first section 2002 to the second section 2020.

An embodiment includes the system wherein the small molecules have an average molecular weight of from 18 g/mol to 46 g/mol.

An embodiment includes the system further comprising a burner or other heat source 1924 configured to heat the first section 2002 and/or the second section 2020.

An embodiment includes the system wherein the burner or other heat source 1924 is configured to receive an air supply from an air treatment/odor control system 1928, e.g., FIG. 13, 1300 for the Plan.

An embodiment includes the system wherein the burner or other heat source 1924 is configured to send exhaust gas 1926 to an exhaust gas recovery system 700, 700A, e.g. FIG. 7A or 7B for the Plan.

An embodiment includes the system configured to separate the treated biomass water slurry 1910 into one or more layers in the boiler 1922.

An embodiment includes the system wherein a layer comprises water 2012, light oil/biomass 2006, heavy oil/biomass 2009 and/or residuals 2009.

An embodiment includes the system wherein the boiler 1922 comprises a drain 2018 in communication with the first section 2002.

An embodiment includes the system wherein the boiler 1922 comprises a second drain 2016 in communication with the first section 2002 and positioned below the first drain 2018.

An embodiment includes the system wherein the boiler 1922 comprises a third drain 2014 in communication with the first section 2002 and positioned below the second drain 2016.

An embodiment includes the system wherein water 2012 is below the first drain 2018.

An embodiment includes the system wherein the second drain 2016 is in communication with water 2012.

An embodiment includes the system further configured to drain the light oil/biomass layer 2006 and/or the optional heavy oil/biomass layer 2009 and/or residuals 2009 and/or optionally water 2012, and a remaining water layer transferred to the second section 2020 and/or drained 2021.

An embodiment includes the system wherein the second section 2020 is configured to vaporize the water 2012 and/or the small molecules optionally comprising steam 1902, and optionally trace biomass, biocrude, and/or biofuel 1902.

An embodiment includes the system wherein the vaporized water and/or small molecules 1902 are directed to drive a turbine 1904 to provide a downstream fluid optionally comprising steam 1906, water 1906, and optionally small molecules comprising biomass, biocrude, and/or biofuel 1906.

An embodiment includes the system wherein the downstream fluid 1906 is sent to a refinery module 1908; a BPP module 1908; and/or an optional condensing unit 1918, which partially separates biofuel and water 1912 and recovers heat 1914, 1916 to the Plan, for example, FIG. 2.

An embodiment includes the system wherein the partially separated biofuel and water 1912 are sent to the refinery module 1908 and/or BPP module 1908.

An embodiment includes the system further configured to transfer the light oil/biomass layer 1927 and/or the optional heavy oil biomass/residuals layers 1927 and optionally water 1927 to a refinery module 1929 and/or BPP module 1929.

An embodiment includes the system further comprising one or more outflows 1925 from the refinery module 1929 and/or BPP 1929.

An embodiment includes the system wherein the one or more outflows 1925 are optionally directed to modules for the recovery and reuse in the Plan of heat 1930, e.g., FIG. 2, water 1930, e.g., FIG. 3, and/or pressure 1930, e.g., FIG. 23.

An embodiment includes the system wherein the first 2002 and/or second 2020 boiler section comprises a cross-sectional shape selected from: a cylinder; an elliptical cylinder; an elliptical cylinder with a longer half ellipse on one side and a shorter half ellipse on the opposite side; and/or any vertical cross section of the above shapes wherein they are divided to comprise both boiler sections 2002, 2020.

An embodiment includes the system wherein the boiler 1922 comprises one or more of the following features: a treated biomass/water slurry entry point 2008; an optional lid 2004, which may be movable or stationary; a light oil/biomass drain 2018; a heavy oil/biomass drain 2014; a water layer drain 2016; an optional drain on the bottom of the second section 2021; a lip on the top of the second section 2020 that extends above the first section 2002; an optional inlet 2019 to the second section 2020 for additional water supply to the second section 2020 of the boiler 1922; one or more agitation devices 2003 in the first section 2002 to stir the water 2012 in order to unclog the selective filtering division 2010 (e.g., remove biomass oil or other materials from the selective filtering division 2010); and/or aside from the features depicted, the boiler may also make use of any other accessories used in boilers that are known to those skilled in the art including but not limited to optionally: pressure controls, safety valves, water level indicators, sight glass, water gauge or water column, bottom blowdown valves, continuous blowdown valves, flash tanks, automatic blowdown/continuous heat recovery system, hand holes, steam drum internals, low-water cutoffs, surface blowdown line, circulating pump, feedwater check valve, clack valve, top feed, desuperheater tubes or bundles, and/or chemical injection lines.

An embodiment includes the system wherein the steam system 1902, 1904 used with the boiler may also optionally make use of steam system accessories known to those in the art.

In reference to FIGS. 19-20, an embodiment of the disclosure includes a method for transferring heat from a boiler 1922 within the system 1900 to a module, unit, or subunit in the system comprising providing a treated biomass/water slurry 1910, heating the slurry 1910 in the boiler 1922 to provide a working fluid, and transferring the working fluid to the module, unit or subunit in the system.

The thermal plant may provide heat and/or cooling (e.g., cogenerated cooling) for biomass and/or biofuel refining by HTP and/or other biomass and/or biofuel processing methods, as shown in FIG. 1, represented by the arrows labeled as "Heat and/or Cooling" exiting the thermal plant and entering the boxes "Refinery", and "BPP (Downstream Processing)", and/or for other processes e.g., FIGS. 1 and/or 2.

Figure 11:
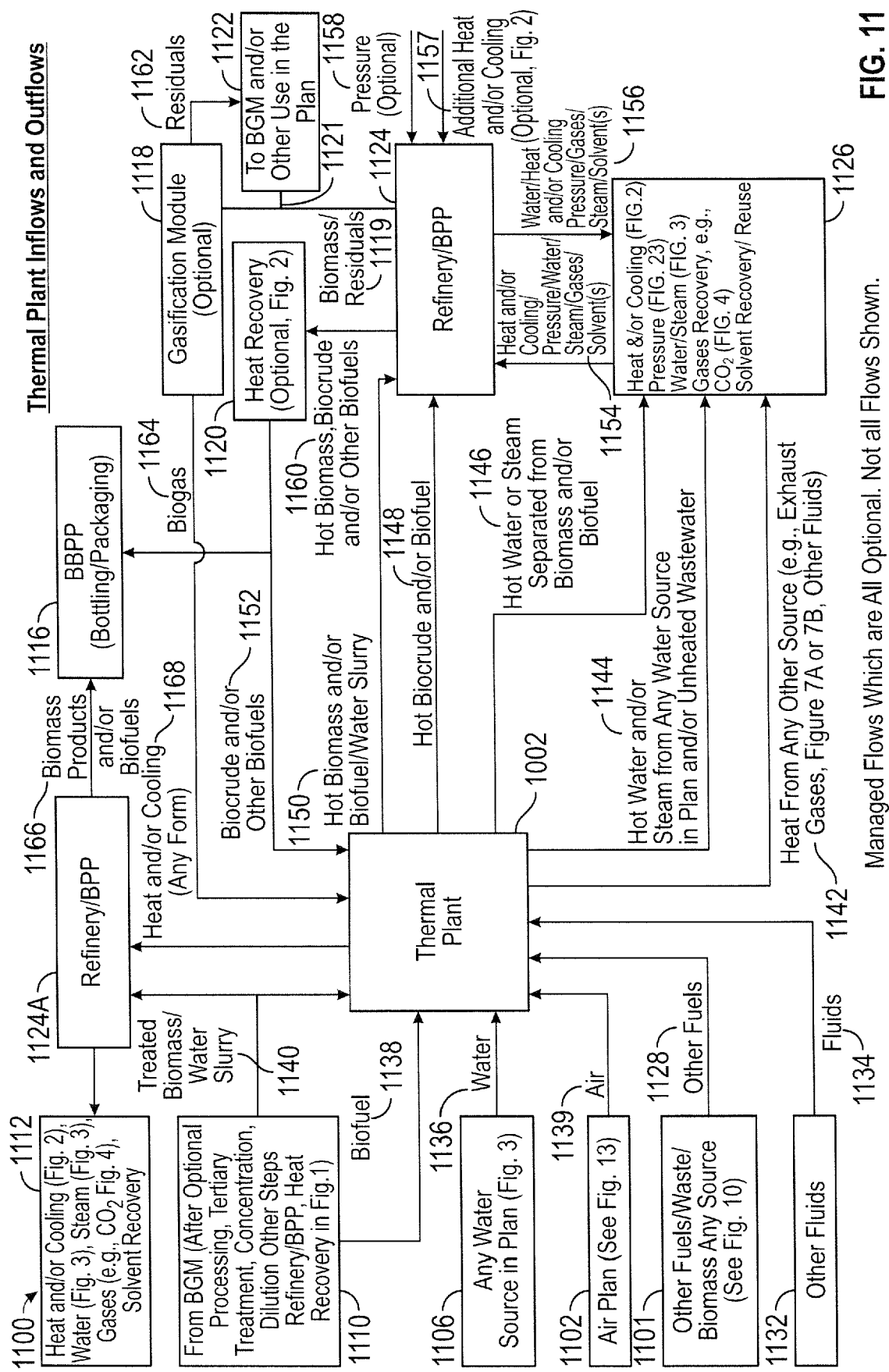
FIG. 11 is a schematic representation of thermal plant inflows and outflows according to the present disclosure.

In an embodiment, FIG. 11 shows different examples as to how thermal plant heat may be provided for these processes using flows of different fluid streams into and/or out of the thermal plant. With reference to FIG. 11, 1100, some possible relevant inflows into the thermal plant 1002 may be shown (not all inflows): a treated biomass/water slurry 1140 from a BGM 1110 after optional processing steps e.g., FIG. 1, 100, biofuels 1138 optionally processed after generation in the BGM 1110, water 1136 from any water source e.g., in the Plan 1106, air 1139 optionally from air treatment/odor control module 1102, 1300, other fluids 1134 from any source 1132, biogas 1164 from a gasification module 1118, biocrude and/or other biofuels 1152 from a refinery and/or BPP 1124, and/or other fuels 1128 from any source 1101, optionally comprising waste, biomass, and sources in IG. 10, 1000. Any or all of these inputs may be used in the thermal plant 1002, and the water and/or air or other fluid inputs may be used to cool the thermal plant 1002, and in the process, capture heat from the thermal plant 1002. FIG. 11 shows some possible outflows of the thermal plant 1002 (not all outflows) once these substances may be heated, comprising heat and/or cooling for downstream processing 1168, a hot biomass and/or biofuel/water slurry 1150, hot biocrude and/or biofuel 1148, hot water and/or steam separated from biomass and/or biofuel 1146, hot water and/or steam from any water source in the design and/or unheated wastewater 1144, heat from any other source 1142, which may comprise heat captured by combusted air if used in a Thermal Process (e.g., 700 or 700A), air and/or any other fluid used in a heat exchanger and/or other heat transfer process, comprising organic compounds used in an organic Rankine cycle 1142, and heat in any form and/or cogenerated cooling 1168. The hot biomass and/or biofuel/water slurry 1150 and/or hot biocrude and/or biofuel 1148 streams, may be then directed to a Refinery and/or BPP for HTP and/or other extraction and/or separation and/or processing methods 1124.

Additional possible inputs to these processes may be shown, comprising optional pressure 1158 and optionally additional heat 1157. Outflows of these processes comprise hot biocrude, biofuels and/or biomass 1160, and water, pressure, heat, cooling, gases, and solvent(s) which may be recovered 1126. Hot biocrude and/or biofuels and/or biomass 1160 produced in the Refinery and/or BPP 1124, from which heat may be recovered 1120, may then be directed back to the thermal plant as fuels 1152, and/or to a BBPP (for bottling/packaging) 1116. Water, heat, pressure, gases, solvent(s), and/or cooling from these processes 1156 may be recovered 1126 for reuse e.g., in the Plan e.g., FIG. 2 (heat and/or cogenerated cooling), FIG. 3 (water), and FIG. 23 (pressure). Additionally, any portion of the aforementioned thermal plant outflows may be sent to a gasification module 1118 to produce biogas 1164. The biogas may be directed to the thermal plant 1002 as a fuel, with any residuals 1162 being directed to the BGM and/or other use e.g., in the Plan, e.g., as described herein 1122. The following thermal plant discharges: hot water and/or steam separated from biomass and/or biofuel 1146, and hot water and/or steam and/or unheated wastewater from any water source e.g., in the Plan 1144, heat from any other source 1142 and/or water, steam, heat, pressure, gases, cooling, and/or solvents reclaimed from the Refinery and/or BPP 1124A, 1126, 1112 may be used to provide the following resources to the Plan: heat/cogenerated cooling e.g., FIG. 2, water (FIG. 3), gases, comprising carbon dioxide (FIG. 4), solvents, and pressure recovery e.g., as described herein and/or e.g., FIG. 23. These resources may be directed to the refinery and/or BPP 1124, and/or elsewhere e.g., in the Plan as needed. Heat in any form and/or cogenerated cooling 1168 may be directed to a BPP 1124 for downstream processing of biomass, which may take place at the BPP 1124 to assist in processes there. Biomass products 1166 derived from the BPP processes may be directed for Bottling/Packaging at the BBPP 1116, as well as part or all of the biocrude and/or other biofuels and/or biomass from the refinery after optional heat recovery 1120. Biomass/residuals from the Refinery/BPP 1124 may be directed 1119 to the Gasification Module (Optional) 1118, and/or 1121 to the BGM and/or Other Use e.g., in the Plan 1122. Heat and/or cooling, water, steam, carbon dioxide and/or other gases, and/or solvents from BPP processes may be recovered for reuse e.g., in the Plan 1112, 1126 e.g., FIGS. 2, 3, and/or 4 (Heat/cooling, water, and/or carbon dioxide). All of the flows shown in FIG. 11, and throughout this disclosure may be optional managed flows, and all flows may not be used in all embodiments.

In reference to FIG. 11, an embodiment of the disclosure includes a system configured to provide resources to and/or receive resources from a thermal plant module comprising flows to and/or from a thermal plant module 1002 wherein the flows are selected from: a treated biomass/water slurry 1140; biofuel 1138, 1152; biogas 1164; biocrude 1152; biomass 1101; waste 1101; other fuels 1128; air 1139; water 1136; anhydrous fluid(s) 1132, 1134; mixture of water and anhydrous fluid(s) 1132, 1134, 1136; a hot biomass and/or biofuel/water slurry 1150; hot biocrude and/or biofuel 1148; hot water or steam separated from biomass and/or biofuel 1146; hot water and/or steam from any water source in the Plan, for example, FIG. 3 1144; unheated wastewater 1144; and/or heat and/or cooling 1142, 1168 from any one or more of: a treated biomass/water slurry 1140; biofuel 1138, 1152; biogas 1164; biocrude 1152; biomass 1101; waste 1101; other fuels 1128; air 1139; water 1136; anhydrous fluid(s) 1132, 1134; mixture of water and anhydrous fluid(s) 1132, 1134, 1136; a hot biomass and/or biofuel/water slurry 1150; hot biocrude and/or biofuel 1148; hot water or steam separated from biomass and/or biofuel 1146; hot water and/or steam from any water source in the Plan, for example, FIG. 3 1144; unheated wastewater 1144; and/or any other source in the Plan, for example, FIG. 7A or 7B.

An embodiment includes the system wherein optionally a portion of the biofuel comes from a BGM outflow fluid that is optionally processed (termed a "treated biomass/water slurry") 1140.

An embodiment includes the system wherein the BGM outflow fluid 1140 is the product of processing which optionally comprises: tertiary treatment 1110, 114; gravity thickener process and/or other methods known to a person of ordinary skill in the art (for example, author Shelef, et. al, 1984 and Pandey et. al, 2013 pgs. 85-110) to concentrate/separate biomass and water 1110, 118; dilution 1110, 118; treatment in a refinery and/or BPP module 1110, 120; and/or treatment in a heat recovery module 1110, 135.

An embodiment includes the system wherein optionally a portion of the treated biomass/water slurry 1140 is directed to a refinery and/or BPP module 1124A.

An embodiment includes the system wherein biomass products and/or biofuels 1166 are sent from the refinery and/or BPP module 1124A to a BBPP module 1116.

An embodiment includes the system wherein heat and/or cooling 1112, for example, FIG. 2, water 1112, for example, FIG. 3, steam 1112, for example, FIG. 3, gases 1112, e.g. CO2, for example, FIG. 4, pressure 1112, for example, FIG. 23, and/or solvent(s) 1112 are recovered for use in the Plan from the refinery and/or BPP module 1124A.

An embodiment includes the system wherein heat and/or cooling 1168 from the thermal plant module 1002 are optionally provided to the refinery and/or BPP module 1124A.

An embodiment includes the system wherein the hot biomass and/or biofuel/water slurry 1150 is processed in a refinery and/or BPP module 1124.

An embodiment includes the system wherein the hot biocrude and/or biofuel 1148 are processed in the refinery and/or BPP module 1124.

An embodiment includes the system wherein the refinery and/or BPP module 1124 generates an output of: biomass 1119; residuals 1119; hot biomass, biocrude and/or other biofuels 1160; water 1156; steam 1156; heat and/or cooling 1156; pressure 1156; gases 1156; and/or solvent(s) 1156.

An embodiment includes the system wherein the hot biomass, biocrude and/or other biofuels 1160 are sent to an optional heat recovery module 1120.

An embodiment includes the system wherein the hot biomass, biocrude and/or other biofuels 1160 optionally processed in the heat recovery module 1120, wherein the biocrude and/or other biofuels 1150 are provided to the thermal plant module 1002.

An embodiment includes the system wherein optionally biomass 1119 and/or residuals 1119 are sent from the refinery and/or BPP module 1124 to a gasification module 1118, and/or are sent to and/or received from 1121 a BGM 1122.

An embodiment includes the system wherein the gasification module 1118 generates biogas 1164 and/or residuals 1162 from a CHG module, and/or an anaerobic digestion module.

An embodiment includes the system wherein the biogas 1164 is provided to the thermal plant module 1002.

An embodiment includes the system wherein the residuals 1162 are sent to a BGM 1122 or for other use in the Plan 1122.

An embodiment includes the system wherein optional additional heat and/or cooling 1157 is provided to the refinery and/or BPP module 1124. "Additional heat" may comprise the portion of heat needed to complete a refining or BPP process which is not supplied by the Thermal Plant.

An embodiment includes the system wherein the optional additional heat and/or cooling 1157 is provided by the thermal plant module 1002.

An embodiment includes the system wherein additional pressure optionally from the Plan (e.g., FIG. 23) 1158 is provided to the refinery and/or BPP module 1124.

An embodiment includes the system further comprising optionally recovered 1126 for use in the Plan: heat and/or cooling, for example, FIG. 2; pressure, for example, FIG. 23; water, for example, FIG. 3; steam, for example, FIG. 3; and/or gases, e.g. CO2, for example, FIG. 4, 1142, 1144, 1146 from the thermal plant module 1002; and/or heat and/or cooling 1156, for example, FIG. 2; pressure 1156, for example, FIG. 23; solvent(s) 1156, gases 1156, e.g. CO2, for example, FIG. 4; water 1156, for example, FIG. 3; and/or steam 1156, for example, FIG. 3 from the refinery and/or BPP module 1124.

An embodiment includes the system wherein recovered 1126 for use in the Plan: heat and/or cooling 1154, for example, FIG. 2; pressure 1154, for example, FIG. 23; water 1154, for example, FIG. 3; steam 1154, for example, FIG. 3; gases 1154, e.g. CO2, for example, FIG. 4; and/or solvent(s) 1154 are provided to the refinery and/or BPP module 1124.

In reference to FIG. 11, an embodiment of the disclosure includes a method of providing resources to and receiving resources from the thermal plant module 1002 comprising providing the system 1100 with one or more flows of: a treated biomass/water slurry 1140; biofuel 1138, 1152; biogas 1164; biocrude 1152; biomass 1101, 1128; waste 1101, 1128; other fuels 1128; air 1139; water 1136; anhydrous fluid(s) 1132, 1134; mixture of water and anhydrous fluid(s) 1132, 1134; a hot biomass and/or biofuel/water slurry 1150; hot biocrude and/or biofuel 1148; hot water or steam separated from biomass and/or biofuel 1146; hot water and/or steam from any water source in the Plan, for example, FIG. 3 1144; unheated wastewater 1144; and/or heat and/or cooling from any one or more of: a treated biomass/water slurry 1140; biofuel 1138, 1152; biogas 1164; biocrude 1152; biomass 1101, 1128; waste 1101, 1128; other fuels 1128; air 1139; water 1136; anhydrous fluid(s) 1132, 1134; mixture of water and anhydrous fluid(s) 1132, 1134; a hot biomass and/or biofuel/water slurry 1150; hot biocrude and/or biofuel 1148; hot water or steam separated from biomass and/or biofuel 1146; hot water and/or steam from any water source in the Plan, for example, FIG. 3 1144; unheated wastewater 1144; and/or any other source in the Plan, for example, FIG. 7A or 7B 1142, 1168; and directing the flows to and from the thermal plant module 1002.

FIGS. 12A through 12E and 15A and 15B illustrate in some embodiments how heat or cooling may be transferred from any source to another within the Plan. FIGS. 15A, 15B, and FIGS. 16-20D illustrate in some embodiments how heat may be transferred to the inflows shown in FIG. 11 which may be used to cool the thermal plant, and how the heated outflows shown in FIG. 11 may result, and heat and/or cooling from those heated. The examples may be illustrative only. Any means known to those of skill in the art may be used to transfer heat and/or cooling.

The biomass, biocrude, and/or biofuel and water mixture that may be the product of the BGM, after additional possible treatment and/or concentration/separation and/or dilution techniques (See FIG. 1), called the "treated biomass/water slurry" or "TBW slurry" may be used as a cooling fluid in any thermodynamic cycle, and/or in any other thermal process, and/or possibly as the working fluid in such processes in the same way that water may be normally used in any of these processes. Some examples may be presented below. The following may be only examples, and may be not intended to limit the use of heat transfer in any manner with respect to the Plan. Any means of heat transfer known to those of skill the art may be used to heat and/or cool either in a standard fashion known to the art, and/or by simple substitution of the TBW slurry where water would normally be used, and processing of the heated TBW slurry e.g., as described herein.

One way the treated biomass/water slurry may be used may be as the cooling fluid in any thermodynamic cycle, in particular, the condensing stage of a cycle.

FIGS. 15A and 15B depict two possible modules that may be used to transfer heat from the thermal plant and/or other heat and/or cooling sources to the Plan.

FIG. 15A depicts a module which uses the treated biomass/water slurry as a cooling fluid in any thermal process, comprising possibly a thermodynamic cycle. The TBW slurry may be pumped into a heat exchanger and cools the working fluid, capturing waste heat in the process. In an embodiment, e.g., FIGS. 2, 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, the waste heat may be used to refine the TBW slurry, and/or to elevate its temperature to reduce the amount of heat needed for HTP and/or other refining processes. Depending on the operating temperature and/or pressure reached in the heat exchanger, some or all of the biomass contained in the heated TBW slurry may be converted to biocrude and/or possibly other biofuels in situ (that is, while being conveyed through this process) via HTP or another mechanism.

The temperature, pressure, and/or any other factors involved in a conversion of the TBW slurry's biomass to biocrude and/or biofuel may be controlled to optimize the process in light of engineering and/or other concerns. For example, if it may be determined that conversion of the biomass in situ (i.e., in the line used to move the TBW slurry) using such a process may cause fouling of the equipment and/or detrimentally hinder the flow of materials through the process to the refinery and/or BPP, which cannot be corrected through earlier removal of some of the materials e.g., 1510, and/or other techniques known to those in the art, the heat exchanger involved in heat transfer to the TBW slurry may be designed to transfer only enough heat to the TBW slurry to provide additional heat for downstream HTP and/or other refining processes at the refinery, but not enough heat to produce an in-situ HTP process in the heat exchanger or the line carrying the TBW slurry. Depending on the thoroughness of conversion, and the amount of heat that may be captured in this process, the outputs may vary and further refining may be necessary to fully convert the heated TBW slurry into biocrude and/or biofuels. The heated TBW slurry may be optionally routed through another heat exchange process of any description e.g., in the Plan to provide more heat to the TBW Slurry and limited cooling of other applications and then may undergo some initial separation steps 1510 and then may be conveyed to a refinery and/or BPP 1512, 1513, 1514 for any other separation/refining steps (which may be ideally located nearby in order to reduce the loss of heat). Heat, water, and pressure from refining processes may be recovered and reused e.g., in the Plan (FIGS. 2 & 3 heat, water), and/or pressure e.g., FIG. 23. In an embodiment, the heated TBW slurry may be routed to the BGM. In an embodiment, the TBW slurry may be heated by any number of heat exchange processes to an optimal temperature for biomass growth using a heat exchange process in the thermal plant and/or another source of heat within the Plan. In an embodiment, any of the processes described may be regulated by sensors and computerized controls to account for temperature variations which may be integrated with computer control and automation systems with sensors and computer controls to sense parameters of operation of the entire Plan, and to send signals to control systems to adjust and optimize performance (e.g., and industrial control system optionally with adaptive controls and/or artificial intelligence), e.g., FIG. 24E.

In one or more embodiments, if in-situ conversion of the BGM biomass to biocrude and/or biofuels has been fully completed (a converted TBW slurry), the outflow may be directed to a refinery, and/or an initial separation of the resulting products from the water may occur before being directed to a refinery and/or BPP (e.g., when movement through piping leading to the refinery would be hindered by oil in the converted TBW slurry), and the heated TBW slurry and initially separated components may be routed to the refinery and/or BPP for more complete separation of these products from water, and possible further refining of these products.

In an embodiment, if conversion of the TBW slurry's biomass to biocrude and/or biofuels has not been fully completed in situ, the heated TBW slurry may be routed to the refinery and/or BPP for HTP and/or another process suited to separating biomass from water and refining it and/or to the BPP to undergo a process suited to the purpose of refining biomass into other products, and/or for separation from water. If HTP and/or other process(es) requiring additional heat may be used in the refinery and/or BPP, the heated TBW slurry may be heated additionally using another heat exchanger either as disclosed herein and/or in any manner known to those of skill in the art, a separate burner, heat from the thermal plant (e.g., primary process heat), and/or another heat source in order to achieve and maintain the heat needed for HTP and/or other refining processes. HTL may be conducted e.g., using the process in FIG. 9. Heat, water, and/or pressure in the converted TBW slurry and other stages of these processes may be reclaimed (e.g., FIGS. 2 & 3 heat and water, respectively, and pressure e.g., FIG. 23), and used e.g., in the Plan.

In an embodiment, alternatively or additionally, the process of FIG. 15A may be used to heat the TBW slurry, and heated TBW slurry may then be directed back to the BGM. In this manner, the TBW slurry would serve as a thermal plant cooling fluid, and also be heated to a higher temperature directly by this process that may be beneficial for its use in the BGM. This application of the process in FIG. 15A would likely be at much lower temperature than the preceding process wherein the goal may be the refining of biomass.

FIG. 15B depicts another module by which heat may be transferred to the Plan. A normal fluid (e.g., water from any source e.g., in the Plan (FIG. 3), other liquid, and/or gas from any source, not necessarily containing biomass and/or biofuel), may be used as cooling fluid in any Thermal Process, comprising possibly thermodynamic process or a thermodynamic cycle, and/or to reclaim heat from any fluid and transfer it to another use within the Plan. The heat captured by the cooling fluid may be used to supply heat to the Plan through direct use, such as use as new water substrate for the BGM, direct routing of heated salt water to a desalination plant and/or other processes, through heat exchangers, comprising heat used for the biomass/biofuel separation and/or refining process, processes depicted in FIGS. 12A-12E, comprising possibly cogenerated cooling, and/or any other process requiring heat/cooling e.g., FIG. 2. Fluid and/or pressure generated from this process may be recovered and reused e.g., in the Plan (FIG. 3 for water), pressure e.g., FIG. 23. Fluids of any type in this disclosure may be recovered and redirected where needed e.g., in the Plan and/or for discharge by any means herein disclosed and/or known to those of skill in the art.

In an embodiment, e.g., FIGS. 2, 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, depending on the amount of heat needed for HTP or HTP preheating, if used, and/or other processes and/or project parameters, such as the type, size, and/or operating temperature of thermal plant working fluid in use, the volume of water available from the TBW slurry and/or other sources e.g., in the Plan, and the amount of cooling needed in the thermal plant to achieve a desired result (e.g., to complete condensation step in any thermodynamic cycle), only one or more than heat transfer module or heat exchange process, e.g., 15A or 15B, using either the TBW slurry and/or any other fluid source may be used cool the thermal plant and to transfer thermal plant waste heat to the Plan, and in any sequence. For example, a heat exchanger containing the TBW slurry may be used first in the condensation step of a thermodynamic cycle, and another heat exchanger containing another fluid source may be used second, and another heat exchanger using a third fluid source may be used as a third step in cooling the working fluid and transferring heat to the Plan.

In one or more embodiments, an initial heat exchange process, due to the higher temperatures attainable, may be used to provide heat for high temperature HTP of the TBW slurry, where a second or third heat exchange process may be needed to further reduce the temperature of the working fluid to complete the condensation stage of a thermodynamic cycle. In an embodiment, the waste heat from a second or third heat exchange process may be directed to lower heat applications e.g., in the Plan, such as heating the BGM, cellulosic ethanol, and/or to processes where any amount of heating/preheating may be desirable, such as desalination. In an embodiment, any residual heat after other processes e.g., in the Plan requiring heat have been supplied, may be directed toward desalination, where present in certain embodiments.

Alternately, only one or more than two different heat exchange processes using either type of cooling fluid may be used in any thermal process (e.g., FIGS. 15A, 15 B, 16, 17, 18, or other thermal processes) depending on design considerations, e.g., whether it may be preferable to perform HTP and/or another process in situ, and/or at the refinery.

In an embodiment, the TBW Slurry and/or any other fluid source may be heated progressively also in two or more heat exchangers also where beneficial, for example, where it may be beneficial to more gradually heat the TBW slurry to avoid problems in the system such as biofouling. In this embodiment, for example, the TBW slurry at ambient temperature may be directed to one heat exchange process which raises its temperature to a certain point (e.g., 120 degrees C.), and then may be directed to another heat exchange process and/or other heating process to further elevate its temperature to 350 degrees C., for example, or another temperature beneficial to the preheating for or performance of HTP. Likewise, any other fluid source e.g., in the Plan (e.g., FIG. 15B) may also be routed through two or more heat exchangers in the design (comprising step 1520) before use e.g., in the Plan/Recovery 1524 in order to optimize engineering considerations, and to provide the optimal quantity and temperature of heated fluid for any application e.g., in the Plan. These heat exchange processes may occur in the same thermal process, thermodynamic cycle, in different thermal plant technologies, and/or in any other process where heat maybe either generated and/or reclaimed. In an embodiment, all needs for heat and/or cogenerated cooling (which may be generated by heat) e.g., in the Plan may be considered, and heat/waste heat of different temperatures may be prioritized and budgeted for all needs for heat and/or cooling within the Plan, with some or all of the heat being supplied by any heat exchange process in the condensation stage of a thermodynamic cycle, by any other any thermal process in the thermal plant, comprising possibly primary process heat, and/or by heat and/or reclaimed heat from any heat source(s) e.g., in the Plan (See FIG. 2). In an embodiment, the need for heat in all processes may also be planned in accordance with the need for cooling of all thermal plant technologies, such that adequate cooling may be provided, and any leftover heat after all other processes requiring heat have been heated, may be directed to the desalination plant, if present e.g., in the Plan, and/or possibly to discharge.

In an embodiment, the present disclosure may be directed to a novel method, design Plan for the production of fuel and/or other products, reduction of $CO_2$ emissions, and innovative methods of conservation of water and energy in performing these vital processes. The method, design and Plan may be adapted to the geography, available resources, and needs of a particular location.

In an embodiment, the Plan and method relate to the minimization of $CO_2$ emitted by a major $CO_2$ emission source and/or sources, e.g., a hydrocarbon-burning, or biofuel-burning thermal plant and/or thermal power plant. In an embodiment, the percentage of carbon removed from the waste stream of the thermal plant and incorporated as biomass growth into the aqueous effluent(s) and/or discharge(s) of the biomass growth module may be from about 30% to 80% of the waste stream carbon, or from about 50% to 100%, or from about 75% to 100%, or from about 80% to 100%, or from about 80% to 95%.

In an embodiment, a thermal plant and biomass growth module may be preferably located at a common locus, e.g., in close proximity, and may be arranged for convenient transfer of the $CO_2$ to the biomass growth module. $CO_2$ may be captured from a thermal plant by pre-combustion capture, post-combustion capture, and/or oxy-fuel process combustion capture. Carbon dioxide may also be generated by the WWTP, WWTP sludge processing, biomass, biomass refining, WWTP sludge, other organic source anaerobic digestion, other processes (See FIG. 4) and/or offsite sources. Carbon dioxide may be directly piped and/or treated and then piped to a biomass growth module, to the biofuel refining/separation plant for use in biomass refining and/or separations techniques, comprising supercritical fluids extraction, piped to the water bottling/biomass packaging plant for use in carbonation of liquids, and/or other uses, and/or stored either as a gas, compressed gas and/or compressed solid (dry ice), and/or may be marketed offsite. Carbon dioxide may be distributed using such technologies as blowers, piping, spargers, and/or any other technologies suited to the purpose.

In an embodiment, water, an aqueous solution, steam, air and/or other gases may be used for the capture and/or distribution of heat, pressure and/or other energy from the thermal plant to the biomass growth module and/or other facilities to assist refining, processing and return of biomass and/or biofuels from the BGM as fuel to the thermal plant, for the production of other products, and/or for other processes e.g., as described herein.

In an embodiment, a biomass growth module (BGM) may contain one or more biomass growth units (BGUs). The BGUs may be used separately, or in combination with each other, possibly sharing and/or exchanging resources and/or flows, to form the BGM. (See FIG. 5).

In one or more embodiments, a biomass growth unit may comprise a growing subunit optionally comprising one or more of the following: one or more open pond(s), photobioreactor(s), non-photosynthetic bioreactor(s) and/or other growing subunit(s) (See FIG. 6). These growing subunits may also work in conjunction with other BGU supporting subunits (e.g., the subunits of FIG. 6), such as nutrient storage, mixing unit(s), stressing, and/or others, wherein all subunits besides the growing subunit as optional supporting components of a BGU, which may be included or excluded, and when included may be tailored to meet the operating conditions and/or desired goals in the use of a particular BGU. In this manner the elements of the disclosure system and/or Plan present a flexible system for optimization of the use of biomass growth in many applications.

In an embodiment, using an autotrophic BGU the biomass growth module provides a continuous flow system such that inflows of $CO_2$, wherein the inflow of $CO_2$ and/or other sources of bioavailable carbon may substantially equal the carbon content of a crude biomass, e.g., FIG. 6.

In an embodiment, a nutrient feed into a biomass growth module which may comprise raw sewage, pre-treated sewage, farm runoff, other wastewater, and/or any combination of the foregoing, which may be combined with another water source of any description may be treated either partially or fully in the biomass growth module to remove contamination and restore water quality, while using $CO_2$ from the thermal plant, generating biofuel/biomass, cooling the thermal plant, and capturing heat from the thermal plant for use in biomass/biofuel refining processes and/or other processes.

Aquatic algae and/or other biomass can be used effectively in some stages of the treatment of municipal wastewater instead of traditional bacterial-based wastewater treatment systems (WWTPs). Algae-based systems may be more cost-effective, energy efficient, and generate better quality of water treatment in these stages than traditional wastewater treatment systems. Algae-based systems may be more effective in remediating nutrients in water (such as nitrates) than traditional wastewater treatment systems at lower cost.

In an embodiment, e.g., those of FIG. 14, non-fuel products derived from the biomass grown in wastewater, comprising select portions of it, or its residue after processing by anaerobic digestion and/or by any other method may also be produced, comprising animal feed, fish feed, soil amendments, bio-polymers, bio-plastics, paints, dyes, colorants, lubricants, and/or other products. Some products may be derived by mixing the above biomass, biomass portions and/or residues optionally with other materials. In this manner, there may be provided a manufacturing process for such products from the collocated modules of the Plan.

In reference to FIG. 14 an embodiment of the disclosure includes a system 1400 for processing biomass comprising a separation module 1404 configured to receive 1405 biomass and water 1402 and wherein the separation module 1404 is configured to receive 1442 heat 1418 from the Plan, for example, FIG. 2.

Another embodiment includes the system wherein the separation module 1404 comprises a biomass output 1403 and a water output 1406 and wherein the water output 1406 is optionally configured for reclamation of water use in the Plan, for example, FIG. 3.

Another embodiment includes the system wherein optionally any portion of a second biomass output 1404A is processed by a whole cell products processing module 1412.

Another embodiment includes the system wherein an output of whole cell products 1412A from the whole cell products processing module 1412 is provided to a BBPP module 1480.

Another embodiment includes the system wherein optionally any portion of the biomass output 1403 is processed by a cell disruption module 1408.

Another embodiment includes the system wherein the cell disruption module 1408 comprises a cell disruption biomass output 1417A.

Another embodiment includes the system wherein optionally any portion of the biomass output 1403 and/or cell disruption biomass output 1417A is provided to a drying module 1410.

Another embodiment includes the system wherein heat 1418A from the Plan, for example, FIG. 2, is optionally provided 1446 to the drying module 1410.

Another embodiment includes the system wherein air 1425A is transferred from an air treatment/odor control module 1300 in the Plan, for example, FIG. 13, to the drying module 1410.

Another embodiment includes the system wherein air 1425B is transferred from the drying module 1410 to the air treatment/odor control module 1300 in the Plan, for example, FIG. 13.

Another embodiment includes the system wherein the drying module 1410 comprises a dried biomass output 1411.

Another embodiment includes the system wherein the dried biomass output 1411 is transferred to a powdered product processing module 1414.

Another embodiment includes the system wherein the powdered product processing module 1414 comprise a powdered products output 1413.

Another embodiment includes the system wherein the powdered products output 1413 is transferred to a BBPP module 1480.

Another embodiment includes the system wherein the cell disruption module comprises a second biomass 1417B output.

Another embodiment includes the system wherein the second biomass 1417B output is transferred to one or more optional mixing module(s) 1420.

Another embodiment includes the system wherein the optional mixing module(s) 1420 further comprises inputs of: solvent(s) containing extracted biomass 1416, 1441; biomass 1471B; solvent 1421; and/or recovered solvent 1437, 1440.

Another embodiment includes the system wherein any of the mixing module(s) is configured to optionally receive heat 1418 optionally from the Plan, for example, FIG. 2.

Another embodiment includes the system wherein the mixing module(s) 1420 comprise(s) a solvent and biomass output 1444.

Another embodiment includes the system wherein the solvent and biomass 1444 is optionally provided to a separation module 1422.

Another embodiment includes the system wherein the separation module 1422 comprises the following outputs: solvent and biomass 1445; and/or residual biomass 1426.

Another embodiment includes the system wherein the solvent and biomass output 1445 is provided to an evaporation module 1424.

Another embodiment includes the system wherein heat 1418B from the Plan, for example, FIG. 2, is optionally provided 1448 to the evaporation module 1424.

Another embodiment includes the system wherein the evaporation module 1424 is optionally configured to evaporate solvent under a vacuum 1427 by air flow 1425.

Another embodiment includes the system wherein air flow 1427 is directed 1447 to the air treatment/odor control module 1300 in the Plan, for example, FIG. 13.

Another embodiment includes the system wherein the evaporation module 1424 optionally provides outputs optionally selected from: formulated products in oil 1449, 1430; recovered solvent 1437; and/or solvent vapor 1436.

Another embodiment includes the system wherein the recovered solvent output 1437 is optionally provided to the following: the mixing module(s) 1420; and/or a BGM 212B.

Another embodiment includes the system wherein the solvent vapor output 1436 is provided to a condensing module 1438.

Another embodiment includes the system wherein optionally cooling 1439, for example, FIG. 2, from the Plan or other source is provided 1451 to the condensing module 1438.

Another embodiment includes the system wherein an output of the condensing module 1438 comprises recovered solvent 1440.

Another embodiment includes the system wherein the recovered solvent 1440 is optionally provided to the mixing module(s) 1420 and/or a BGM 212.

Another embodiment includes the system wherein the formulated products in oil 1430 are provided 1450 to the BBPP module 1480.

Another embodiment includes the system wherein the residual biomass output 1426 is provided to: a refinery module 1428; a gasification module 1428; and/or a BGM 212A.

Another embodiment includes the system wherein the refinery module 1428 and/or the gasification module 1428 provide an output of biofuel 1434.

Another embodiment includes the system wherein the biofuel output 1434 is optionally configured to fuel the thermal plant, or otherwise in the Plan 1000, for example, FIG. 10.

Another embodiment includes the system wherein the biomass and water 1402 is supplied by a BGU, for example, FIG. 6, 603, 648.

Another embodiment includes the system wherein the solvent containing extracted biomass 1416 is supplied by a BGU 600 output 644, for example, FIG. 6.

In reference to FIG. 14 an embodiment of the disclosure includes a system 1400 configured to process solvent comprising a solvent and biomass input 1445 in operative communication with an evaporation module 1424 wherein heat 1418B from the Plan, for example, FIG. 2, is provided to 1448 the evaporation module 1424.

Another embodiment includes the system wherein the evaporation module 1424 optionally comprises outputs selected from the following: formulated products in oil 1449, 1430; recovered solvent 1437; solvent vapor 1436; and/or air 1425.

In reference to FIG. 14 an embodiment of the disclosure includes a system 1400 configured to process solvent and biomass comprising a mixing module(s) 1420 wherein heat 1418 from the Plan, for example, FIG. 2, is provided to 1443 the mixing module(s) 1420.

Another embodiment includes the system wherein any of the mixing module(s) 1420 may receive inputs optionally selected from: biomass 1403, 1417B; solvent 1421; solvent containing extracted biomass 1416, 1441; and/or recovered solvent 1437, 1440.

Another embodiment includes the system wherein an output of the mixing module(s) 1420 is solvent and biomass 1444.

In reference to FIG. 14 an embodiment of the disclosure includes a system 1400 configured to dry biomass comprising a drying module 1410 wherein heat 1418A from the Plan, for example, FIG. 2, is provided to 1446 the drying module 1410.

Another embodiment includes the system wherein the drying module 1410 is configured to receive inputs selected from: biomass 1403, 1417A; and/or air 1425A.

Another embodiment includes the system wherein the drying module 1410 comprises outputs selected from: dried biomass 1411; and/or air 1425B.

In reference to FIG. 14 an embodiment of the disclosure includes a system 1400 configured to dry biomass comprising a drying module 1410 wherein ambient, reclaimed, purified and/or deodorized air from an air treatment/odor control module 1300 in the Plan, for example, FIG. 13, is configured to provide air to 1425A and/or receive air from 1425B the drying module 1410.

Another embodiment includes the system wherein the drying module 1410 is configured to receive inputs selected from: biomass 1403,1417A; and/or heat 1418A, 1446.

Another embodiment includes the system wherein the drying module 1410 is configured to provide an output of dried biomass 1411.

In reference to FIG. 14 an embodiment of the disclosure includes a system 1400 configured to process solvent vapor comprising a solvent vapor input 1436 in operative communication with a condensing module 1438 wherein cooling 1439 from the Plan, for example, FIG. 2, is provided to 1451 the condensing module 1438.

Another embodiment includes the system wherein the condensing module 1438 comprises an output of recovered solvent 1440.

In reference to FIG. 14 an embodiment of the disclosure includes a system 1400 configured to grow biomass comprising a recovered solvent input 1437 configured to provide recovered solvent 1437 to a BGM 212B.

Another embodiment includes the system wherein an evaporation module 1424 is in operative communication with the recovered solvent input 1437.

In reference to FIG. 14 an embodiment of the disclosure includes a system 1400 configured to grow biomass comprising a recovered solvent input 1440 of a BGM 212 wherein a condensing module 1438 is in operative communication with the recovered solvent input 1440.

In reference to FIG. 14 an embodiment of the disclosure includes a system 1400 configured to reclaim residual biomass comprising a residual biomass input 1426 in operative communication with a BGM 212A; a refinery module 1428; and/or a gasification module 1428.

Another embodiment includes the system wherein a separation module 1422 is in operative communication with the residual biomass input 1426.

Another embodiment includes the system wherein the refinery module 1428 and/or gasification module 1428 are configured to produce biofuel(s) 1434.

Another embodiment includes the system wherein the biofuel(s) 1434 are optionally used to fuel the thermal plant, for packaging, storage, and/or use in other combustion processes or otherwise in the Plan 1000, for example, FIG. 10.

In reference to FIG. 14 an embodiment of the disclosure includes a system 1400 configured to bottle and/or package biomass comprising a BBPP module 1480 which receives inputs selected from: formulated products in oil 1430, 1450; powdered products 1413; and/or whole cell products 1412A.

Another embodiment includes the system wherein the BBPP module 1480 is collocated with a BGM 212, and/or a BPP module 1400.

Another embodiment includes the system wherein the BGM 212, and/or the BPP module 1400 provide inputs to the BBPP module 1480.

In reference to FIG. 14 an embodiment of the disclosure includes a system 1400 to provide evacuation of air comprising an air input 1447 in operative communication with an air treatment/odor control module 1300 in the Plan, for example, FIG. 13.

Another embodiment includes the system further comprising an evaporation module 1424 which provides the air input 1447 to the air treatment/odor control module 1300 in the Plan, for example, FIG. 13, optionally configured to create a vacuum 1427.

Another embodiment includes the system wherein the air flow 1447 and/or vacuum 1427 is optionally used to evaporate solvents creating solvent vapor 1436.

Another embodiment includes the system wherein the solvent vapor 1436 is optionally condensed in a condensing module 1438.

In reference to FIG. 14. an embodiment of the disclosure includes a method of processing biomass comprising providing the system 1400 and introducing a biomass and water 1402 to the separation module 1404.

In reference to FIG. 14. an embodiment of the disclosure includes a method of processing solvent comprising providing the system 1400 and providing 1448 heat 1418B from the Plan, for example, FIG. 2, to the evaporation module 1424.

In reference to FIG. 14. an embodiment of the disclosure includes a method of processing solvent and biomass comprising providing the system 1400 and providing 1443 heat 1418 from the Plan, for example, FIG. 2, to the mixing module(s) 1420.

In reference to FIG. 14. an embodiment of the disclosure includes a method of drying biomass comprising providing the system 1400 and providing 1446 heat 1418A from the Plan, for example, FIG. 2, to the drying module 1410.

In reference to FIG. 14. an embodiment of the disclosure includes a method of drying biomass comprising providing the system 1400 and conveying air to 1425A and from 1425B the drying module 1410.

In reference to FIG. 14. an embodiment of the disclosure includes a method of processing solvent vapors comprising providing the system 1400 and providing 1451 cooling 1439 from the Plan, for example, FIG. 2, to the condensing module 1438.

In reference to FIG. 14. an embodiment of the disclosure includes a method of growing biomass comprising providing the system 1400 and conveying a recovered solvent 1437 to a BGM 212B.

In reference to FIG. 14. an embodiment of the disclosure includes a method of growing biomass comprising providing the system 1400 and conveying a recovered solvent 1440 to a BGM 212.

In reference to FIG. 14. an embodiment of the disclosure includes a method of reclaiming residual biomass comprising providing the system 1400 and conveying the reclaimed residual biomass 1426 to the BGM 212A, the refinery module 1428, and/or the gasification module 1428.

In reference to FIG. 14. an embodiment of the disclosure includes a method of bottling and/or packaging biomass comprising providing the system 1400 and conveying the inputs 1412A, 1413, 1430, 1450 to the BBPP module 1480.

In reference to FIG. 14. an embodiment of the disclosure includes a method of evacuating air comprising providing the system 1400 and conveying air to 1447 the air treatment/odor control module 1300 in the Plan, for example, FIG. 13.

In an embodiment, thermal plant $CO_2$ emissions may be combined and converted into a renewable energy source using a BGM, which supplies fuel to the thermal plant, the water discharge(s) from the biomass growth module may be used to cool the thermal plant, and heat and power from the thermal plant may be used productively in the biomass/biofuel refining process and/or other processes e.g., in the Plan. In this embodiment, a wide variety of useful products may be generated in the biomass growth module and/or downstream processes, comprising nutritional supplements for human consumption, e.g., pharmaceuticals, food, feed, other products such as cosmetics, biopolymers and/or other products as known to a person of ordinary skill in the art. For example, see U.S. Provisional Application No. 62/173,905, filed Jun. 10, 2015, Appendix 1 incorporated herein by reference and relied upon and Pandey, Ashok, Lee, Duu-Jong, and Chisti, Yusuf, eds. Biofuels from Algae. Amsterdam, NLD: Elsevier Science & Technology, 2013. 205-233. ProQuest ebrary. Web. 16 Sep. 2015, incorporated herein by reference and relied upon in this specification for such products and/or processes that may produce them.

Alternatively, in other embodiments, a wide variety of other water sources may be used to grow biomass for use as fuel and/or to produce many useful products, while abating carbon dioxide, comprising partially treated wastewater, fresh water, salt water, high salinity salt water, other water types, or any combination of the foregoing. There may be hundreds of thousands of algae species and other plant species worldwide. The biodiversity of plant species, in particular, algae, allows for strategic strain selection to optimize a biomass growth system for a wide variety of different growing conditions, climates, water substrates, desired outputs, and/or other factors. This disclosure specifically seeks to include all water substrates available in any location for potential use and optimization based on local resources in the biomass growth module (BGM), a biomass growth system.

In one or more embodiments, solid waste, such as municipal sanitary waste, and/or industrial waste may be used for fuel to produce power in a waste-to-energy unit, comprised by the thermal plant, and the carbon dioxide from that process may be used in biomass growth, and heat generated by it may be used productively to process and/or refine biofuel and/or biomass generated in the biomass growth module, and/or for other uses e.g., in the Plan (See FIG. 2). Biomass/biofuels generated in the biomass growth module may be used as fuel for the combustion component of the waste-to-energy unit, biomass combustion unit, and/or in other power systems, and/or other useful products may be synthesized from the biomass.

The biomass and/or fuels generated by it and/or from refining its composition in the disclosed Plan may be utilized as a fuel for power generation and/or production of other useful products by a variety of downstream processing methods such as filtration, screening, coagulation, centrifugation, sedimentation, flocculation, bio-flocculation, flotation (comprising dissolved air and hydrogen), gravity settling, gravity thickener, cell disruption, bacterial extraction (e.g., a bacterial process for processing biomass, for example, see http://www.soleybio.com/extractor-bacteria.html incorporated herein by reference and relied upon); ultrasound, microwave, solvent, cold press, transesterification, evaporation, electrophoresis, electroflotation, adsorption, ultrafiltration, precipitation, chromatography, crystallization, desiccation, lyophilization, drying, sterilization, hydrothermal processing, and/or other methods suitable for processing biomass and/or biofuels known to the person of skill in the art. For example, see, Pandey, Ashok, Lee, Duu-Jong, and Chisti, Yusuf, eds. Biofuels from Algae. Amsterdam, NLD: Elsevier Science & Technology, 2013. 85-110. ProQuest ebrary. Web. 16 Sep. 2015, incorporated herein by reference and relied upon and Shelef, G., A. Sukenik, and M. Green. *Microalgae harvesting and processing: a literature review*. No. SERI/STR-231-2396. Technion Research and Development Foundation Ltd., Haifa (Israel), 1984, incorporated herein by reference and relied upon. Shelef et al., is incorporated in U.S. Provisional Application No. 62/173,905, a priority document of this specification, filed Jun. 10, 2015 as an Appendix to the Specification, also incorporated by reference in its entirety and relied upon. Depending on the biomass strain used, some types of fuel may be generated directly by the biomass in the biomass growth module. In an embodiment, e.g., those of FIG. 1 and/or FIG. 10, these fuels may be separated from the water in the biomass growth module, either by evaporation and/or other means, and/or may be used directly as fuel and/or further refined and then used as fuel for the thermal plant and/or other use. These fuels may follow the process path shown in 106 and 102 of FIG. 1, FIG. 10, and/or may be routed to the Refinery and/or BPP and/or to the BBPP.

Processing of the biomass in a gasification module (e.g., 124 of FIG. 1) using CHG, anaerobic digestion and/or other technologies know to the art to gasify biomass may be used to produce biogas, which may be used as fuel. Hydrogen and/or other gaseous fuels may also be produced using other methods. Gaseous fuels may also be used in fuel cells to produce power for use e.g., in the Plan.

Wet and/or dry biomass may be combusted to produce power in the thermal plant. Biomass may be dried using waste heat from the power and/or WTE plant, either in a drying module attached to the thermal plant, and/or in a separately powered biomass drying facility. Water captured from the drying process may be re-introduced into the biomass growth module and/or elsewhere e.g., in the Plan (See FIG. 3).

In one or more embodiments, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, a biomass/water slurry generated by the biomass growth module may be heated by waste heat generated in the thermal plant and "flash refined" in a process referred to as hydrothermal processing, which may comprise hydrothermal liquefaction, RTP, catalytic hydrothermal gasification and/or any other hydrothermal processing method. The heated biomass/water slurry may be pressurized if necessary for the specific HTP process and/or operating conditions, and the outputs of these processes may be primarily water and biocrude oil and/or methane and carbon dioxide. For example, the following references are incorporated by reference herein and relied upon: http://www.genifuel.com/text/20150125%20 Genifuel%20Hydrothermal%20Overview.pdf.

Other references to HTL include:

Elliott D C, T R Hart, A J Schmidt, G G Neuenschwander, L J Rotness, Jr, M V Olarte, A H Zacher, K O Albrecht, R T Hallen, and J E Holladay. 2013. "Process Development for Hydrothermal Liquefaction of Algae Feedstocks in a Continuous-Flow Reactor." Algal Research 2(4):445-454.
http://www.sciencedirect.com/science/article/pii/S2211926413000878.
Biddy M J, R Davis, S B Jones, and Y Zhu. 2013. Whole Algae Hydrothermal Liquefaction Technology Pathway. PNNL-22314, Pacific Northwest National Laboratory, Richland, Wash.
http://www.pnl.gov/main/publications/external/technical_reports/PNNL-22314.pdf.
Jones S B, Y Zhu, D B Anderson, R T Hallen, D C Elliott, A J Schmidt, K O Albrecht, T R Hart, M G Butcher, C Drennan, L J Snowden-Swan, R Davis, and C Kinchin. 2014. Process Design and Economics for the Conversion of Algal Biomass to Hydrocarbons: Whole Algae Hydrothermal Liquefaction and Upgrading. PNNL-23227, Pacific Northwest National Laboratory, Richland, Wash.
http://www.pnnl.gov/main/publications/external/technical_reports/PNNL-23227.pdf.
Elliott, Douglas C., et al. "Review: Hydrothermal Liquefaction of Biomass Developments from Batch to Continuous Process." Bioresource Technology 178. (2015): 147-156. ScienceDirect. Web. 24 Sep. 2015. http://www.sciencedirect.com/science/article/pii/S0960852414013911.

Other references to CHG include:

U.S. Pat. No. 8,877,098, Nov. 4, 2014. "Methods for sulfate removal in liquid-phase catalytic hydrothermal gasification of biomass." Douglas C Elliott and James R. Oyler,
http://www.google.com.ar/patents/US8877098.
Mian, Alberto, Adriano V. Ensinas, and Frangois Marechal. "Multi-objective optimization of SNG production from microalgae through hydrothermal gasification." Computers & Chemical Engineering (2015).
http://www.sciencedirect.com/science/article/pii/S0098135415000150.

In an embodiment, the biocrude and/or gaseous fuels that may be a result of HTP may be used either directly as fuel (e.g., in the thermal plant and/or elsewhere), and/or further refined and used as fuel in a variety of applications. In this embodiment, a biomass/water slurry serves as a source of cooling water for the thermal plant either directly or indirectly, and also reclaims a significant portion of waste heat generated in the thermal plant. This results in a fast and efficient means to obtain biofuel while also meeting the needs of the thermal plant for cooling, and making efficient use of waste heat.

Alternatively, in an embodiment, the biomass may be separated from the water substrate generated by the biomass growth module using any mechanical, chemical, thermal, physical, and/or other type of method(s) herein disclosed and/or known by the person of skill in the art, and then refined for use as fuel and/or to make other products.

Alternatively, in an embodiment, the biomass may be processed on a limited basis through various extraction techniques, wherein portions of the water/biomass solution may be extracted for use to make fuels and/or products (e.g., milking), and the biomass substrate itself and/or portions thereof may be preserved and reused, and/or then processed by one of the other methods given herein.

In an embodiment, two or more hydrothermal processing methods and/or other refining methods may be used in combination, in parallel and/or in series anywhere HTP may be referenced e.g., in the Plan, comprising in-situ, in the Refinery and/or BPP to produce specific types or blends of fuels and/or products.

In one or more embodiments, biomass will grow in the biomass growth module and its growth may be optimized as disclosed herein. The biomass may produce some types of fuels directly in the biomass growth unit(s) within the biomass growth module. These fuels may be processed as necessary by any means known to those in the art, and optionally routed to the thermal plant as fuel.

In an embodiment, fuels, useful products and/or their precursors may be generated by a combination of these methods and/or by other methods either directly in the biomass growth module, and/or through any other means of processing the biomass growth module outputs.

With reference to FIG. 10, Design 1000 comprises optional flows of fuels e.g., in the Plan wherein thermal plant 1002 receives inputs from modules optionally present in an embodiment of the Plan comprising: Biofuel in gaseous and/or liquid form, biocrude and/or biocoal 1058 from refinery and/or BPP 1054; biomass and/or biofuel in liquid and/or gaseous form 1060 from BGM 1048; biogas that has been optionally processed 1034 from gasification module 1036; Waste oil 1032 from all onsite systems 1040; biomass and/or waste for use as fuels (e.g., waste-to-energy, biomass combustion) 1030 from recycling/waste receiving module 1028; gases 1023 from landfill 1021; and fuels of any description from offsite source(s) 1064. Thermal plant's optional power plant technologies, comprising combustion based power plants and/or waste-to-energy power generation technologies 1004 optionally receive fuels 1006 from other optionally present thermal plant technologies which may produce fuels 1008 comprising: pyrolysis submodule 1009; HTP submodule 1010, cellulosic ethanol/butanol/isobutanol submodule 1012, desorber/condenser submodule 1016, and/or other thermal plant technologies capable of generating fuels 1018. Optional thermal plant submodules rotary kiln incinerator 1022, plasma gasification 1020, and/ or other technologies capable of processing hazardous waste 1024 optionally receive hazardous waste 1026 from recycling/waste receiving module 1028, and/or thermal plant technologies generating hazardous waste 1026. Thermal Plant 1002 optionally provides optionally heated biomass, biocrude, biofuels, and/or biocoal 1062 to refinery and/or BPP 1054 for refining into fuels 1056 and/or processing into products. Refinery and/or BPP 1054 optionally receive biomass and/or biofuel (gaseous and/or liquid) 1060 for processing from BGM 1048 and provide(s) and/or receive(s) residuals 1049 to/from BGM 1048 and/or gasification module 1036. Gasification module 1036 optionally receives biomass, sludge and/or residuals/or water 1038 from BGM 1048. BBPP 1052 receives optionally biomass 1050 from BGM 1048 and/or biomass, biocrude, biofuels and/or biocoal 1056 from refinery and/or BPP 1054 for bottling/packaging. Bottled/packaged biocrude, biofuels, biomass and/or biocoal 1046 may be provided for use in thermal plant 1042, for storage 1043, and/or for export offsite 1044. A Desalination Unit 1053 may provide Brine 1061 to a Brine Electrolysis Unit 1055, which in turn may provide Hydrogen 1063 as fuel to the Thermal Plant 1002 or to the Refinery 1054 for optional hydrotreating and upgrading of raw biocrude.

In reference to FIG. 10, an embodiment of the disclosure includes a system 1000 configured to provide fuels to a thermal plant module or another module comprising a thermal plant module 1002 configured to receive fuel from a module and/or an input comprising: a pyrolysis module 1009; a HTL module 1010; a CHG module 1010; a RTP module 1010; other hydrothermal processing module 1010; a cellulosic ethanol module 1012; a cellulosic butanol and/or isobutanol module 1012; a desorber/condenser module 1016; biomass 1030 and/or waste 1030; hazardous waste 1026; waste oil 1032, for example, from all onsite systems 1040; biogas (optionally processed) 1034; hydrogen 1063 optionally from brine electrolysis 1055; biomass 1060; biofuel (liquid) 1058, 1060; biofuel (gaseous) 1058, 1060; biocrude 1058; biocoal 1058; landfill gases (optionally processed) 1023; other fuel-generating technologies 1018; and/or other fuels imported from offsite (e.g., outside the Plan) 1064.

An embodiment includes the system wherein the biogas 1034 is unprocessed.

An embodiment includes the system wherein the biogas 1034 is processed.

An embodiment includes the system further comprising a gasification module 1036.

An embodiment includes the system wherein the gasification module 1036 further comprises: a catalytic hydrothermal gasification module; and/or an anaerobic digestion module.

An embodiment includes the system wherein the landfill gases 1023 optionally comprising biogas are received at the thermal plant module 1002 unprocessed from a landfill 1021 and/or after processing.

An embodiment includes the system wherein processing comprises drying, pollutant removal, purification, and/or combination with another gas.

An embodiment includes the system wherein a BGM 1048 is configured to supply biomass 1038, water 1038, sludge 1038 and/or residuals 1038 to a gasification module 1036 or process.

An embodiment includes the system wherein the BGM 1048 is optionally configured to supply biomass 1060, biofuel (gaseous) 1060, and/or biofuel (liquid) 1060 to the thermal plant module 1002.

An embodiment includes the system wherein the BGM 1048 is configured to supply biomass 1050 to a BBPP module 1052.

An embodiment includes the system wherein the thermal plant module 1002 is configured to supply biomass 1062, biocrude 1062, biofuel 1062, and/or biocoal 1062, after optionally heating the biomass 1062, biocrude 1062, biofuel 1062, and/or biocoal 1062, to: a refinery module 1054; and/or a BPP module 1054.

An embodiment includes the system wherein the BGM 1048 is configured to supply biomass 1060 and/or biofuel 1060 optionally to: a refinery module 1054; and/or a BPP module 1054.

An embodiment includes the system wherein the biofuel 1060 comprises liquid biofuel 1060.

An embodiment includes the system wherein the biofuel 1060 comprises gaseous biofuel 1060.

An embodiment includes the system wherein the biofuel 1060 comprises a mixture of gaseous and liquid biofuel 1060.

An embodiment includes the system wherein the refinery module 1054 and/or BPP module 1054 optionally supply biofuel 1058, 1060, biocrude 1058, biocoal 1058 and/or biomass 1060 to the thermal plant module 1002.

An embodiment includes the system wherein the refinery module 1054 and/or BPP module 1054 optionally supply biofuel 1056, biocrude 1056, biocoal 1056 and/or biomass 1056 to the BBPP module 1052.

An embodiment includes the system wherein the BBPP module 1052 is configured to package biofuel (liquid) 1046, biofuel (gaseous) 1046, biocrude 1046, biocoal 1046 and/or biomass 1046. Package or packaging may mean to bottle, preserve, cut, pelletize, box, containerize, compress and/or pressurize.

An embodiment includes the system wherein any portion of the packaged biofuel (liquid) 1046, biofuel (gaseous) 1046, biocrude 1046, biocoal 1046 and/or biomass 1046 is configured to minimize transport of the portion and/or requirements for storage for later use and/or holding in: a thermal plant module 1042; storage 1043; and/or offsite export (e.g., outside the Plan) 1044.

An embodiment includes the system wherein residuals 1049 may be transferred for additional processing or use among any two or more of the following: the refinery module 1054; the BPP module 1054; the BGM 1048; and/or the gasification module 1036.

An embodiment includes the system wherein any portion of module and/or input: a pyrolysis module 1009; a HTL module 1010; a CHG module 1010; a RTP module 1010; other hydrothermal processing module 1010; a cellulosic ethanol module 1012; a cellulosic butanol and/or isobutanol module 1012; a desorber/condenser module 1016; biomass 1030 and/or waste 1030; hazardous waste 1026; waste oil 1032, for example, from all onsite systems 1040; biogas (optionally processed) 1034; hydrogen 1063 optionally from brine electrolysis 1055; biomass 1060; biofuel (liquid) 1058, 1060; biofuel (gaseous) 1058, 1060; biocrude 1058; biocoal 1058; landfill gases (optionally processed) 1023; other fuel-generating technologies 1018; and/or other fuels imported from offsite (e.g., outside the Plan) 1064 may undergo any of the following at any stage of any process shown in, for example, FIG. 10: storage; processing in any way known to those in the art; and/or blending with other materials.

An embodiment includes the system wherein a desalination module 1053 provides brine 1061 to an electrolysis module 1055.

An embodiment includes the system wherein the electrolysis module 1055 provides hydrogen 1063 to the thermal plant module 1002 as a fuel, and/or to the refinery module 1054 and/or BPP module 1054 for hydrotreating and upgrading raw biocrude.

An embodiment includes the system wherein the pyrolysis module 1009, the HTL module 1010, the CHG module optionally comprised by either the HTP module 1010 and/or gasification module 1036, the RTP optionally comprised by the HTP module 1010, other hydrothermal processing module 1010, cellulosic ethanol module 1012, cellulosic butanol and/or isobutanol module 1012, and/or a gasification module 1036, optionally comprised by the thermal plant module 1002 is configured to receive in parallel, in series, or simultaneously BGM sludge 1038, WWTP sludge optionally comprised by BGM sludge 1038, and/or biomass comprising agricultural biomass 1030, WTE biomass 1030, and/or BGM biomass 1060.

An embodiment includes the system wherein the biogas input 1034, thermal plant module 1002 and/or CHG module 1010, 1036 comprises a biogas module.

An embodiment includes the system wherein the biogas module is configured for biogas purification, treatment, storage and/or heating comprising a shared infrastructure wherein the following are in operative communication with the biogas module: an HTP module 1010; a natural gas input or output comprised by offsite fuels 1064 e.g., a natural gas line delivering natural gas and/or biogas to the biogas module and/or a line removing it; an anaerobic digestion module comprised by gasification module 1036; a WWTP module comprised by BGM 1048; a BGM 1048; a gasification module 1036, and/or a landfill module 1021.

An embodiment includes the system wherein gases generated in one or more modules: an HTP module 1010; a natural gas input or output 1064; an anaerobic digestion module 1036; a WWTP module 1048; a BGM 1048; a gasification module 1036, and/or a landfill module 1021 are combusted in one or more thermal plant module 1002 technolog(ies).

In reference to FIG. 10, an embodiment of the disclosure includes a system 1000 comprising a BGM 1048, a refinery module 1054, and/or a BPP module 1054 wherein the system is configured to transmit fuel and/or biomass to and from the refinery module 1054 and/or the BPP module 1054 wherein the fuels are: biomass 1060; biofuel (liquid) 1060; biofuel (gaseous) 1060; and/or residuals 1049.

An embodiment includes the system wherein the fuels and/or biomass are provided to and/or from the refinery module 1054 and/or BPP module 1054 by: a thermal plant module 1002; a BGM 1048; a gasification module 1036; and/or a BBPP module 1052.

An embodiment includes the system wherein the thermal plant module 1002 provides to and/or receives from the refinery module 1054 and/or BPP module 1054 the following inputs: biomass (optionally heated) 1062; biofuel (liquid)—optionally heated 1058, 1062; biofuel (gaseous)—optionally heated 1058, 1062; biocrude (optionally heated) 1058, 1062; and/or biocoal (optionally heated) 1058, 1062.

An embodiment includes the system wherein the refinery module 1054 and/or BPP module 1054 provide an output to the BBPP module 1052 of: biomass 1056; biofuel (liquid) 1056; biofuel (gaseous) 1056; biocrude 1056; and/or biocoal 1056.

An embodiment includes the system wherein BBPP module 1052 provides packaged fuel 1046 and/or biomass products 1046 for export 1044, for storage 1043 and/or for use in a thermal plant module 1042 wherein the packaged fuel comprises: biomass 1046; biofuel (liquid) 1046; biofuel (gaseous) 1046; biocrude 1046; and/or biocoal 1046.

An embodiment includes the system wherein the refinery module 1054, BPP module 1054, thermal plant module 1002, BGM 1048, gasification module 1036, and/or BBPP module 1052 are collocated.

In reference to FIG. 10, an embodiment of the disclosure includes a system 1000 configured to packaging fuels and/or biomass products wherein the system comprises a BBPP module 1052 configured to receive inputs of: biomass 1050, 1056; biofuel (liquid) 1056; biofuel (gaseous) 1056; biocrude 1056; and/or biocoal 1056.

An embodiment includes the system wherein the fuels 1056 and/or biomass 1050, 1056 are provided to the BBPP module 1052 by: a refinery module 1054; a BPP module 1054; and/or a BGM 1048.

An embodiment includes the system wherein the BBPP module 1052 provides packaged fuel 1046 and/or biomass products 1046 for export 1044, for storage 1043 and/or for use in a thermal plant module 1042 wherein the packaged fuel comprises: biomass 1046; biofuel (liquid) 1046; biofuel (gaseous) 1046; biocrude 1046; and/or biocoal 1046.

An embodiment includes the system wherein the refinery module 1054, BPP module 1054, BBPP module 1052, and/or BGM 1048 are collocated.

In reference to FIG. 10, an embodiment of the disclosure includes a method of distributing fuels within the system 1000, the method comprising: receiving at a first module and/or an input: a pyrolysis module 1009; a HTL module 1010; a CHG module 1010; a RTP module 1010; other hydrothermal processing module 1010; a cellulosic ethanol module 1012; a cellulosic butanol and/or isobutanol module 1012; a desorber/condenser module 1016; biomass 1030 and/or waste 1030; hazardous waste 1026; waste oil 1032, for example, from all onsite systems 1040; biogas (optionally processed) 1034; hydrogen 1063 optionally from brine electrolysis 1055; biomass 1060; biofuel (liquid) 1058, 1060; biofuel (gaseous) 1058, 1060; biocrude 1058; biocoal 1058; landfill gases (optionally processed) 1023; and/or other fuel-generating technologies 1018; a fuel from a second module and/or input: a pyrolysis module 1009; a HTL module 1010; a CHG module 1010; a RTP module 1010; other hydrothermal processing module 1010; a cellulosic ethanol module 1012; a cellulosic butanol and/or isobutanol module 1012; a desorber/condenser module 1016; biomass 1030 and/or waste 1030; hazardous waste 1026; waste oil 1032, for example, from all onsite systems 1040; biogas (optionally processed) 1034; hydrogen 1063 optionally from brine electrolysis 1055; biomass 1060; biofuel (liquid) 1058, 1060; biofuel (gaseous) 1058, 1060; biocrude 1058; biocoal 1058; landfill gases (optionally processed) 1023; and/or other fuel-generating technologies 1018; optionally processing the fuel at the first module and/or input: a pyrolysis module 1009; a HTL module 1010; a CHG module 1010; a RTP module 1010; other hydrothermal processing module 1010; a cellulosic ethanol module 1012; a cellulosic butanol and/or isobutanol module 1012; a desorber/condenser module 1016; biomass 1030 and/or waste 1030; hazardous waste 1026; waste oil 1032, for example, from all onsite systems 1040; biogas (optionally processed) 1034; hydrogen 1063 optionally from brine electrolysis 1055; biomass 1060; biofuel (liquid) 1058, 1060; biofuel (gaseous) 1058, 1060; biocrude 1058; biocoal 1058; landfill gases (optionally processed) 1023; and/or other fuel-generating technologies 1018; optionally storing the fuel or processed fuel at a third module and/or input: a pyrolysis module 1009; a HTL module 1010; a CHG module 1010; a RTP module 1010; other hydrothermal processing module 1010; a cellulosic ethanol module 1012; a cellulosic butanol and/or isobutanol module 1012; a desorber/condenser module 1016; biomass 1030 and/or waste 1030; hazardous waste 1026; waste oil 1032, for example, from all onsite systems 1040; biogas (optionally processed) 1034; hydrogen 1063 optionally from brine electrolysis 1055; biomass 1060; biofuel (liquid) 1058, 1060; biofuel (gaseous) 1058, 1060; biocrude 1058; biocoal 1058; landfill gases (optionally processed) 1023; and/or other fuel-generating technologies 1018; and/or converting the fuel or processed fuel to energy at a fourth module and/or input: a pyrolysis module 1009; a HTL module 1010; a CHG module 1010; a RTP module 1010; other hydrothermal processing module 1010; a cellulosic ethanol module 1012; a cellulosic butanol and/or isobutanol module 1012; a desorber/condenser module 1016; biomass 1030 and/or waste 1030; hazardous waste 1026; waste oil 1032, for example, from all onsite systems 1040; biogas (optionally processed) 1034; hydrogen 1063 optionally from brine electrolysis 1055; biomass 1060; biofuel (liquid) 1058, 1060; biofuel (gaseous) 1058, 1060; biocrude 1058; biocoal 1058; landfill gases (optionally processed) 1023; and/or other fuel-generating technologies 1018.

An embodiment includes the method wherein the fuel is a biofuel.

An embodiment includes the method wherein the fuel is a biogas.

An embodiment includes the method wherein the fuel is biocrude.

An embodiment includes the method wherein the fuel is a biocoal.

An embodiment includes the method wherein the fuel is a hydrogen.

An embodiment includes the method further comprising packaging the fuel.

In reference to FIG. 10, an embodiment of the disclosure includes a method of generating, distributing, and processing biomass into fuel and non-fuel biomass products comprising processing the biomass into biofuel (liquid), biofuel (gaseous), biocrude, biocoal and/or non-fuel biomass products at a refinery module 1054 and/or BPP module 1054.

In reference to FIG. 10, an embodiment of the disclosure includes a method of packaging biomass and/or biofuel comprising processing into packages the biomass, biofuel (liquid), biofuel (gaseous), biocrude, and/or biocoal at the BBPP module 1052.

FIG. 10 depicts some fuel flows through Plan, not all material flows, comprising other materials that may be mixed with fuels. All depicted fuels/materials may be sent to storage, processed and/or blended with other materials in any manner known to the art before use in the next process step or module shown.

In an embodiment, raw biocrude from HTP, e.g., HTL can be burned as fuel optionally in the same Thermal Plant that provided carbon dioxide to the BGM.

In a further embodiment, the raw biocrude can be stabilized by adding about 10% of a hydrogen-donor solvent such as methanol or ethanol, to extend the time it can be stored before re-polymerization raises its viscosity to unacceptable levels. This avoids the cost of upgrading raw biocrude with hydrogen generated by steam reforming of natural gas, which would be required before refining to produce liquid transportation fuels.

In an embodiment, biogas from CHG can be burned as fuel optionally in the same Thermal Plant that provided the carbon dioxide to the BGU and/or others.

In a further embodiment, biogas from CHG, and/or raw biocrude from HTP, e.g., HTL (stabilized or unstabilized) can be used as a supplemental fuel for a coal-fired Thermal Plant, optionally the same one that provided the carbon dioxide to the BGU and/or others.

In a further embodiment, biogas from CHG, and/or raw biocrude from the HTL (stabilized or unstabilized) and/or biomass can be used as a supplemental fuel for a WTE Thermal Plant, optionally the same one that provided the carbon dioxide to the BGU and/or others.

In an embodiment, municipal wastewater, other wastewater, salt water, ultra-high concentration salt water (e.g., brine), or any other type or combination of water resources may be delivered to a biomass growth module. Nutrients may be added to the BGUs comprising the BGM as needed. In certain embodiments, the CO2 produced in a thermal plant may be delivered to the biomass growth module. With the addition of a CO2 source, a photosynthetic biomass production process increases in efficiency. The treatment and processing of biomass and/or fuels may be optimized based on the water resource and/or other resources comprising the biomass growth module, and/or the types of products and/or fuels desired to be developed from the biomass growth module.

In one or more embodiments, e.g. FIG. 10, different technologies, comprising conventional power plants and/or WTE systems within the thermal plant may serve as backups for each other to a point to meet power generation goals, contingencies, and/or margins. Fuels and/or wastes may be stored in manners known to the industry to allow for optimal power generation for the Plan and/or for the grid over time (e.g., daily and/or seasonal fluctuations in power needs, fuel availability, and backup capacity).

In one or more embodiments, e.g. FIG. 10, an oil/water mixture(s) generated in systems in the Plan and/or from offsite may be separated. In an embodiment, waste oil may be sent to the thermal plant as a fuel to produce power. Thermal plant technologies used for waste oil may comprise a WTE incinerator, HTP, Plasma gasification unit, rotary kiln incinerator, and/or other technologies.

In one or more embodiments, e.g. FIG. 10, some solid, liquid, and/or blended wastes may be generated in the thermal plant which may be considered to be hazardous wastes.

If these wastes may be legally and efficiently disposed of using recycling, the WTE incinerator, plasma unit, the rotary kiln incinerator, alternate thermal plant technologies, HTP, and/or a landfill, any of these options and/or others suited to the purpose may be utilized in the Plan.

In one or more embodiments, e.g., FIG. 10, the Plan may comprise fuel heaters which may be fired with natural gas and/or biogas and/or methane/other fuel mixture from sources onsite and/or methane from offsite and/or may be heated using Thermal plant heat and/or heat recovered from other heat-intensive processes in the Plan per FIG. 2 as needed to heat natural gas and/or other gaseous fuels in the Plan above the dew point.

In one or more embodiments, e.g., FIG. 10 a municipal waste incinerator (MSW) may incinerate waste from cities, industry, agriculture and/or other sources and generate power. An MSW incinerator thus reduces land use for landfills, greenhouse methane gas generation, and produces power and heat and thus may be incorporated within a system and/or Plan as a thermal plant technology. That is, a thermal plant may comprise an MSW incinerator. Other example WTE technology options that may be incorporated into the Plan are discussed below. In one or more embodiments, WTE technologies may be used to dispose of waste and/or biomass generated by technologies in the Plan and/or offsite in an environmentally friendly manner and/or to recover energy from waste/biomass for power production. In an embodiment, an end product of incineration and/or other direct-combustion WTE technologies may be ash, which may be used to produce cement. In one or more embodiments, oil from an optional desorber plant and/or waste oil from all site facilities and/or offsite sources may be burned in a rotary kiln incinerator, MSW incinerator, alternate direct combustion units, a plasma gasification unit, pyrolysis-based WTE systems, and/or processed by HTP module(s) in the Plan to produce power and/or fuels for use in the thermal plant.

In one or more embodiments, e.g., FIG. 10, oil from an optional desorber plant and/or waste oil from all site facilities and/or offsite sources may be burned in a rotary kiln incinerator, MSW incinerator, alternate direct combustion units, a plasma gasification unit, pyrolysis-based WTE systems, and/or processed by HTP module(s) in the Plan to produce power and/or fuels for use in the thermal plant.

In one or more embodiments, e.g., FIG. 10, a rotary kiln incinerator may be part of the thermal plant, e.g., the thermal plant comprises a rotary kiln incinerator. An MSW incinerator may not be suitable for handling industrial wastes, many of which would be categorized under US, European and/or other law as "hazardous wastes." In an embodiment, an alternative for handling these would be a rotary kiln incinerator. A rotary kiln incinerator may be fed liquid, solid, containerized and/or gaseous waste, comprising dust and/or acid gases.

In one or more embodiments, e.g., FIG. 10, pyrolysis-based and/or other WTE technologies may generally replace waste removal and/or waste burning technologies, as WTE technologies are generally more efficient, better environmentally, and more viable than incinerators in some applications. In general, these technologies use lower heat than incinerators to anaerobically pyrolize organic waste to obtain combustible products, such as oil, and/or a coal-like product. These products may then be combusted in a thermal plant to generate power and/or may be exported offsite, e.g., outside a system or Plan. In an embodiment, WTE comprises two processes: first, a lower temperature and/or anaerobic degradation) theoretically results in fewer harmful chemical reactions, and therefore fewer harmful emissions upon subsequently combusting products of the first process. In an embodiment, greater power can be generated per unit volume of municipal sanitary waste (MSW) and/or biomass than incinerators, and that other marketable solids, liquids and/or gases may be generated and/or reclaimed. In an embodiment, the Thermal Plant may comprise these types of technology options in whole or in part. These processes may be similar in nature to hydrothermal processing (HTP) such as HTL, a process used to flash separate and/or refine biocrude from biomass in water. The synergies of these systems in the Plan are the same as those of the incinerator described above, but in addition, coal, oil, and/or other products generated in these processes may be combusted in the thermal plant onsite to generate power for the Plan and/or exported offsite. Biomass, biocrude, and/or other fuels derived from the BGM may be combusted in a second step of the process in the thermal plant either in combination with pyrolysis-generated fuels or separately.

In one or more embodiments, e.g., FIG. 10, fuels generated in these and/or other processes may be combined in whole or in part and combusted in a thermal plant, and/or separately combusted in a thermal plant onsite to generate power for the Plan and/or exported offsite. In one or more embodiments, fuels generated by cellulosic ethanol/butanol/isobutanol technologies and/or any other technologies that convert biomass into biofuel may be combined with biomass, biocrude, and/or other fuels derived from the BGM, waste HTP, and/or other biomass HTP, and/or subsequent processing steps and/or may be combusted separately and/or in combination with other fuels produced in the Plan and/or imported to it.

In one or more embodiments, e.g., FIG. 10, an indirect desorber/condenser system may also be used and/or added to other technologies as part of the thermal plant. The indirect desorber/condenser is configured to treat organic waste, vaporizing/distilling/azeotropically distilling the organic compounds therein or produced upon heating, and/or condensing the organic compounds to recover their fuel value. Example feed streams are API separator sludges from refinery operations, and/or petroleum contaminated soils. This system may take on these wastes from offsite sources, and/or onsite sources, routinely and in emergencies, e.g., in the event of an oil spill. The recovered fuels may be used to generate power in the thermal plant.

In one or more embodiments, e.g., FIG. 24K and/or FIG. 10, brine electrolysis provides hydrogen gas. The hydrogen may be used in a fuel cell to produce electricity, and/or returned to the thermal plant for combustion.

In one or more embodiments, e.g., FIG. 10, and/or FIG. 3, a waste handling/recycling plant may be added optionally as part of the Plan to sort a waste stream (e.g., municipal sanitary waste, construction waste, agricultural waste and/or other biomass, such as wood waste) for recycling, landfilling, and/or use to provide feedstock for WTE and/or other technologies in the thermal plant to generate power. In general, construction and demolition wastes and municipal sanitary waste (MSW) may be collected and handled separately. Construction and demolition wastes may be handled by large equipment in an outdoor setting that allows for large stockpile areas for materials. This may be conducted remotely from the site, and/or in a large building or open area which may be collocated. In an embodiment, the waste handling/recycling facility design may allow for drainage and use/treatment of liquids. Waste oils from the waste stream may be processed in the thermal plant to generate power.

In one or more embodiments, e.g., FIG. 10, landfills may be used to contain waste that cannot be recycled and/or ash from the thermal plant, if not used in cement production. Landfills may be used to supplement WTE technologies used in the thermal plant, providing disposal space for WTE ash and/or excess waste, a temporary repository for waste to be used in WTE system(s), and/or may also be used as a substitute for WTE system(s) should these technologies not be pursued. Gas generated by landfill waste decomposition (typically 50 percent methane and 50 percent carbon dioxide) may be used beneficially to power the thermal plant. It may share power generation technology used to combust methane and/or biogas with other possible systems in the Plan that produce and/or combust gaseous fuels, such as the gasification module (e.g., CHG, anaerobic digestion) used for biomass and/or sludge and/or gas-fired combustion power generators. Landfill-generated CO2 may be directed to the BGM and/or other processes requiring CO2 in the Plan (e.g., FIG. 4), either before and/or after the burn off of methane. In one or more embodiments, e.g., FIG. 4, carbon dioxide transport and/or storage infrastructure may be shared with the other systems described herein that generate CO2. In one or more embodiments, e.g., FIG. 3 and/or FIG.

10, the optional landfill may be lined with a liner system possibly made of IDPE capable of containing leachate generated by the waste materials. The leachate collection system may be installed to remove leachate from the facility for temporary storage and future treatment at a water treatment facility. In an embodiment, landfill leachate may be sent to the WWTP and/or oil separation and used for power generation in a WTE plant rotary kiln incinerator, plasma gasification unit, and/or other WTE technology.

In one or more embodiments, e.g., FIG. 10 and/or FIG. 24K bottle blowing, washing, filling, and/or capping may be combined into one integrated system. Integrated systems reduce bacteriological loading (disinfection), reduce production costs, decrease line footprint, reduce bottle costs, and increase line efficiency. A bottle to bottle recycling facility may be included in the Plan to allow for direct use of recycled PET and/or other materials for plastic bottle manufacture. This type of facility may be coupled with the waste handling/recycling plant.

In one or more embodiments, e.g., FIG. 10 and/or FIG. 24K, plastic may be recycled from the waste receiving and processing area. The end product of the recycled plastic would be cleaned, disinfected, and shredded plastic material. This material may then be utilized in the bottle manufacturing process at the BBPP. Packaging materials for the BBPP and/or other modules in the Plan, such as the refinery may also come from the waste handling/recycling plant described herein, including possibly plastic, cardboard, and wood pallets. Bottle to bottle recycling facility may be included in the Plan to allow for direct use of recycled PET and/or other materials for plastic bottle manufacture. This type of facility may be coupled with the waste handling/recycling plant. The end product of the recycled plastic would be cleaned, disinfected, and/or shredded plastic material. This material may then be utilized in the bottle manufacturing process at the BBPP. Packaging materials for the BBPP may also come from the waste handling/recycling plant described herein, including possibly plastic, glass, cardboard, wood pallets and/or other recycled materials. Waste heat from the thermal plant and/or heat recovered from other sources in the Plan (e.g., FIG. 2) may be used to generate cooling, such as air conditioning and/or refrigeration for cooling buildings and/or for refrigeration of biomass products, for cooling the BGM where beneficial, and/or for other uses.

In an embodiment, e.g., FIGS. 10 and/or 24B, solids and/or sludge from the WWTP, WWTBGU, MFWBGU, and/or other BGUs described herein may be processed in a gasification module (e.g., CHG, anaerobically digested) to produce biogas for power generation in the thermal plant. In one or more embodiments, all or part of the biomass from the BGM may also be processed in a gasification module along with the solids referenced or separately using the same gasification equipment, to produce a biogas; and/or WWTP and/or WWTBGU solids may be injected into the WWTBGU for use in biomass growth; and/or any of the solids referenced may be processed in an HTP system (either the biomass HTP system described herein and/or a separate one) to produce biocrude for power generation in the thermal plant, with the remaining residue being processed by any of the above methods; and/or the solids may be processed in another WTE and/or other technology to produce power and/or fuel (e.g., pyrolysis-based WTE, cellulosic ethanol and/or other methods) for use in the thermal plant.

In one or more embodiments, e.g., FIGS. 10, 24B, and/or 24C, biogas generated by processing biomass in a gasification module (e.g., using CHG and/or anaerobic digesters), and optionally from a landfill used in any onsite process may be used to generate power in the thermal plant. The biogas from the gasification module technologies may undergo processing to prepare it for use as fuels and/or storage, comprising drying, hydrogen sulfide and/or other pollutant removal, blending with other fuels, condensation to liquids, and/or other techniques known to those of ordinary skill in the art. Gasification module(s), such as CHG module(s), anaerobic digesters and/or gas purification, drying, condensation to liquids, treatment, storage and/or heating and/or related infrastructure may be shared by BGM biomass, BGM sludge, and/or WWTP sludge and/or the resulting biogas and/or other biogas sources, such as an optional landfill, and/or other optional sources of natural gas, such as natural gas imported from offsite. Any thermal plant technologies utilizing gaseous fuels (e.g., natural gas-fired combustion turbines) and/or related infrastructure may be shared by any or all of the foregoing systems, and/or also other sources of combustible gas, such as natural gas delivered from offsite for use in the thermal plant.

In one or more embodiments, e.g., FIG. 10, and/or FIG. 24B, HTP comprises a primary method of "flash separating" biomass from water and/or converting the biomass to a biocrude and/or other fuels using a process involving heat and possibly pressure. In one or more embodiments, the biocrude that is the product of liquid-based HTP processes such as HTL or RTP may be combusted directly e.g., in burners, heavy motors, e.g., an engine normally combusting diesel or heavier fuels, and/or other select thermal plant technologies to produce power, and/or may be further refined to many major fuel types, which may be combusted if more efficient than biocrude given additional refining costs. In an embodiment HTP may convert other biomass and/or waste to biocrude. In an embodiment, HTP may be used as a full substitute for other WTE technologies, or a partial replacement in the Plan. In this embodiment, the waste may be heated and/or possibly pressurized, and the organic portion may be liquefied to a form of biocrude (this process is termed "Waste HTP"). In an embodiment, the biocrude may be combusted and/or further refined and then combusted to generate power, depending on its properties. It is an optional system in the disclosed Plan for waste-to-energy, comprising optionally the incorporation of biomass streams, such as agricultural material, wood and/or other organic materials into one or more HTP processes. The synergies with the Plan are the same as those described for pyrolysis-based WTE Systems described above, plus the following. In an embodiment, Waste HTP infrastructure may be shared with BGM Biomass HTP infrastructure, and/or other biomass HTP (Such as agricultural biomass, wood, energy crops, etc.), and the processes may be fully combined or partially combined.

In an embodiment, the biomass growth unit(s) within a biomass growth module may comprise may comprise a "growing subunit" which may comprise one or more photobioreactor(s), fermentation tank(s), other reactor(s), pond(s), and/or any other system(s) designed for growth of biomass. In an embodiment using photosynthetic biomass, CO2 from the exhaust of the thermal plant, either by use of the thermal plant exhaust gases directly, or after optionally passing through a pollution entrainment module and/or other processing technology suited to the purpose (e.g., FIGS. 7A and 7B, further described herein, as two example systems that may be used for this purpose), may be delivered to the biomass growth module. In an embodiment, a biomass feedstock source may be introduced into the stream at the proper entry point to facilitate growth, based on the biomass growth module technology in use.

In an embodiment, e.g., FIG. 2, and/or figures or description relevant to heat transfer and/or capture, the water containing biomass discharged from the biomass growth module, or "BGM outflow fluid" comprising a biomass/water slurry optionally after the processing steps shown in FIG. 1, may be sent to the thermal plant to provide cooling and heat capture in a variety of ways. The BGM outflow fluid containing biomass from a BGM may be used directly to cool the thermal plant, may be further processed and then used to cool the thermal plant, and/or may be used in a heat exchange system with another fluid cooling the thermal plant whereby it cools and captures heat from the thermal plant indirectly, depending on the nature of the BGM outflow fluid, the water quality, flow rate, volume, and/or other needs of the particular thermal plant technology type(s) in use, and/or other factors. Alternatively, heat from the thermal plant may be transferred by any other means to the biomass/water slurry.

In one or more embodiments, e.g., FIGS. 1, 2, 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer and/or water transfer, water that has been separated from biomass in a BGM outflow fluid or biomass/water slurry after it may be processed and/or refined may be used to cool the thermal plant and capture heat for use e.g., in the Plan.

In an embodiment, e.g., FIGS. 2, 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, heat captured from a thermal plant may be used productively to refine biofuels generated directly in the biomass growth module, and/or the biomass in a biomass/water slurry, optionally processed in any manner known to those in the art, without harvesting by the use of such methods as hydrothermal processing, and/or any other method of refining the biomass growth module output, especially those without harvesting, and/or to preheat for any of the foregoing. Alternatively or additionally, biomass may be processed and/or harvested by any or a combination of the methods described supra and/or by any other method that produces biomass and/or biofuel that may be useful for fuels and/or other products, and/or in the synthesis of fuels and/or other products.

In an embodiment, some portion of the energy produced by the thermal plant may be utilized to provide light that enables the photosynthetic process to proceed during overnight hours of operation when power demand declines. In an embodiment, biomass may be grown heterotrophically (in the absence of light while utilizing organic carbon) and/or mixotrophically (in the presence or absence of light while utilizing organic carbon). In an embodiment, e.g. FIG. 6, oxygen from daylight photosynthesis in the BGM may be stored and optionally directed back into the BGM at night for a heterotrophic and/or mixotrophic growth process(es), or otherwise provided by the Plan, e.g., FIG. 25. In an embodiment, e.g. FIG. 6, carbon dioxide generated in heterotrophic growth processes may be stored at night, and optionally directed back to the BGM during the day for autotrophic biomass growth process(es). In an embodiment, e.g. FIG. 6, and/or other figures and/or description relating to transfer of gases, any gases that may be generated in any process or stage likewise may be stored and reused at any other process/stage of biomass growth as may be beneficial (See FIG. 6) and/or elsewhere e.g., in the Plan. In an embodiment, e.g., FIG. 6, a biomass growth module and/or BGUs it comprises may operate heterotrophically exclusively, and an organic (biologically based) carbon and an oxygen stream may be added to facilitate growth. In an embodiment, e.g., FIGS. 5 and/or 6, different BGUs comprised by the BGM operate autotrophically, heterotrophically, and/or mixotrophically during the same time of day (e.g., an autotrophic BGU exposed to the sun and a heterotrophic BGU in a closed reactor), and/or at different times of the day, and may exchange carbon dioxide and/or oxygen and/or other resources in regulated flows. In an embodiment, carbon dioxide flow, other nutrient flows, light exposure, temperature, biomass collection rate, and many other aspects affecting a biomass growth module may be optimized based on the strain of biomass, climate, daylight cycle, and/or other factors, using sensors, flow regulators, manual and/or automated (e.g., computerized) controls, and/or other devices adapted to the purpose.

In an embodiment, e.g., FIG. 5, a biomass growth module may comprise several biomass growth units in any configuration, comprising any number of the same or different BGUs used and/or connected in parallel with fully separate components, any number of BGUs used and/or connected in series, any number of BGUs connected at any stage of their processes (e.g. sharing of subunits in whole or in part, sharing combined flows in whole or in part, and/or BGUs sharing different components and/or equipment, such as a nutrient source, stressing unit, filtration unit, milking unit, holding tank, piping, heat transfer equipment, carbon dioxide source, extraction unit, and/or any other component, resource, and/or byproduct of the Plan, such as carbon dioxide, heat, water, oxygen, growth medium, carbon source, solvent, and/or other light organic material, (e.g., volatile organic compounds, such as a C1-C10 hydrocarbon, alcohol, ether, ester, acid and the like, wherein the volatile compound may be combustible), and/or biomass. (See some example configurations in FIG. 5).

Thus, the present disclosure provides an integrated approach to minimization of $CO_2$ emissions, power generation, biofuel production, efficient use of heat and water, as well as production of biomass-derived non-fuel products, treatment of wastewater and/or waste-to-energy in some embodiments. Various embodiments provide for a wide variety of other water sources or combinations to be used to provide optionally $CO_2$ abatement, and a medium for biomass and/or biofuel production with conservation of water and/or heat energy.

In certain embodiments, e.g., FIGS. 4, 7A and/or 7B, a thermal plant and a biomass growth module may be operatively linked to provide a regulated continuous or discontinuous flow of carbon dioxide from the thermal plant, via a stack or other conveyance therefrom, to the biomass growth module. In certain embodiments, control systems may be implemented to provide affirmative control of the thermal plant and/or BGM, monitoring, or both. For example, the constituents, temperatures, humidity, and/or chemical constitution of gases and/or liquids emanating to and/or from the thermal plant, and/or any condition(s) in the BGM (e.g., carbon dioxide levels, temperature, chemical concentrations, etc.), may be monitored and/or regulated, and any portion of the gases and/or any liquids generated (e.g., using pollution control and/or pollution entrainment modules) routed either directly to the BGM, the gases routed through an optional pollution entrainment module and/or other technologies when necessary to prepare the gases and/or liquids for the BGM in order to optimize the input of carbon dioxide, and/or other inputs to the BGM. The exhaust gas recovery module and/or pollution entrainment modules may be controlled to adjust the functioning of these modules based on the measurements of the thermal plant and/or BGM (e.g., pollution controls may be increased or reduced based on changes to the exhaust gases, and/or heat, pollutants entrained, and/or water flows may be regulated based on measurements in the BGM). The thermal plant and/or biomass growth module and/or any of its components may be monitored and/or adjusted by sensors and controls either manually or automatically and/or dynamically to control operating parameters and/or any inputs and/or outputs. These sensors and controls may be integrated with computer control and automation systems for the entire Plan with sensors and computer controls to sense parameters of operation of the Plan, and to send signals to control systems to adjust and optimize performance (e.g., and industrial control system optionally with adaptive controls and/or artificial intelligence). In an embodiment, e.g., FIG. 7A or 7B, the thermal plant stack or other conveyance and/or attached modules, such as an exhaust gas recovery module as in FIGS. 7A and 7B, may use dynamic controls (e.g., computerized controls interfaced with hardware) that may automatically adjust to measurements anywhere e.g., in the Plan also to divert a controlled portion of the exhaust gases to the BGM/BGU and to direct another portion to be treated for release into the environment. The portion treated for release into the environment may use pollution control technologies as necessary to reduce emissions and/or heat exchangers to capture the heat in that portion of the exhaust gases for use e.g., in the Plan. The resultant treated exhaust gases may be released into the environment.

In an embodiment, the biomass growth module may be used as a means of water remediation. In such case, for example, organic carbon waste, nitrates, metals, and/or other potential contaminants in the biomass growth module feed water may be reduced by digestion, incorporation and/or other means in the growth of biomass. BOD5 in the wastewater may be reduced by approximately 88-100%.

In an embodiment, wastewater, e.g. municipal wastewater, farm effluent, animal waste effluent, and/or other wastewater may be used as a feed water source for the biomass growth module. When wastewater may be included as any part of the biomass growth module water source, additional pretreatment steps may be undertaken before use in the biomass growth module (e.g., primary wastewater treatment) and/or post-biomass growth module treatment steps (e.g., tertiary wastewater treatment) may be used to further treat the water in order to obtain comprehensive wastewater treatment, to prepare the water for use in other processes, and/or for release into the environment.

In an embodiment, e.g., FIGS. 1, 3 and/or 6, using a wastewater as the source, and the aforementioned system as a wastewater treatment methodology, additional, traditional bacteria-based or other wastewater treatment technology may be provided alongside the biomass growth module or BGU within a BGM to handle additional and/or fluctuating wastewater treatment needs, e.g., when the whole volume of wastewater treatment needed cannot be accomplished by the biomass growth module. In an embodiment, e.g., FIGS. 1, 3, 5, and/or 6, salt water, high salinity salt water, fresh water, wastewater (either partially treated or raw), and/or other water types may be used either in separate biomass growth units or combined as desired in certain BGUs or individual BGU subunits within the BGM, and/or several variations of BGUs may be used concurrently and/or sequentially. Further illustration of different optional BGUs and their components may be given FIG. 6, and described herein.

With reference to FIGS. 7A and 7B, in an embodiment, heat from thermal plant combustion exhaust may be delivered via a conveyance and employed to heat a BGM, individual BGU(s), and/or individual BGU components maintaining an optimal biological growth and/or reproduction rate in the biomass growth module 222. As biomass growth may be typically temperature-dependent, during colder seasons, and/or with daily temperature changes, and/or other temperature fluctuations, such heat, e.g., waste heat, assists biological growth in many cases; and/or such heat may be used in other processes, comprising heating water for any process and/or purpose e.g., in the Plan (See FIG. 2). Waste heat may also be converted to cooling in order to regulate BGM, individual BGU, and/or BGU component temperatures to prevent overheating, in refining/processing biomass (e.g., to condense solvents), to cool/refrigerate biomass products, and/or for any other use e.g., in the Plan (See FIG. 2).

In an embodiment, e.g., FIG. 1, and/or FIG. 9, an exemplary biomass refining technique that may be used may be a hydrothermal processing (HTP) method known as hydrothermal liquefaction (HTL). FIG. 9 may be an exemplary process for performing HTL. Such a liquefaction process typically produces a biocrude and water. In a first step, the biomass/water slurry may be processed by a tertiary treatment, optionally concentrated by a gravity thickener, and/or by another concentrating technique known to a person of skill in the art, e.g., centrifugation, and/or may be diluted with water from any source. Then biomass grown in a biomass growth module containing water and/or a biomass/water slurry may be heated by the thermal plant and undergo HTP in situ, and/or the heated mixture may be sent to a refinery where it may be fed to a hydrothermal liquefaction module.

In an embodiment, e.g., those embodiments of FIGS. 15A, 15B, 16, 17, and/or 18, notwithstanding the concentration of biofuel in the biomass, a biomass/water slurry may be transferred to thermal plant to be used as a cooling fluid. A biomass/water slurry may pass through a heat exchanger to provide cooling for a thermal power plant, e.g., the cooling/condensation stage of a thermodynamic cycle (e.g., Rankine cycle, other), and/or other process steps where cooling water may be needed in any thermal plant. Optionally, thermal plant waste heat may be transferred to the biomass/water slurry using a different configuration of water sources and/or heat exchangers, e.g., any water and/or other fluid source may be used to cool the thermal plant, and then to transfer heat to the biomass/water slurry via heat exchange and/or any other method, and/or other process(es) used to convey heat that may be not a heat exchanger. In thermal plant thermal processes where air may be used in firing a boiler and/or to cool the working fluid, a heat exchanger may be used to transfer heat from the cooling air to the biomass/water slurry (See FIGS. 7A and 7B, further described herein, for possible example configurations of systems that may be used to reclaim heat from exhaust gases). The figures presented may be examples only, and any viable configuration to reclaim exhaust heat may be used. In an embodiment, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, and FIG. 23, and/or other figures and/or description relevant to pressure use and/or transfer, once heat has been absorbed by the biomass/water slurry, the slurry may be optionally directed to a refinery for refinement and/or further processing, which refinery may comprise HTP module, such as the HTL module in FIG. 9, and/or another hydrothermal process module, where the temperature may be elevated as necessary and maintained (e.g., at or above about 350 degrees Celsius (662 F) for HTL) by additional heating (from the thermal plant and/other source(s), comprising heat recovery from any aspect of the Plan, See FIG. 2), and pressure may be elevated as necessary for the particular HTP method (e.g., for HTL, approximately 3000 PSI and maintained for approximately 1 hour). In an embodiment, a closed reactor may be heated from 500-1300 degrees F. with rapid heating, and the processing time may be about one minute. For example see the following references are incorporated by reference herein and relied upon: http://www.greencarcongress.com/2012/11/savage-201211-08.html, http://pubs.acs.org/doi/abs/10.1021/ef301925d and/or http://www.biofuelsdigest.com/bdigest/2015/02/22/algae-liquefaction-what-is-is-and-why-it-might-be-the-key-to-affordable-drop-in-algae-biofuels.

In an embodiment, the Envergent Technologies, LLC RTP process, or a similar process wherein algae may be heated at ambient pressure and converted to biofuel. The pressure, temperature, speed at which heat may be increased, and/or duration of the process may be adjusted based on the biomass strain in use, different combinations of heat, pressure and time under varying conditions, improvements in the methodology, and/or other specific factors. In an embodiment, e.g., FIG. 1, heat and/or energy may be supplied to an HTP module by the thermal plant and/or a separate heating process optionally powered by the thermal plant. Once the hydrothermal processing may be complete, the HTP module may release the products of the process, e.g., for HTL or RTP, typically mostly a biocrude and water; for CHG, biogas. The HTP module may be a static container of any design, or a moving conveyance of any description where HTP may be performed, depending on design preferences. It may utilize a batch method, constant flow, intermittent flow, or another flow method. The biocrude may be used directly as a fuel source for the thermal plant, or may be further dried and/or refined, and then used as a fuel source for the thermal plant. Hydrothermal conversion may be a thermochemical process to re-form biomass in hot compressed water. Under elevated temperature and/or pressure, specifically when exceeding the critical point (374.31 C and 22.1 MPa) of water, the density, static dielectric constant and ion dissociation constant of water drop drastically, which can accelerate the reaction rate substantially. Due to those superior properties of hot pressurized water, it acts as a non-polar solvent and benign reactant with high diffusivity, excellent transport properties and solubility. Consequently, hydrothermal conversion technology has been widely applied for fuels and chemicals recovery from wet biomass and/or organic waste with high moisture content in the last two decades. Hydrothermal conversion can be divided into (1) hydrothermal carbonization (180-250 C) for hydrochar production, (2) hydrothermal liquefaction (about 200-370 C, with pressures between 4 and 20 MPa) for heavy oil production and (3) hydrothermal gasification (near-critical temperatures up to about 500 C) to generate hydrogen rich gas under various conditions. From the perspectives of fossil energy shortage and environmental impacts, renewable hydrogen recovery from readily available wet biomass using hydrothermal gasification may be desired in the long run. It may be of particular interest to integrate catalytic process into thermochemical biomass conversion process to improve the yield and quality of gas and/or liquid fuels. Introduction of catalyst(s) (either homogeneous or heterogeneous) in hydrothermal gasification could achieve good gasification performance under mild temperatures and/or pressures, lowering the equipment investment and operating cost.

For example, see the following references are incorporated by reference herein and relied upon: http://www.genifuel.com/text/Genifuel%20Combined%20HTL-CHG%20-BFD.pdf, and http://www.researchgate.net/profile/Apostolos_Giannis/publication/265230800_Hydrothermal_gasification_of_sewage_sludge_and_model_compounds_for_renewable_hydrogen_production_A_review/links/5453 04b-d0cf26d5090a38456.pdf, and/or http://www.adktroutguide.com/files/Elliott hydrothermal_gasification_of_biomass.pdf.

The figures below depict a flow diagram of the basic system for continuous-flow catalytic hydrothermal gasification.

The temperature used in the operation of hydrothermal gasification of biomass can have several significant effects. Three temperature regions for hydrothermal gasification may be identified: Region I (500-700° C. supercritical water) biomass decomposes and activated carbon catalyst may be used to avoid char formation or alkali catalyst facilitates the water-gas shift reaction. Region II (374-500° C., supercritical water) biomass hydrolyzes and metal catalysts facilitate gasification. Region III (below 374° C., subcritical water) biomass hydrolysis may be slow and catalysts may be required for gas formation.

Figure 26:
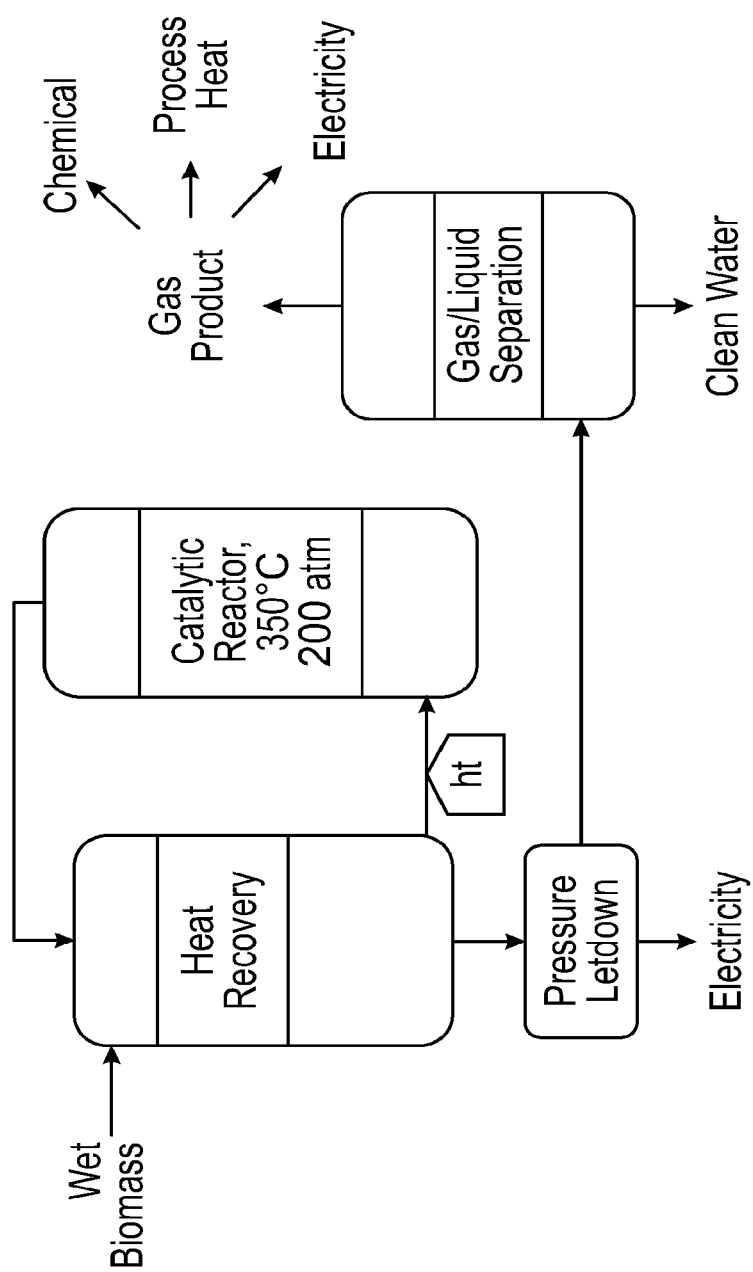
FIG. 26 is a schematic representation of a Catalytic Hydrothermal Gasification system at subcritical conditions for use e.g., in the Plan of the present disclosure.
Figure 27:
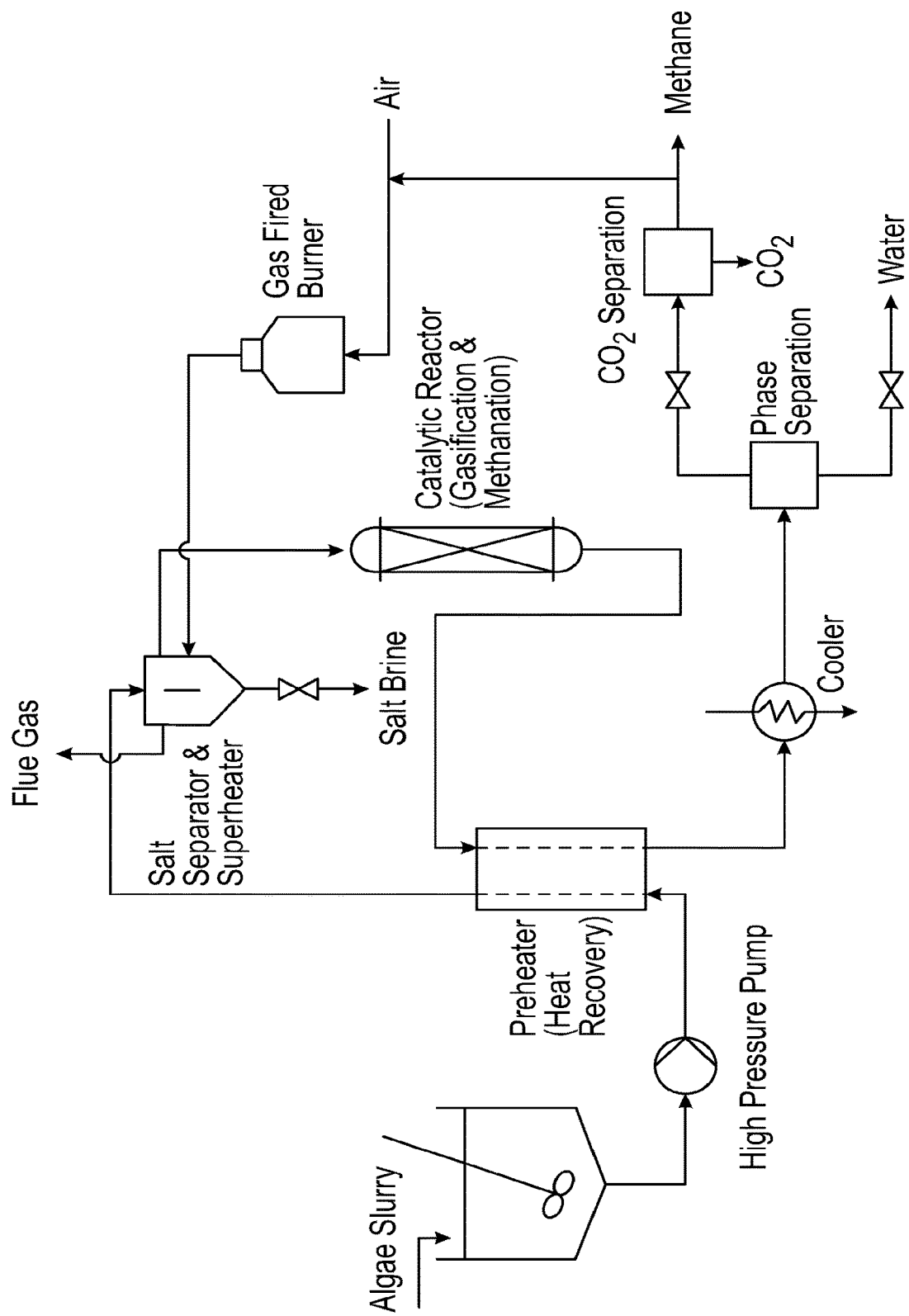
FIG. 27 is a schematic representation of a Catalytic Hydrothermal Gasification system for use e.g., in the Plan of the present disclosure.

In reference to FIG. 26 and/or FIG. 27, when operating in a system which reaches thermodynamic equilibrium, the resulting gas product composition will be determined by the pressure and temperature. Operation at subcritical temperature results in a product gas high in methane and less hydrogen while operations at supercritical temperatures will produce more hydrogen and less methane. A confounding factor may be that the partial pressure of water in the system will also affect the gas product composition in that lower biomass concentration in the reactor system—and therefore higher water content—will move the equilibrium toward hydrogen and away from methane by known steam-reforming mechanisms. A useful catalyst for gasification of biomass structures will also be a useful catalyst for methane synthesis and reforming. The use of a catalyst can allow low-temperature operation while maintaining useful kinetics. The use of low temperature will also impact the mechanical systems for containing the reaction. Lower temperature operation allows lower capital costs because of lower pressure operation, requiring less containment structure, and less severe attack on the reactor walls, which allows the use of less costly alloys.

The figure above may be another example of a CHG process, and was taken from an article "Catalytic gasification of algae in supercritical water for biofuel production and carbon capture" 2009, Energy & Environmental Science. The figure may be described as "FIG. 2 Sketch of PSI's catalytic hydrothermal gasification and methanation process." And, in further description, "An important finding was that sulfate, added as sodium sulfate to the feed solution, may be a strong poison for the ruthenium catalyst. We have, therefore, integrated a salt separation step before the catalytic reactor in our continuous process (see FIG. 2)." In an embodiment, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, energy used to generate pressure and/or heat may be recovered once a hydrothermal liquefaction and/or other HTP process may be completed. Such energy may then be transferred to generate supplemental power and/or increase the efficiency of the Plan and/or method e.g., FIG. 23.

In an embodiment, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, the heated biocrude that may be the product of HTP processes such as HTL, may be further refined while still containing the heat from HTP. For example, for HTL it may be typically necessary to raise the temperature of the biocrude to about 350 degrees C. or higher, which may be approximately the temperature needed for additional refining to other fuels. Other HTP processes, likewise may yield heated fuels possibly mixed with water. This heated mixture may optionally be dried (chemically and/or otherwise), and/or otherwise processed to separate it from water and/or other constituents, and then sent as heated for refining to produce all other refined fuels that may be derived from the type of biomass being used. For example, most algae biomass processed through HTP may be converted to the same fuels that can be derived from petroleum, comprising LPG, gasoline, jet fuel, diesel, heating oil, fuel oil, and/or bitumen. Use of the already heated biocrude from HTP may save energy in reheating to further refine the biocrude after it has cooled. Likewise, gaseous fuels that may be the product of HTP processes, such as CHG, may utilize heat in the resultant gaseous biofuel possibly mixed with steam in a similar way to provide heat for separation from water and/or further refining of the biofuel. All heat used in any refining activities may be reclaimed e.g., as described herein, and/or reused e.g., in the Plan e.g., FIG. 2.

In an embodiment, e.g., FIGS. 2, 15A, 15B, 16, 17, 18, 19 and/or 23, heated water and/or biocrude may be directed through other heat exchangers to reclaim heat used in processing the biomass. Pressure may be recovered and/or reclaimed using standard technologies such as turbine or Pelton wheel, turbocharger, pressure exchanger (such as DWEER, the rotary pressure exchanger, and Dannfoss iSave), energy recovery pump (such as the Clark pump, the Spectra Pearson pump, and/or other technologies suited to the purpose) and used to generate pressure for another portion of heated biomass/water slurry being prepared to undergo hydrothermal processing, for movement of liquids through the process, for power generation, for desalination, for other processes e.g., in the Plan, and/or other applications e.g., FIG. 23.

In an embodiment, e.g., FIGS. 2, 7A, 7B and/or other figures and/or description relevant to heat capture and/or transfer, recovered heat from thermal plant exhaust gases, thermal plant cooling, comprising embodiments using HTP of a biomass/water slurry, and/or any other process e.g., in the Plan may be reused for any hydrothermal processing method and/or other refining processes for water, biomass and/or biofuel, comprising distillation of fuels, drying of biomass for preheating the biomass growth module water source, for either directly and/or indirectly heating the biomass growth module, for heating anaerobic digestion (when used) to increase efficiency, biofuel, and/or waste in preparation for combustion and/or other processes, in cellulosic ethanol/butanol/isobutanol processes, in supercritical fluids extraction, for increasing the efficiency of an optional desalination unit, for HTP of any organic waste which may mixed with biomass and water and/or another fluid, and/or for other processes or uses e.g., in the Plan (See FIG. 2). In an embodiment, e.g., FIG. 7A, 7B, and/or FIG. 3, water that may be the substrate for any of the foregoing processes may be reused anywhere e.g., in the Plan where water may be utilized, including as source water for the BGM, cooling the thermal plant, to dilute brine discharge of the optional desalination system, and/or for other uses (See FIG. 2). Heat exchangers and/or other known technologies may be used to transfer heat from any system e.g., in the Plan to another.

In an embodiment, e.g., FIG. 2, 7A, 7B, 12A, 12B, 12C, 12D, and/or 12E, and/or figures or description relevant to heat transfer and/or capture, heat may be generated/reclaimed for use in above applications and/or for other applications e.g., in the Plan by the following: The thermal plant's waste heat in the form of exhaust gases and that heat which may be captured by thermal plant cooling water, primary process heat generated by the thermal plant (e.g., primary combustion process non-waste heat), heat generated by any other thermal plant process, heat recovered from HTP and/or other water/biofuel/biomass refining, heat that may be recovered in processes used to cool the BGM, additional solar thermal techniques of any type, comprising solar troughs and/or towers, optional desalination plant discharge, and/or any other process e.g., in the Plan where heat may be captured and/or recovered, comprising reclamation of heat resulting from any process herein disclosed and/or known to the person of skill in the art. Heat exchangers and/or other known technologies may be used to transfer heat from one system to another and/or from one substrate to another (e.g., water, vapor, solids to another substrate) and/or different supplies of the same substrate type (e.g., wastewater to separate water supply used in different processes, gases to other gases, etc.), which may transfer heat where needed e.g., in the Plan, for example, see FIGS. 12A-12E.

In an embodiment, e.g., FIG. 3, following hydrothermal processing e.g., FIG. 1, and/or other processes such as the harvesting of the biomass material from the biomass growth module discharge stream, a subsequent purifying filter, ultraviolet light, tertiary wastewater treatment (e.g., when wastewater may be used in the BGM) and/or other water treatment methods known to those of ordinary skill in the art may be used to further treat the water discharge before use in other applications where necessary.

Water processed through this system and/or optional subsequent refining steps can be made suitable for many uses, e.g. as a potable water stream, a non-potable stream, for discharge to the environment, for reuse in the disclosed Plan wherever water may be needed (See FIG. 3).

With reference to FIGS. 1, 4, and 6, in an embodiment, a majority, e.g., the percentages described earlier, or all of the carbon dioxide in the exhaust gas delivered to the biomass growth module may be consumed as raw material for photosynthetic growth of a biomass and thereby converted into useful organic compounds. Fuel, nutraceuticals, food and feed, pharmaceuticals, pigments, vitamins, antioxidants, biopolymers, cosmetics, paper, lubricants, fertilizer, chemicals and/or other product types may be produced in such production processes as known to a person of ordinary skill in the art per Pandey, et. al 2013 pgs. 205-233. Optionally, carbon dioxide may be used in some water, biomass, and/or biofuel refining techniques, such as supercritical fluids extraction, in the desalination process, in the water bottling/packaging plant to carbonate water and/or other liquids (likely after some purification), and/or may for other purposes (See FIG. 4).

In an embodiment, optionally, an artificial light source, optionally powered by a thermal plant, may be provided for use as required, e.g., during off-peak, non-daylight conditions, for photosynthetic growth of the biomass. In this manner, the biomass growth module may be operational at least from 80% to 100%, or from 85% to 95%, or from 90% to 100% of a 24 hour day. In an embodiment the percentage of operation per day may be 80, 81, 82, 83, 84, 85, 86, 87, 88, 89, 90, 91, 92, 93, 94, 95, 96, 97, 98, 99, or 100 percent or from one integer to another integer in the preceding list, for example from 83% to 92%. This percentage may include nighttime growth by supplying a carbon source with light (e.g., autotrophic or mixotrophic) and/or without light (e.g., heterotrophic or mixotrophic). Different growth methods may be used concurrently in different BGUs within the BGM.

In an embodiment, e.g., FIG. 6, 600 a supplemental nutrient supply line(s) 620 may optionally deliver a controlled amount of nutrients (such as nitrogen and/or phosphorus) from nutrient supply controlled by a motive device such as a variable speed pump, which receives an input signal from a water and/or biomass measurement and/or other parameter measurement device such that a control signal may be sent to the motive device to regulate the inflow of nutrients into the BGM or any other component thereof.

One or more measurement device(s) may be set to measure water content of essential nutrients in the system, biomass density, pH, temperature, gases of different types, and/or any number of other factors, and optionally send the information to a computerized system, which may then send a signal back to one or more automated systems to make an adjustment(s) to any operational parameter(s) (e.g., initiating an input or output, changing the flow of an input our output, changing some other aspect of the system in response to the sensed and/or measured information). All systems e.g., in the Plan may have sensors and/or automated or manual valves and/or other flow rate controls to dispense materials, apply heat and/or cooling, add or reduce carbon dioxide and/or other gases, add or reduce additional water flows of any type, and/or to meet any other needs of all systems in the BGM. These systems may comprise integrated computer control and automation systems with sensors and computer controls to sense parameters of operation of the entire Plan, and to send signals to control systems to adjust and optimize performance (e.g., and industrial control system optionally with adaptive controls and/or artificial intelligence).

In an embodiment, municipal wastewater, where used as the water source for the biomass growth module, in whole or in part, may be treated more completely to remove contaminants and dissolved carbon, for example, in the disclosed Plan, than in a standard wastewater treatment plant or a biomass-based wastewater treatment plant known to the person of ordinary skill in the art. The colocation and/or integration of beneficial inputs described herein from the other modules of the Plan (e.g., abundant carbon dioxide, heat, etc.), and flow controls may be used to optimize the biomass's ability both to grow and to remediate contaminants. For example, municipal wastewater effluent may contain a substantial concentration of waste pharmaceuticals and metabolites thereof, e.g., hormones, antibiotics, cardiovascular drugs, etc., that the biomass (e.g., algae) may use as a feed source. Recently, algae have become significant organisms for biological purification of wastewater since they may be able to accumulate plant nutrients, heavy metals, pesticides, antibiotics, medicines, hormones, antibodies, proteins, viruses, and the like, and/or other human xenobiotic substances, organic and inorganic toxic substances and radioactive matters in their cells/bodies with their bioaccumulation abilities. For example, see the following references may be incorporated by reference herein and relied upon: Bulent Sen, Mehmet Tahir Alp, Feray Sonmez, Mehmet Ali Turan Kocer and Ozgur Canpolat (2013). Relationship of Algae to Water Pollution and Waste Water Treatment, Water Treatment, Dr. Walid Elshorbagy (Ed.), ISBN: 978-953-51-0928-0, InTech, DOI: 10.5772/51927. Available from: http://www.intechopen.com/books/water-treatment/relationship-of-algae-to-water-pollution-and-waste-water-treatment and http://www.ncbi.nlm.nih.gov/pmc/articles/PMC4052567/. Abdel-Raouf, N., A. A. Al-Homaidan, and I. B. M. Ibraheem. "Microalgae and wastewater treatment." Saudi Journal of Biological Sciences 19.3 (2012): 257-275. In an embodiment, municipal wastewater and/or agricultural and/or runoff wastewater may comprise a large concentration of fertilizer, pesticides, and the like that serves as a feed source for algae. The embodied system may be idealized, controlled and regulated to optimize the growth of biomass such as algae, and thus, greatly increase the efficiency of the uptake of contaminants. In an embodiment, the effluent from the biomass growth module may contain a lower concentration of nitrates, phosphorus and/or other pollutants than in the wastewater delivered to the biomass growth module. Similarly, carbon dioxide and other gases and contaminants (e.g., NOx and SOx, particulates) may be discharged to the environment in the effluent from the biomass growth module at a lower rate per unit time than the rate per unit time than the carbon dioxide and other gases and particulates may be delivered to the biomass growth module from the exhaust gas of the thermal plant.

With reference to FIG. 6, in an embodiment, the biomass growth module comprises a BGU 600 with a growing subunit 602, which optionally receives exhaust gases, or the treated exhaust gases and/or liquids e.g., from the pollution entrainment module 712, pollution control module 704 and/or other treatment technology, wherein they may be combined with a water source, optional nutrient stream 620 and/or other elements to promote growth. A biomass "seed" source, may be added to start and/or support or enable biomass growth. In photosynthetic embodiments, carbon dioxide and/or other gases, e.g., harmful gases, may be used to produce biomass, and oxygen may be released. The oxygen may be stored and/or transferred; the oxygen may be used in other processes e.g., in the Plan; and/or the oxygen may be marketed e.g., FIG. 25.

In an embodiment, e.g., FIG. 25, the oxygen produced in the BGM and/or from other sources e.g., FIG. 25 may be injected in whole or in part into the inflow of any thermal plant combustion technology as a means to reduce the formation of NOx in thermal plant emissions, and/or to provide other potential benefits in combustion processes.

In an embodiment, one or more bioreactors may be used in the biomass growth module and/or in any BGU comprised by the BGM, and/or in any growing subunit comprised by a BGU.

In an embodiment a bioreactor may be a partially or fully enclosed structure comprising water, gases, nutrients and/or other elements used to grow biomass, inlets to allow entry of required elements, and/or outlets for biomass, biofuel, water, gases, and/or other elements to be released. A bioreactor that allows for penetration of light into the biomass for use in photosynthetic processes may be termed a photobioreactor.

In an embodiment, e.g., FIG. 6, BGUs comprised by the BGM which may be used in an embodiment comprise open ponds, closed ponds, channels, high rate ponds, waste stabilization ponds, other ponds of any description and/or other water bodies or portions thereof, whether covered or open to the environment, and/or other open or closed systems of any kind adapted for biomass growth. BGUs may comprise nutrient streams, water streams, external and/or internal lighting, water jets, paddle wheels and/or other liquid movement and/or agitation technologies, gas delivery technologies for the delivery of CO2 and/or other gases, and/or any of the wide variety of technologies employed to enhance biomass growth and/or processing.

In an embodiment, solar energy may be captured for use in the method and/or systems described herein. For example solar energy may be captured in the form of a closed or open basin of any configuration comprising the use of water in decorative water features such as pools, fountains, lakes, etc. (e.g., used to enhance the visual appeal the Plan), and/or a solar thermal technology, such as a solar tower, solar trough, and/or other solar thermal unit of any description, may be used to heat water to an elevated temperature before entrance into the BGM and/or other modules of the Plan, to heat the intake water for an optional desalination unit, and/or for any other use of water e.g., in the Plan (e.g., FIG. 3). In colder climates, or at cooler times of day, where cold water may be advantageous, the water comprised by the basin may be used to bring cooling to the Plan.

Generally, most aquatic biomass species may be believed to grow effectively only between approximately 37° N and 37° S latitude, and when overnight temperatures drop, and/or daytime temperatures may be too high, aquatic biomass growth can slow or stop. Photosynthetic biomass may have sufficient light resource in many parts of the world where temperature limitations prevent or slow growth. The disclosed Plan may be intended to provide a solution to the issue of temperature limitations in growing biomass worldwide. In an embodiment, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, and/or FIG. 6, heat, e.g., waste heat, and/or cogenerated cooling from the thermal plant, the water discharge from HTP, and/or other heat-intensive process e.g., in the Plan (e.g., FIG. 2) may be provided to counteract temperature variations in the biomass growth module, a BGU within the BGM, and/or any component(s) of any BGU due to e.g., ambient temperature change and/or other reasons that may be detrimental to optimal biomass growth. In this manner the co-location of the thermal plant and/or other heat sources and biomass growth module may enable daily and/or year-around operation and optimization of the biomass growth module, e.g., a 24/7 operation, and use in temperate climates where biomass, such as algae cannot grow effectively at ambient temperatures for all or part of the year, or even in extremely cold climates, like arctic regions, where it may be much too cold to grow biomass effectively in a normal biomass growth system. In an embodiment, e.g., FIGS. 2, 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer and/or FIG. 6, cooling from the thermal plant (e.g., using cogenerated cooling technologies), and/or other means to bring cooling into the Plan and/or reclaim cooling, e.g., FIG. 2, and as otherwise disclosed herein and/or in any manner know to those skilled in the art, may allow for biomass growth in warm or even in extremely hot environments (e.g., deserts) which could normally hinder growth rates and/or limit the species available for use. Cooling generated in this fashion may also be used to generate cooling such as air conditioning and/or refrigeration for cooling buildings, for cooling and/or refrigeration of biomass products, for use in biomass refining, such as condensing solvents evaporated off after extraction, for condensing and/or cooling other process gases, liquids and/or solids throughout the Plan, and/or for other uses potentially onsite and/or offsite.

In an embodiment related to biomass growth methods and systems and plans therefor, e.g., FIG. 6, the biomass growth module, certain BGUs comprising it, and/or certain components comprising a BGU may be installed in contact with the ground, partially or fully underground, in contact with water, and/or partially or fully submerged in water as may be most beneficial to the location with consideration of temperature stability and optimization. For example, in Artic/Antarctic cold climates, the biomass growth module and/or any of its components (e.g., a bioreactor) may be preferably fully or partially underground, and/or in a container (e.g., a tank) filled with water, air and/or other fluid. Either the ground, the water, the surrounding air, and/or any other material in contact with, and/or flowing into a BGM, BGU, or BGU subunit (e.g., source water) may be heated by the thermal plant e.g., using waste heat and/or primary process heat e.g., as described herein, and/or other heat source e.g., in the Plan (e.g., FIG. 2), and/or cooled e.g., using cogenerated cooling from the thermal plant heat, optionally waste heat, and/or other cool fluid source (e.g., FIG. 2, as otherwise disclosed herein, and/or as known to those in the art), to maintain a beneficial temperature for biomass growth. In an embodiment, discharges from the BGM, piping, and/or other components e.g., in the Plan, likewise may be installed partially or wholly underground. The ground which contacts the BGM, BGM component(s) and/or other components e.g., in the Plan may be heated and/or cooled using heat and/or cogenerated cooling from the thermal plant and/or heat from other sources e.g., in the Plan and/or other sources (e.g., geothermal heat, if locally available, solar thermal technologies such as solar troughs and/or towers, and/or other sources or technologies). In an embodiment, the BGM or any of its components may be designed to float on the top of water, where the water helps to regulate the temperature, and the movement of water in contact with the BGM component (e.g., waves and/or currents) may be utilized in mixing the biomass and/or other elements contained in the BGM. In an embodiment, if the BGM may be in contact with and/or partially or fully submerged in water, a water tank, pool, and/or other water structure may be used to contain the water, and heat and/or cooling, generated by the thermal plant, its output and/or other heat source(s) e.g., in the Plan (e.g. FIG. 2) may be used to regulate the temperature in the water structure in order to maintain optimal temperature in the biomass growth module or its component(s). In one or more embodiments, the biomass growth module may alternatively or additionally comprise devices and/or structures to contain and/or control the flow of air around the biomass growth module or any of its components and to the heat and/or cool the air in order to regulate the biomass growth module or its components' temperature using air, other gas, and/or vapor. Heated air, other gas and/or vapor and/or cogenerated cooling air may be generated from the thermal plant and/or other sources e.g., in the Plan, and/or other sources may be used for this purpose (e.g., waste heat and/or cooling in air may be directed to a greenhouse or other structure containing the BGM). In an embodiment, heat exchangers, repositioning, restructuring, covers, heat to and/or from the biomass growth module or any of its components, electricity, heat and/or cooling generated by the thermal plant and/or other sources e.g., in the Plan evaporative techniques and/or any other means and/or structure suitable to transferring to conserve heat and/or release or otherwise mitigate excess heat may be used to regulate the temperature of a BGM, a BGU, a subunit and/or any of its components, optionally using sensors with automation (e.g., to measure temperature or other aspect of the system and/or Plan and enact a change to the system), and/or any other method known to those of skill in the art where feasible in the implementation and operation of these techniques.

In an embodiment, biomass growth may be performed in a batch method, semi-continuous, or continuous method in any BGU. Feedwater for any BGU or BGU component may be treated to remove or reduce constituents of any kind that may be detrimental to biomass growth, for example, if metals levels may be too high, and would be lethal to the biomass, the water may be treated to remove metals before use in the BGU. Feedwater for any BGU and/or BGU component may be used from any source e.g., in the Plan (See FIG. 3), and may also be treated in any other way known to the art to optimize biomass growth, for example, the addition of chemicals to adjust pH, the addition of nutrients, minerals, combination with other water sources and/or any other treatment method known to the art to optimize biomass growth based on the particular conditions of the system, comprising the biomass strain(s) in use, climate, temperature variations, and/or any other factor which may affect the growth of biomass.

In an embodiment, feedwater may also be preheated in any manner water and/or a water/biomass slurry may be heated or cooled e.g., as described herein, comprising any process(es) in FIG. 2, 3, 7*a*, 7B, 11, 12, or 14-22, may be preheated or precooled by use in decorative water features, such as pools, fountains, and/or lakes, preheated using solar thermal technology (e.g., solar towers and/or solar troughs), and/or in any manner known to the person of skill in the art, and afterwards directed to the BGU in whole or in part as feedwater for the BGM or any BGM component.

In an embodiment, e.g., FIG. 1, a WWTP or any of its components may be adapted for use as a BGM, or to support the function of a BGM. WWTP ponds may be generally too deep to be optimal for biomass growth, such as algae. The WWTP ponds may be filled in to provide more shallow ponds suitable to aquatic biomass, and stirring and a carbon dioxide source may be added, e.g., a raceway design. Alternatively, lighting may be added below the pond surface to light the deep WWTP ponds in order to make them suitable for biomass growth, such as algae. If beneficial, WWTP ponds and/or other structures may be used to contain water that may be in contact with BGM or any of its components in order to regulate the temperature of the BGM or any of its components. For example, BGU bioreactors may be fully and/or partially submerged in or otherwise put in contact with (e.g. floating on) ponds currently or formerly used as part of a WWTP in order to create a more stable temperature in the bioreactor. Also, WWTP ponds and/or other structures may be heated and/or cooled using heat and/or cooling generated in the thermal plant, and/or from other sources (e.g., in the Plan, e.g., FIG. 3) in order to optimize the BGM or any of its components. Any of these adaptations of a WWTP to support a BGM may be used with active WWTPs to the extent practical, and/or those that may be converted over or retrofitted to function as or support the operations of BGMs, BGUs, and/or other components of BGMs, and may be no longer used as WWTPs.

In an embodiment, heat transfer mechanisms not specifically described herein for generating power from heat by way of steam, electricity, or otherwise, or for extracting heat from water, gases, or otherwise, and may be known by the person of ordinary skill in the art may be used e.g., in the Plan wherever heat transfer may occur.

In an embodiment, e.g., FIG. 1, and/or description regarding BGU operation and/or design, notwithstanding the construction and/or operation of the biomass growth module(s) comprising embodiments that include photosynthesis, non-photosynthetic, and/or a mixture of processes for biomass growth, the design may include structures to partially block, redirect, filter, concentrate, and/or otherwise modify light being introduced into the biomass growth module or individual BGUs, BGU subunits, and/or other BGU components. For example, in an embodiment, a photosynthetic bioreactor used to grow biomass using light may be configured to grow an organism or organisms also in the dark by selectively blocking and/or filtering sunlight at predefined times and/or in response to detected conditions and selectively unblocking and/or removing such filters of the sunlight at other times and/or under other detected and/or selected conditions. Different wavelengths of light may also be directed to a BGU or subunit or filtered out where beneficial (e.g., FIG. 8) either using equipment outside of the bioreactor, and/or by modifying the bioreactor itself (e.g., the bioreactor coating may be configured to selectively filter light).

Figure 8:
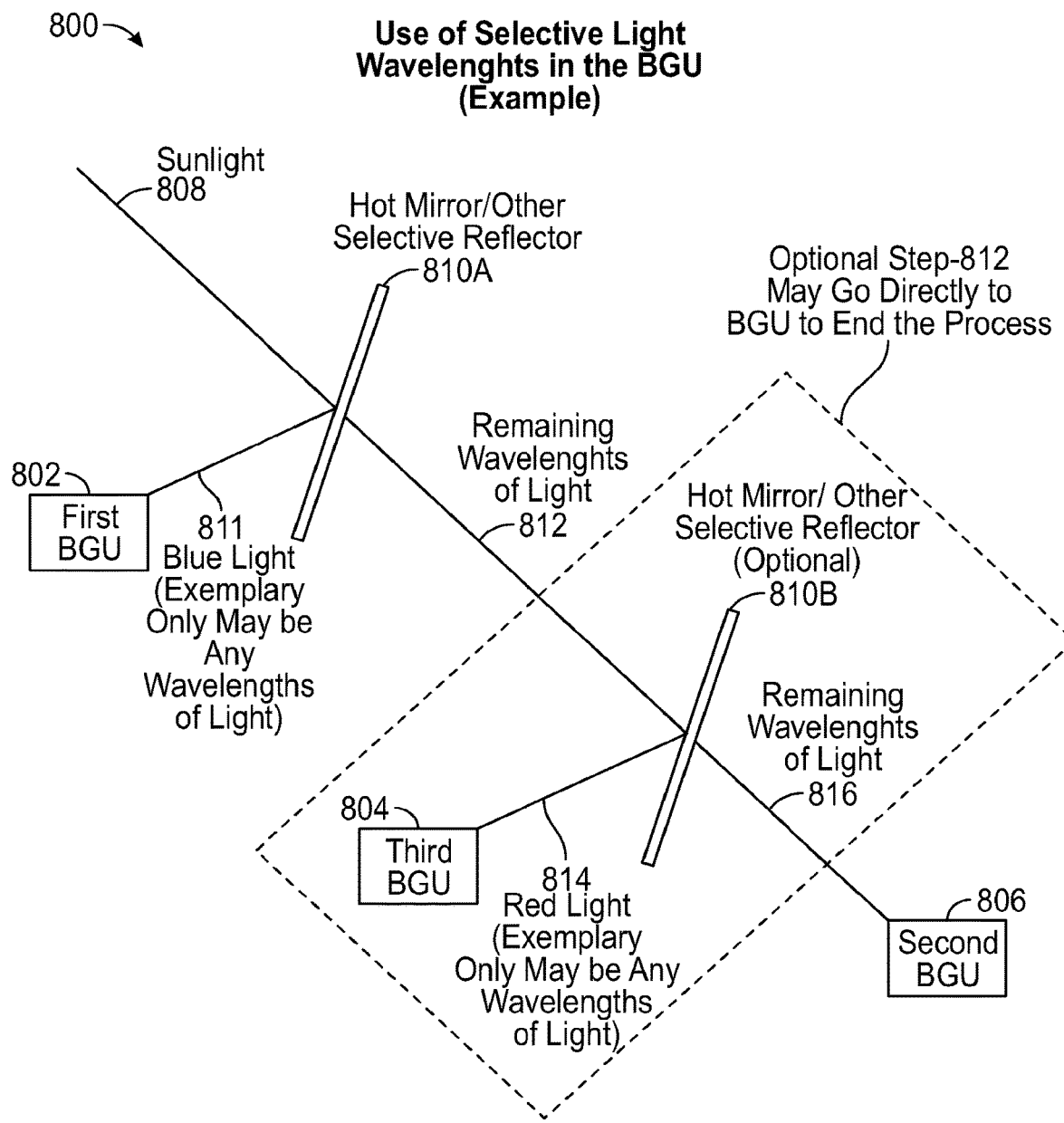
FIG. 8 is a schematic representation of a design for light wavelength selection in a biomass growth unit according to the present disclosure.

In an embodiment, e.g., FIG. 8, a system and method may be used to select a portion of the spectrum of light and using it to photostress an organism, e.g., algae, using filters, selectively reflective surfaces and/or BGU materials, and/or other means to alter light in a way most suitable to the growth of desirable biomass and/or products generated therefrom (e.g., stressing through the use of certain wavelengths of light). These processes may be used to alter and/or select light frequencies directed to any subunit of any BGU. For example, with reference to FIG. 8, in an embodiment, hot mirror 810A or other technology suited to the purpose receives sunlight and/or artificial light source, and reflects predominantly blue light 811 into a first BGU 802 while allowing other wavelengths of light 812 to pass through to a second stage reflector 810B, which reflects predominantly red light 814 into another BGU 804, and all remaining wavelength of light 816 may be allowed to pass through to another BGU 806. Alternatively, the remaining wavelengths of light 812 may go directly to a BGU without 810B to end the process. Alternatively, the BGU 806 may be eliminated from any of these configurations, wherein remaining wavelengths may be not directed to a BGU. Red and blue light in FIG. 8 may be only exemplary. Any wavelengths of light in the visible and/or invisible ranges may be used similarly. In this manner, or using other variations of sequence or different wavelengths of light in reflection in the same manner, or in other ways known to those in the art, different wavelengths of light may be used where most beneficial in the biomass growth process.

In reference to FIG. 8 an embodiment of the disclosure includes a system 800 configured to provide selected wavelengths of light to a BGU or a component thereof comprising a hot mirror or other light-selective surface 810A in operative communication with the BGU and which mirror or other surface is configured to selectively reflect, or direct a wavelength or range of wavelengths of light 811, 812 to a BGU or a component thereof 802, 806. An embodiment includes the system wherein selective wavelengths of light 812 are allowed to pass through the hot mirror or other light-selective surface 810A. An embodiment includes the system wherein the selective wavelengths of light 812 are directed to a BGU or BGU component 806. An embodiment includes the system wherein the selected wavelengths of light 812 are directed to a second hot mirror or other light-selective surface 810B. An embodiment includes the system wherein selected wavelengths of light 814 are reflected or directed from the second hot mirror or other light-selective surface 810B into or onto a BGU or BGU component 804. An embodiment includes the system wherein selective wavelengths of light 816 are allowed to pass through the hot mirror or other light-selective surface 810B. An embodiment includes the system wherein the selective wavelengths of light 816 are directed to a BGU or BGU component 806.

In reference to FIG. 8 an embodiment of the disclosure includes a method for providing selected wavelengths of light to one or more BGUs or BGU components comprising receiving light onto a hot mirror or other light-selective surface 810A wherein the hot mirror or other light-selective surface is in operative communication with the BGU, and selectively reflecting or directing the wavelengths of light, and directing the selective wavelengths of light 811, 812 to a BGU or a BGU component 802, 806. An embodiment includes the method wherein selective wavelengths of light 812 are allowed to pass through the hot mirror or other light-selective surface 810A. An embodiment includes the method wherein the selective wavelengths of light 812 are directed to a BGU or BGU component 806. An embodiment includes the method further comprising directing the selected wavelengths of light 812 to a second hot mirror or other light-selective surface 810B, and selectively reflecting or directing the second selected wavelengths 814, 816 to a BGU or a BGU component 804, 806. An embodiment includes the method wherein selected wavelengths of light 816 are allowed to pass through the hot mirror or other light-selective surface 810B. An embodiment includes the method wherein the selected wavelengths of light 816 are directed to a BGU or BGU component 806.

In an embodiment, e.g., FIG. 6, the biomass growth module may contain adequate structures, control modules, hardware and software, such as valves to inject or release gases, liquids, and/or solids as necessary to maintain optimal biomass growth. Sensors may be used to detect any condition in the BGM or any of its components, atmosphere, and/or surrounding systems, to send a signal to a control system, which may then trigger an automatic response to make an adjustment to BGM and/or its supporting systems (e.g., systems connected to and/or in operative communication with, and/or otherwise providing inputs, receiving outputs and/or otherwise interacting with the BGM in any way to affect its operations, e.g., in the Plan). For example, a sensor may monitor BGM component temperature, and trigger an automated response to release additional heated water into a pool, heating a BGM component to optimize its temperature. This automated system may be controlled by computer. The computer software may employ algorithms based on data and/or intelligent adaptive controls.

In an embodiment, e.g., FIG. 25, oxygen and/or other gases released from a BGU may be collected and stored and/or rerouted for use in heterotrophic biomass growth processes, in a WWTP, in other processes beneficial to the Plan, and/or may be marketed. In an embodiment, oxygen collected from a BGU may be injected in whole or in part into thermal plant combustion processes to reduce NOx emissions.

In an embodiment, e.g., FIG. 6 the BGM may comprise not only one technology design, but possibly an array of different BGUs which may use an array of bioreactors, tanks, ponds, with any necessary supporting subunits e.g., FIG. 6, other designs suited to the purpose and/or any combination of technologies designed to grow and/or process biomass.

In an embodiment, A BGM may be composed of one or more BGUs e.g., FIG. 5. A BGU may be any system for growing/developing/preparing biomass, comprising a growing subunit, and any supplementary subunits to support biomass growth within that particular BGU, such as a nutrient supply, stressing subunit, and/or any other subunits necessary to the BGU's system (e.g., FIG. 6 and Patent US 2009/'0197322 A1, incorporated herein by reference in the U.S. Provisional Application No. 62/173,905, filed Jun. 10, 2015, Appendix 2) and/or other possible components and/or processes that may be used in a BGU. In an embodiment, other systems and/or components may be used that may be suitable to support biomass growth.

In an embodiment, e.g., FIG. 5, one or more BGUs of any configuration composing a BGM may be used and/or connected in series and/or in parallel, may share any component(s), may flow into each other in whole or in part. FIG. 5 represents some example configurations of the BGM. In FIG. 5, lines with arrows indicate inflows and outflows, and lines without arrows represent sharing, comprising sharing from one BGU to another or back and forth of any material (comprising inflows and/or outflows) from any subunit(s) comprised by the BGUs. Example 1: A Single BGU, Example 2: BGUs in series, Example 3: BGUs in parallel with no sharing. Example 4: BGUs in parallel with sharing. 5.) BGUs in parallel with sharing and only one outflow. 6.) Multiple BGUs in a variety of sharing and inflow and outflow configurations. The illustrated configurations may be only examples, and any configuration of BGUs may be used to comprise the BGM.

In an embodiment, e.g., FIG. 6, or other figures and/or description regarding BGUs, in lieu of ponds or photobioreactors to grow biomass, any of the biomass BGUs may utilize other technologies, such as those involving fermentation processes, heterotrophic biomass growth (requiring no sunlight), mixotrophic biomass growth, and/or any other system herein disclosed and/or known to those in the art that may be viable in producing biomass and/or biofuels. Any other systems that work differently to produce fuels and/or consume carbon dioxide, or new systems developed in the future that perform these functions may also be used in the same fashion to perform the function of a BGU. The biomass, fuel(s), and/or products produced from any of these systems may be used e.g., as described herein.

In an embodiment, different processes may be used for refining/separating biomass, e.g., in a Refinery and/or BPP, represented in some figures of this disclosure as "Refinery/BPP". Currently HTP may be considered a preferred technology for biomass separation from water and/or partial refining for biocrude and/or other fuels. Any equivalent technology and/or method that may be available to the person of ordinary skill in the art may be used for these processes in the design or Plan to allow for flexible use of different technologies known to the art where most beneficial in biomass separation and/or refining. The resultant fuels may be used e.g., as described herein.

In an embodiment, in making other biomass-derived products from biomass generated e.g., in the disclosed Plan (e.g., FIGS. 6, and 14), comprising higher value products such as pharmaceuticals and nutraceuticals as known to a person of ordinary skill in the art per Pandey, et. al 2013 pgs. 205-233.

Other methods may be used to process biomass comprising: filtration, screening, centrifugation, flotation (comprising dissolved air and hydrogen), flocculation, bio-flocculation, gravity settling, gravity thickener, and/or other techniques as known to a person of ordinary skill in the art, e.g., Shelef, et. al, 1984 and Pandey et. al, 2013 pgs. 85-110.

In reference to FIG. 14 the separation unit 1404 separates biomass 1404a and/or 1403 from water 1406 and may be achieved through filtration, screening, centrifugation, flotation (comprising dissolved air and hydrogen), flocculation, bio-flocculation, gravity settling, gravity thickener, and/or other techniques as known to a person of ordinary skill in the art and/or e.g., Shelef, et. al, 1984 and Pandey et. al, 2013 pgs. 85-110.

In one or more embodiments, e.g., FIGS. 7A and/or 7B, and unexpectedly, sulfur capture may be affected by the process of the disclosure. Sulfur may be often a constituent in fuels burned in the thermal plant. When burned, sulfur produces primarily sulfur dioxide (SO2). In the presence of water, sulfur dioxide forms sulfurous acid (H2SO3), a weak acid. Thus, oxides of sulfur that may be often problematic in gaseous exhaust, requiring scrubbers and/or other technologies to clean up thermal plant exhaust, may here be used to advantage to promote additional remediation of exhaust gases and/or the water in the system, whether exhaust gases may be processed through a pollution entrainment module in an exhaust gas recovery module, and/or a pollution control module (e.g., FIG. 7A or 7B) and/or other technology suited to the purpose, and/or used directly in the biomass growth module. In an embodiment, e.g., FIGS. 7A, 7B, and/or 22, sulfurous acid may be collected from the pollution entrainment module, and/or pollution control module (e.g., FIGS. 7A and/or 7B), a wet scrubber, and/or a two pass wet scrubber's first pass and/or second pass 2240, 2276 (e.g. FIG. 22), and/or other exhaust gas purification technology and/or used to further remediate exhaust gases and/or alkaline and/or salty soils or water.

In an embodiment, the Plan may comprise one or more of the following features: a biomass growth module using wastewater and serving some functions of a wastewater treatment plant, a freshwater BGU, a saltwater BGU, a brackish water BGU and/or other BGU type(s) e.g., as described herein; a traditional bacteria-based wastewater treatment plant; a sludge processing plant; a thermal plant, which may comprise power generation from fuels and/or waste, and/or other heat-intensive processes; a desalination plant; a biofuel/biomass processing plant; a waste-handling and/or recycling plant; a biofuel research center; a water bottling/biomass products bottling/packaging plant; a non-technical facility such as a shipping area; a site maintenance facility; non-production office space; an assembly area, such as a convention center, a tower, decorative and/or water-treatment fountain (e.g., oxygenation of water) pool(s) and/or a lake(s) and/or other body of water e.g., for discharge of water to the environment, or as a water reservoir for supply of water to the biomass growth module, thermal plant, and/or other modules herein disclosed.

In an embodiment, a thermal plant may provide heat and/or optionally power for the Plan and/or optionally for the grid. Solid waste may be processed and waste recycled when possible or used in a WTE technology to produce energy. A WWTBGU may treat wastewater, mitigate carbon dioxide produced onsite, produce biofuel for use as a power source onsite, and/or may use other water source(s) to produce an array of fuels and other products for export offsite. A conventional wastewater treatment plant may exist prior to, and/or alongside, biomass growth unit-based WWT plant, or WWTBGU.

The resultant treated water from either process may be used for industrial, firefighting, landscaping, irrigation and/or other purposes. A sludge processing plant may process sludge from WWTBGU(s) and/or WWTP(s) and use it to produce soils substrates, fertilizer, fuels (by hydrothermal processing and/or other methods), and/or other products. A saltwater and/or brackish water biomass growth unit may produce biofuel and/or other valuable products from seawater while mitigating carbon dioxide emissions. Water may be brought in from the sea, desalinated in the desalination plant, and used e.g., for drinking and/or many other functions of the Plan and the community.

All of the production products and byproducts produced e.g., in the Plan may be used synergistically to provide the maximal ecological benefit. In an embodiment, the facility may be substantially self-contained and self-sustainable with respect to energy use, water use, mitigation of CO2 and other harmful emissions, wastewater treatment and/or waste treatment.

Wastewater Treatment Biomass Growth Unit/Conventional Wastewater Treatment Plant: In an embodiment, A BGU may grow biomass using wastewater as the water source, and simultaneously perform wastewater treatment of municipal wastewater, farm runoff, and/or other wastewater in whole or in part. Other process steps known to one skilled in the art may be added to achieve certain wastewater treatment goals. Such a BGU, with optional modules added as necessary for additional treatment may be termed a "Wastewater Treatment BGU" (WWTBGU).

In an embodiment, e.g., FIG. 6 or other figures and/or description regarding BGUs, one or more traditional bacteria-based wastewater treatment plant (WWTP), WWTBGU, both, or optionally more than one of each may be located proximate to where wastewater treatment may be implemented in any embodiment. In this sense, optionally being collocated, the WWTP(s), and/or the WWTBGU(s) may form a locus of wastewater treatment. These systems may also be operably connected to share infrastructure in common, and/or may exchange gases (e.g., a photosynthetic WWTBGU may supply oxygen to a WWTP, and/or a WWTP may supply CO2 to a photosynthetic WWTBGU, e.g., as described herein, e.g., FIGS. 4 and 25). In an embodiment, one of these plants or BGU system types may be built first, followed later by the other, wherein the original system may continue to operate, or may be later partially or fully converted to the other system type for treating wastewater (e.g., a WWTP may be built first, and a WWTBGU may be added later to operate concurrently or to replace a WWTP in whole or in part). Consequently, the design, system or Plan may have either system, or both. Synergies exist between the two systems when collocated, and also in the case where a WWTP exists first, and it may be then converted to a WWTBGU, as described below.

In an embodiment, e.g., with reference to FIG. 3, an unexpected benefit may be synergies of both WWTP and WWTBGU systems with the remainder of the Plan.

Wash water and spilled water and/or biomass from the optional water bottling/biomass products bottling/packaging plant may be sent to the WWTP/WWTBGU for treatment, reclamation of water, or a substantial portion thereof, for example from 60 to 100% of the wash water and/or spilled water, or from 60 to 90% or from 60 to 80% or from 60 to 70% of the water. Wastewater from all other plants e.g., in the Plan may be sent to WWTP/WWTBGU comprising water used to cool the thermal plant, if acceptable to these systems, or may undergo treatment, and then sent to these systems.

In an embodiment, WWTBGUs may use carbon dioxide and produce oxygen, whereas WWTPs may be bacteria-based, and therefore, use oxygen and release carbon dioxide in the wastewater treatment process. WWTBGUs may be generally preferred e.g., in the Plan for this reason, but in certain cases, WWTPs may be preferable and may be implemented either alone or in conjunction with a WWTBGU.

In an embodiment, e.g., FIG. 4, a WWTBGU may be used alongside a WWTP, whereby it may be used to mitigate the CO2 from the WWTP, and provide O2 to the WWTP (e.g., in photosynthetic embodiments) to achieve near zero carbon dioxide release in wastewater treatment. Oxygen generated by a WWTBGU and/or other BGU may also be captured, exported and/or marketed, injected into thermal plant combustion processes for reduction of NOx emissions and/or for other uses e.g., FIG. 25.

In an embodiment, e.g., FIG. 3, HTP discharge water may serve as feedwater for a BGU in whole or in part. This water source may contain higher levels of carbon and/or other materials left after HTP, not unlike wastewater, which may require remediation and/or may facilitate biomass growth. In this case, the water source may be salt water, fresh water, and/or any other water type discussed herein as a possible water source type in a BGU which has been processed through HTP. In addition to treatment of the water by use of the residual carbon and/or possibly other material in the water, the synergies of the BGU using HTP wastewater may be the same as the type of source water used for the HTP process.

In an embodiment, e.g., FIG. 3, HTP wastewater may be processed in a manner similar to BGM outflow fluid 117. Its higher carbon content may provide a concentrated carbon stream which may be mixed with BGM outflow fluid and/or separately processed by taking it through any processing steps undertaken by the BGM outflow fluid 117.

In an embodiment, e.g., FIG. 6 and/or any figure or description relevant to a WWTBGU, a WWTBGU may effectively perform minimally what may be commonly referred to in the wastewater treatment industry as "secondary treatment" of wastewater to a degree that may be superior to that of a traditional WWTP. Primary and possibly tertiary treatment may be needed to complete the process to typical municipal wastewater treatment standards. If a standard WWTP may be in operation, and may be later adapted into a WWTBGU as understood by a person of ordinary skill in the art, and/or in accordance with embodiments in this disclosure, or if operating alongside the WWTBGU, the primary and/or tertiary treatment infrastructure initially developed for the WWTP may also be adapted for use in the WWTBGU or shared with the WWTBGU, and if a WWTP may be adapted to a WWTBGU, possibly parts or all of the secondary treatment infrastructure may be adapted for use in the WWTBGU. If only a WWTBGU may be built, and some aspects of primary and/or tertiary treatment may be not needed, those steps may be eliminated, reducing infrastructure and operation and maintenance costs.

In an embodiment, biomass from the BGM may be used to generate a large variety of useful products for use onsite and/or export offsite. Some examples for onsite use include bioplastics, which may be used in the water bottling/biomass products bottling/packaging plant for packaging, and biomass-based lubricants that may be used in machinery throughout the site. In an embodiment, e.g. FIGS. 2, 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, thermal plant waste heat and/or primary process heat and/or cogenerated cooling may be used in many applications to process biomass. In an embodiment e.g., FIGS. 1 and/or 14, biomass products requiring bottling may be bottled in a collocated water bottling/biomass products bottling/packaging plant (BBPP). In an embodiment, solid biomass products and/or biomass products in oil may also be packaged in this plant.

Infrastructure Synergy: In an embodiment, e.g., FIG. 24, an HTP module or unit, which may be used e.g., as described herein to process biomass, and/or similar methods, may also be used as a means of converting waste into energy. HTP and/or equivalent technologies to a person of ordinary skill may be used to convert a wide variety of organic materials to produce biocrude. An HTP module or unit or equivalent processing systems set up for biomass may be shared with those being used to process solid waste. HTL may be conducted in accordance with the PNNL process patent WO 2013/184317A1 e.g., FIG. 9. Other variations of HTP and/or similar processes suited to the purpose may also be used.

Other Freshwater Biomass Growth Units: In an embodiment, a BGU may use other fresh water sources besides wastewater. A BGU which uses fresh water without wastewater content may be termed a Freshwater BGU (FWBGU). Such fresh water sources may comprise water drawn from lakes, streams, WWTP/WWTBGU outputs, and/or other sources when not containing significant amounts of wastewater. A FWBGU may carry the same synergies with the Plan as a WWTBGU, except that wastewater will not be treated.

In one or more embodiments, a BGU may also use fresh water that may be partly wastewater and partly non-wastewater. Such as system may be termed a Mixed Freshwater BGU (MFWBGU). The likelihood of nutrient deficiency for biomass growth may be greater in non-wastewater or partial wastewater sources. An additional nutrient stream may be added to any BGU water source where needed to facilitate biomass growth. The nutrient stream may comprise nitrates, phosphorus, and/or possibly other nutrients appropriate to biomass growth.

Salt Water Biomass Growth Unit (Salt water/Brine Water/Brackish Water): In an embodiment, a salt water BGU uses salt water as a primary medium comprising optionally any one or any combination of salt water sources (e.g., sea water, brine water, and/or brackish water). A salt water BGU (SWBGU) would carry all of the same benefits and/or synergies with the Plan as a WWTBGU, except that the water used in a SWBGU and the SWBGU discharge water would be salt water, so wastewater would not be treated by this process, and some pretreatment and/or post treatment steps used for wastewater may not be necessary. The SWBGU discharge water would be used as appropriate for salt water e.g., in the Plan.

In an embodiment, e.g., FIG. 1, FIG. 2, and/or FIG. 3, a salt water BGU discharge from any module e.g., in the Plan, or biomass/water slurry, and/or treated biomass/water slurry after BGM post treatment steps as noted in FIG. 1, which comprises a biomass and/or biofuel laden salt water may operate substantially free of primary and/or tertiary treatment, and/or may be used in the same methods and/or systems described for other BGU discharges e.g., in the Plan, comprising: use as cooling water in the thermal plant; to perform hydrothermal processing (HTP); to preheat for HTP, and/or other biomass processing technologies, in decorative water features, and/or in other functions e.g., in the Plan. If the BGU and/or BGU discharge may be heated in any manner, the heat may be reclaimed before discharge by one of the methods given herein. After biomass production and/or other uses within the Plan, the salt water used may be mixed and/or discharged along with the optional desalination plant brine discharge, providing some dilution effect to the brine discharge, and/or may be reclaimed and used as noted e.g., in the Plan (See FIG. 3).

In an embodiment, a SWBGU may be used instead of or concurrently with a WWTBGU and/or other BGU.

In an embodiment, a SWBGU may share infrastructure with the optional desalination plant, comprising, for example, the water intake from the sea, pumps, pipes, heat use, water use and/or an outfall. In an embodiment, a SWBGU may use salt water separately from the desalination plant, it may receive brine as source water from the desalination plant, and/or its output may be directed to the desalination plant (see description in desalination section).

In an embodiment, e.g., FIG. 3 and/or FIG. 14, a SWBGU may use regular salt water, such as seawater and/or may use the brine discharge (reject high salinity water from the optional desalination plant) to grow biomass. The resultant discharge water from a brine water SWBGU may be treated the same way as brine discharge described herein, but may be lower in nutrient content, lower in some mineral content, biological materials, and/or other chemicals than seawater, after processing through a SWBGU, which may allow for the production of different biomass products, salt, and/or other products from the brine than seawater, and/or production of the same products more efficiently (e.g., more easily isolated from contaminants). The high salinity of a brine water SWBGU may also be more effective than other water sources at preventing invasive biomass species from invading a BGU, as fewer plant species can grow in high salinity water.

With reference to FIG. 5, in an embodiment, a SWBGU may be used concurrently with a WWTBGU and/or FWBGU, either using separate water supplies, or BGU water sources and/or system components may be partially or completely combined at any stage of their respective processes, to form a "brackish water biomass growth module" (BWBGU), where the combined water biomass system uses a brackish water combination of salt water and fresh water, and/or r a BWBGU may receive brackish water input(s) (e.g., from a brackish water lagoon), and/or a mixture of water of different salinities from different intakes, offsite sources and/or mixtures from onsite module, unit, or subunit water outputs. The discharge brackish water from the combined water biomass system may be used to dilute the optional desalination plant brine discharge using any brine discharge method. Optionally, as suitable, brackish water brought into the Plan from any source(s), and/or the BWBGU's discharge brackish water may be used as source water for desalination.

In an embodiment, e.g. FIG. 3, a BWBGU may be implemented by the use of a combination of any fresh and saltwater sources optionally comprising wastewater of any description, salt water, brine water (e.g., from the optional desalination plant), non-waste fresh water and/or other water sources. It may have the combined synergies of a system that would normally use the water sources being combined, but the resulting brackish water discharge may be discharged e.g., as in the desalination plant, used to dilute the brine discharge, and/or may be reused in manners determined to be acceptable for cooling and/or other purposes, e.g., as in the treated wastewater system, given resultant salinity. The resulting discharge if not useful otherwise, may be discharged to the sea and/or by other salt water disposal methods either with or without dilution.

In an embodiment, e.g. FIG. 3, after desalination, the desalination plant brine discharge may be diluted to about the salinity of seawater using wastewater, fresh water, salt water and/or other water source(s). The combined water substrate may then be used in the BGM to grow biomass. This embodiment may provide a greater volume of useful water than using only wastewater and/or other fresh water in the BGM, wherein the BGM water discharge may be later combined with the brine discharge to dilute it for discharge to sea. Working with water in the BGM that has a salinity comparable with ocean salinity allows for the use of biomass growth systems that have been developed on the market to operate using salt water, and in the case of a brine water combination with wastewater, the mixture may provide a better source of nutrients than may be present in salt water alone, and, result in better biomass growth and/or production, while also treating wastewater.

Biomass Growth Units Combined to Meet Different Project Goals: In an embodiment, e.g., FIGS. 1, 4, 5, 6, 11, and/or other figures and/or description relevant to integration of Plan components with BGUs, all BGUs described herein may be implemented in different combinations, in multiples, in connection and/or communication (e.g., FIG. 5, connected systems depicted), and/or different orders of priority to achieve particular project goals. For example, in order to mitigate all carbon dioxide and to treat all wastewater available to the Plan, in an embodiment, a WWTBGU may be built first to treat all of the wastewater available, and a SWBGU or FWBGU not using wastewater may be designed and implemented to mitigate any remaining CO2 in the event a WWTBGU's use of CO2 may be maximized given the wastewater supply, and additional CO2 from the thermal plant still remains to be used. In this embodiment, the SWBGU or FWBGU not using wastewater may be scaled according to the remaining CO2 supply to achieve zero net carbon dioxide production onsite. Any other BGU type(s) may also be used instead of or in addition to the WWTBGU and/or SWBGU or FWBGU not using wastewater in this example if considered more advantageous. For example, a FWBGU may be used instead of a WWTBGU where wastewater treatment may be not feasible or desirable as a component of a particular project.

Potable Water: In an embodiment, a WWTP and/or WWTBGU with additional processing steps may be designed to produce potable water in the event of emergency or where local society accepts it for consumption.

WWTP/WWTBGU/MFWBGU Solids/Sludge: In an embodiment, e.g., FIG. 24B, solids and/or sludge from the WWTP, WWTBGU, MFWBGU, and/or other BGUs described herein may be processed in a gasification module (e.g., CHG, anaerobically digested) to produce biogas for power generation in the thermal plant. In an embodiment, all or part of the biomass from the BGM may also be processed in a gasification module along with the solids referenced or separately using the same gasification equipment, to produce a biogas; and/or WWTP and/or WWTBGU solids may be injected into the WWTBGU for use in biomass growth; and/or any of the solids referenced may be processed in an HTP system (either the biomass HTP system described herein and/or a separate one) to produce biocrude for power generation in the thermal plant, with the remaining residue being processed by any of the above methods; and/or the solids may be processed in another WTE and/or other technology to produce power and/or fuel (e.g., pyrolysis-based WTE, cellulosic ethanol and/or other methods) for use in the thermal plant.

In an embodiment, optionally, sludge as generated in any of these systems, and/or the portion remaining after processing in a gasification module and/or another process above may be used as generated, and/or composted and/or treated with lime, carbon, ash from WTE processes, biomass from the BGM, and/or other additives to produce a soil amendment for agricultural purposes in a sludge processing plant.

In an embodiment, e.g., FIGS. 24B, 24C and 10, biogas generated by processing biomass in a gasification module (e.g., using CHG and/or anaerobic digesters), and optionally from a landfill used in any onsite process may be used to generate power in the thermal plant. The biogas from the gasification module technologies may undergo processing to prepare it for use as fuels and/or storage, comprising drying, hydrogen sulfide and/or other pollutant removal, blending with other fuels, condensation to liquids, and/or other techniques known to those of ordinary skill in the art. Gasification module(s), such as CHG module(s), anaerobic digesters and/or gas purification, drying, condensation to liquids, treatment, storage and/or heating and/or related infrastructure optionally may be shared by BGM biomass, BGM sludge, and/or WWTP sludge and/or the resulting biogas and/or other biogas sources, such as an optional landfill, and/or other optional sources of natural gas, such as natural gas imported from offsite. Any thermal plant technologies utilizing gaseous fuels (e.g., natural gas-fired combustion turbines) and/or related infrastructure may be shared by any or all of the foregoing systems, and/or also other sources of combustible gas, such as natural gas delivered from offsite for use in the thermal plant.

Description of Anaerobic Digesters: In an embodiment, thermophilic digestion, mesophilic digestion and/or another method of anaerobic digestion and/or a combination of several methods may be used to treat sludge and/or biomass. Biogas generated by anaerobic digestion may be used in fuel cells, turbines, internal combustion engines, and/or other technologies suited to the purpose. In an embodiment, anaerobic digesters may be heated to maintain optimal temperature or when the outside temperature may be less than 35° C. Equipment for the anaerobic digesters may comprise heat exchangers using hot water or other heat sources. The heat may be supplied by the thermal plant and/or from heat recovery and/or heated water discharge from the HTP process, other heat intensive biomass refining processes, and/or other processes e.g., in the Plan from which heat may be recovered e.g., FIG. 2, and/or using a heat source dedicated to the anaerobic digester system.

In an embodiment, e.g., FIG. 24D, ponds, settling tanks and/or other technologies used in secondary WWTP may be used in a WWTBGU as well, and/or may share infrastructure if operating together, or in the event of a switchover of a WWTP system to a WWTBGU, adaptation of initial WWTP ponds, tanks and/or other infrastructure to later WWTBGU and/or other BGU implementation, depending on design needs. In an embodiment, this may also comprise primary treatment infrastructure for wastewater, comprising screens, clarifiers, flocculation technologies, settling technologies, and/or other suitable primary wastewater treatment technologies, and/or tertiary treatment technologies for wastewater, which may comprise tertiary clarifiers, disinfection technologies such as UV, and/or other suitable tertiary wastewater treatment technologies. For example, a UV treatment system may be shared between a WWTBGU and WWTP where both may be used concurrently, or it may be adapted for use in a WWTBGU in the event a WWTBGU may be implemented to replace a WWTP.

Electrical: In an embodiment, e.g., FIG. 24D, an electric substation near the influent pumping equipment may be shared by the WWTBGU and WWTP, or adapted for replacement of the WWTP by a WWTBGU. Sensors, computer controls, control modules, software, hardware and/or other electrical systems may also be shared among these systems, adapted from one to the other, and may be integrated with the rest of the modules, units, subunits, technologies, and/or other features of the system and/or Plan.

In an embodiment, e.g., FIG. 24D, an air/oxygen delivery system used for any purpose (e.g., a preexisting system used in a WWTP) may be adapted and/or converted to a Carbon Dioxide delivery system, e.g., to support a photosynthetic WWTBGU, or to an oxygen or air delivery system suited to biomass growth in a BGU type that requires oxygen or air, or to an oxygen, air and/or carbon dioxide delivery system to support BGUs with these requirements.

Construction: In an embodiment, a shared construction process and structures, such as conduits may be utilized to reduce the materials needed and the costs of installing water lines to convey wastewater, gray water (partially or fully treated wastewater), salt water (comprising brackish and brine water), potable water and other water lines for specific use in various purposes in the system and/or Plan e.g., FIG. 2 (e.g., high temperature fresh water containing biomass/water slurry, low temperature salt water, ambient temperature brackish water, warm fresh water, etc.) when various different water lines may be used together to convey water in the Plan (e.g., when a WWTBGU and a desalination plant may be used together, and the water lines for both systems may be installed in the same conduit).

In an embodiment, numerous thermal plant technologies may be used individually or together to comprise the thermal plant, from factories to portable power generation systems. There may be many possible variations in thermal plants, comprising thermal power plants that may be used e.g., in the Plan, a wide variety of fuels that may be produced onsite and/or exported or imported from offsite (which may be determined individually for each project), using the ability onsite to use biomass-generated fuels, some waste-to-energy technologies, HTP, cellulosic ethanol/butanol/isobutanol, and/or other processes to produce a wide variety of fuels, supplemented by fuels selected from offsite (offsite fuels) based on local availability and any needs and/or efficiencies that may be gained by using and/or supplementing the Plan with offsite fuels (e.g., using offsite fuels to blend with biofuels produced onsite for better and/or different burn characteristics, using offsite fuels to produce additional power while mitigating emissions e.g., using the Plan, using the biomass generated to produce products, other uses described herein and/or known to those of skill in the art). Technologies used to produce fuels and/or fuel precursors may also comprise components of the thermal plant, such as pyrolysis technologies, cellulosic ethanol, and others as herein disclosed.

In an embodiment, e.g., FIG. 1, thermal plant technologies of any kind which may predate implementation of the Plan may be incorporated into the Plan as the thermal plant module or a component or technology of the thermal plant module (e.g., an pre-existing coal-fired plant may be retrofitted to the Plan, and become part of the thermal plant module, which connects to the rest of the Plan). In an embodiment, any other pre-existing component, technology, unit, subunit, feature, and/or module which may be retrofitted to become a technology, unit, subunit, feature and/or module and/or a means of connection and/or communication between modules, units, subunits, technologies and/or other features of the Plan, or to otherwise to be comprised by any feature of the Plan, may be retrofitted and included into the Plan (e.g., a waste-to-energy system, a WWTP, a BGM, a refinery, a BPP, a waste handling plant, recycling plant, a solar thermal technology, a desalination plant, a BBPP, a water intake, water lines, and/or any other module, unit, subunit technology and/or other component of the system and/or Plan).

FIG. 10 shows, in an embodiment how some fuels may be generated, directed and utilized e.g., in the Plan.

In an embodiment, a thermal plant may be designed to utilize any one or a number of different fuels, comprising potentially methane gas/natural gas/biomass biogas, ethanol (produced by biomass plants, refined from biomass, and/or from the cellulosic ethanol process) other fuels that may be derived from algae and/or other biomass biocrude, (comprising gasoline, diesel, jet fuel, fuel oil, and/or other fuels), hydrogen gas, butanol and/or isobutanol from the cellulosic butanol and/or isobutanol process, biocrude from HTP processes such as HTL (both biomass-derived and/or MSW and/or possibly other biomass-derived biocrudes, bio-oil, coal-like products (bio-coal), and/or other organic outputs from some WTE technologies utilizing waste (municipal, agricultural, construction, demolition, industrial, waste oil, and/or other wastes), other fuels that may be generated by any technology onsite to produce power, and/or various fuels imported from offsite as well, comprising possibly natural gas, light oil, and/or other fuels. Any of the foregoing, may be treated in any manner known to those of skill in the art, stored and/or used directly and/or blended with other fuels for use in whole or in part in the thermal plant. Any of the foregoing may be stored in any manner suited to the purpose prior to use for any purpose. Any precursors to any of the above fuels, such as biomass and/or waste of any kind, may be stored in any manner suited to the purpose before processing into fuel in processes that use these materials to generate fuel. Every system e.g., in the Plan may use sensors and/or automated controls that make measurements and adjust the systems as needed to change inputs/outputs of any parameter supporting the performance of any system e.g., in the Plan. In an embodiment, e.g., FIGS. 1, 2, 3, 4, 7A, 7B, 10, 11, 22 and/or 25 and/or any other figures and/or description relation to resources, heat and/or cooling, and/or other aspects of a thermal plant, thermal plant technologies, fuel type and/or flow, air flow and/or content, water selection, water flow, and/or any other aspect of performance known to those in the art may be controlled with sensors and/or dynamic controls.

In an embodiment, these fuels may be used to produce power in conventional power generation processes, such as combustion turbines (simple or combined cycle), oil fired units, boilers, and/or other power generation and/or other thermal plant systems of various types, comprising any WTE process.

Examples of a thermal plant or thermal plant technology comprise a conventional power generation systems, e.g. employing a combustible fuel, nuclear power and/or solar radiation, and waste-to-energy (WTE) systems. These and/or other technologies fitting the definition of a "Thermal Plant", e.g., industrial facilities which generate heat, such as cement factories, steel mills, and glass factories may serve as the thermal plant, or any combination of thermal plant technologies may be used in the same location or different locations on the same site or different sites, and may constitute the "thermal plant".

In an embodiment, e.g., FIG. 24E and/or FIG. 24H, one or more connections, communications, and/or synergies described herein between the thermal plant and other processes e.g., in the Plan may be established using any number of the different technologies comprising the "thermal plant" (e.g., carbon dioxide may be supplied to the BGM from either a combustion turbine or a waste-to-energy incinerator, or both, and/or any other thermal plant technologies generating carbon dioxide when these technologies may be in use as the thermal plant). In an embodiment, different technologies and/or fuel sources may be used to comprise the thermal plant, comprising conventional power generation systems, waste-to-energy, and/or other thermal plant technologies may be integrated to share infrastructure and/or resources, e.g., fuels, heat, water, power, emission control modules, sensors, computer systems, computer controls or modules, and/or other resources. Infrastructure sharing may comprise one or more electrical substations, transmission lines, other electrical infrastructure known to the person of ordinary skill in the art, exhaust gas conveyances, stacks, pollution control modules, pollution entrainment modules (e.g., FIG. 7A or 7B) and/or other emission controls, carbon dioxide, methane, biogas, oxygen and/or other gas transport lines and/or storage, water, water/biomass slurry, biofuel, other fuel, chemical storage, piping for water, chemicals and/or other materials, other liquid transportation and/or storage, cooling systems, heat exchangers, and/or other components that may be shared between thermal plants. In some embodiments, fuels may be generated/processed by one technology in the thermal plant and used to generate power and/or heat using another thermal plant technology, e.g., fuels may be generated in a WTE technology, processed with thermal plant heat, and combusted in a power plant comprised by the thermal plant.

In an embodiment, e.g., FIG. 2, FIGS. 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer, a thermal plant may generate waste heat and/or primary process heat which may be exported to water desalination in the desalination plant, biomass processing, and/or for other industrial uses. Heat may be used to perform desalination and/or to enhance the desalination process, depending on the desalination method selected.

In an embodiment, e.g. FIG. 3, a thermal plant wastewater (optionally after heat recovery) may be directed to the WWTP and/or WWTBGU.

In an embodiment, e.g. FIG. 10, different technologies, comprising conventional power plants and/or WTE systems within the thermal plant may serve as backups for each other to a point to meet power generation goals, contingencies, and/or margins. Fuels and/or wastes may be stored in manners known to the industry to allow for optimal power generation for the Plan and/or for the grid over time (e.g., daily and/or seasonal fluctuations in power needs, fuel availability, backup capacity).

In an embodiment, WTE systems may share most of the same synergies with the Plan as conventional power systems, but more synergies may also apply depending on the WTE system(s) used, some of which generate fuels from waste and/or biomass that may be used in other power systems, such as ethanol, butanol, isobutanol, bio-coal, and/or bio-oil products.

In an embodiment, collocated modules and/or technologies may be integrated by coupling a waste heat source to the modules and/or technologies.

Power: In an embodiment, all or some power needed for the Plan may be provided by the thermal plant, and power, fuels, or both may be exported offsite.

In an embodiment, e.g. FIG. 3, demineralized water from an optional desalination plant may be utilized during firing of light oil and/or other fuels to reduce the combustion temperature and/or the generation of NOx emissions from combustion turbines (CTs) and/or other thermal plant systems. In an embodiment, desalinated water from the optional desalination plant may be used for relatively small volumes of water needed for CT inlet air cooling, NOx injection water, and/or potable water, and/or for similar uses in other thermal plant power generation systems.

In an embodiment, the thermal plant may produce unheated wastewater, heated air, steam and/or a mixture, heated wastewater, and/or e.g., FIG. 11, possibly a heated biomass and/or biofuel and water slurry and/or HTP separated hot biocrude and/or biofuel and hot water from which heat may recovered. Much of the thermal plant discharge water may be heated, and the heat may be used either for other processes e.g., FIG. 2, either while in the discharge water, and/or otherwise transferred to another substrate e.g., in the Plan using any heat transfer technology suited to the purpose, e.g., FIGS. 12A-12E, 15-20, and/or in any other manner known to those in the art, with the water used in these processes to be recovered, treated as necessary, and reused, e.g., FIG. 3.

In an embodiment, e.g., FIGS. 2, 7A, 7B, 11, 12A, 12B, 12C, 12D, 12E, 15A, 15B, 16, 17, 18, 19, 20A, 20B, 20C, 20D and/or other figures and/or description relevant to heat capture and/or transfer and/or FIG. 3, and/or other figures and/or description relevant to water use and/or movement, cooling water from any source may be used to cool the thermal plant, and then routed for optional primary treatment (per module 104 of FIG. 1) and then for direct use as source water in the BGM, mixed with another water source and used as source water in the BGM, or simply used to transfer heat to water used in the BGM and/or another process. In any of these and/or other manners disclosed herein, temperature in the BGM, individual BGUs, subunits, components and/or other features may be regulated either directly or indirectly by water outflows from the thermal plant in combination optionally with other water sources. Gases and/or other fluid outflows from the thermal plant, likewise may be used alone or in combination with other sources of heat to regulate the temperature of the BGM and/or other components of the Plan, (e.g., FIGS. 7A, 7B, 12A, 12B, 12C, 12D, and/or 12E). If cooling may be needed, any of the aforementioned sources of heat may be used to produce, convey and/or cogenerate cooling, which may be supplied to the Plan e.g., FIG. 2.

In an embodiment, e.g. FIGS. 1 and/or 3, a portion, e.g., most, of the wastewater discharged from the thermal plant (after heat use or recovery), may be routed to primary treatment (per module 104 of FIG. 1) and then to the WWTP and/or WWTBGU. Some thermal plant water wastes, depending on contamination levels, may be used to dilute the desalination plant brine discharge without further treatment in order to reduce the environmental impact of the brine (e.g., when discharged). Storm water runoff may be sent to a storm water retention pond or first run through an oil/water separator if it contains oil, and then sent to a storm water retention pond. This wastewater may then be routed for primary treatment (per module 104 of FIG. 1), and then to the WWTP and/or WWTBGU. Chemical cleaning wastewater and/or other chemically treated wastewater may be maintained onsite and tested and, if non-hazardous, according to a person of ordinary skill, may be routed to primary treatment (per module 104 of FIG. 1) and then to the WWTP and/or WWTBGU with the other wastewaters or directed to an evaporation pond if suitable.

In an embodiment, e.g., FIG. 3 and/or FIG. 1 any other wastewater source(s) e.g., in the system or Plan may be routed to primary treatment (per module 104 of FIG. 1) and then to the WWTP and/or WWTBGU.

In an embodiment, e.g. FIG. 10, an oil/water mixture(s) generated in systems e.g., in the Plan or from offsite may be separated. In an embodiment, waste oil may be sent to the thermal plant as a fuel to produce power. Thermal plant technologies used for waste oil may comprise a WTE incinerator, HTP, Plasma gasification unit, rotary kiln incinerator, and/or other technologies.

In an embodiment, e.g. FIG. 10, some solid, liquid, and/or blended wastes may be generated in the thermal plant which may be considered to be hazardous wastes. If these wastes may be legally and efficiently disposed of using recycling, the WTE incinerator, plasma unit, the rotary kiln incinerator, alternate thermal plant technologies, HTP, and/or a landfill, any of these options and/or others suited to the purpose may be utilized e.g., in the Plan.

Emissions: In an embodiment, biomass (e.g., algae) fuels generally burn cleaner in thermal plant technologies than petroleum fuels and may mitigate other harmful emissions besides carbon dioxide when exhaust gases may be directed to the BGM as described e.g., in the Plan.

In an embodiment, e.g. FIG. 4 and/or FIG. 2 and/or other description related to heat generation and/or transfer, the system or Plan can mitigate a carbon dioxide release (e.g., of a conventional fuel-burning thermal plant) and use the $CO_2$ to generate additional power from any source with the BGM. This presents a very attractive synergy with offsite carbon dioxide producers. In an embodiment, e.g., a local (possibly offsite) thermal plant (e.g., a coal-burning power plant or industrial plant) sends exhaust gases (e.g., stack gases), optionally pretreated to the BGM, which may substantially capture the emissions. This system may provide power with substantially complete carbon capture (e.g., zero or low carbon emissions), mitigation of other emissions, such as SOx, NOx, particulates, and/or metals, and BGM generation of biofuel from the emissions for additional power and/or for export. In an embodiment, examples of additional or alternate sources of power generation which may be used as thermal plant technologies e.g., in the Plan, as offsite thermal plants, or as additional non-thermal power sources comprise plants using coal, petroleum fuels, nuclear, solid fuels (such as petroleum coke, biomass and/or others), wind, solar thermal, solar photovoltaic, geothermal, hydroelectric, micro-hydro generation, combined heat and power, and/or other systems suited to the purpose. These additional systems may be connected to the system or the Plan to provide any combination of the following benefits, and/or other benefits, as identified herein for thermal plants and/or on a project-by-project basis comprise: augmentation of power production; carbon dioxide and/or other emissions mitigation of exhaust from these plants in the BGM; provision of cooling water source from the WWTBGU and/or WWTP; capture of heat for use in HTP, desalination, heating the BGM, BGU(s), and/or their components, and/or for other uses of heat onsite e.g., FIG. 2; and/or for reduction of reserve plant margins.

In an embodiment, e.g., FIG. 24H and/or FIG. 24C, one or more fuel sources both onsite and/or offsite may share power generation technologies in the thermal plant, reducing infrastructure costs (e.g., biomass biocrude, WTE biocrude, HTP biocrude and/or other fuel sources sharing a thermal plant technology). In an embodiment, thermal plant technologies, comprising WTE and/or power generation technologies, may share carbon dioxide transportation and/or distribution infrastructure, cooling water and/or heated water transport, heat use equipment, emission controls (e.g., exhaust gases may share the infrastructure shown, for example in FIG. 7B or 7B), and/or all other infrastructure in common to these technologies. Air Emissions Controls: In an embodiment, the Plan may have in place all of the modern air pollution controls, as needed, for the emissions being generated.

In an embodiment, e.g., FIG. 7A, and/or 7B, exemplary designs for pollution control and/or the use of exhaust gases for the Plan may be described. In an embodiment, any other equivalent technology suited to the purpose of treating emissions may be used e.g., in the Plan, being known by those of ordinary skill in the art. In an embodiment, biomass-based fuels generated (e.g., from algae systems) potentially used in the BGM may have lower emissions than petroleum fuels under many burning conditions, thus reducing harmful emissions, and reducing costs of infrastructure and maintenance of some types of emission control systems in the thermal plant as compared to traditional systems.

In an embodiment, e.g., FIG. 10, the Plan may comprise fuel heaters which may be fired with natural gas and/or biogas and/or methane/other fuel mixture from sources onsite and/or methane from offsite and/or may be heated using Thermal Plant heat and/or heat recovered from other heat-intensive processes e.g., in the Plan per FIG. 2 as needed to heat natural gas and/or other gaseous fuels e.g., in the Plan above the dew point.

In an embodiment, e.g., FIG. 3 and/or FIG. 24H, the Plan may use solar thermal technologies (e.g., solar troughs) for preheating seawater for desalination, a BGM output for HTP, for power generation, and/or for introduction of heat into the Plan wherever needed (e.g., FIG. 3). If a solar thermal technology may be used, it may share steam turbines with those already in thermal plant.

WASTE-TO-ENERGY (WTE) SYSTEM EXAMPLE TECHNOLOGIES WHICH MAY BE USED AS THERMAL PLANT TECHNOLOGIES—GENERAL DESCRIPTION: WTE systems for the purpose of this disclosure comprise systems which generate fuel, fuel precursors and/or power in any form from waste, biomass and/or any other material. In an embodiment, WTE may use any method(s), optionally comprising combustion, chemical methods, biological methods and/or thermal methods either separately or in combination.

Most WTE systems operate similarly, utilizing waste as fuel for combustion and/or other thermal processes to produce power. The differences affecting interactions, connections and/or communications creating greater efficiencies with the Plan (synergies) may be mostly related to whether the waste or other material may be directly combusted (incinerator and/or other direct-combustion methods), directly thermally destructed anaerobically to produce power (gasification, plasma gasification), or whether intermediate steps may be used to transform the waste into another fuel before combustion (e.g., pyrolysis-based methods, HTL, CHG, anaerobic digestion, cellulosic ethanol). A few different synergies with the Plan, e.g., efficiencies, may be created with systems that use intermediate steps. There may be other technologies known to those of skill in the art that may also be used similarly, so the Plan, system and disclosure comprises and allows for the incorporation of other systems performing the same function(s), and/or other WTE technologies. The scale of any individual project, the other systems comprising a local project, and/or project-specific priorities may affect WTE technology and/or other thermal plant technology selection for a given project. The base system being discussed may be the incinerator, and synergies with the Plan for this system may be given below. Synergies for the other WTE systems may be discussed relative to those listed for an incinerator.

In an embodiment, the technical connections, communications and/or synergies described herein for all thermal plants with the Plan also apply to WTE systems, where applicable. Where heat may be produced by a WTE system, where not used for power generation, it may be captured by heat exchangers and/or other technologies and used e.g., in the Plan e.g., FIG. 2. Exhaust gases/carbon dioxide and other emissions may also be processed e.g., FIGS. 7A and 7B, for optional use in the BGM e.g., as described herein for thermal plants, and/or using another technology known to those in the art, and the carbon dioxide and other emissions optionally mitigated by the BGM in whole or in part, biomass may be produced, and the carbon dioxide used e.g., in the Plan as noted in FIG. 4. The uses of water (e.g., FIG. 3), biomass (e.g., FIGS. 1, 10, 11 and others), fuel (e.g., FIG. 10), heat (e.g., FIG. 2), carbon dioxide (e.g., FIG. 4), and/or other resources or byproducts as described for thermal plants in general in this disclosure may also be applied to WTE Technologies as applicable. WTE Power may be used to power the Plan and/or for export, along with power from other technologies that may comprise the thermal plant. Additional synergies, connections, and/or communications of particular WTE technologies to the Plan may be described below.

EXAMPLES OF WASTE-TO-ENERGY (WTE) SYSTEMS which may be incorporated as thermal plant technologies comprise one or more of the following types:

In an embodiment, e.g., FIG. 10 a municipal waste incinerator (MSW) may incinerate waste from cities, industry, agriculture and/or other sources and generate power. An MSW incinerator thus reduces land use for landfills, greenhouse methane gas generation, and produces power and heat and thus may be incorporated within a system and/or Plan as a thermal plant or thermal plant technology used as a component of the thermal plant, optionally along with other thermal plant technologies. That is, a thermal plant may comprise an MSW incinerator. Other example WTE technology options that may be incorporated into the Plan may be discussed below. In an embodiment, WTE technologies may be used to dispose of waste and/or biomass generated by technologies e.g., in the Plan and/or offsite in an environmentally friendly manner and to recover energy from waste/biomass for power production. In an embodiment, e.g., 24K, an end product of incineration or other direct-combustion WTE technologies may be ash, which may be used to produce cement. In an embodiment, e.g., FIG. 10, oil from an optional desorber plant and/or waste oil from all site facilities and/or offsite sources may be burned in a rotary kiln incinerator, MSW incinerator, alternate direct combustion units, a plasma gasification unit, pyrolysis-based WTE systems, and/or processed by HTP module(s) e.g., in the Plan to produce power and/or fuels for use in the thermal plant.

Plasma Gasification Unit (Plasma): In an embodiment, thermal gasification to syngas may be a system used in the thermal plant. Syngas may be used for energy production and/or condensed to oils and/or waxes. Plasma may be similar to an incinerator in generating power from waste and/or other organic material, but may be able to accept more hazardous wastes also. Plasma also uses high temperatures. All cooling and/or heat recovery systems and/or synergies with the Plan involved with an incinerator also apply to a plasma gasification unit (See Incinerator above).

In an embodiment, e.g., FIG. 10, a rotary kiln incinerator may be part of the thermal plant, e.g., the thermal plant comprises a rotary kiln incinerator. An MSW incinerator may not be suitable for handling industrial wastes, many of which would be categorized under US, European and/or other law as "hazardous wastes." In an embodiment, an alternative for handling these would be a rotary kiln incinerator. A rotary kiln incinerator may be fed liquid, solid, containerized and/or gaseous waste, optionally comprising dust and/or acid gases.

Alternative Waste-to-Energy/Biomass Systems: Current public sentiment may be trending away from use of incinerators for Waste-to-Energy/Biomass, e.g., due to environmental concerns. In an embodiment, the Plan comprises the use of alternate technologies to replace the incinerator, or to be used in combination with it, and/or with each other in order to generate power from organic material such as waste and/or biomass. In an embodiment, systems performing these functions may be incorporated into the Plan as part of the thermal plant, optionally comprising:

Direct Combustion Systems: There may be some differently-designed MSW and/or agricultural/wood waste direct combustion systems that may be used instead of incinerators (e.g., AgriPower, Inc., Turboden, Inc. systems). These systems may be advertised as less expensive, more efficient, and more environmentally friendly than incinerators. The synergies of these systems with the Plan may be the same as those described for incinerators above.

In an embodiment, e.g., FIG. 10, Pyrolysis-based and/or other WTE technologies may generally replace waste removal or waste burning technologies, as WTE technologies may be generally more efficient, better environmentally, and/or more viable than incinerators in some applications. In general, these technologies use lower heat than incinerators to anaerobically pyrolize organic waste to obtain combustible products, such as oil, and/or a coal-like product. These products may then be combusted in a thermal plant to generate power and/or may be exported offsite, e.g., outside a system or Plan. In an embodiment, WTE comprises two processes: first, a lower temperature and/or anaerobic degradation) theoretically results in fewer harmful chemical reactions, and therefore fewer harmful emissions upon subsequently combusting products of the first process. In an embodiment, greater power can be generated per unit volume of municipal sanitary waste (MSW) or biomass than incinerators, and that other marketable solids, liquids and/or gases may be generated and/or reclaimed. In an embodiment, the Thermal Plant may comprise these technologies in whole or in part. Pyrolysis-based processes may be similar in nature to hydrothermal processing (HTP) such as HTL, a process used to flash separate and refine biocrude from biomass in water. The synergies of these systems e.g., in the Plan may be the same as those of the incinerator described above, but in addition, coal, oil, and/or other products generated in these processes may be combusted in the thermal plant onsite to generate power for the Plan and/or exported offsite. Biomass, biocrude, and/or other fuels derived from the BGM may be combusted in a second step of the process in the thermal plant either in combination with pyrolysis-generated fuels or separately.

Hydrothermal Processing (HTP): In an embodiment, e.g., FIG. 24B, HTP comprises a primary method of "flash separating" biomass from water and converting the biomass to a biocrude and/or other fuels using a process involving heat and possibly pressure. In an embodiment, the biocrude that may be the product of liquid-based HTP processes such as HTL or RTP may be combusted directly e.g., in burners, heavy motors, e.g., an engine normally combusting diesel or heavier fuels, and/or other select thermal plant technologies to produce power, and/or may be further refined to many major fuel types, which may be combusted if more efficient than biocrude given additional refining costs. In an embodiment HTP may convert other biomass and/or waste to biocrude. In an embodiment, HTP may be used instead of, in conjunction with other WTE technologies, and/or as full or partial replacement e.g., in the Plan. In this embodiment, the waste may be heated and possibly pressurized, and the organic portion may be liquefied to a form of biocrude (this process may be termed "Waste HTP"). In an embodiment, the biocrude may be combusted and/or further refined and then combusted to generate power, depending on its properties. It may be an optional system in the disclosed Plan for waste-to-energy, comprising optionally the incorporation of biomass streams, such as agricultural material, wood and/or other organic materials into one or more HTP processes. The synergies with the Plan comprise the same benefits as those described for pyrolysis-based WTE Systems described above, plus the following. In an embodiment, Waste HTP infrastructure may be shared with BGM Biomass HTP infrastructure, and/or other biomass HTP (Such as agricultural biomass, wood, energy crops, etc.), and the processes may be fully combined or partially combined in any manner as herein disclosed or known to those in the art. In an embodiment, e.g., FIG. 2 or other description related to heat generation and/or transfer, waste heat and/or primary process heat from Thermal Plant technologies may be used for Waste HTP and/or other biomass HTP (e.g., wood and/or agricultural waste) in the same way it may be described herein for an HTP processing of a biomass/water slurry. In an embodiment, a fuel generated e.g., in the Plan or by system processes e.g., in the Plan may be used in a thermal plant onsite to generate power for the Plan and/or exported offsite. In an embodiment, biomass, biocrude, and/or other fuels derived from the BGM and/or its downstream processes may be combusted in the thermal plant either in combination with fuels generated by Waste HTP, other biomass HTP, the other WTE processes described herein and/or separately possibly using the same equipment.

Cellulosic Ethanol/Butanol/Isobutanol: In an embodiment, FIG. 2 and/or FIG. 10 and/or other description related to fuel and/or heat generation and/or transfer, the system may comprise cellulosic ethanol, butanol and/or isobutanol production. In an embodiment, these fuels may be combusted on-site to power the Plan and/or for power export offsite, and/or the fuels may be exported offsite. Cellulosic ethanol/butanol/isobutanol technologies may be used as a full or partial replacement for incineration to produce fuels for combustion, and/or to produce sugars to feed biomass (e.g., algae). In an embodiment, other technologies that produce compounds useful as fuels and/or as biomass feedstock from cellulose and/or other organic materials either currently or in the future may also be used in the same manner. In an embodiment, FIG. 2, waste heat and/or primary process heat may be utilized from the Thermal Plant in a pretreatment stage, celluloytic process, distillation process, and/or possibly other steps of these processes requiring heat. In an embodiment intermediate fuels may be produced by cellulosic alcohol technologies (e.g., ethanol, butanol, and/or isobutanol) that may be combusted in the thermal plant and/or exported offsite. In an embodiment, thermal plant waste heat may be utilized in steps of this process, and/or as otherwise noted herein for all systems (See FIG. 2). Depending on technology selection, water may also be needed for these processes. Incoming water may be taken from any source(s) e.g., in the Plan, e.g., FIG. 3. In an embodiment, e.g., FIG. 4, carbon dioxide may be released in the cellulosic ethanol/butanol/isobutanol production phase and/or as part of the thermal plant activities combusting the resultant fuels. Thus, carbon dioxide may be captured and/or used in other aspects of the Plan. This and other sources and uses of Carbon dioxide e.g., in the Plan may be given in FIG. 4, and discussed herein. In an embodiment, e.g., FIG. 10, fuels generated in these and/or other processes may be combined in whole or in part and combusted in a thermal plant, and/or separately combusted in a thermal plant onsite to generate power for the Plan and/or exported offsite. In an embodiment, fuels generated by cellulosic ethanol/butanol/isobutanol technologies and/or any other technologies that convert biomass into biofuel may be combined with biomass, biocrude, and/or other fuels derived from the BGM, waste HTP, and/or other biomass HTP, and/or subsequent processing steps and/or may be combusted separately and/or in combination with other fuels produced e.g., in the Plan or imported to it.

In an embodiment, cellulosic ethanol/butanol/isobutanol technology and/or similar technologies may be used e.g., in the Plan to provide sugars to a heterotrophic and/or mixotrophic BGU. In this embodiment, the cellulosic ethanol/butanol/isobutanol technology may be carried through only the steps necessary to break down cellulose into sugars, and the sugars may be used as a feedstock for the biomass (e.g., algae) e.g., module 636. In an embodiment, supercritical water hydrolysis may be used as another process by which sugars may be made from biomass, and used also as a feedstock for any BGU in the BGM. In an embodiment, any other technology which may be used to convert cellulosic biomass to sugars may be used similarly to provide a feedstock for the biomass in the BGM.

Other WTE Technologies: In an embodiment, numerous other technologies which may convert waste and/or biomass of any kind to fuels and/or energy may be used e.g., in the Plan. The synergies of these systems with the Plan may be similar to one or more of the technology types described herein. Therefore, this disclosure seeks specifically to include any technologies which may perform the same functions, optionally producing intermediate fuels of organic content, and which may benefit the Plan using the same or similar synergies with the Plan.

In an embodiment, e.g., FIG. 7A and/or FIG. 7B and/or FIG. 24H, thermal plant exhaust gases may be discharged into the atmosphere in whole or in part, and/or in the exhaust gas recovery modules used to capture pollutants before introduction into the BGM, e.g., FIG. 7A or 7B, and pollution control technologies herein disclosed, and/or standard pollution control technologies known to those in the art may be used to mitigate harmful emissions. For example, a 2 pass wet scrubber may be used to reduce NOx and/or other pollutants, e.g. FIG. 22, the hot gases may be passed through a lime slurry spray drier to remove sulfur and/or chlorine compounds and/or may be sent into a baghouse or bag filter or fabric filter to remove particulates. Activated carbon may be associated with and/or incorporated into the baghouse to remove mercury and/or dioxins. Any technolog(ies) known to the art may be used to treat emissions in these systems, optionally comprising: activated carbon, hearth furnace cokes, zeolites, lime, chlorine, sprayers, sorbents, filtration, catalyst(s), photochemical methods, selective catalytic reduction, dry scrubber(s), and/or wet scrubber(s) (e.g., spray tower, tray tower, packed bed tower, and/or other wet scrubber types).

In an embodiment, these and/or other pollution control measures may be used in all thermal plant technologies, as needed. These and/or other pollution control technologies may be used also to treat exhaust gases e.g., in the pollution control module 705, or pollution entrainment module 713 of an exhaust gas recovery module 707, 709 e.g., FIGS. 7A, 7B and/or by another means known to the art, either for use in the BGM, for other use e.g., in the Plan, and/or for discharge.

In an embodiment, thermal plant technologies may share the infrastructure and/or treatment methods to perform pollution control by combining the exhaust gases emitted from any combination of different thermal plant technologies using piping and/or motivating technologies for water and/or other fluids, such as chemicals, for example piping and/or motive devices, such as blowers/fans that carry the gases to one combined conveyance designed for a sufficiently large enough flow volume for the two flows coming together. In an embodiment, the combined conveyance exhaust gases may be treated as noted herein for single exhaust gas flows through a stack or other conveyance (e.g., e.g., FIG. 7A or 7B). In an embodiment, exhaust gases and/or liquids from an exhaust gas recovery module in the combined flow system described may be directed to the BGM and/or other use e.g., in the Plan e.g., FIGS. 7A and 7B, and any discharge to the environment may be drawn off of the single large discharge section or stack, or other combined conveyance for the combined exhaust gas streams, in the same way e.g., FIGS. 7A and 7B. Combination of exhaust gas streams may be selective, based on the emissions and/or treatment requirements of different emissions streams generated by different thermal plant technologies. In an embodiment, different thermal plant exhaust gas emissions systems may remain separate. In an embodiment, different thermal plant technology emissions systems may remain initially separate, or may predate implementation of the Plan, but may later combine to form as combined infrastructure systems. In an embodiment, any number of thermal plant technologies may share infrastructure and/or processes (e.g., in FIG. 7A or 7B) as follows: pollution control modules 704, heat recovery modules 710, and/or pollution entrainment modules 712 and/or processes that follow after these processes (such as discharge or introduction into the BGM or other heat and/or CO2 storage, and/or use e.g., in the Plan 718) e.g., FIG. 7A or 7B. Only select processes may share infrastructure as suited to the application.

In an embodiment, e.g., FIG. 10, an indirect desorber/condenser system may also be used or added to other technologies as part of the thermal plant. The indirect desorber/condenser may be configured to treat organic waste, vaporizing/distilling/azeotropically distilling the organic compounds therein or produced upon heating, and/or condensing the organic compounds to recover their fuel value. Example feed streams may be API separator sludges from refinery operations, and petroleum contaminated soils. In an embodiment, this system may take on these wastes from offsite sources, and/or onsite sources, routinely and/or in emergencies, e.g., in the event of an oil spill. The recovered fuels may be used to generate power in the thermal plant.

In an embodiment, one or more of these technologies or modules may be co-located together in a common building or shelter; or the technologies or modules may be co-located at separate buildings or shelters and/or then connected.

DESALINATION, DESALINATION PLANT (DP) In an embodiment, a seawater intake system, capable of delivering water requirements with minimal impacts on the marine environment, may be implemented using a desalination plant (DP) to provide a source of water for potable water production, cooling water, firewater supply, etc. The water may be processed to produce desalinated water and a brine (high-salinity water) discharge. Example technology types that may be used separately or in combination as the DP may be as follows: filtration-based processes, comprising for example: reverse osmosis, electrodialysis reversal and/or other technologies using a membrane; and distillation-based processes comprising multi-stage flash distillation, multi-effect distillation, vapor compression distillation and/or other technologies using evaporation to produce desalinated water.

In an embodiment, e.g., FIG. 2, and/or other description related to heat generation and/or transfer desalination plant filtration-based processes and distillation-based processes both may use waste heat and/or primary process heat from the Thermal Plant.

In an embodiment, filtration-based processes may utilize heat to increase the efficiency of the filtration process, e.g., in any manner known to those of skill in the art. In an embodiment, distillation-based processes may use heat to distill water, and/or to preheat water in order to lower the heating requirements at a distillation plant.

In an embodiment, e.g., FIG. 2 and/or FIG. 24K, waste heat may be used for power generation to achieve electrolysis, e.g., sodium hypochlorite (bleach) may be synthesized from DP brine discharge using brine electrolysis. The bleach may be used throughout the Plan for disinfection, cleaning, and/or other uses, and/or exported offsite. In an embodiment, e.g., FIG. 24K and/or FIG. 10, brine electrolysis provides hydrogen gas. The hydrogen may be used in a fuel cell to produce electricity, and/or returned to the thermal plant for combustion.

In an embodiment, e.g., FIG. 3 and/or FIG. 24K, sea salt may be manufactured from the DP brine discharge and sold off-site. In an embodiment, e.g., FIG. 3, DP demineralized water may be supplied for use in the thermal plant where needed in any thermal plant system (e.g., combustion turbines, if used, and in other power systems). In an embodiment, e.g., FIG. 3, DP desalinated water (with minerals added back) may be supplied for use as appropriate in the thermal plant (e.g., combustion turbines and in other power systems).

Intake/Salt Water: In an embodiment, e.g., FIG. 3 and/or FIG. 24A, the DP may share an intake with a SWBGU, a saltwater cooling source for the thermal plant (if needed), or any of these modules/uses for salt water may have separate intakes. Any of these modules/sources' intakes, if separate, or the combined intake if combined may share some piping and/or other equipment with wastewater treatment plant, BGM, and/or brine discharge outfall. In an embodiment, e.g., FIG. 3, the water intake(s), shown as fresh water source 302, and/or water intake (salt water) 314, may provide a source of cooling for any process e.g., in the Plan, wherein water from an intake out to sea, especially a deep-water intake, which in many climates should be significantly cooler than ambient temperature on land and can provide cooling, or an intake of any kind with a warmer water source may provide heat. In an embodiment, saltwater intake water may be used as source water for a SWBGU and/or BWBGU in a hot climate to regulate its temperature. In an embodiment, the salt water from the intake may be used to provide cooling either alone or combined with other water sources to fill pools or other structures surrounding any BGU or BGU component in order to provide cooling and/or temperature modulation, particularly in hot environments. In an embodiment, after use in this manner and/or in other cooling applications, decorative application, and/or in any other manner described for heat and/or cooling transfer, comprising possibly heat transfer from the thermal plant to the Plan, the water may be then routed to the DP for desalination and/or other processes where warmer water may be beneficial. In this manner, water and/or cooling may be provided where needed e.g., in the Plan (See FIGS. 2 and 3), and in the process, the salt water may be elevated in temperature, which allows for a lower energy requirement in the desalination process and/or other processes e.g., in the Plan where warmer water may be beneficial. In an embodiment, hot or warm water may also be used in a prioritization of uses which allows for productive tiered uses of heat in many systems as the water cools. For example, water mixed with a biomass water slurry may be heated to approximately 350 C, separated from biomass, biocrude and/or biofuels, then routed to a heat exchanger to heat salt water to be used for desalination, and then used, possibly still at a temperature above ambient temperature, as a heated source water for the BGM. In this manner, water use and/or heat use may be prioritized in the Plan to produce unexpected novel efficiencies in the use of water, heat and/or cooling (e.g. FIGS. 2 and 3).

Additional Technologies which may produce desalinated water: In an embodiment, e.g., FIG. 2 and/or FIG. 3, salt water processed through HTP and/or another heating process e.g., in the Plan (heated water) may be used to produce desalinated water after heating may be conducted by the release of pressure of the heated water, such that steam may be formed, released from the solution (e.g., using a valves and/or other technology known to those in the art, separated from the solution, and condensed as desalinated water. In this fashion, water in a solution that has been heated may be desalinated by distillation. Alternatively, heated may be routed to the desalination plant, preferably while still heated from HTP, for standard desalination processes, e.g., as described herein.

In an embodiment, e.g., FIGS. 1 and/or 3, desalinated water may be produced through various processes known to the art in processing water through a BGM and subsequent BGM outflow fluid processing steps in the Plan.

Water Conservation: In an embodiment, e.g., FIG. 3, water reuse from the BGM and/or WWTP may be used for landscape irrigation, firefighting, water features, fountains, lakes, industrial cooling (Comprising cooling in the thermal plant), and/or cleaning processes e.g., in the Plan, as opposed to using DP desalinated water. This may greatly reduce the needed amount of desalinated water and consequently the power requirement e.g., in the Plan. It will require only additional piping. In an embodiment, e.g., FIG. 3, optionally salt water, or salt water mixed with reclaimed wastewater or another water source either from the BGM, WWTP and/or another source may be used for: cooling water, firewater supply, water features, fountains, lakes, and/or other uses to conserve reclaimed BGM and/or WWTP water and/or DP desalinated water e.g., in the Plan. Where usable as cooling water, salt water may be used to cool the thermal plant and/or other heat sources directly or indirectly (via heat exchange), and may be then routed to the DP for desalination. This may save energy in the DP, as higher temperature water may be easier to desalinate per No. 1 above. Treatment of any water supply may be performed either before and/or after its use in the thermal plant and/or any other modules and/or processes e.g., in the Plan in accordance with techniques known to the art.

In an embodiment, e.g., FIG. 3, certain salt water and/or other bioreactors may produce desalinated water, possibly mixed with biofuel by evaporation, and once separated from biofuel as necessary, the water may be potable. In an embodiment, a SWBGU, a BWBGU, or other BGU may produce desalinated drinking water either in the place of desalination technologies or to supplement desalination technologies e.g., in the Plan. Brine produced by such a system may be treated as discussed herein for other desalination technologies.

In an embodiment, e.g., FIG. 3, as required, for a reverse osmosis desalination process, a Clean In Place (CIP) cycle may be used to clean a DP membrane (filtration-based processes only). In an embodiment, waste from this process may be disposed of to the WWTP and/or BGM.

In an embodiment, e.g., FIG. 23, standard energy recovery technologies known to a person of ordinary skill in the art may be used to recover DP high pressure pump energy expenditure (for desalination filtration technologies) and the recovered pressure may be used for additional desalination pressure, to pressurize a biomass/water slurry coming from the BGM for HTP harvesting/separation and/or another biomass processing method, and/or other uses e.g., in the Plan e.g., FIG. 23.

In reference to FIG. 23, an embodiment of the disclosure includes a system 2300 configured to use and reclaim pressure wherein such pressure 2302 is generated by and/or reclaimed from: a desalination module 2304; a thermal plant heat and/or pressure-intensive processes module 2306; a BBPP module 2308; an HTP module(s) or processes 2316; a pressure generated to create movement of substances of any kind in the Plan module 2314 by turning a turbine, creating a vacuum, pressurizing a pump, and/or directing a pressurized substance into a conveyance; a refinery module 2312; a BPP module 2312; and/or a power generation module 2310—the system comprising: capturing fluid pressure from a desalination module 2304; a thermal plant heat and/or pressure-intensive processes module 2306; a BBPP module 2308; an HTP module(s) or processes 2316; a pressure generated to create movement of substances of any kind in the Plan module 2314 by turning a turbine, creating a vacuum, pressurizing a pump, and/or directing a pressurized substance into a conveyance; a refinery module 2312; a BPP module 2312; and/or a power generation module 2310 and directing a portion of that fluid pressure to another a desalination module 2304; a thermal plant heat and/or pressure-intensive processes module 2306; a BBPP module 2308; an HTP module(s) or processes 2316; a pressure generated to create movement of substances of any kind in the Plan module 2314 by turning a turbine, creating a vacuum, pressurizing a pump, and/or directing a pressurized substance into a conveyance; a refinery module 2312; a BPP module 2312; and/or a power generation module 2310. An embodiment includes the system wherein pressure reclaimed 2302 from: a desalination module 2304; a thermal plant heat and/or pressure-intensive processes module 2306; a BBPP module 2308; an HTP module(s) or processes 2316; a pressure generated to create movement of substances of any kind in the Plan module 2314 by turning a turbine, creating a vacuum, pressurizing a pump, and/or directing a pressurized substance into a conveyance; a refinery module 2312; a BPP module 2312; and/or a power generation module 2310 may be supplied 2302 to: a desalination module 2304; a thermal plant heat and/or pressure-intensive processes module 2306; a BBPP module 2308; an HTP module(s) or processes 2316; a pressure generated to create movement of substances of any kind in the Plan module 2314 by turning a turbine, creating a vacuum, pressurizing a pump, and/or directing a pressurized substance into a conveyance; a refinery module 2312; a BPP module 2312; and/or a power generation module 2310.

With reference to Table 4, a system configured to use and reclaim pressure wherein such pressure is generated by and/or reclaimed from:

a desalination module;
a thermal plant heat and/or pressure-intensive processes module;
a BBPP module;
an HTP module(s) or processes;
a pressure generated to create movement of substances of any kind by turning a turbine, creating a vacuum, pressurizing a pump, and/or directing a pressurized substance into a conveyance;
a refinery module;
a BPP module; and/or
a power generation module—the system comprising: capturing fluid pressure from a module a-h and directing a portion of that fluid pressure to another module a-h.

Thus, Table 4 provides a combination that may be an embodiment of the system.

In one or more embodiments, e.g., FIG. 23, standard energy recovery technologies known to a person of ordinary skill in the art may be used to recover DP high pressure pump energy expenditure (for desalination filtration technologies) and the recovered pressure may be used for additional desalination pressure, to pressurize a biomass/water slurry coming from the BGM for HTP harvesting/separation and/or another biomass processing method, and/or other uses in the Plan as in FIG. 23.

In reference to FIG. 23 an embodiment of the disclosure includes a method of using and reclaiming pressure wherein such pressure 2302 is generated by and/or reclaimed from: a desalination module 2304; a thermal plant heat and/or pressure-intensive processes module 2306; a BBPP module 2308; an HTP module(s) or processes 2316; a pressure generated to create movement of substances of any kind in the Plan module 2314 by turning a turbine, creating a vacuum, pressurizing a pump, and/or directing a pressurized substance into a conveyance; a refinery module 2312; a BPP module 2312; and/or a power generation module 2310—the method comprising: capturing fluid pressure from a desalination module 2304; a thermal plant heat and/or pressure-intensive processes module 2306; a BBPP module 2308; an HTP module(s) or processes 2316; a pressure generated to create movement of substances of any kind in the Plan module 2314 by turning a turbine, creating a vacuum, pressurizing a pump, and/or directing a pressurized substance into a conveyance; a refinery module 2312; a BPP module 2312; and/or a power generation module 2310 and directing a portion of that fluid pressure to another a desalination module 2304; a thermal plant heat and/or pressure-intensive processes module 2306; a BBPP module 2308; an HTP module(s) or processes 2316; a pressure generated to create movement of substances of any kind in the Plan module 2314 by turning a turbine, creating a vacuum, pressurizing a pump, and/or directing a pressurized substance into a conveyance; a refinery module 2312; a BPP module 2312; and/or a power generation module 2310. An embodiment includes the method wherein pressure reclaimed 2302 from: a desalination module 2304; a thermal plant heat and/or pressure-intensive processes module 2306; a BBPP module 2308; an HTP module(s) or processes 2316; a pressure generated to create movement of substances of any kind in the Plan module 2314 by turning a turbine, creating a vacuum, pressurizing a pump, and/or directing a pressurized substance into a conveyance; a refinery module 2312; a BPP module 2312; and/or a power generation module 2310 may be supplied 2302 to: a desalination module 2304; a thermal plant heat and/or pressure-intensive processes module 2306; a BBPP module 2308; an HTP module(s) or processes 2316; a pressure generated to create movement of substances of any kind in the Plan module 2314 by turning a turbine, creating a vacuum, pressurizing a pump, and/or directing a pressurized substance into a conveyance; a refinery module 2312; a BPP module 2312; and/or a power generation module 2310.

In an embodiment, e.g., FIG. 4, reverse osmosis water output remineralization may be performed using CO2 addition with Dolomitic limestone and Sodium Carbonate, or if feasible, CO2 may be added from purified thermal plant exhaust, other CO2 source(s) e.g., in the Plan, and/or by another technique.

In an embodiment, e.g., FIG. 3, treated wastewater from the WWTP and/or BGM may be used to dilute the DP plant brine discharge to reduce or eliminate environmental impacts. If a deep sea diffuser brine discharge outfall may be used, up to 5% salinity above the naturally occurring salinity may be generally acceptable. However, In an embodiment, with freshwater dilution, the salinity may be reduced in-pipe to match the naturally occurring salinity or a salinity that may be acceptable, and discharged near the shore, instead of out to sea, eliminating the significant infrastructure expense associated with a deep sea discharge. The typical salinity of ocean water may be between 3% and 5%, and a typical reverse osmosis desalination plant rejection rate (rate of brine discharge as a percentage of the initial intake volume) may be generally about 50%. In an embodiment the following formula may be used to calculate the amount of dilution necessary to restore the brine discharge to a target salinity:

$$S_B V_B + S_D V_D = S_T(V_B + V_D), \text{ where:}$$

$S_B$=Salinity of Brine, $V_B$=Volume of Brine,
$S_D$=Salinity of Diluent, $V_D$=Volume of Diluent, and
$S_T$=Target Salinity.

In one or more embodiments, an example of BGM and/or WWTP dilution may be utilized as follows: Assuming a WWBGU, FWBGU or WWTP may be the source with a salinity of 0.5%, assuming ocean salinity of 4.5%, and assuming a desalination 50% rejection rate, for a near shore discharge, using the formula above, the brine would be diluted with approximately 1.125 liters of BGU and/or WWTP discharge water per liter of brine discharge water to reach background salinity. For a deep sea discharge, the brine would be diluted with approximately 1.012 liters of BGU and/or WWTP discharge water per liter of brine discharge water in order to reach 5% above background salinity, a recommended discharge salinity level. The brine discharge may also be diluted with salt water either from a saltwater BGU and/or a brackish water BGU, and/or another salt water source, and/or another water source e.g., in the Plan. In an embodiment, any water source(s) e.g., in the Plan in combination with or without the BGU and/or WWTP discharge (FIG. 3) may be used in order to meet desalination plant brine discharge salinity goals. In an embodiment, the water source(s) used for dilution may be strategically selected and/or combined such that water most valuable to the Plan and/or community may be preserved as much as possible, and water of lesser value may be used for dilution (e.g., treated wastewater, brackish water). In one or more embodiments, in the case where there may be multiple possible dilution sources, the above formula may be modified as follows calculate the volumes of each diluent water source that may be combined to achieve a target salinity:

$$S_B V_B + (S_{D1} V_{D1} + S_{D2} V_{D2} + S_{D3} V_{D3} \ldots) = S_T(V_B + V_{D1} + V_{D2} + V_{D3} \ldots), \text{ where:}$$

The numbers represent different diluent water sources. As many diluent sources as may be available may be added in the same way (denoted by " . . . " above).

In an embodiment, the disclosed Plan provides a novel means and method of planning and/or combining water resources strategically by use of this formula and strategic selection of water sources to generate salinity targets as mentioned above. This process and/or method may be used to dilute the brine to the same or similar salinity as naturally occurring salinity for near shore discharge, or an acceptable salinity for deep sea discharge, or possibly some salinity between the two for a sea discharge between the two distances. In an embodiment, if the brine may be heated due to processing through desalination or another reason, after optional heat recovery to the Plan, if the brine temperature may be impacting on the local environment, or regulated by law, dilution strategies may also incorporate calculations and/or diluent source water selections to adjust the heat of the brine discharge to appropriate levels. As may be known to the person of ordinary skill in the art, mathematical and/or physical modeling and/or other studies may be needed to determine actual numbers, based on discharge design, local features and/or other considerations.

In an embodiment, e.g., FIG. 2, or other description related to heat generation and/or transfer heat may be transferred to the DP from the heated water, biocrude and/or biofuel that result from HTP and/or other processing methods used to process biofuel, biomass and/or a biomass/water slurry using heat exchangers and/or other technologies, and/or from any other heat source(s) e.g., in the Plan, e.g., FIG. 2. The method may beneficially raise the temperature of the feed water prior to desalination.

In an embodiment, e.g., FIG. 2, and/or other description related to heat generation and/or transfer; and/or FIG. 3, a saltwater BGU may use salt water to produce biomass initially, and subsequently, a water output may be directed in whole or in part to the DP for the desalination process after biomass separation from the water (possibly using HTP, other currently known biomass separation/refining methods, and/or methods that may be developed in the future). The biomass action on the salt water may remove organic materials, nutrients, and/or some minerals, which may result in a more efficient desalination process than regular salt water. Also the salt water after HTP or a similar process (if used) may have been heated, and that heat may increase the efficiency of the desalination process.

DP Brine Disposal Technologies: Brine Disposal to Sea— Discharge to Sea or another water body: In an embodiment, e.g., FIG. 2, and/or FIG. 3 and/or other description related to heat generation and/or transfer and/or water transfer, DP brine discharge to sea and/or by other methods may be diluted with water output from the BGM and/or WWTP, as needed to mitigate salinity to reduce or eliminate environmental damage due to high-salinity and/or high temperature brine. In an embodiment, e.g., FIG. 24A, a DP brine discharge outfall may share some piping and/or other equipment with the WWTP/BGM outfall, and/or may utilize the same piping and/or outfall. In an embodiment, e.g., FIG. 3, brine may be discharged to land using zero liquid discharge.

In an embodiment, e.g., FIG. 3, brine may be discharged underground and/or by another means known to the person of ordinary skill in the art.

WASTE HANDLING/RECYCLING PLANT: In one or more embodiments, e.g., FIG. 10, and/or FIG. 3, a waste handling/recycling plant may be added optionally as part of the Plan to sort a waste stream (e.g., municipal sanitary waste, construction waste, agricultural waste and/or other biomass, such as wood waste) for recycling, landfilling, and/or use to provide feedstock for WTE and/or other technologies in the thermal plant to generate power. In general, construction and/or demolition wastes and municipal sanitary waste (MSW) may be collected and handled separately.

Construction and/or demolition wastes may be handled by large equipment in an outdoor setting that allows for large stockpile areas for materials. This may be conducted remotely from the site, or in a large building or open area which may be collocated. In an embodiment, the waste handling/recycling facility design may allow for drainage and use/treatment of liquids. Waste oils from the waste stream may be processed in the thermal plant to generate power. In an embodiment, e.g., FIG. 3, wastewater may be directed to a WWTP and/or WWTBGU.

In an embodiment, e.g., FIG. 3, wastewater from all onsite modules and optionally from offsite sources may be directed to a WWTP and/or WWTBGU.

In an embodiment, e.g., FIG. 10, landfills may be used to contain waste that cannot be recycled and/or ash from the thermal plant, if not used in cement production. In an embodiment, landfills may be used to supplement WTE technologies used in the thermal plant, providing disposal space for WTE ash and/or excess waste, a temporary repository for waste to be used in WTE system(s), and/or may also be used as a substitute for WTE system(s) in certain embodiments. In an embodiment, gases generated by landfill waste decomposition (landfill gases), which may be typically 50 percent methane and 50 percent carbon dioxide may be used beneficially to power the thermal plant. In an embodiment, landfill gases may share power generation technology used to combust methane and/or biogas with other possible systems e.g., in the Plan that produce and/or combust gaseous fuels, such as the gasification module (e.g., CHG, anaerobic digestion) used for biomass and/or sludge and gas-fired combustion power generators. In an embodiment, landfill-generated $CO_2$ may be directed to the BGM and/or other processes requiring $CO_2$ e.g., in the Plan (e.g., FIG. 4), either before and/or after a burn off of methane in the thermal plant. In an embodiment, e.g., FIG. 4, carbon dioxide transport and storage infrastructure may be shared with the other systems described herein that generate $CO_2$. In an embodiment, e.g., FIG. 3 and/or FIG. 10, the optional landfill may be lined with a liner system possibly made of HDPE capable of containing leachate generated by the waste materials. The leachate collection system may be installed to remove leachate from the facility for temporary storage and future treatment at a water treatment facility. In an embodiment, landfill leachate may be sent to a WWTP, BGM, and/or oil separation and used for power generation in a WTE plant rotary kiln incinerator, plasma gasification unit, and/or other WTE technology.

BOTTLING AND PACKAGING PLANT (BBPP): In an embodiment, e.g., FIGS. 1, 3, 6, 10,11, and/or 14, a water bottling/biomass products bottling/packaging plant (BBPP) may be added optionally as part of the Plan. In an embodiment, any one or more of the components within the BBPP may be used (e.g., water bottling only, biomass bottling only, and/or other biomass packaging types only.) Water bottling lines may be used to bottle treated drinking water generated from the DP. In an embodiment, water bottling may product carbonated water optionally using any carbon dioxide source in the Plan (e.g., FIG. 4). In an embodiment, e.g., FIGS. 1, 3, 6, 10, 11, and/or 14, the desalinated water used for water bottling may require additional disinfection prior to bottling. Heat from the thermal plant and/or any other source(s) e.g., in the Plan (e.g., FIG. 2) may be used for this purpose and/or for other purposes in the BBPP. The BBPP can provide drinking water for daily per capita consumption, stockpiled for emergency, and/or produced for export, if desired. In an embodiment, the BBPP may also package liquid and/or solid biomass-derived products. It may produce carbonated water and/or biomass products using carbon dioxide from any source e.g., in the Plan, e.g., FIG. 4. It may have a separate section from the water bottling section to package biocrude and/or other biofuels. Packaging may comprise bottling, barreling, preserving, cutting, pelletizing, boxing, containerizing, compressing, pressurizing and putting into tanks, and/or other means of preparing products for storage, export and/or marketing.

In an embodiment, e.g., FIGS. 1, 3, 6, 10, 11, and/or 14 the BBPP may have warehouse space to store these products before shipment offsite and/or use e.g., in the Plan. In an embodiment, e.g., FIGS. 1, 3, 6, 10, 11, and/or 14, biomass products produced onsite, most notably liquid and/or solid biomass products, may also be bottled/packaged quickly after production and/or otherwise preserved in the BBPP. In an embodiment, the biomass products may be cooled using cogenerated cooling from the thermal plant or other sources before and/or after packaging to preserve freshness. The prompt packaging and cooling (such as refrigeration), where needed, may preserve delicate products promptly onsite and prepare them for market in the most beneficial way.

In an embodiment, e.g., FIG. 1, a portion or all of the BBPP equipment for disinfecting desalinated water before bottling may be shared with the WWTP and/or WWTBGU, such as disinfection treatment (e.g. UV treatment). A portion or all of the BBPP equipment for disinfecting desalinated water before bottling may be shared with the WWTP and/or WWTBGU, such as disinfection treatment (e.g. UV). In an embodiment, e.g., FIG. 2, or other description related to heat generation and/or transfer, a BBPP may use heat from any source e.g., in the Plan for disinfection or any other processes requiring heat. In an embodiment, e.g., FIG. 10 and/or FIG. 24K bottle blowing, washing, filling, and capping may be combined into one integrated system.

Integrated systems reduce bacteriological loading (disinfection), reduce production costs, decrease line footprint, reduce bottle costs, and increase line efficiency. In an embodiment, e.g., FIG. 10 and/or FIG. 24K, plastic may be recycled from the waste receiving/recycling area and/or any waste processing area. The end product of the recycled plastic would be cleaned, disinfected, and shredded plastic material. This material may then be utilized in the bottle manufacturing process at the BBPP. In an embodiment, packaging materials for the BBPP and/or other modules e.g., in the Plan, such as the refinery may also come from the waste handling/recycling plant described herein, comprising possibly plastic, cardboard, and wood pallets. In an embodiment, a bottle to bottle recycling facility is included e.g., in the Plan in the BBPP module to allow for direct use of recycled PET and/or other materials for plastic bottle manufacture. In an embodiment, this type of facility may be coupled with the waste handling/recycling plant. The end product of the recycled plastic would be cleaned, disinfected, and shredded plastic material. This material may then be utilized in the bottle manufacturing process at the BBPP. In an embodiment, packaging materials for the BBPP may also come from the waste handling/recycling plant described herein, comprising possibly plastic, glass, cardboard, wood pallets and/or other recycled materials. In an embodiment, e.g., FIG. 2, and/or other description related to heat generation and/or transfer, waste heat from the thermal plant and/or heat recovered from other sources e.g., in the Plan (e.g., FIG. 2) may be used to generate cooling, such as air conditioning and/or refrigeration for cooling buildings and/or for refrigeration of biomass products, for cooling the BGM where beneficial, and for other uses.

BIOFUEL RESEARCH CENTER: A biofuel research center (BRC) may be added to the Plan to provide ongoing research and development into all phases of the biomass and biomass fuel production systems, including the BGM and any of its BGUs, and testing to improve biomass yields, fuel yields, biomass processing technologies, to reduce costs, and to make all processes more environmentally beneficial. The BRC may also develop and implement methods of producing a wide array of non-fuel biomass products for use onsite and/or for export. The BRC may also work to develop, implement, and improve on WTE processes and/or other processes which produce fuels. Because the BRC may be located onsite, biomass and/or other testing research may benefit from the opportunity to perform in-process testing, and/or to pilot, and to share infrastructure needed onsite without extra expense, excluding infrastructure that may need to be used for closed research systems (e.g., for testing new biomass strains without comingling with biomass in a BGU).

REFINERY: In an embodiment, a refinery may be utilized e.g., in the Plan to perform any process related to processing biomass, water, fuel precursors, gases, and/or fuels of any type from one state to any other more beneficial or usable state. The systems used in the refinery for the purposes of this disclosure will not be limited to those in a petroleum refinery, rather the refinery may employ systems and/or methods needed for the Plan. For example, the refinery may employ any technique(s) needed to separate water, biomass, biocrude and/or biofuels. It may further refine biocrude and/or biofuels into more pure components, certain ranges of carbon molecular weights, volatility, or in other ways. It may perform all of the usual functions of a petroleum refinery, adapted as necessary to the refining of biomass, and/or may use refining techniques more typical of biofuels of various types and/or other techniques. The refinery may comprise HTP modules of any kind. It may use HTP modules to perform HTP for the flash refining of a biomass/water slurry, such as HTL, HTC with or without IST, and/or RTP.

It may comprise a module for catalytic hydrothermal gasification. It may comprise modules to refine biocrude or bio-coal that may be the result of other processes e.g., in the Plan, e.g., pyrolysis-based and/or other WTE processes which generate fuels. It may comprise modules to refine the outputs of cellulosic ethanol/butanol/isobutanol systems. It may process the residue from anaerobic digestion, for example by HTP. It may comprise methods to dry, purify, and/or treat gaseous fuels, such as biogas, natural gas, methane, and/or hydrogen. It may use pyrolysis, micro emulsion, transesterification, thermal depolymerization, bacterial processing, and/or other methods. The refinery may comprise a wide variety of different methods in order to handle any refining needs of any system e.g., in the Plan. These methods may be known to those skilled in the art, and will not be described herein. In an embodiment, any of the foregoing modules and/or systems comprised by the refinery may be used not only for biomass from the BGM, but also any other source of biomass, such as farm waste, wood, municipal waste, energy crops, and/or other sources of biomass. In an embodiment, processing of these other sources of biomass may be done in combination with the various means to process the BGM outflow fluid, fuels generated directly in the BGM, and/or separately. In an embodiment, the technologies chosen for refining in any embodiment may vary based on project goals (e.g., what biomass type(s) may be used, what fuel type(s) may be most beneficial, and other project-specific considerations), therefore the disclosed Plan may use any technique or other means suited to the purpose, comprising the methods e.g., as described herein and/or any others available to the person of ordinary skill in the art for refining and/or processing biomass. In an embodiment, heat and/or cooling needed in the refinery may be provided by the thermal plant and/or other sources e.g., in the Plan, e.g., FIG. 2, and/or by separate sources in the refinery. In an embodiment, heat and/or cooling used in the refinery may be recovered and reused e.g., in the Plan. In an embodiment, all solvents used in the refinery may be recovered and reused as much as possible, or may be used as a fuel in any thermal plant technology. In an embodiment, the refinery may have bottling/barreling and storage functions to package and store biocrude and/or biofuel onsite and/or for export offsite. In an embodiment, it may also have pumps and piping to pipe these and/or other fuels to the thermal plant and/or offsite. In an embodiment, it may have sources of chemical additives (e.g., to stabilize fuels and/or to change their burn characteristics) and/or fuels from offsite, such as petro fuels which may be stored and/or piped in, which may be combined with biocrude and/or biofuels before being packaged, stored and/or sent out of the refinery as described above. In an embodiment, any residuals or other outflows of the refinery may optionally be processed in a BPP.

BIOMASS PROCESSING PLANT (BPP)_In an embodiment, e.g., FIGS. 1-4, 6, 10-12, and/or 14-19, a biomass processing plant (BPP) may be included to process biomass derived from the BGM and/or other systems in certain embodiments in addition to, or instead of the aforementioned refinery. In various embodiments, a BPP may be represented in FIGS. 1-4, 6, 10-12, and/or 14-19 as the module e.g., in the Plan for "BPP" or "BPP (Downstream Processing)" of biomass. This module may be shown along with the refinery in some figures as "Refinery and/or BPP", as, in an embodiment, either or both may be selected in an embodiment of the Plan, and they may be either separate plants or may be collocated or combined into one plant. In an embodiment, a possible configuration, comprising many optional components for a BPP may be shown in FIG. 14, and/or additional possible configurations may be shown in FIGS. 3 through 9 of patent No. US20090197322 A1. These figures may be incorporated in U.S. Provisional Application No. 62/173,905, filed Jun. 10, 2015, Appendix 2, also incorporated by reference in its entirety and relied upon. In an embodiment, any system or method suited to purpose of the separation and/or processing of biomass may be used in the BPP. In an embodiment, the BPP may focus more on using biomass for non-fuel product production, and the Refinery may focus more on producing fuels, however, each may produce either products and/or fuels. The BPP may use any methods suitable for separation/extraction/refining biomass, comprising thermal, chemical, biological, and/or mechanical means and/or other means suited to the purpose, comprising the methods e.g., as described herein and/or any others available to the person of ordinary skill in the art. The BPP may use harvesting methods such as flocculation, flotation, sedimentation, expansion, expeller press, extraction, milking, cavitation, nanotechnologies, bacterial extraction and/or other bacterial processing, catalytic methods and/or other methods as known to a person of ordinary skill in the art e.g., Shelef, et. al, 1984 and Pandey et. al, 2013 Pgs. 85-110. The BPP may be used to produce many products besides fuels from biomass. Some examples of biomass products may be bioplastics, adhesives, paints, dyes, colorants, nanocellulose, fertilizers and other soil amendments, animal feed, glycerol, nutraceuticals, pharmaceuticals, cosmetics, food ingredients, fine chemicals (e.g., industrial enzymes, esters, resins), oxygen, and many other possible products for use onsite and/or for export as known to a person of ordinary skill in the art per Pandey, et. al 2013 pgs. 205-233. Fuels of all types may also be produced. In an embodiment, any resultant fuels may be routed to the refinery for further refining, for use onsite and/or for offsite export e.g., FIG. 10. In an embodiment, residual biomass and/or biomass that has been milked or otherwise processed may be directed to the BGM for reuse in biomass growth and/or to the refinery for processing into fuels and/or other products (See FIG. 14).

In an embodiment, e.g., FIG. 14, non-fuel products derived from biomass grown in wastewater, e.g., in a WWTBGU comprising select portions of it, or its residue after processing by HTP, anaerobic digestion and/or by any other method known to those of skill in the art may also be produced, comprising animal feed, fish feed, soil amendments, bio-polymers, bio-plastics, paints, dyes, colorants, lubricants, and/or other products. In an embodiment, some products may be derived by mixing the above biomass, biomass portions and/or residues with other materials.

Biomass Processing Plant 1400 comprises a biomass and water supply 1402, 1405 feeding into a separation unit 1404. Biomass 1403 may be sent to optional cell disruption unit 1408 and water 1406 may be reused (e.g., see FIG. 3) and/or discharged. Biomass 1417A may be transferred to drying unit 1410; and/or biomass 1417B may be transferred to one or more mixing modules 1420 that receive(s) solvent 1421. Mixing modules 1420 may also or alternatively receive a mixture of solvent and biomass 1416 1441 in the same or in separate mixing modules. Solvent and biomass may be transferred from mixing module 1420 to separation module 1422. Residual biomass 1426 may be optionally sent to BGM 21A and/or to module 1428 and refined to biofuel 1434. Biofuel use 1000, e.g., FIG. 10 may be one terminus to provide a downstream product.

Solvent may be recaptured in evaporation unit 1424 by conversion to a vapor 1436 where it may be condensed in unit 1438. Cooling of unit 1438 may be from 1451 cooling module 1439 (cooling optionally from FIG. 2). Recovered solvent 1440 may be then transferred back to mixing module 1420 or to BGM 212. BGM 212, BGM 212A and/or BGM 212B may be the same or different BGM's.

Other recovered solvent 1437 from evaporation module 1424 may be reused in mixing module 1420 and/or BGM 212B. Exhaust air 1425 may be removed by vacuum unit 1427 and transferred 1447 to optional odor control unit 1300 (e.g., from FIG. 13).

Treated air 1425A may be circulated to drying unit 1410 and returned air 1425b transferred back to optional unit 1300.

Dried biomass 1411 emerging from drying unit 1410 may be submitted to unit 1414 whereupon powdered products 1413 may be transferred to BPPP 1480.

Biomass 1404A emerging from separation unit 1404 may be transferred to whole cell products processing unit 1412 wherein whole cell products 1412A may be transferred to BPPP 1480.

Biomass emerging from evaporation unit 1424 become formulated products in oil 1430, which may be then transferred to BPPP 1480.

Both separation module 1404 and/or mixing module 1420 may receive heat from module 1418 (heat optionally from FIG. 2). Drying unit 1410 receives heat from unit 1418A (heat optionally from FIG. 2). Evaporation unit 1424 receives heat from unit 1418B (heat optionally from FIG. 2). Units 1418, 1418A and/or 1418B may be the same or different heat units.

One or more different biomass and water 1402 or solvent containing extracted biomass 1416 inputs may be processed using any subset of the steps and modules depicted.

In reference to FIG. 14 the separation unit 1404 separates biomass 1404A and/or 1403 from water 1406 and may be achieved through filtration, screening, centrifugation, flotation (comprising dissolved air and hydrogen), flocculation, bio-flocculation, gravity settling and/or other techniques as known to a person of ordinary skill in the art e.g., Shelef, et. al, 1984 and Pandey et. al, 2013 pgs. 85-110.

The optional cell disruption unit 1408 breaks down the cell wall of the biomass 1403 in order to release the contents of the cell through mechanical means such as crushing, sonication, homogenizing, temperature adjustments (freezing or microwaving) and/or non-mechanical means such as using enzymes or chemicals and/or other techniques as known to a person of ordinary skill in the art.

The drying unit 1410 dries the biomass 1417A by spray drying, freeze drying, drum drying, sun drying and/or other techniques as known to a person of ordinary skill in the art.

Mixing module(s) 1420 mixes biomass 1417B and/or solvent(s) containing extracted biomass 1416 with solvent for the purpose of extracting useful products from the biomass.

The separation unit 1422 separates biomass from solvent and may be achieved through filtration, screening, centrifugation, flotation (comprising dissolved air and hydrogen), flocculation, bio-flocculation, gravity settling, gravity thickener, and/or other techniques as known to a person of ordinary skill in the art per author Shelef, et. al, 1984 and Pandey et. al, 2013 pgs. 85-110.

The refinery and/or gasification module 1428 functions to produce biofuel 1434 from residual biomass 1426.

The evaporation unit 1424 evaporates off solvent leaving formulated products in oil 1430. The evaporation process preferably may be done under vacuum 1427 and/or with supplemental heat 1418B (heat optionally from FIG. 2).

The condensing unit 1438 condenses the solvent vapor 1436 to recover solvent 1440 using cooling 1439 (cooling optionally from FIG. 2).

The whole cell products processing unit 1412 functions to process whole cell products from biomass 1404A in preparation for the BBPP 1480.

The powdered products processing unit 1414 functions to process powdered products from the dried biomass 1411 in preparation for the BBPP 1480.

FIG. 14 shows the major steps involved in the downstream processing of the various products 1400. In an embodiment for the production of whole cell products 1412A biomass and water 1402 may be separated 1404 aided by heat 1418 (heat optionally from FIG. 2) and the resulting biomass 1404A may be sent to whole cell products processing 1412.

In an embodiment for the production of powered products 1413, biomass and water 1402 may be separated 1404 aided by heat 1418 (heat optionally from FIG. 2). The resulting biomass 1403 may be dried 1410 using heat 1418A and the dried biomass 1411 may be sent to powdered products processing 1414.

In an embodiment for the production of powdered products 1413 biomass and water 1402 may be separated 1404 aided by heat 1418 (heat optionally from FIG. 2). The resulting biomass 1403 optionally goes through cell disruption 1408 and the biomass 1417a may be dried 1410 using heat 1418A (heat optionally from FIG. 2). Exhaust air 1425B from drying 1410 optionally goes to air treatment/odor control 1300 (FIG. 13) and treated air 1425a may be optionally returned. The resulting dried biomass 1411 may be sent to powdered products processing 1414.

In an embodiment for the production of formulated products in oil 1430, biomass and water 1402 may be separated 1404 aided by heat 1418 (heat optionally from FIG. 2). The resulting biomass 1403 may be transferred to one or more mixing modules 1420 aided by heat 1418 with the addition of solvent 1421 and/or recovered solvent 1437 and/or 1440. Mixing modules 1420 may also or alternatively receive a mixture of solvent and biomass 1416 in the same or in separate mixing modules 1420. The residual biomass 1426 may be separated 1422 and the solvent containing the desired product goes through evaporation 1424 facilitated by vacuum 1427 and heat 1418B to produce the formulated product in oil 1430. The solvent 1437 may be recovered directly from the evaporation unit 1424 and/or from solvent vapor 1436 which may be condensed 1438 using cooling 1439. The recovered solvent 1440 can be used in the BGM 212. The recovered solvent 1437 and/or the residual biomass 1426 can be used in the BGM 212A.

In an embodiment for the production of formulated products in oil 1430 biomass and water 1402 may be separated 1404 aided by heat 1418 (heat optionally from FIG. 2) and go through optional cell disruption 1408. The resulting biomass 1417B may be transferred to one or more mixing modules 1420 aided by heat 1418 (heat optionally from FIG. 2) with the addition of solvent 1421 and/or recovered solvent 1437 and/or 1440. Mixing modules 1420 may also or alternatively receive a mixture of solvent and biomass 1416 in the same or in separate mixing modules 1420. The residual biomass 1426 may be separated 1422 and the solvent containing the desired product goes through evaporation 1424 facilitated by vacuum 1427 and heat 1418B (heat optionally from FIG. 2) to produce the formulated product in oil 1430. Exhaust air 1425 from vacuum 1427 may be optionally treated for odor control 1300 (FIG. 3). The solvent 1437 may be recovered directly from the evaporation unit 1424 and/or from solvent vapor 1436 which may be condensed 1438 using cooling 1439 (cooling optionally from FIG. 2). The recovered solvent 1440 can be used in the BGM 212. The recovered solvent 1437 and/or the residual biomass 1426 can be used in the BGM 212A.

In one or embodiments for the production of biofuel 1434 biomass and water 1402 may be separated 1404 aided by heat 1418. The resulting biomass 1403 may be transferred to one or more mixing modules 1420 aided by heat 1418 with the addition of solvent 1421 and/or recovered solvent 1437 and/or 1440. Mixing modules 1420 may also or alternatively receive a mixture of solvent and biomass 1416 in the same or in separate mixing modules 1420. The residual biomass 1426 may be separated 1422 and sent to the refinery and/or gasification module 1428 to produce biofuel 1434 for fuel use 1000 (FIG. 10).

In an embodiment for the production of biofuel 1434 biomass and water 1402 may be separated 1404 aided by heat 1418 (heat optionally from FIG. 2) and go through optional cell disruption 1408. The resulting biomass 1417B may be transferred to one or more mixing modules 1420 aided by heat 1418 (heat optionally from FIG. 2) with the addition of solvent 1421 and/or recovered solvent 1437 and/or 1440. Mixing modules 1420 may also or alternatively receive a mixture of solvent and biomass 1416 in the same or in separate mixing modules 1420. The residual biomass 1426 may be separated 1422 and sent to the refinery and/or gasification module 1428 to produce biofuel 1434 for fuel use 1000 (FIG. 10).

In an embodiment, the BPP and Refinery may be co-located in order to allow sharing of systems, resources and/or processes. In an embodiment, any or all flows into and out of these facilities may be shared, e.g., biomass, biofuels, water, heat, cooling, carbon dioxide, as well as stores of materials used in processing biomass and/or biofuels. Some biomass heating, separation and/or other refining techniques may be shared with the Refinery. In an embodiment, these processes may be performed at the Refinery and the outflows further processed at the BPP, or vice versa. Any residual biomass from the BPP may be sent to the BGM for reuse, to a separate gasification module, to a gasification module such as a CHG or anaerobic digestion unit in the thermal plant, and/or to the Refinery for processing into fuels by HTP or other methods.

Location of the Refinery and BPP: Many of the possible separation and/or refining processes for biomass in the Refinery and BPP involve the use of heat. One current separation/refining technology type—HTP, and alternate processes also require heat. Some processing steps may also require cooling, such as condensation of solvents. In an embodiment, waste heat from the thermal plant and/or any other source e.g., in the Plan may be used for these purposes, e.g., FIG. 2. In an embodiment, the Refinery and/or BPP may be located in such as way onsite to make the best use possible of waste heat from the heat-intensive processes. In an embodiment, some aspects of refining/separation/processing of biomass may be performed in the thermal plant and/or any other heat generation and/or reclamation processes described herein, and the resultant output may be directed to the Refinery and/or BPP in order to use heat more efficiently. In an embodiment, these plants may also be located with consideration of efficient transportation of biomass products both onsite and preparation for export (i.e., proximity to the BBPP).

AIR TREATMENT/ODOR CONTROL SYSTEM: In an embodiment, e.g., FIG. 13, a Sludge processing module, gasification module, BGM, WWTP, BPP, Refinery, BBPP, Waste Handling/Recycling Plant, WTE Plant, and/or Cellulosic Ethanol/butanol/Isobutanol unit(s) when used in an embodiment of the Plan, and/or possibly other thermal plant technologies may emit odors and possibly other gaseous forms of pollution. In an embodiment, these facilities may be put under vacuum or draft (e.g., negative air pressure), and the air drawn from them used to feed combustion processes in the thermal plant in order to remove odors and/or other undesirable gases. In an embodiment, fresh portions of air may be provided using ambient air, air from other modules, and/or purification technologies may be used to treat the air and/or circulate air back to these units and/or for discharge. In an embodiment, this system may also be used to circulate air through any system e.g., in the Plan that may require air flow for other reasons, such as drying of biomass in the BPP and/or Refinery and/or recycled products in the recycling facility and/or BBPP. In an embodiment, heated air (e.g., from the thermal plant and/or other module, e.g., FIG. 2) may be used for these processes, and/or after optional heat recovery, the gases may be routed back into this system, as shown. In an embodiment, after exiting a combustion process, the air may be processed for heat recovery and/or pollution control (e.g., FIG. 7A or 7B), or by another method, and then sent for reuse, e.g., the BGM and/or other uses where carbon dioxide may be beneficial (See FIG. 4) and/or released into the environment. These plants may also or alternatively make use of regenerative thermal oxidizer technology, and/or other air treatment, odor reduction and/or purification technologies.

With reference to FIG. 13, design 1300 comprises an air treatment odor control configuration wherein optionally present refinery and/or BPP 1302, sludge processing module 1304, gasification module 1306, BGM/WWTP 1308, BBPP 206, waste handling/recycling module 1318, and thermal plant 1002 optionally comprising combustion processes 1326, waste-to-energy module(s) 1328, cellulosic ethanol/butanol/isobutanol module 1330, and/or other thermal plant processes 1332 may be in fluid communication with ambient air source 1310. Air purification module 1316 and/or heat recovery module 1314 may optionally process any air flow or flows in 1300, and one or more storage modules 1312 may store air from any one or more flows in 1300. Modules 1302, 1304, 1306, 1308, 206, 1312, 1314, 1316, 1318, 1328, 1330, and/or 1332 may deliver air to combustion processes 1326 in the Thermal plant 1002. Thermal plant combustion processes combust intake air from these modules, and the exhaust gases may be routed to heat recovery and/or pollution control 1324 and either reuse 1322 or discharge of gases 1320. 1324, 1322 and/or 1320 may be comprised by FIG. 7A, module 700 or 7B, module 700A, or by another means known to those in the art.

In reference to FIG. 13 an embodiment of the disclosure includes a system 1300 configured to use ambient air and optionally reclaim, purify and deodorize used air wherein the ambient 1310 and/or used air is provided to and/or from: a thermal plant module 1002; a sludge processing module 1304; a WWTP module 1308; a BGM 1308; a gasification module 1306; a waste handling/recycling module 1318; a heat recovery module 1314; a refinery module 1302; a BPP module 1302; a BBPP module 206; an air storage module 1312; and/or an optional air purification module 1316. An embodiment includes the system wherein an ambient 1310 and/or used air outflow(s) from any one or more of the modules: a thermal plant module 1002; a sludge processing module 1304; a WWTP module 1308; a BGM 1308; a gasification module 1306; a waste handling/recycling module 1318; a heat recovery module 1314; a refinery module 1302; a BPP module 1302; a BBPP module 206; an air storage module 1312; and/or an optional air purification module 1316 is provided to the thermal plant module 1002. An embodiment includes the system wherein the thermal plant module 1002 is configured to process the air outflow(s) using a combustion process 1326. An embodiment includes the system wherein the combustion process 1326 comprises the combustion of fuels to generate heat and/or power. An embodiment includes the system wherein the air outflow(s) from the thermal plant module 1002 is provided to a heat recovery and/or pollution control module 1324. An embodiment includes the system wherein the air outflow(s) from the heat recovery and/or pollution control module 1324 is optionally reused 1322 by any one or more of the modules: a thermal plant module 1002; a sludge processing module 1304; a WWTP module 1308; a BGM 1308; a gasification module 1306; a waste handling/recycling module 1318; a heat recovery module 1314; a refinery module 1302; a BPP module 1302; a BBPP module 206; an air storage module 1312; and/or an optional air purification module 1316 and/or discharged 1320 external or outside the system.

In reference to FIG. 13 an embodiment of the disclosure includes a method for using ambient air 1310 and optionally reclaiming, purifying and deodorizing used air wherein the ambient 1310 and/or used air is provided within a system 1300 to and/or from: a thermal plant module 1002; a sludge processing module 1304; a WWTP module 1308; a BGM 1308; a gasification module 1306; a waste handling/recycling module 1318; a heat recovery module 1314; a refinery module 1302; a BPP module 1302; a BBPP module 206; an air storage module 1312; and/or an optional air purification module 1316, comprising receiving ambient and/or used air from a module, optionally purifying the ambient and/or used air, and providing the ambient and/or used air to another module or discharging the ambient and/or used air. An embodiment includes the method further comprising providing an air outflow(s) from any one or more of the modules: a thermal plant module 1002; a sludge processing module 1304; a WWTP module 1308; a BGM 1308; a gasification module 1306; a waste handling/recycling module 1318; a heat recovery module 1314; a refinery module 1302; a BPP module 1302; a BBPP module 206; an air storage module 1312; and/or an optional air purification module 1316, comprising receiving ambient and/or used air from a module, optionally purifying the ambient and/or used air, and providing the ambient and/or used air to another module or discharging the ambient and/or used air to the thermal plant module 1002 wherein the air comprises ambient 1310, reclaimed, purified, and/or deodorized air. An embodiment includes the method further comprising directing air to a thermal plant combustion unit or module 1002. An embodiment includes the method further comprising directing air from a thermal plant combustion unit or module 1002 to a heat recovery and/or pollution control module 1324.

In one or more embodiments, e.g., FIG. 13, a Sludge processing module, gasification module, BGM, WWTP, BPP, Refinery, BBPP, Waste Handling/Recycling Plant, WTE Plant, and/or Cellulosic Ethanol/butanol/Isobutanol unit(s) when used in one or more embodiments of the Plan, and/or possibly other thermal plant technologies may emit odors and/or possibly other gaseous forms of pollution. In an embodiment, these facilities may be put under draft (e.g., negative air pressure), and the air drawn from them used to feed combustion processes in the thermal plant in order to remove odors and/or other undesirable gases. In one or more embodiments, fresh portions of air may be provided using ambient air, air from other modules, and/or purification technologies may be used to treat the air and/or circulate air back to these units. In an embodiment, this system may also be used to circulate air through any system in the Plan that may require air flow for other reasons, such as drying of biomass in the BPP and/or Refinery and/or recycled products in the recycling facility and/or BBPP. In one or more embodiments, heated air may be used for these processes, and after optional heat recovery, the gases may be routed back into this system, as shown. After exiting a combustion process, the air may be processed for heat recovery and/or pollution control (e.g., FIG. 7A or 7B), and/or by another method, and then sent for reuse, such as in the BGM and/or other uses where carbon dioxide may be beneficial (See FIG. 4) and/or released into the environment. These plants may also or alternatively make use of regenerative thermal oxidizer technology, and/or other air treatment, odor reduction and/or purification technologies.

Pressure anywhere e.g., in the Plan may be recovered and reused wherever present e.g., in the Plan. With reference to FIG. 23, 2300, pressure may be recovered from and/or provided back to any of the optionally present modules: desalination module 2304, thermal plant 2306, BBPP 2308, power generation module 2310, refinery and/or BPP 2312, HTP 2316 and/or energy for the movement of materials within the Plan 2314. Pressure recovery and reuse 2302 may be accomplished by any method know to those in the art. Some examples of pressure recovery technologies which may be used for this purpose may be a turbine or Pelton wheel, turbocharger, pressure exchanger (such as DWEER, the rotary pressure exchanger, and Dannfoss iSave), and energy recovery pumps (such as the Clark pump, the Spectra Pearson pump, and/or other technologies suited to the purpose).

Due to the collocation of different technology types, some of which may share aspects of infrastructure, inputs, outputs, resources and/or other aspects in common, infrastructure may be shared. Also, certain products may be synthesized or reclaimed and used e.g., in the Plan in unexpected beneficial ways due to the collocation of these typically separate technologies and/or modules e.g., in the Plan. FIGS. 24A through 24J depict aspects of infrastructure which may be shared, or other synergies created e.g., in the Plan which may be related to infrastructure. FIG. 24K shows products that may be reclaimed or synthesized within the Plan (in addition to those previously discussed), and shows how some of these products may be used/reused e.g., in the Plan. FIGS. 24L and 24M give some examples of synergies created in embodiments where a refinery, BPP, and/or BBPP may be used.

With reference to FIG. 24A: In an embodiment, piping and piping installation and conduit infrastructure may be shared between a saltwater BGM, TP salt water cooling (e.g., salt water used to cool a thermal plant and/or other process), a desalination plant, BGM/WWTP discharge(s), and/or brine discharge.

With reference to FIG. 24B: In an embodiment, HTP infrastructure, comprising HTP transportation infrastructure and HTP processing infrastructure and/or anaerobic digestion infrastructure and/or other biomass gasification technologies may be shared to process WWTP sludge, BGM sludge, Biomass to and from any source, and/or BGM biomass.

With reference to FIG. 24C: In an embodiment, biogas purification, treatment, storage and/or heating infrastructure may be shared between optionally HTP gaseous output, natural gas input/output, anaerobic digestion, WWTP/BGM biogas, and/or gasification module(s).

With reference to FIG. 24D: In an embodiment, air supply/gas supply, automation and flow controls, primary treatment and tertiary treatment infrastructure and/or modules optionally may be shared by WWTP, BGM, and/or WWTP when converted to a BGM.

With reference to FIG. 24E: In an embodiment, sensors, computerized controls, and systems to automate and optimize all functions of the design and/or Plan may be implemented to control and/or optimize inputs, outputs, comprising flow rates and/or other features of the whole of the Plan, design, or system. These systems may comprise an automation system with controls, or automation system with flow controls comprising an optionally computer-controlled system capable of sensing and/or regulating any condition, process, flow, input, output, in the Plan (e.g., temperature, pH, gas content, flow rate(s), density, dissolved solids, pollutant concentrations, nutrient levels, light intensity, salinity, and/or other measureable characteristics), receiving data, processing it optionally via computer, optionally using artificial intelligence or other adaptive controls to determine if adjustments to any operational parameters may be needed, sending one or more signals to one or more systems, which then makes one or more physical adjustment(s) in the operational parameters of the Plan (e.g., a change in a flow rate of fluids, a release of materials, the startup, increased rate, or decreased rate of function of a process or technology, directing materials to storage and/or other module, and/or other operational adjustments to the modules, units, subunits, technologies, and/or communications comprising the Plan). In an embodiment, any of the processes, technologies, and controls may be integrated for all systems in the Plan with computer control and automation systems with sensors and computer controls to sense parameters of operation of the entire Plan, and to send signals to control systems to adjust and optimize any aspect of performance, optionally using one or more controller interfaces, and/or robust and/or adaptive controls and/or artificial intelligence (e.g., and industrial control system optionally with adaptive controls and/or artificial intelligence).

With reference to FIG. 24E: In an embodiment, electrical power distribution may be shared between all modules, units, subunits, connections, communications, flows, and/or all other features of the system and/or Plan.

With reference to FIG. 24F: In an embodiment, intake piping infrastructure may optionally be shared by a saltwater BGU, TP salt water cooling (e.g., salt water used to cool a thermal plant or other process), a desalination plant, and/or salt water for any other selected use e.g., in the Plan.

With reference to FIG. 24G: In an embodiment, water lines may be installed in the same conduit to reduce infrastructure installation process for the supply or discharge of salt water, brine water, brackish water, fresh water, grey water, and/or potable water.

With reference to FIG. 24H: In an embodiment, any thermal plant technologies and/or solar thermal technologies optionally present in any embodiment may share an exhaust gas conveyance, stack, pollution control module(s), pollution entrainment module(s), turbine(s), water/other fluid source(s), conveyances in and/or out, CO2 storage and/or distribution systems, chemical storage and/or piping, water piping, fuels, sensors and/or electronic controls, other infrastructure in common between systems, and/or resources and/or outputs in common.

With reference to FIG. 24I: In an embodiment, heat and/or cooling transmission and/or storage infrastructure may optionally be shared between and/or with any two or more modules with heat and/or cooling outputs and/or solar thermal modules.

With reference to FIG. 24J: In an embodiment, infrastructure for HTP processes and/or combustion of fuels may be shared by BGM biomass, WTE biomass, and/or agricultural biomass.

With reference to FIG. 24K: In an embodiment, other byproducts of the Plan or byproducts converted to other products e.g., in the Plan may comprise any of the following: ash (from TP combustion processes) to cement, brine (e.g., from desalination) to hydrogen gas by electrolysis, brine to bleach, brine to sea salt, and from recycling plant module (comprised by waste receiving/recycling module 206): plastic to plastic bottles, straps, and/or packing materials for BBPP, other plastic uses, rubber to rubber chips, wood to pressed wood (e.g., pressed board), glass to glass products, metals to metal products and/or raw materials, paper to paper for cardboard and/or paper products, and other standard recycling.

With reference to FIG. 24L: In an embodiment, a refinery and/or a BPP may provide synergies due to colocation with other modules e.g., in the Plan as follows: Prompt processing of biomass into fuels and/or non-fuel products for use onsite, for storage, and/or for export offsite. Any of the fuels discussed herein may be used onsite. The following non-fuel products may be synthesized from biomass onsite and used in systems e.g., in the Plan: lubricants, bioplastics, paper, soil amendments, fertilizer, paints, chemicals, and other useful products. When a refinery and BPP may be both present any one or more embodiments, they may share any infrastructure in common, resources, inputs, outflows, and/or the outputs or byproducts of a BPP may be processed in a refinery or vice versa.

With reference to FIG. 24M: In an embodiment, a BBPP may provide synergies when integrated into the Plan as follows: Prompt processing and/or bottling of desalinated water from DP to preserve freshness; carbonation of water onsite using optionally purified carbon dioxide from Plan (FIG. 4); ability to store and/or transport water from source, which creates a versatile water supply, and which may allow for generation of a reserve water supply to meet varying needs or to store for emergencies; prompt packaging of biomass products after synthesis to preserve optimal freshness; optional carbonation of biomass liquids onsite using optionally purified carbon dioxide from Plan (FIG. 4); may use heat comprising possibly waste heat from thermal plant for processing; may use cogenerated cooling from thermal plant heat comprising waste heat for rapid preservation of water and/or biomass products.

DP Brine Disposal Technologies: Brine Disposal to Sea—Discharge to Sea or another water body: In an embodiment, e.g., FIG. 24A and/or FIG. 3 a DP brine discharge outfall may share some piping and/or other equipment with the WWTP/BGM outfall, and/or may utilize the same piping and/or outfall. In an embodiment, brine may be discharged to land using zero liquid discharge. In an embodiment, brine may be discharged underground and/or by another means known to the person of ordinary skill in the art.

In one or more embodiments, e.g., FIG. 24A and/or FIG. 3, a SWBGU may share infrastructure with the optional desalination plant, comprising, for example, the water intake from the sea, pumps, pipes, heat use, water use and/or an outfall. In an embodiment, a SWBGU may use salt water separately from the desalination plant, it may receive brine as source water from the desalination plant, and/or its output may be directed to the desalination plant (see description in desalination section).

In one or more embodiments, e.g., FIG. 3 and/or FIG. 24A, the DP may share an intake and/or piping throughout the Plan with a SWBGU, a saltwater cooling source for the thermal plant (if needed), or any of these modules/uses for salt water may have separate intakes. Any of these modules/sources' intakes, if separate, or the combined intake if combined may share some piping and/or other equipment with wastewater treatment plant, BGM, and/or brine discharge outfall. In one or more embodiments the intake(s) may provide a source of cooling for any process in the Plan, wherein water from an intake out to sea, especially a deep-water intake, may be significantly cooler than ambient temperature on land and may provide cooling. In an embodiment, saltwater intake water may be used as source water for a SWBGU and/or BWBGU in a hot climate to regulate its temperature. In an embodiment, the salt water from the intake is used to fill pools and/or other structures surrounding any BGU and/or BGU component in order to provide cooling and/or temperature modulation, particularly in hot environments. After use in this manner and/or in other cooling application(s), decorative application(s), and/or in any other manner described for heat and/or cooling transfer, comprising possibly heat transfer from the thermal plant to the Plan, the water may be then routed to the DP for desalination. In this manner, water and/or cooling are provided where needed in the Plan (See FIGS. 2 and 3), and in the process, the salt water is elevated in temperature, which allows for a lower energy requirement in the desalination process.

In an embodiment, e.g., FIG. 24B and/or FIG. 3, an HTP module or unit, which may be used as described herein to process biomass, and/or similar methods, may also be used as a means of converting waste into energy. HTP and/or equivalent technologies to a person of ordinary skill may be used to convert a wide variety of organic materials to produce biocrude. An HTP module, unit or equivalent processing system(s) set up for biomass may be shared with those being used to process solid waste. HTL may be conducted in accordance with the PNNL process patent WO 2013/184317A1 as shown in FIG. 9. Other variations of HTP or similar processes suited to the purpose may also be used.

WWTP/WWTBGU/MFWBGU Solids/Sludge: In an embodiment, e.g., FIGS. 24B, and/or 10 solids and/or sludge from the WWTP, WWTBGU, MFWBGU, and/or other BGUs described herein may be processed in a gasification module (e.g., CHG, anaerobically digested) to produce biogas for power generation in the thermal plant. In one or more embodiments, all or part of the biomass from the BGM may also be processed in a gasification module along with the solids referenced or separately using the same gasification equipment, to produce a biogas; and/or WWTP and/or WWTBGU solids may be injected into the WWTBGU for use in biomass growth; and/or any of the solids referenced may be processed in an HTP system (either the biomass HTP system described herein and/or a separate one) to produce biocrude for power generation in the thermal plant, with the remaining residue being processed by any of the above methods; and/or the solids may be processed in another WTE and/or other technology to produce power and/or fuel (e.g., pyrolysis-based WTE, cellulosic ethanol and/or other methods) for use in the thermal plant.

In one or more embodiments, e.g., FIGS. 24B, 24C and 10, biogas generated by processing biomass in a gasification module (e.g., using CHG and/or anaerobic digesters), and optionally from a landfill used in any onsite process may be used to generate power in the thermal plant. The biogas from the gasification module technologies may undergo processing to prepare it for use as fuels and/or storage, comprising drying, hydrogen sulfide and/or other pollutant removal, blending with other fuels, condensation to liquids, and/or other techniques known to those of ordinary skill in the art. Gasification module(s), such as CHG module(s), anaerobic digesters and/or gas purification, drying, condensation to liquids, treatment, storage and/or heating and/or related infrastructure may be shared by BGM biomass, BGM sludge, and/or WWTP sludge and/or the resulting biogas and/or other biogas sources, such as an optional landfill, and/or other optional sources of natural gas, such as natural gas imported from offsite. Any thermal plant technologies utilizing gaseous fuels (e.g., natural gas-fired combustion turbines) and/or related infrastructure may be shared by any or all of the foregoing systems, and/or also other sources of combustible gas, such as natural gas delivered from offsite for use in the thermal plant.

In one or more embodiments, e.g., FIG. 24B, and/o FIG. 10 HTP comprises a primary method of "flash separating" biomass from water and/or converting the biomass to a biocrude and/or other fuels using a process involving heat and possibly pressure. In one or more embodiments, the biocrude that is the product of liquid-based HTP processes such as HTL or RTP may be combusted directly e.g., in burners, heavy motors, e.g., an engine normally combusting diesel or heavier fuels, and/or other select thermal plant technologies to produce power, and/or may be further refined to many major fuel types, which may be combusted if more efficient than biocrude given additional refining costs. In an embodiment HTP may convert other biomass and/or waste to biocrude. In an embodiment, HTP may be used as a full substitute for other WTE technologies, or a partial replacement in the Plan. In this embodiment, the waste may be heated and/or possibly pressurized, and the organic portion may be liquefied to a form of biocrude (this process is termed "Waste HTP"). In an embodiment, the biocrude may be combusted and/or further refined and then combusted to generate power, depending on its properties. It is an optional system in the disclosed Plan for waste-to-energy, comprising optionally the incorporation of biomass streams, such as agricultural material, wood and/or other organic materials into one or more HTP processes. The synergies with the Plan are the same as those described for pyrolysis-based WTE Systems described above, plus the following. In an embodiment, Waste HTP infrastructure may be shared with BGM Biomass HTP infrastructure, and/or other biomass HTP (Such as agricultural biomass, wood, energy crops, etc.), and the processes may be fully combined or partially combined.

In one or more embodiments, e.g., FIG. 24D, and/or FIG. 3, if a standard WWTP is in operation, and is later adapted into a WWTBGU as understood by a person of ordinary skill in the art, the primary and/or tertiary treatment infrastructure initially developed for the WWTP may also be adapted for use in the WWTBGU, and/or possibly parts or all of the secondary treatment infrastructure as well.

In one or more embodiments, e.g., FIG. 24D and/or FIG. 3, ponds, settling tanks and/or other technologies used in secondary treatment at a WWTP may be used in one or more WWTBGUs as well, and may share infrastructure if operating together, and/or in the event of the retrofit or partial or full adaptation of a WWTP system to a WWTBGU, adaptation of initial WWTP ponds, tanks and/or other infrastructure to later WWTBGU and/or other BGU implementation, depending on design needs. In one or more embodiments, this may also comprise primary treatment infrastructure for wastewater, comprising screens, clarifiers, flocculation technologies, settling technologies, and/or other suitable primary wastewater treatment technologies, and/or tertiary treatment technologies for wastewater, which may comprise tertiary clarifiers, disinfection technologies such as UV, and/or other suitable tertiary wastewater treatment technologies. For example, a UV treatment system may be shared between one or more WWTBGUs and WWTPs where both are used concurrently, or it may be adapted for use in a WWTBGU in the event a WWTBGU is implemented to replace a WWTP.

Electrical: In one or more embodiments, e.g., FIG. 24D, an electric substation near the influent pumping equipment may be shared by one or more WWTBGUs and WWTPs, or adapted for replacement of a WWTP by a WWTBGU. Sensors, computer controls, control modules, software, hardware and/or other electrical systems may also be shared among these systems, adapted from one to the other, and may be integrated with the rest of the modules of the Plan.

In one or more embodiments, e.g., FIG. 24D and/or FIG. 6, an air/oxygen delivery system used for any purpose in a system or Plan may be adapted and/or converted to a Carbon Dioxide delivery system, e.g., to support a photosynthetic WWTBGU, or to an oxygen or air delivery system suited to biomass growth in a BGU type that requires oxygen or air, or to an oxygen, air or carbon dioxide delivery system to support BGUs with these requirements.

In one or more embodiments, e.g., FIG. (table) 24E and/or FIG. (table) 24H, one or more connections, communications, and/or synergies described herein between the thermal plant and other processes in the Plan may be established using any number of the different technologies comprising the "thermal plant" (e.g., carbon dioxide may be supplied to the BGM from either a combustion turbine or a waste-to-energy incinerator, both, and/or any other thermal plant technologies generating carbon dioxide when these technologies are in use as the thermal plant). In one or more embodiments, different technologies and/or fuel sources may be used to comprise the thermal plant, comprising conventional power generation systems, waste-to-energy, and/or other thermal plant technologies may be integrated to share infrastructure and/or resources, e.g., fuels, heat, water, power, emission control modules, computer controls or modules, and/or other resources. Infrastructure sharing may comprise one or more electrical substations, transmission lines, other electrical infrastructure known to a person of ordinary skill in the art, exhaust gas conveyances, stacks, pollution control modules, pollution entrainment modules (e.g., as in FIG. 7A or 7B) and/or other emission controls, carbon dioxide, methane, biogas, oxygen and/or other gas transport lines and/or storage, water, water/biomass slurry, biofuel, other fuel, other liquid transportation and/or storage, cooling systems, heat exchangers, and/or other components that may be shared between thermal plants. In some embodiments, fuels may be generated/processed by one technology in the thermal plant and used to generate power and/or heat using another thermal plant technology, e.g., fuels may be generated in a WTE technology, processed with thermal plant heat, and/or combusted in a power plant comprised by the thermal plant.

In one or more embodiments, e.g., FIG. 24H and/or FIG. 24C, and/or FIG. 10 one or more fuel sources onsite and/or offsite may share power generation technologies in the thermal plant, reducing infrastructure costs (e.g., biomass biocrude, WTE biocrude, HTP biocrude and/or other fuel sources sharing a thermal plant technology). In one or more embodiments, thermal plant technologies, comprising WTE and/or power generation technologies, may share carbon dioxide transportation and/or distribution infrastructure, cooling water and/or heated water transport, heat use, emission controls (e.g., exhaust gases may share the infrastructure shown, for example in FIG. 7B or 7B), and/or all other infrastructure in common to these technologies. Air Emissions Controls: In one or more embodiments, the Plan will have in place all of the modern air pollution controls, as needed, for the emissions being generated.

In one or more embodiments, e.g., FIG. 3 and/or FIG. 24H, the Plan may use solar thermal technologies (e.g., solar troughs) for preheating seawater for desalination, a BGM output for HTP, for power generation, or for introduction of heat into the Plan wherever needed (e.g., FIG. 3). If a solar thermal technology is used, it may share steam turbines with those already in thermal plant.

In an embodiment, e.g., 24K, an end product of incineration and/or other direct-combustion WTE technologies may be ash, which may be used to produce cement. In one or more embodiments, e.g., FIG. 2 and/or FIG. 24K, waste heat may be used for power generation to achieve electrolysis, e.g., sodium hypochlorite (bleach) may be synthesized from DP brine discharge using brine electrolysis. The bleach may be used throughout the Plan for disinfection, cleaning, and/or other uses, and/or exported offsite.

In one or more embodiments, e.g., FIG. 24K and/or FIG. 10, brine electrolysis provide hydrogen gas. The hydrogen may be used in a fuel cell to produce electricity, and/or returned to the thermal plant for combustion.

In one or more embodiments, e.g., FIG. 3 and/or FIG. 24K, sea salt may be manufactured from the DP brine discharge and sold off-site. In one or more embodiments, e.g., FIG. 3, DP demineralized water may be supplied for use in the thermal plant where needed in any thermal plant system (e.g., combustion turbines, if used, and/or other power systems). In one or more embodiments, e.g., FIG. 3, DP desalinated water (with minerals added back) may be supplied for use as appropriate in the thermal plant (e.g., combustion turbines and/or other power systems).

In one or more embodiments, e.g., FIG. 10 and/or FIG. 24K bottle blowing, washing, filling, and/or capping may be combined into one integrated system. Integrated systems reduce bacteriological loading (disinfection), reduce production costs, decrease line footprint, reduce bottle costs, and increase line efficiency. A bottle to bottle recycling facility may be included in the Plan to allow for direct use of recycled PET and/or other materials for plastic bottle manufacture. This type of facility may be coupled with the waste handling/recycling plant.

In one or more embodiments, e.g., FIG. 10 and/or FIG. 24K, plastic may be recycled from the waste receiving and processing area. The end product of the recycled plastic would be cleaned, disinfected, and/or shredded plastic material. This material may then be utilized in the bottle manufacturing process at the BBPP. Packaging materials for the BBPP and/or other modules in the Plan, such as the refinery may also come from the waste handling/recycling plant described herein, including possibly plastic, cardboard, and/or wood pallets. Bottle to bottle recycling facility may be included in the Plan to allow for direct use of recycled PET and/or other materials for plastic bottle manufacture. This type of facility may be coupled with the waste handling/recycling plant. The end product of the recycled plastic would be cleaned, disinfected, and/or shredded plastic material. This material may then be utilized in the bottle manufacturing process at the BBPP. Packaging materials for the BBPP may also come from the waste handling/recycling plant described herein, comprising possibly plastic, glass, cardboard, wood pallets and/or other recycled materials. Waste heat from the thermal plant and/or heat recovered from other sources in the Plan (e.g., FIG. 2) may be used to generate cooling, such as air conditioning and/or refrigeration for cooling buildings and/or for refrigeration of biomass products, for cooling the BGM where beneficial, and/or for other uses.

With reference to FIG. 25, design 2500, in an embodiment oxygen source(s) in the Plan may be supplied to modules and/or technologies using, storing, transporting, and/or processing oxygen. For example, WWTP/BGM 402 optionally comprises any of the following: WWTP 402A; autotrophic BGU 402B; mixotrophic BGU 402C; heterotrophic BGU 402D. In an embodiment, thermal plant 222 optionally comprises oxy-fuel processes 2508 (e.g. to reduce NOx emissions) and/or other processes using oxygen 2510, such as those generating fuels of various kinds (e.g., cellulosic ethanol/butanol/isobutanol) which may require or benefit from oxygen (e.g., oxygen concentrations higher than air, or replenishment of oxygen where it may be being depleted by a process). The following modules or technologies optionally present in any embodiment may generate and/or supply oxygen, and/or may release it after performing functions for reuse in the grid: autotrophic BGU 402B; mixotrophic BGU 402C; module(s) for oxygen distribution for use, reuse, storage, purification and/or other processing in any manner known to those in the art 2504, and/or offsite oxygen sources 2502. Any one or more of these sources of oxygen may provide oxygen optionally to modules requiring oxygen or which may be benefitted by oxygen, optionally comprising any of the following: refinery and/or BPP 202; WWTP 402A, sludge processing 404, mixotrophic BGU(s) 402C, heterotrophic BGU(s), BBPP 206; Thermal plant 222, modules for oxygen distribution for use, reuse, storage, purification and/or other processing in any manner known to those in the art 2504, and/or for export and/or discharge 2506.

With reference to FIG. 25, in an embodiment, the use of oxygen in the Refinery and/or BPP may comprise any processes where oxygen may be needed or may be beneficial to processing biomass (e.g., bacterial processing of biomass into fuels and/or other products, other separation and/or refining techniques). Mixotrophic BGUs may both use and emit oxygen. Oxygen may be used in Thermal Plant oxy-fuel processes wherein oxygen may be injected into the intake for combustion processes of any kind, increasing the oxygen content of the gases used for combustion, and decreasing nitrogen content. The resulting combustion discharge gases may be lower in NOx emissions. In an embodiment, autotrophic and/or mixotrophic BGUs provide an oxygen stream for use in thermal plant oxy-fuel processes.

With reference to FIG. 25 an embodiment of the disclosure includes a system 2500 for power generation and fuel production, configured to use and reclaim oxygen wherein the oxygen is provided to the system by: an autotrophic BGU(s) 402B configured to generate oxygen; a mixotrophic BGU(s) 402C configured to generate oxygen; an offsite oxygen source(s) 2502; and/or a module(s) for oxygen use, reuse, distribution, purification, and/or processing 2504. An embodiment includes the system wherein oxygen is provided to: a refinery module 202; a BPP module 202; a traditional WWTP module 420A; a mixotrophic BGU(s) 402C; a heterotrophic BGU(s) 402D; a BBPP module 206; a sludge processing module 404; a thermal plant module 222; a module(s) for oxygen use, reuse, distribution, purification, and/or processing 2504; and/or a module(s) for oxygen export and/or discharge 2506. An embodiment includes the system wherein oxygen is provided by an autotrophic BGU(s) 402B configured to generate oxygen. An embodiment includes the system wherein oxygen is provided by a mixotrophic BGU(s) 402C configured to generate oxygen. An embodiment includes the system wherein oxygen is supplied to one or more thermal plant oxy-fuel process module(s) 2508, 2510. An embodiment includes the system wherein oxygen is supplied to a mixotrophic BGU(s) 402C. An embodiment includes the system wherein oxygen is supplied to a heterotrophic BGU(s) 402D.

In reference to FIG. 25 an embodiment of the disclosure includes a method for using and reclaiming oxygen wherein the oxygen is provided by: an autotrophic BGU(s) 402B; a mixotrophic BGU(s) 402C; an offsite oxygen source(s) 2502; and/or a module(s) for oxygen use, reuse, distribution, purification, and/or processing 2504, the method comprising capturing oxygen from: an autotrophic BGU(s) 402B; a mixotrophic BGU(s) 402C; an offsite oxygen source(s) 2502; and/or a module(s) for oxygen use, reuse, distribution, purification, and/or processing 2504 and providing the oxygen to another module. An embodiment includes the method wherein oxygen is provided to: a refinery module 202; a BPP module 202; a traditional WWTP module 420A; a mixotrophic BGU(s) 402C; a heterotrophic BGU(s) 402D; a BBPP module 206; a sludge processing module 404; a thermal plant module 222; a module(s) for oxygen use, reuse, distribution, purification, and/or processing 2504; and/or a module(s) for oxygen export and/or discharge 2506. An embodiment includes the method wherein oxygen is provided by an autotrophic BGU(s) 402B. An embodiment includes the method wherein oxygen is provided by a mixotrophic BGU(s) 402C. An embodiment includes the method wherein oxygen is supplied to one or more thermal plant oxy-fuel process module(s) 2508, 2510, optionally comprising oxy-fuel combustion and/or other means known to the art to increase the ratio of oxygen to other gases in combustion processes. An embodiment includes the method wherein oxygen is supplied to a mixotrophic BGU(s) 402C. An embodiment includes the method wherein oxygen is supplied to a heterotrophic BGU(s) 402D.

In one or more embodiments, e.g., FIG. 25, oxygen and/or other gases released from a BGU may be collected and/or stored and/or rerouted for use in heterotrophic biomass growth processes, in a WWTP, in other processes beneficial to the Plan, and/or may be marketed.

In one or more embodiments, e.g., FIG. 25, oxygen produced in the BGM and/or produced and/or reclaimed from other sources as in FIG. 25 may be injected in whole or in part to comprise in whole or in part the gaseous inflow of any thermal plant combustion technology in any means known to those in the art as a means: to reduce the formation of NOx in thermal plant emissions; to reduce fuel consumption (e.g., by reducing the amount of nitrogen in the air that is both heated and converted into NOx emissions); to reduce the volume of exhaust gas produced in combustion; to reduce heat loss in the exhaust gas; to produce a higher proportion of CO2 in exhaust; to concentrate pollutants in a smaller volume of exhaust gas to allow for easier separation from the exhaust gases; to make the exhaust gases more condensable to allow for compression separation; to recapture heat of condensation; and/or to provide other potential benefits in combustion processes.

In one or more embodiments, e.g., FIG. 25, injection of oxygen may comprise oxy-fuel processes, optionally comprising oxy-fuel combustion, and/or other processes involving partial or total replacement of inflow gas with oxygen, and/or injection of oxygen as only a part of thermal plant inlet gas content. For example, oxygen that is substantially pure, or gases which comprise 30 to 80% oxygen, or 40-85% oxygen, or 50-90% oxygen, or 60-95% oxygen may be collected from one or more BGU growing subunit(s) and/or other BGU subunits and/or other modules and/or offsite sources and supplied to one or more thermal plant combustion process at a rate of 10% to 50% of the gases consumed, or 25% to 100%, or 30% to 80%, or 50% to 90%, or 35% to 95%, with the rest of the gases used in combustion comprising another gas or mixture of gases, e.g. air. In one or more embodiments, oxygen may be injected in variable amounts and/or proportions to other thermal plant inflow gas source(s) at different times based on any operating parameter(s) in the thermal plant, and/or Plan operational goals and/or limits (e.g., combustion rates, inflow air requirements, emissions requirements, amount of oxygen available, and/or other considerations). Sensors throughout the Plan, comprising those which measure operational parameters (e.g., combustion rate(s) in the thermal plant, gas flow rate(s), oxygen production rate in the BGM, temperatures, emissions, and/or other parameters) may be used to send signals to an automated system which may adjust the flow of oxygen, air and/or fuel injected into thermal plant gas inflows and/or other operational characteristics of the Plan, comprising thermal plant operations.

FIG. 28 depicts a high-level view 2800 of many aspects of the disclosed Plan, design, and/or system (or "the Plan") in an embodiment, with many optional features depicted. In various embodiments, the Plan of the disclosure may offer a flexible platform for local resource optimization (e.g., use of water, fuels, waste, heat, gases, etc.) by the integration of different modules, units, subunits, technologies and/or components and connections, interactions and/or communications e.g., between them, which may be selected as described herein to implement embodiments of the Plan of the present disclosure effectively in various embodiments (e.g., based on climate, environmental issues, waste streams, water availability, existing infrastructure which may be incorporated into embodiments of the Plan, etc.). As such, the disclosed Plan may describe many features which may be optional in some embodiments. Other figures disclosed herein illustrate many features in greater detail, such as optional connections and/or communications depicted between modules, technologies and/or other features, which are depicted by lines and arrows between features of the Plan in FIG. 28. With reference to FIG. 28, in an embodiment, the Plan comprises optionally:

A thermal plant module 108 optionally comprising one or more technologies which may generate carbon dioxide and/or heat, systems which generate fuels or fuel precursors, and/or systems which may communicate with, connect to, and/or otherwise support thermal plant technologies or systems, comprising one or more of: power plant technologies; waste-to-energy technologies; such as an incinerator; other direct combustion systems 108; a plasma gasification unit 1020; an HTP unit 1010; a pyrolysis unit 1009; and a cellulosic ethanol/cellulosic butanol/cellulosic isobutanol unit (cellulosic ethanol/IsoB) 1012, a desorber/condenser unit 1016, and/or other fuel-producing technologies unit(s) 1018; a rotary kiln incinerator unit 226, and/or other technologies fitting the definition of a thermal plant. The systems, technologies and/or other features of a thermal plant may share infrastructure as described herein (e.g., FIGS. 24B, 24C, 24E, 24H, 24I, 24J).

The thermal plant module 108 may comprise inputs of one or more of the following from other modules, units, subunits, technologies and/or features of the Plan as depicted: water 160, 314 of one or more water types (e.g., FIG. 3); biogas 127, 132; other biofuels comprising: biocrude, ethanol, refined biofuels, biogas, biomass, and/or hydrogen 132, 1058, 1060; a biomass/water slurry and/or biofuel/water slurry 130; combustible fuels (e.g., from other thermal plant fuel-generating technologies) 1006; treated wastewater (e.g. FIG. 3); waste oil 1032; waste (for fuel) 1030; offsite fuels 1064; hazardous waste 1026; and air optionally from an odor control system (e.g., FIG. 13). The thermal plant may comprise outputs of the following to the Plan: Power 2082 (e.g., electricity), Heat 134 for use in the Plan (e.g., FIG. 2); biofuels 1062; carbon dioxide for use in the Plan (e.g., FIG. 4); wastewater for use in the Plan (e.g., FIG. 2); and/or Ash for cement production (e.g., FIG. 24K).

A WWTP module and/or BGM 110, 212, may comprise one or more of: a traditional WWTP 402A, a wastewater BGU 402B, a freshwater BGU 402C, a saltwater BGU 402D, and/or a brackish water BGU 402E. Other BGU types may be present, being comprised by those given, such as a brine water BGU, and/or a mixed fresh water BGU. These modules may share water sources and/or may mix different water sources (e.g., FIG. 3), the WWTP module and BGM or any BGU comprised by the BGM when present in certain embodiments, may exchange carbon dioxide and oxygen e.g., FIG. 4, FIG. 25 and/or may share some infrastructure among the different modules e.g., FIG. 24B, 24D, 24F, 24G.

The WWTP module and/or BGM 110, 212 may comprise one or more inputs from the Plan of: heat and/or cooling, e.g., FIG. 2; carbon dioxide 412; water optionally comprising: wastewater, salt water, brine water, and/or fresh water (non-wastewater) e.g., FIG. 3, 302. The WWTP/BGM 110, 212 may comprise outputs to the Plan selected from one or more of: a biomass/water slurry or biofuel/water slurry 130; a water discharge e.g., FIG. 3; treated wastewater e.g., FIG. 3, and/or a sludge 128.

A sludge processing module 126, 131 optionally comprises a gasification module 125 which optionally comprises: a CHG unit; an anaerobic digestion unit; and/or other technologies to process sludge 128. The sludge processing plant may comprise an input from the Plan of sludge 128, and may comprise optional outputs to the Plan of fuel (e.g., biogas) 127, soil amendments and/or fertilizer e.g., FIG. 24L. Other functions of the gasification module are herein disclosed.

A refinery module 202 and/or BPP module 202 may comprise: an HTP module 202A; an anaerobic digestion module 202B, a supercritical fluids extraction module 202C; and/or other processes to separate, refine, process, alter, mix, prepare, and otherwise process materials (e.g., systems and/or methods herein disclosed and/or known to the person of skill in the art to process e.g., biomass, portions of biomass, biogas, biofuels, biocrude, petro fuels, hydrogen, water, solvents, other fluids, and/or residuals, etc.) 202D.

The refinery and/or BPP may comprise inputs from the Plan of: a biomass/water slurry and/or biofuel/water slurry 130; biomass products, biocrude, ethanol, biogas and/or other biofuels 132; biofuels 1062, and/or sludge 128. The refinery and/or BPP may comprise outputs to the Plan of: biomass and/or fuel 1046, biomass products, biocrude, ethanol, biogas and/or other biofuels 132; water e.g., wastewater, FIG. 3.

An optional desalination module 145 may optionally comprise: filtration-based technologies and/or distillation-based technologies, and/or other technologies capable of performing desalination, comprising optionally BGUs which may produce fresh water from salt water 402D. The desalination module may also comprise energy recovery/pressure recovery for use in the Plan e.g., FIG. 23.

The desalination module 145 may comprise inputs from the Plan of: salt water e.g., FIG. 3; heat e.g., FIG. 2; and/or carbon dioxide e.g., FIG. 4. The desalination module may comprise outputs to the Plan of: water (e.g., drinking water) e.g., FIG. 3; brine water e.g., FIG. 3, bleach e.g., FIG. 24K, Sea Salt e.g., FIG. 24K, and/or wastewater e.g., FIG. 2.

The desalination module 145 may comprise a brine discharge outfall e.g., FIG. 2, FIG. 24A, which may share some infrastructure with the WWTP/BGM 110, 212 and/or thermal plant module 108. The brine discharge module may receive inputs from the Plan of brine water e.g., FIG. 3, and/or other water types (e.g., those of lower salinity) e.g., FIG. 3.

A solar thermal module 230 may provide an input or output of heat to the Plan (e.g., FIG. 2).

An optional BBPP module which may comprise processing, preserving, bottling, packaging and/or storage of materials (e.g., processing and/or bottling water, liquid biomass products, and/or other liquids comprising fuels, packaging gases, and/or processing and/or packaging solid biomass products) 144.

The BBPP may comprise inputs to the Plan of: water e.g., FIG. 3; biomass and/or fuel 1046; and/or recycled products e.g., FIG. 24K. The BBPP may comprise outputs to the Plan of: biomass, fuel (e.g., biofuel), and/or products (e.g., biomass and/or biomass-derived products) 1044; and/or wastewater e.g., FIG. 3.

An optional recycling/waste receiving module comprises facilities to receive, sort, recycle and/or otherwise process waste (e.g., municipal sanitary waste, hazardous waste, construction and/or demolition waste) 206. The recycling/waste receiving module 206 optionally provides outputs to the Plan of: recycled products (e.g., FIG. 24K); waste for fuel 1030; hazardous waste 1026; wastewater (e.g., FIG. 3), and air optionally to an odor reduction system (e.g., FIG. 13).

Modules are provided for the export of products generated and/or packaged in the Plan 1044, optionally comprising: bottled water (e.g., FIG. 3); biomass products, biocrude, ethanol, biogas and/or other biofuels 1044, 132, 1058, 1060; bleach (e.g., FIG. 24K), and/or sea salt (e.g., FIG. 24K).

Modules for irrigation, firefighting, fountains and/or lakes 307 may be comprised by the Plan, and may receive input(s) from the Plan of water (e.g., treated wastewater, e.g., FIG. 2).

Optional connections and/or communications e.g., between particular modules, units, subunits, technologies, components and/or features are depicted by lines and arrows between them on FIG. 28 and are labeled with other figure numbers and/or feature reference numbers in the Plan, and are further illustrated in other figures of the disclosure and described herein. Other modules, units, subunits, technologies, components and features and connections and/or communications not depicted in FIG. 28 may be disclosed in other figures, and/or description of the present disclosure (e.g., the Plan).

In the Figures, like reference numerals refer to like parts throughout the various views unless otherwise indicated. For reference numerals with letter character designations such as "102A" or "102B", the letter character designations may differentiate two like parts or elements present in the same Figure. Letter character designations for reference numerals may be omitted when it may be intended that a reference numeral to encompass all parts having the same reference numeral in all Figures. FIG. 6 and/or U.S. Provisional Application No. 62/173,905, filed Jun. 10, 2015, Appendix 2 show some possible processing steps that may be used in the growth and downstream processing of biomass. FIGS. 2A-2E from Appendix 2 show various process variations for generation of useful products and based respectively on autotrophic, heterotrophic, or mixotrophic cultivation. These and/or other downstream processing methods may be used to process biomass. FIG. 6 shows an example BGU with a biomass growth subunit and several possible supporting subunits. Any or all of these subunits may be used to comprise a BGU, or other subunits or systems suited to the purpose of biomass growth. Patent US20090197322 A1, FIG. 3 from Appendix 2 shows some other examples of the major steps involved in the downstream processing of the various useful products which may be used to process biomass in the disclosed Plan. FIGS. 4 to 9 from Appendix 2 show downstream processing for extraction of useful products consistent with respective products of cultivation.

TABLE 1

| Any combination herein is optionally collocated: |
| --- |

A thermal plant module provides heat and/or cooling to and/or reclaims heat and/or cooling from a) a BGM;
A thermal plant module provides heat and/or cooling to and/or reclaims heat and/or cooling from b) a refinery module;
A thermal plant module provides heat and/or cooling to and/or reclaims heat and/or cooling from c) a BPP module;
A thermal plant module provides heat and/or cooling to and/or reclaims heat and/or cooling from d) an air conditioning/heating module;
A thermal plant module provides heat and/or cooling to and/or reclaims heat and/or cooling from e) a recycling module;
A thermal plant module provides heat and/or cooling to and/or reclaims heat and/or cooling from f) a BBPP module;
A thermal plant module provides heat and/or cooling to and/or reclaims heat and/or cooling from g) a products storage module;
A thermal plant module provides heat and/or cooling to and/or reclaims heat and/or cooling from h) a desalination module;
A thermal plant module provides heat and/or cooling to and/or reclaims heat and/or cooling from i) a waste to energy module;
A thermal plant module provides heat and/or cooling to and/or reclaims heat and/or cooling from j) a biogas storage module;
A thermal plant module provides heat and/or cooling to and/or reclaims heat and/or cooling from k) a heat/cooling storage module;
A thermal plant module provides heat and/or cooling to and/or reclaims heat and/or cooling from l) a heat/cooling recovery module;
A thermal plant module provides heat and/or cooling to and/or reclaims heat and/or cooling from m) heating/cooling for use outside of the Plan;
A thermal plant module provides heat and/or cooling to and/or reclaims heat and/or cooling from n) heating/cooling for discharge; and/or
A thermal plant module provides heat and/or cooling to and/or reclaims heat and/or cooling from o) a module optionally comprised by the thermal plant module selected from:
A thermal plant module provides heat and/or cooling to and/or reclaims heat and/or cooling from o. 1) a pyrolysis processes module;
A thermal plant module provides heat and/or cooling to and/or reclaims heat and/or cooling from o. 2) a hydrothermal processing module;
A thermal plant module provides heat and/or cooling to and/or reclaims heat and/or cooling from o. 3) a cellulosic ethanol/butanol/isobutanol module; and/or
A thermal plant module provides heat and/or cooling to and/or reclaims heat and/or cooling from o. 4) a desorber/condenser module.
A BGM provides heat and/or cooling to and/or reclaims heat and/or cooling from a) a BGM;
A BGM provides heat and/or cooling to and/or reclaims heat and/or cooling from b) a refinery module;
A BGM provides heat and/or cooling to and/or reclaims heat and/or cooling from c) a BPP module;
A BGM provides heat and/or cooling to and/or reclaims heat and/or cooling from d) an air conditioning/heating module;
A BGM provides heat and/or cooling to and/or reclaims heat and/or cooling from e) a recycling module;
A BGM provides heat and/or cooling to and/or reclaims heat and/or cooling from f) a BBPP module;
A BGM provides heat and/or cooling to and/or reclaims heat and/or cooling from g) a products storage module;
A BGM provides heat and/or cooling to and/or reclaims heat and/or cooling from h) a desalination module;
A BGM provides heat and/or cooling to and/or reclaims heat and/or cooling from i) a waste to energy module;
A BGM provides heat and/or cooling to and/or reclaims heat and/or cooling from j) a biogas storage module;
A BGM provides heat and/or cooling to and/or reclaims heat and/or cooling from k) a heat/cooling storage module;
A BGM provides heat and/or cooling to and/or reclaims heat and/or cooling from l) a heat/cooling recovery module;
A BGM provides heat and/or cooling to and/or reclaims heat and/or cooling from m) heating/cooling for use outside of the Plan;
A BGM provides heat and/or cooling to and/or reclaims heat and/or cooling from n) heating/cooling for discharge; and/or
A BGM provides heat and/or cooling to and/or reclaims heat and/or cooling from o) a module optionally comprised by the thermal plant module selected from:
A BGM provides heat and/or cooling to and/or reclaims heat and/or cooling from o. 1) a pyrolysis processes module;
A BGM provides heat and/or cooling to and/or reclaims heat and/or cooling from o. 2) a hydrothermal processing module;
A BGM provides heat and/or cooling to and/or reclaims heat and/or cooling from o. 3) a cellulosic ethanol/butanol/isobutanol module; and/or
A BGM provides heat and/or cooling to and/or reclaims heat and/or cooling from o. 4) a desorber/condenser module.

TABLE 1-continued

| Any combination herein is optionally collocated: |
|---|

A refinery module provides heat and/or cooling to and/or reclaims heat and/or cooling from a) a BGM;
A refinery module provides heat and/or cooling to and/or reclaims heat and/or cooling from b) a refinery module;
A refinery module provides heat and/or cooling to and/or reclaims heat and/or cooling from c) a BPP module;
A refinery module provides heat and/or cooling to and/or reclaims heat and/or cooling from d) an air conditioning/heating module;
A refinery module provides heat and/or cooling to and/or reclaims heat and/or cooling from e) a recycling module;
A refinery module provides heat and/or cooling to and/or reclaims heat and/or cooling from f) a BBPP module;
A refinery module provides heat and/or cooling to and/or reclaims heat and/or cooling from g) a products storage module;
A refinery module provides heat and/or cooling to and/or reclaims heat and/or cooling from h) a desalination module;
A refinery module provides heat and/or cooling to and/or reclaims heat and/or cooling from i) a waste to energy module;
A refinery module provides heat and/or cooling to and/or reclaims heat and/or cooling from j) a biogas storage module;
A refinery module provides heat and/or cooling to and/or reclaims heat and/or cooling from k) a heat/cooling storage module;
A refinery module provides heat and/or cooling to and/or reclaims heat and/or cooling from l) a heat/cooling recovery module;
A refinery module provides heat and/or cooling to and/or reclaims heat and/or cooling from m) heating/cooling for use outside of the Plan;
A refinery module provides heat and/or cooling to and/or reclaims heat and/or cooling from n) heating/cooling for discharge; and/or
A refinery module provides heat and/or cooling to and/or reclaims heat and/or cooling from o) a module optionally comprised by the thermal plant module selected from:
A refinery module provides heat and/or cooling to and/or reclaims heat and/or cooling from o. 1) a pyrolysis processes module;
A refinery module provides heat and/or cooling to and/or reclaims heat and/or cooling from o. 2) a hydrothermal processing module;
A refinery module provides heat and/or cooling to and/or reclaims heat and/or cooling from o. 3) a cellulosic ethanol/butanol/isobutanol module; and/or
A refinery module provides heat and/or cooling to and/or reclaims heat and/or cooling from o. 4) a desorber/condenser module.
A BPP module provides heat and/or cooling to and/or reclaims heat and/or cooling from a) a BGM;
A BPP module provides heat and/or cooling to and/or reclaims heat and/or cooling from b) a refinery module;
A BPP module provides heat and/or cooling to and/or reclaims heat and/or cooling from c) a BPP module;
A BPP module provides heat and/or cooling to and/or reclaims heat and/or cooling from d) an air conditioning/heating module;
A BPP module provides heat and/or cooling to and/or reclaims heat and/or cooling from e) a recycling module;
A BPP module provides heat and/or cooling to and/or reclaims heat and/or cooling from f) a BBPP module;
A BPP module provides heat and/or cooling to and/or reclaims heat and/or cooling from g) a products storage module;
A BPP module provides heat and/or cooling to and/or reclaims heat and/or cooling from h) a desalination module;
A BPP module provides heat and/or cooling to and/or reclaims heat and/or cooling from i) a waste to energy module;
A BPP module provides heat and/or cooling to and/or reclaims heat and/or cooling from j) a biogas storage module;
A BPP module provides heat and/or cooling to and/or reclaims heat and/or cooling from k) a heat/cooling storage module;
A BPP module provides heat and/or cooling to and/or reclaims heat and/or cooling from l) a heat/cooling recovery module;
A BPP module provides heat and/or cooling to and/or reclaims heat and/or cooling from m) heating/cooling for use outside of the Plan;
A BPP module provides heat and/or cooling to and/or reclaims heat and/or cooling from n) heating/cooling for discharge; and/or
A BPP module provides heat and/or cooling to and/or reclaims heat and/or cooling from o) a module optionally comprised by the thermal plant module selected from:
A BPP module provides heat and/or cooling to and/or reclaims heat and/or cooling from o. 1) a pyrolysis processes module;
A BPP module provides heat and/or cooling to and/or reclaims heat and/or cooling from o. 2) a hydrothermal processing module;
A BPP module provides heat and/or cooling to and/or reclaims heat and/or cooling from o. 3) a cellulosic ethanol/butanol/isobutanol module; and/or
A BPP module provides heat and/or cooling to and/or reclaims heat and/or cooling from o. 4) a desorber/condenser module.
An air conditioning/heating module provides heat and/or cooling to and/or reclaims heat and/or cooling from a) a BGM;

TABLE 1-continued

| Any combination herein is optionally collocated: |
| --- |

An air conditioning/heating module provides heat and/or cooling to and/or reclaims heat and/or cooling from b) a refinery module;
An air conditioning/heating module provides heat and/or cooling to and/or reclaims heat and/or cooling from c) a BPP module;
An air conditioning/heating module provides heat and/or cooling to and/or reclaims heat and/or cooling from d) an air conditioning/heating module;
An air conditioning/heating module provides heat and/or cooling to and/or reclaims heat and/or cooling from e) a recycling module;
An air conditioning/heating module provides heat and/or cooling to and/or reclaims heat and/or cooling from f) a BBPP module;
An air conditioning/heating module provides heat and/or cooling to and/or reclaims heat and/or cooling from g) a products storage module;
An air conditioning/heating module provides heat and/or cooling to and/or reclaims heat and/or cooling from h) a desalination module;
An air conditioning/heating module provides heat and/or cooling to and/or reclaims heat and/or cooling from i) a waste to energy module;
An air conditioning/heating module provides heat and/or cooling to and/or reclaims heat and/or cooling from j) a biogas storage module;
An air conditioning/heating module provides heat and/or cooling to and/or reclaims heat and/or cooling from k) a heat/cooling storage module;
An air conditioning/heating module provides heat and/or cooling to and/or reclaims heat and/or cooling from l) a heat/cooling recovery module;
An air conditioning/heating module provides heat and/or cooling to and/or reclaims heat and/or cooling from m) heating/cooling for use outside of the Plan;
An air conditioning/heating module provides heat and/or cooling to and/or reclaims heat and/or cooling from n) heating/cooling for discharge; and/or
An air conditioning/heating module provides heat and/or cooling to and/or reclaims heat and/or cooling from o) a module optionally comprised by the thermal plant module selected from:
An air conditioning/heating module provides heat and/or cooling to and/or reclaims heat and/or cooling from o. 1) a pyrolysis processes module;
An air conditioning/heating module provides heat and/or cooling to and/or reclaims heat and/or cooling from o. 2) a hydrothermal processing module;
An air conditioning/heating module provides heat and/or cooling to and/or reclaims heat and/or cooling from o. 3) a cellulosic ethanol/butanol/isobutanol module; and/or
An air conditioning/heating module provides heat and/or cooling to and/or reclaims heat and/or cooling from o. 4) a desorber/condenser module.
A recycling module provides heat and/or cooling to and/or reclaims heat and/or cooling from a) a BGM;
A recycling module provides heat and/or cooling to and/or reclaims heat and/or cooling from b) a refinery module;
A recycling module provides heat and/or cooling to and/or reclaims heat and/or cooling from c) a BPP module;
A recycling module provides heat and/or cooling to and/or reclaims heat and/or cooling from d) an air conditioning/heating module;
A recycling module provides heat and/or cooling to and/or reclaims heat and/or cooling from e) a recycling module;
A recycling module provides heat and/or cooling to and/or reclaims heat and/or cooling from f) a BBPP module;
A recycling module provides heat and/or cooling to and/or reclaims heat and/or cooling from g) a products storage module;
A recycling module provides heat and/or cooling to and/or reclaims heat and/or cooling from h) a desalination module;
A recycling module provides heat and/or cooling to and/or reclaims heat and/or cooling from i) a waste to energy module;
A recycling module provides heat and/or cooling to and/or reclaims heat and/or cooling from j) a biogas storage module;
A recycling module provides heat and/or cooling to and/or reclaims heat and/or cooling from k) a heat/cooling storage module;
A recycling module provides heat and/or cooling to and/or reclaims heat and/or cooling from l) a heat/cooling recovery module;
A recycling module provides heat and/or cooling to and/or reclaims heat and/or cooling from m) heating/cooling for use outside of the Plan;
A recycling module provides heat and/or cooling to and/or reclaims heat and/or cooling from n) heating/cooling for discharge; and/or
A recycling module provides heat and/or cooling to and/or reclaims heat and/or cooling from o) a module optionally comprised by the thermal plant module selected from:
A recycling module provides heat and/or cooling to and/or reclaims heat and/or cooling from o. 1) a pyrolysis processes module;
A recycling module provides heat and/or cooling to and/or reclaims heat and/or cooling from o. 2) a hydrothermal processing module;
A recycling module provides heat and/or cooling to and/or reclaims heat and/or cooling from o. 3) a cellulosic ethanol/butanol/isobutanol module; and/or
A recycling module provides heat and/or cooling to and/or reclaims heat and/or cooling from o. 4) a desorber/condenser module.
A BBPP module provides heat and/or cooling to and/or reclaims heat and/or cooling from a) a BGM;

TABLE 1-continued

Any combination herein is optionally collocated:

A BBPP module provides heat and/or cooling to and/or reclaims heat and/or cooling from b) a refinery module;
A BBPP module provides heat and/or cooling to and/or reclaims heat and/or cooling from c) a BPP module;
A BBPP module provides heat and/or cooling to and/or reclaims heat and/or cooling from d) an air conditioning/heating module;
A BBPP module provides heat and/or cooling to and/or reclaims heat and/or cooling from e) a recycling module;
A BBPP module provides heat and/or cooling to and/or reclaims heat and/or cooling from f) a BBPP module;
A BBPP module provides heat and/or cooling to and/or reclaims heat and/or cooling from g) a products storage module;
A BBPP module provides heat and/or cooling to and/or reclaims heat and/or cooling from h) a desalination module;
A BBPP module provides heat and/or cooling to and/or reclaims heat and/or cooling from i) a waste to energy module;
A BBPP module provides heat and/or cooling to and/or reclaims heat and/or cooling from j) a biogas storage module;
A BBPP module provides heat and/or cooling to and/or reclaims heat and/or cooling from k) a heat/cooling storage module;
A BBPP module provides heat and/or cooling to and/or reclaims heat and/or cooling from l) a heat/cooling recovery module;
A BBPP module provides heat and/or cooling to and/or reclaims heat and/or cooling from m) heating/cooling for use outside of the Plan;
A BBPP module provides heat and/or cooling to and/or reclaims heat and/or cooling from n) heating/cooling for discharge; and/or
A BBPP module provides heat and/or cooling to and/or reclaims heat and/or cooling from o) a module optionally comprised by the thermal plant module selected from:
A BBPP module provides heat and/or cooling to and/or reclaims heat and/or cooling from o. 1) a pyrolysis processes module;
A BBPP module provides heat and/or cooling to and/or reclaims heat and/or cooling from o. 2) a hydrothermal processing module;
A BBPP module provides heat and/or cooling to and/or reclaims heat and/or cooling from o. 3) a cellulosic ethanol/butanol/isobutanol module; and/or
A BBPP module provides heat and/or cooling to and/or reclaims heat and/or cooling from o. 4) a desorber/condenser module.
A products storage module provides heat and/or cooling to and/or reclaims heat and/or cooling from a) a BGM;
A products storage module provides heat and/or cooling to and/or reclaims heat and/or cooling from b) a refinery module;
A products storage module provides heat and/or cooling to and/or reclaims heat and/or cooling from c) a BPP module;
A products storage module provides heat and/or cooling to and/or reclaims heat and/or cooling from d) an air conditioning/heating module;
A products storage module provides heat and/or cooling to and/or reclaims heat and/or cooling from e) a recycling module;
A products storage module provides heat and/or cooling to and/or reclaims heat and/or cooling from f) a BBPP module;
A products storage module provides heat and/or cooling to and/or reclaims heat and/or cooling from g) a products storage module;
A products storage module provides heat and/or cooling to and/or reclaims heat and/or cooling from h) a desalination module;
A products storage module provides heat and/or cooling to and/or reclaims heat and/or cooling from i) a waste to energy module;
A products storage module provides heat and/or cooling to and/or reclaims heat and/or cooling from j) a biogas storage module;
A products storage module provides heat and/or cooling to and/or reclaims heat and/or cooling from k) a heat/cooling storage module;
A products storage module provides heat and/or cooling to and/or reclaims heat and/or cooling from l) a heat/cooling recovery module;
A products storage module provides heat and/or cooling to and/or reclaims heat and/or cooling from m) heating/cooling for use outside of the Plan;
A products storage module provides heat and/or cooling to and/or reclaims heat and/or cooling from n) heating/cooling for discharge; and/or
A products storage module provides heat and/or cooling to and/or reclaims heat and/or cooling from o) a module optionally comprised by the thermal plant module selected from:
A products storage module provides heat and/or cooling to and/or reclaims heat and/or cooling from o. 1) a pyrolysis processes module;
A products storage module provides heat and/or cooling to and/or reclaims heat and/or cooling from o. 2) a hydrothermal processing module;
A products storage module provides heat and/or cooling to and/or reclaims heat and/or cooling from o. 3) a cellulosic ethanol/butanol/isobutanol module; and/or
A products storage module provides heat and/or cooling to and/or reclaims heat and/or cooling from o. 4) a desorber/condenser module.
A desalination module provides heat and/or cooling to and/or reclaims heat and/or cooling from a) a BGM;

TABLE 1-continued

| Any combination herein is optionally collocated: |
|---|

A desalination module provides heat and/or cooling to and/or reclaims heat and/or cooling from b) a refinery module;
A desalination module provides heat and/or cooling to and/or reclaims heat and/or cooling from c) a BPP module;
A desalination module provides heat and/or cooling to and/or reclaims heat and/or cooling from d) an air conditioning/heating module;
A desalination module provides heat and/or cooling to and/or reclaims heat and/or cooling from e) a recycling module;
A desalination module provides heat and/or cooling to and/or reclaims heat and/or cooling from f) a BBPP module;
A desalination module provides heat and/or cooling to and/or reclaims heat and/or cooling from g) a products storage module;
A desalination module provides heat and/or cooling to and/or reclaims heat and/or cooling from h) a desalination module;
A desalination module provides heat and/or cooling to and/or reclaims heat and/or cooling from i) a waste to energy module;
A desalination module provides heat and/or cooling to and/or reclaims heat and/or cooling from j) a biogas storage module;
A desalination module provides heat and/or cooling to and/or reclaims heat and/or cooling from k) a heat/cooling storage module;
A desalination module provides heat and/or cooling to and/or reclaims heat and/or cooling from l) a heat/cooling recovery module;
A desalination module provides heat and/or cooling to and/or reclaims heat and/or cooling from m) heating/cooling for use outside of the Plan;
A desalination module provides heat and/or cooling to and/or reclaims heat and/or cooling from n) heating/cooling for discharge; and/or
A desalination module provides heat and/or cooling to and/or reclaims heat and/or cooling from o) a module optionally comprised by the thermal plant module selected from:
A desalination module provides heat and/or cooling to and/or reclaims heat and/or cooling from o. 1) a pyrolysis processes module;
A desalination module provides heat and/or cooling to and/or reclaims heat and/or cooling from o. 2) a hydrothermal processing module;
A desalination module provides heat and/or cooling to and/or reclaims heat and/or cooling from o. 3) a cellulosic ethanol/butanol/isobutanol module; and/or
A desalination module provides heat and/or cooling to and/or reclaims heat and/or cooling from o. 4) a desorber/condenser module.
A waste to energy module provides heat and/or cooling to and/or reclaims heat and/or cooling from a) a BGM;
A waste to energy module provides heat and/or cooling to and/or reclaims heat and/or cooling from b) a refinery module;
A waste to energy module provides heat and/or cooling to and/or reclaims heat and/or cooling from c) a BPP module;
A waste to energy module provides heat and/or cooling to and/or reclaims heat and/or cooling from d) an air conditioning/heating module;
A waste to energy module provides heat and/or cooling to and/or reclaims heat and/or cooling from e) a recycling module;
A waste to energy module provides heat and/or cooling to and/or reclaims heat and/or cooling from f) a BBPP module;
A waste to energy module provides heat and/or cooling to and/or reclaims heat and/or cooling from g) a products storage module;
A waste to energy module provides heat and/or cooling to and/or reclaims heat and/or cooling from h) a desalination module;
A waste to energy module provides heat and/or cooling to and/or reclaims heat and/or cooling from i) a waste to energy module;
A waste to energy module provides heat and/or cooling to and/or reclaims heat and/or cooling from j) a biogas storage module;
A waste to energy module provides heat and/or cooling to and/or reclaims heat and/or cooling from k) a heat/cooling storage module;
A waste to energy module provides heat and/or cooling to and/or reclaims heat and/or cooling from l) a heat/cooling recovery module;
A waste to energy module provides heat and/or cooling to and/or reclaims heat and/or cooling from m) heating/cooling for use outside of the Plan;
A waste to energy module provides heat and/or cooling to and/or reclaims heat and/or cooling from n) heating/cooling for discharge; and/or
A waste to energy module provides heat and/or cooling to and/or reclaims heat and/or cooling from o) a module optionally comprised by the thermal plant module selected from:
A waste to energy module provides heat and/or cooling to and/or reclaims heat and/or cooling from o. 1) a pyrolysis processes module;
A waste to energy module provides heat and/or cooling to and/or reclaims heat and/or cooling from o. 2) a hydrothermal processing module;
A waste to energy module provides heat and/or cooling to and/or reclaims heat and/or cooling from o. 3) a cellulosic ethanol/butanol/isobutanol module; and/or
A waste to energy module provides heat and/or cooling to and/or reclaims heat and/or cooling from o. 4) a desorber/condenser module.
A biogas storage module provides heat and/or cooling to and/or reclaims heat and/or cooling from a) a BGM;

TABLE 1-continued

| Any combination herein is optionally collocated: |
| --- |

A biogas storage module provides heat and/or cooling to and/or reclaims heat and/or cooling from b) a refinery module;
A biogas storage module provides heat and/or cooling to and/or reclaims heat and/or cooling from c) a BPP module;
A biogas storage module provides heat and/or cooling to and/or reclaims heat and/or cooling from d) an air conditioning/heating module;
A biogas storage module provides heat and/or cooling to and/or reclaims heat and/or cooling from e) a recycling module;
A biogas storage module provides heat and/or cooling to and/or reclaims heat and/or cooling from f) a BBPP module;
A biogas storage module provides heat and/or cooling to and/or reclaims heat and/or cooling from g) a products storage module;
A biogas storage module provides heat and/or cooling to and/or reclaims heat and/or cooling from h) a desalination module;
A biogas storage module provides heat and/or cooling to and/or reclaims heat and/or cooling from i) a waste to energy module;
A biogas storage module provides heat and/or cooling to and/or reclaims heat and/or cooling from j) a biogas storage module;
A biogas storage module provides heat and/or cooling to and/or reclaims heat and/or cooling from k) a heat/cooling storage module;
A biogas storage module provides heat and/or cooling to and/or reclaims heat and/or cooling from l) a heat/cooling recovery module;
A biogas storage module provides heat and/or cooling to and/or reclaims heat and/or cooling from m) heating/cooling for use outside of the Plan;
A biogas storage module provides heat and/or cooling to and/or reclaims heat and/or cooling from n) heating/cooling for discharge; and/or
A biogas storage module provides heat and/or cooling to and/or reclaims heat and/or cooling from o) a module optionally comprised by the thermal plant module selected from:
A biogas storage module provides heat and/or cooling to and/or reclaims heat and/or cooling from o. 1) a pyrolysis processes module;
A biogas storage module provides heat and/or cooling to and/or reclaims heat and/or cooling from o. 2) a hydrothermal processing module;
A biogas storage module provides heat and/or cooling to and/or reclaims heat and/or cooling from o. 3) a cellulosic ethanol/butanol/isobutanol module; and/or
A biogas storage module provides heat and/or cooling to and/or reclaims heat and/or cooling from o. 4) a desorber/condenser module.
A heat/cooling storage module provides heat and/or cooling to and/or reclaims heat and/or cooling from a) a BGM;
A heat/cooling storage module provides heat and/or cooling to and/or reclaims heat and/or cooling from b) a refinery module;
A heat/cooling storage module provides heat and/or cooling to and/or reclaims heat and/or cooling from c) a BPP module;
A heat/cooling storage module provides heat and/or cooling to and/or reclaims heat and/or cooling from d) an air conditioning/heating module;
A heat/cooling storage module provides heat and/or cooling to and/or reclaims heat and/or cooling from e) a recycling module;
A heat/cooling storage module provides heat and/or cooling to and/or reclaims heat and/or cooling from f) a BBPP module;
A heat/cooling storage module provides heat and/or cooling to and/or reclaims heat and/or cooling from g) a products storage module;
A heat/cooling storage module provides heat and/or cooling to and/or reclaims heat and/or cooling from h) a desalination module;
A heat/cooling storage module provides heat and/or cooling to and/or reclaims heat and/or cooling from i) a waste to energy module;
A heat/cooling storage module provides heat and/or cooling to and/or reclaims heat and/or cooling from j) a biogas storage module;
A heat/cooling storage module provides heat and/or cooling to and/or reclaims heat and/or cooling from k) a heat/cooling storage module;
A heat/cooling storage module provides heat and/or cooling to and/or reclaims heat and/or cooling from l) a heat/cooling recovery module;
A heat/cooling storage module provides heat and/or cooling to and/or reclaims heat and/or cooling from m) heating/cooling for use outside of the Plan;
A heat/cooling storage module provides heat and/or cooling to and/or reclaims heat and/or cooling from n) heating/cooling for discharge; and/or
A heat/cooling storage module provides heat and/or cooling to and/or reclaims heat and/or cooling from o) a module optionally comprised by the thermal plant module selected from:
A heat/cooling storage module provides heat and/or cooling to and/or reclaims heat and/or cooling from o. 1) a pyrolysis processes module;
A heat/cooling storage module provides heat and/or cooling to and/or reclaims heat and/or cooling from o. 2) a hydrothermal processing module;
A heat/cooling storage module provides heat and/or cooling to and/or reclaims heat and/or cooling from o. 3) a cellulosic ethanol/butanol/isobutanol module; and/or
A heat/cooling storage module provides heat and/or cooling to and/or reclaims heat and/or cooling from o. 4) a desorber/condenser module.
A heat/cooling recovery module provides heat and/or cooling to and/or reclaims heat and/or cooling from a) a BGM;

TABLE 1-continued

Any combination herein is optionally collocated:

A heat/cooling recovery module provides heat and/or cooling to and/or reclaims heat and/or cooling from b) a refinery module;
A heat/cooling recovery module provides heat and/or cooling to and/or reclaims heat and/or cooling from c) a BPP module;
A heat/cooling recovery module provides heat and/or cooling to and/or reclaims heat and/or cooling from d) an air conditioning/heating module;
A heat/cooling recovery module provides heat and/or cooling to and/or reclaims heat and/or cooling from e) a recycling module;
A heat/cooling recovery module provides heat and/or cooling to and/or reclaims heat and/or cooling from f) a BBPP module;
A heat/cooling recovery module provides heat and/or cooling to and/or reclaims heat and/or cooling from g) a products storage module;
A heat/cooling recovery module provides heat and/or cooling to and/or reclaims heat and/or cooling from h) a desalination module;
A heat/cooling recovery module provides heat and/or cooling to and/or reclaims heat and/or cooling from i) a waste to energy module;
A heat/cooling recovery module provides heat and/or cooling to and/or reclaims heat and/or cooling from j) a biogas storage module;
A heat/cooling recovery module provides heat and/or cooling to and/or reclaims heat and/or cooling from k) a heat/cooling storage module;
A heat/cooling recovery module provides heat and/or cooling to and/or reclaims heat and/or cooling from l) a heat/cooling recovery module;
A heat/cooling recovery module provides heat and/or cooling to and/or reclaims heat and/or cooling from m) heating/cooling for use outside of the Plan;
A heat/cooling recovery module provides heat and/or cooling to and/or reclaims heat and/or cooling from n) heating/cooling for discharge; and/or
A heat/cooling recovery module provides heat and/or cooling to and/or reclaims heat and/or cooling from o) a module optionally comprised by the thermal plant module selected from:
A heat/cooling recovery module provides heat and/or cooling to and/or reclaims heat and/or cooling from o. 1) a pyrolysis processes module;
A heat/cooling recovery module provides heat and/or cooling to and/or reclaims heat and/or cooling from o. 2) a hydrothermal processing module;
A heat/cooling recovery module provides heat and/or cooling to and/or reclaims heat and/or cooling from o. 3) a cellulosic ethanol/butanol/isobutanol module; and/or
A heat/cooling recovery module provides heat and/or cooling to and/or reclaims heat and/or cooling from o. 4) a desorber/condenser module.
Heating/cooling for use outside of the Plan provides heat and/or cooling to and/or reclaims heat and/or cooling from a) a BGM;
Heating/cooling for use outside of the Plan provides heat and/or cooling to and/or reclaims heat and/or cooling from b) a refinery module;
Heating/cooling for use outside of the Plan provides heat and/or cooling to and/or reclaims heat and/or cooling from c) a BPP module;
Heating/cooling for use outside of the Plan provides heat and/or cooling to and/or reclaims heat and/or cooling from d) an air conditioning/heating module;
Heating/cooling for use outside of the Plan provides heat and/or cooling to and/or reclaims heat and/or cooling from e) a recycling module;
Heating/cooling for use outside of the Plan provides heat and/or cooling to and/or reclaims heat and/or cooling from f) a BBPP module;
Heating/cooling for use outside of the Plan provides heat and/or cooling to and/or reclaims heat and/or cooling from g) a products storage module;
Heating/cooling for use outside of the Plan provides heat and/or cooling to and/or reclaims heat and/or cooling from h) a desalination module;
Heating/cooling for use outside of the Plan provides heat and/or cooling to and/or reclaims heat and/or cooling from i) a waste to energy module;
Heating/cooling for use outside of the Plan provides heat and/or cooling to and/or reclaims heat and/or cooling from j) a biogas storage module;
Heating/cooling for use outside of the Plan provides heat and/or cooling to and/or reclaims heat and/or cooling from k) a heat/cooling storage module;
Heating/cooling for use outside of the Plan provides heat and/or cooling to and/or reclaims heat and/or cooling from l) a heat/cooling recovery module;
Heating/cooling for use outside of the Plan provides heat and/or cooling to and/or reclaims heat and/or cooling from m) heating/cooling for use outside of the Plan;
Heating/cooling for use outside of the Plan provides heat and/or cooling to and/or reclaims heat and/or cooling from n) heating/cooling for discharge; and/or
Heating/cooling for use outside of the Plan provides heat and/or cooling to and/or reclaims heat and/or cooling from o) a module optionally comprised by the thermal plant module selected from:
Heating/cooling for use outside of the Plan provides heat and/or cooling to and/or reclaims heat and/or cooling from o. 1) a pyrolysis processes module;
Heating/cooling for use outside of the Plan provides heat and/or cooling to and/or reclaims heat and/or cooling from o. 2) a hydrothermal processing module;
Heating/cooling for use outside of the Plan provides heat and/or cooling to and/or reclaims heat and/or cooling from o. 3) a cellulosic ethanol/butanol/isobutanol module; and/or
Heating/cooling for use outside of the Plan provides heat and/or cooling to and/or reclaims heat and/or cooling from o. 4) a desorber/condenser module.

TABLE 1-continued

| Any combination herein is optionally collocated: |
|---|

Heating/cooling for discharge provides heat and/or cooling to and/or reclaims heat and/or cooling from a) a BGM;
Heating/cooling for discharge provides heat and/or cooling to and/or reclaims heat and/or cooling from b) a refinery module;
Heating/cooling for discharge provides heat and/or cooling to and/or reclaims heat and/or cooling from c) a BPP module;
Heating/cooling for discharge provides heat and/or cooling to and/or reclaims heat and/or cooling from d) an air conditioning/heating module;
Heating/cooling for discharge provides heat and/or cooling to and/or reclaims heat and/or cooling from e) a recycling module;
Heating/cooling for discharge provides heat and/or cooling to and/or reclaims heat and/or cooling from f) a BBPP module;
Heating/cooling for discharge provides heat and/or cooling to and/or reclaims heat and/or cooling from g) a products storage module;
Heating/cooling for discharge provides heat and/or cooling to and/or reclaims heat and/or cooling from h) a desalination module;
Heating/cooling for discharge provides heat and/or cooling to and/or reclaims heat and/or cooling from i) a waste to energy module;
Heating/cooling for discharge provides heat and/or cooling to and/or reclaims heat and/or cooling from j) a biogas storage module;
Heating/cooling for discharge provides heat and/or cooling to and/or reclaims heat and/or cooling from k) a heat/cooling storage module;
Heating/cooling for discharge provides heat and/or cooling to and/or reclaims heat and/or cooling from l) a heat/cooling recovery module;
Heating/cooling for discharge provides heat and/or cooling to and/or reclaims heat and/or cooling from m) heating/cooling for use outside of the Plan;
Heating/cooling for discharge provides heat and/or cooling to and/or reclaims heat and/or cooling from n) heating/cooling for discharge; and/or
Heating/cooling for discharge provides heat and/or cooling to and/or reclaims heat and/or cooling from o) a module optionally comprised by the thermal plant module selected from:
Heating/cooling for discharge provides heat and/or cooling to and/or reclaims heat and/or cooling from o. 1) a pyrolysis processes module;
Heating/cooling for discharge provides heat and/or cooling to and/or reclaims heat and/or cooling from o. 2) a hydrothermal processing module;
Heating/cooling for discharge provides heat and/or cooling to and/or reclaims heat and/or cooling from o. 3) a cellulosic ethanol/butanol/isobutanol module; and/or
Heating/cooling for discharge provides heat and/or cooling to and/or reclaims heat and/or cooling from o. 4) a desorber/condenser module.
A pyrolysis processes module optionally comprised by the thermal plant module provides heat and/or cooling to and/or reclaims heat and/or cooling from a) a BGM;
A pyrolysis processes module optionally comprised by the thermal plant module provides heat and/or cooling to and/or reclaims heat and/or cooling from b) a refinery module;
A pyrolysis processes module optionally comprised by the thermal plant module provides heat and/or cooling to and/or reclaims heat and/or cooling from c) a BPP module;
A pyrolysis processes module optionally comprised by the thermal plant module provides heat and/or cooling to and/or reclaims heat and/or cooling from d) an air conditioning/heating module;
A pyrolysis processes module optionally comprised by the thermal plant module provides heat and/or cooling to and/or reclaims heat and/or cooling from e) a recycling module;
A pyrolysis processes module optionally comprised by the thermal plant module provides heat and/or cooling to and/or reclaims heat and/or cooling from f) a BBPP module;
A pyrolysis processes module optionally comprised by the thermal plant module provides heat and/or cooling to and/or reclaims heat and/or cooling from g) a products storage module;
A pyrolysis processes module optionally comprised by the thermal plant module provides heat and/or cooling to and/or reclaims heat and/or cooling from h) a desalination module;
A pyrolysis processes module optionally comprised by the thermal plant module provides heat and/or cooling to and/or reclaims heat and/or cooling from i) a waste to energy module;
A pyrolysis processes module optionally comprised by the thermal plant module provides heat and/or cooling to and/or reclaims heat and/or cooling from j) a biogas storage module;
A pyrolysis processes module optionally comprised by the thermal plant module provides heat and/or cooling to and/or reclaims heat and/or cooling from k) a heat/cooling storage module;
A pyrolysis processes module optionally comprised by the thermal plant module provides heat and/or cooling to and/or reclaims heat and/or cooling from l) a heat/cooling recovery module;
A pyrolysis processes module optionally comprised by the thermal plant module provides heat and/or cooling to and/or reclaims heat and/or cooling from m) heating/cooling for use outside of the Plan;

TABLE 1-continued

Any combination herein is optionally collocated:

A pyrolysis processes module optionally comprised by the thermal plant module provides heat and/or cooling to and/or reclaims heat and/or cooling from n) heating/cooling for discharge; and/or
A pyrolysis processes module optionally comprised by the thermal plant module provides heat and/or cooling to and/or reclaims heat and/or cooling from o) a module optionally comprised by the thermal plant module selected from:
A pyrolysis processes module optionally comprised by the thermal plant module provides heat and/or cooling to and/or reclaims heat and/or cooling from o. 1) a pyrolysis processes module;
A pyrolysis processes module optionally comprised by the thermal plant module provides heat and/or cooling to and/or reclaims heat and/or cooling from o. 2) a hydrothermal processing module;
A pyrolysis processes module optionally comprised by the thermal plant module provides heat and/or cooling to and/or reclaims heat and/or cooling from o. 3) a cellulosic ethanol/butanol/isobutanol module; and/or
A pyrolysis processes module optionally comprised by the thermal plant module provides heat and/or cooling to and/or reclaims heat and/or cooling from o. 4) a desorber/condenser module.
A hydrothermal processing module optionally comprised by the thermal plant module provides heat and/or cooling to and/or reclaims heat and/or cooling from a) a BGM;
A hydrothermal processing module optionally comprised by the thermal plant module provides heat and/or cooling to and/or reclaims heat and/or cooling from b) a refinery module;
A hydrothermal processing module optionally comprised by the thermal plant module provides heat and/or cooling to and/or reclaims heat and/or cooling from c) a BPP module;
A hydrothermal processing module optionally comprised by the thermal plant module provides heat and/or cooling to and/or reclaims heat and/or cooling from d) an air conditioning/heating module;
A hydrothermal processing module optionally comprised by the thermal plant module provides heat and/or cooling to and/or reclaims heat and/or cooling from e) a recycling module;
A hydrothermal processing module optionally comprised by the thermal plant module provides heat and/or cooling to and/or reclaims heat and/or cooling from f) a BBPP module;
A hydrothermal processing module optionally comprised by the thermal plant module provides heat and/or cooling to and/or reclaims heat and/or cooling from g) a products storage module;
A hydrothermal processing module optionally comprised by the thermal plant module provides heat and/or cooling to and/or reclaims heat and/or cooling from h) a desalination module;
A hydrothermal processing module optionally comprised by the thermal plant module provides heat and/or cooling to and/or reclaims heat and/or cooling from i) a waste to energy module;
A hydrothermal processing module optionally comprised by the thermal plant module provides heat and/or cooling to and/or reclaims heat and/or cooling from j) a biogas storage module;
A hydrothermal processing module optionally comprised by the thermal plant module provides heat and/or cooling to and/or reclaims heat and/or cooling from k) a heat/cooling storage module;
A hydrothermal processing module optionally comprised by the thermal plant module provides heat and/or cooling to and/or reclaims heat and/or cooling from l) a heat/cooling recovery module;
A hydrothermal processing module optionally comprised by the thermal plant module provides heat and/or cooling to and/or reclaims heat and/or cooling from m) heating/cooling for use outside of the Plan;
A hydrothermal processing module optionally comprised by the thermal plant module provides heat and/or cooling to and/or reclaims heat and/or cooling from n) heating/cooling for discharge; and/or
A hydrothermal processing module optionally comprised by the thermal plant module provides heat and/or cooling to and/or reclaims heat and/or cooling from o) a module optionally comprised by the thermal plant module selected from:
A hydrothermal processing module optionally comprised by the thermal plant module provides heat and/or cooling to and/or reclaims heat and/or cooling from o. 1) a pyrolysis processes module;
A hydrothermal processing module optionally comprised by the thermal plant module provides heat and/or cooling to and/or reclaims heat and/or cooling from o. 2) a hydrothermal processing module;
A hydrothermal processing module optionally comprised by the thermal plant module provides heat and/or cooling to and/or reclaims heat and/or cooling from o. 3) a cellulosic ethanol/butanol/isobutanol module; and/or
A hydrothermal processing module optionally comprised by the thermal plant module provides heat and/or cooling to and/or reclaims heat and/or cooling from o. 4) a desorber/condenser module.
A cellulosic ethanol/butanol/isobutanol module optionally comprised by the thermal plant module provides heat and/or cooling to and/or reclaims heat and/or cooling from a) a BGM;

TABLE 1-continued

Any combination herein is optionally collocated:

A cellulosic ethanol/butanol/isobutanol module optionally comprised by the thermal plant module provides heat and/or cooling to and/or reclaims heat and/or cooling from b) a refinery module;
A cellulosic ethanol/butanol/isobutanol module optionally comprised by the thermal plant module provides heat and/or cooling to and/or reclaims heat and/or cooling from c) a BPP module;
A cellulosic ethanol/butanol/isobutanol module optionally comprised by the thermal plant module provides heat and/or cooling to and/or reclaims heat and/or cooling from d) an air conditioning/heating module;
A cellulosic ethanol/butanol/isobutanol module optionally comprised by the thermal plant module provides heat and/or cooling to and/or reclaims heat and/or cooling from e) a recycling module;
A cellulosic ethanol/butanol/isobutanol module optionally comprised by the thermal plant module provides heat and/or cooling to and/or reclaims heat and/or cooling from f) a BBPP module;
A cellulosic ethanol/butanol/isobutanol module optionally comprised by the thermal plant module provides heat and/or cooling to and/or reclaims heat and/or cooling from g) a products storage module;
A cellulosic ethanol/butanol/isobutanol module optionally comprised by the thermal plant module provides heat and/or cooling to and/or reclaims heat and/or cooling from h) a desalination module;
A cellulosic ethanol/butanol/isobutanol module optionally comprised by the thermal plant module provides heat and/or cooling to and/or reclaims heat and/or cooling from i) a waste to energy module;
A cellulosic ethanol/butanol/isobutanol module optionally comprised by the thermal plant module provides heat and/or cooling to and/or reclaims heat and/or cooling from j) a biogas storage module;
A cellulosic ethanol/butanol/isobutanol module optionally comprised by the thermal plant module provides heat and/or cooling to and/or reclaims heat and/or cooling from k) a heat/cooling storage module;
A cellulosic ethanol/butanol/isobutanol module optionally comprised by the thermal plant module provides heat and/or cooling to and/or reclaims heat and/or cooling from l) a heat/cooling recovery module;
A cellulosic ethanol/butanol/isobutanol module optionally comprised by the thermal plant module provides heat and/or cooling to and/or reclaims heat and/or cooling from m) heating/cooling for use outside of the Plan;
A cellulosic ethanol/butanol/isobutanol module optionally comprised by the thermal plant module provides heat and/or cooling to and/or reclaims heat and/or cooling from n) heating/cooling for discharge; and/or
A cellulosic ethanol/butanol/isobutanol module optionally comprised by the thermal plant module provides heat and/or cooling to and/or reclaims heat and/or cooling from o) a module optionally comprised by the thermal plant module selected from:
A cellulosic ethanol/butanol/isobutanol module optionally comprised by the thermal plant module provides heat and/or cooling to and/or reclaims heat and/or cooling from o. 1) a pyrolysis processes module;
A cellulosic ethanol/butanol/isobutanol module optionally comprised by the thermal plant module provides heat and/or cooling to and/or reclaims heat and/or cooling from o. 2) a hydrothermal processing module;
A cellulosic ethanol/butanol/isobutanol module optionally comprised by the thermal plant module provides heat and/or cooling to and/or reclaims heat and/or cooling from o. 3) a cellulosic ethanol/butanol/isobutanol module; and/or
A cellulosic ethanol/butanol/isobutanol module optionally comprised by the thermal plant module provides heat and/or cooling to and/or reclaims heat and/or cooling from o. 4) a desorber/condenser module.
A desorber/condenser module optionally comprised by the thermal plant module provides heat and/or cooling to and/or reclaims heat and/or cooling from a) a BGM;
A desorber/condenser module optionally comprised by the thermal plant module provides heat and/or cooling to and/or reclaims heat and/or cooling from b) a refinery module;
A desorber/condenser module optionally comprised by the thermal plant module provides heat and/or cooling to and/or reclaims heat and/or cooling from c) a BPP module;
A desorber/condenser module optionally comprised by the thermal plant module provides heat and/or cooling to and/or reclaims heat and/or cooling from d) an air conditioning/heating module;
A desorber/condenser module optionally comprised by the thermal plant module provides heat and/or cooling to and/or reclaims heat and/or cooling from e) a recycling module;
A desorber/condenser module optionally comprised by the thermal plant module provides heat and/or cooling to and/or reclaims heat and/or cooling from f) a BBPP module;
A desorber/condenser module optionally comprised by the thermal plant module provides heat and/or cooling to and/or reclaims heat and/or cooling from g) a products storage module;
A desorber/condenser module optionally comprised by the thermal plant module provides heat and/or cooling to and/or reclaims heat and/or cooling from h) a desalination module;

TABLE 1-continued

Any combination herein is optionally collocated:

A desorber/condenser module optionally comprised by the thermal plant module provides heat and/or cooling to and/or reclaims heat and/or cooling from i) a waste to energy module;
A desorber/condenser module optionally comprised by the thermal plant module provides heat and/or cooling to and/or reclaims heat and/or cooling from j) a biogas storage module;
A desorber/condenser module optionally comprised by the thermal plant module provides heat and/or cooling to and/or reclaims heat and/or cooling from k) a heat/cooling storage module;
A desorber/condenser module optionally comprised by the thermal plant module provides heat and/or cooling to and/or reclaims heat and/or cooling from l) a heat/cooling recovery module;
A desorber/condenser module optionally comprised by the thermal plant module provides heat and/or cooling to and/or reclaims heat and/or cooling from m) heating/cooling for use outside of the Plan;
A desorber/condenser module optionally comprised by the thermal plant module provides heat and/or cooling to and/or reclaims heat and/or cooling from n) heating/cooling for discharge; and/or
A desorber/condenser module optionally comprised by the thermal plant module provides heat and/or cooling to and/or reclaims heat and/or cooling from o) a module optionally comprised by the thermal plant module selected from:
A desorber/condenser module optionally comprised by the thermal plant module provides heat and/or cooling to and/or reclaims heat and/or cooling from o. 1) a pyrolysis processes module;
A desorber/condenser module optionally comprised by the thermal plant module provides heat and/or cooling to and/or reclaims heat and/or cooling from o. 2) a hydrothermal processing module;
A desorber/condenser module optionally comprised by the thermal plant module provides heat and/or cooling to and/or reclaims heat and/or cooling from o. 3) a cellulosic ethanol/butanol/isobutanol module; and/or
A desorber/condenser module optionally comprised by the thermal plant module provides heat and/or cooling to and/or reclaims heat and/or cooling from o. 4) a desorber/condenser module.

TABLE 2

Any combination herein is optionally collocated:

Water from a fresh water source is provided to, and/or reclaimed from, and/or mixed with water from a) a fresh water source;
Water from a fresh water source is provided to, and/or reclaimed from, and/or mixed with water from b) a fresh water pretreatment module;
Water from a fresh water source is provided to, and/or reclaimed from, and/or mixed with water from c) a salt water intake;
Water from a fresh water source is provided to, and/or reclaimed from, and/or mixed with water from d) a salt water pretreatment module;
Water from a fresh water source is provided to, and/or reclaimed from, and/or mixed with water from e) a preheating/cooling module;
Water from a fresh water source is provided to, and/or reclaimed from, and/or mixed with water from f) a water storage module;
Water from a fresh water source is provided to, and/or reclaimed from, and/or mixed with water from g) irrigation;
Water from a fresh water source is provided to, and/or reclaimed from, and/or mixed with water from h) firefighting;
Water from a fresh water source is provided to, and/or reclaimed from, and/or mixed with water from i) fountains;
Water from a fresh water source is provided to, and/or reclaimed from, and/or mixed with water from j) lakes;
Water from a fresh water source is provided to, and/or reclaimed from, and/or mixed with water from k) cleaning;
Water from a fresh water source is provided to, and/or reclaimed from, and/or mixed with water from l) a BGM;
Water from a fresh water source is provided to, and/or reclaimed from, and/or mixed with water from m) a traditional WWTP module;
Water from a fresh water source is provided to, and/or reclaimed from, and/or mixed with water from n) a refinery module;
Water from a fresh water source is provided to, and/or reclaimed from, and/or mixed with water from o) a BPP module;
Water from a fresh water source is provided to, and/or reclaimed from, and/or mixed with water from p) heating and/or cooling to the Plan;
Water from a fresh water source is provided to, and/or reclaimed from, and/or mixed with water from q) a recycling module;
Water from a fresh water source is provided to, and/or reclaimed from, and/or mixed with water from r) a waste receiving module;

TABLE 2-continued

Any combination herein is optionally collocated:

Water from a fresh water source is provided to, and/or reclaimed from, and/or mixed with water from s) a BBPP module;
Water from a fresh water source is provided to, and/or reclaimed from, and/or mixed with water from t) a desalination module;
Water from a fresh water source is provided to, and/or reclaimed from, and/or mixed with water from u) water for discharge/export;
Water from a fresh water source is provided to, and/or reclaimed from, and/or mixed with water from v) a processing and/or treatment module; and/or
Water from a fresh water source is provided to, and/or reclaimed from, and/or mixed with water from w) a thermal plant module.
Water from a fresh water pretreatment module is provided to, and/or reclaimed from, and/or mixed with water from a) a fresh water source;
Water from a fresh water pretreatment module is provided to, and/or reclaimed from, and/or mixed with water from b) a fresh water pretreatment module;
Water from a fresh water pretreatment module is provided to, and/or reclaimed from, and/or mixed with water from c) a salt water intake;
Water from a fresh water pretreatment module is provided to, and/or reclaimed from, and/or mixed with water from d) a salt water pretreatment module;
Water from a fresh water pretreatment module is provided to, and/or reclaimed from, and/or mixed with water from e) a preheating/cooling module;
Water from a fresh water pretreatment module is provided to, and/or reclaimed from, and/or mixed with water from f) a water storage module;
Water from a fresh water pretreatment module is provided to, and/or reclaimed from, and/or mixed with water from g) irrigation;
Water from a fresh water pretreatment module is provided to, and/or reclaimed from, and/or mixed with water from h) firefighting;
Water from a fresh water pretreatment module is provided to, and/or reclaimed from, and/or mixed with water from i) fountains;
Water from a fresh water pretreatment module is provided to, and/or reclaimed from, and/or mixed with water from j) lakes;
Water from a fresh water pretreatment module is provided to, and/or reclaimed from, and/or mixed with water from k) cleaning;
Water from a fresh water pretreatment module is provided to, and/or reclaimed from, and/or mixed with water from l) a BGM;
Water from a fresh water pretreatment module is provided to, and/or reclaimed from, and/or mixed with water from m) a traditional WWTP module;
Water from a fresh water pretreatment module is provided to, and/or reclaimed from, and/or mixed with water from n) a refinery module;
Water from a fresh water pretreatment module is provided to, and/or reclaimed from, and/or mixed with water from o) a BPP module;
Water from a fresh water pretreatment module is provided to, and/or reclaimed from, and/or mixed with water from p) heating and/or cooling to the Plan;
Water from a fresh water pretreatment module is provided to, and/or reclaimed from, and/or mixed with water from q) a recycling module;
Water from a fresh water pretreatment module is provided to, and/or reclaimed from, and/or mixed with water from r) a waste receiving module;
Water from a fresh water pretreatment module is provided to, and/or reclaimed from, and/or mixed with water from s) a BBPP module;
Water from a fresh water pretreatment module is provided to, and/or reclaimed from, and/or mixed with water from t) a desalination module;
Water from a fresh water pretreatment module is provided to, and/or reclaimed from, and/or mixed with water from u) water for discharge/export;
Water from a fresh water pretreatment module is provided to, and/or reclaimed from, and/or mixed with water from v) a processing and/or treatment module; and/or
Water from a fresh water pretreatment module is provided to, and/or reclaimed from, and/or mixed with water from w) a thermal plant module.
Water from a salt water intake is provided to, and/or reclaimed from, and/or mixed with water from a) a fresh water source;
Water from a salt water intake is provided to, and/or reclaimed from, and/or mixed with water from b) a fresh water pretreatment module;
Water from a salt water intake is provided to, and/or reclaimed from, and/or mixed with water from c) a salt water intake;
Water from a salt water intake is provided to, and/or reclaimed from, and/or mixed with water from d) a salt water pretreatment module;
Water from a salt water intake is provided to, and/or reclaimed from, and/or mixed with water from e) a preheating/cooling module;
Water from a salt water intake is provided to, and/or reclaimed from, and/or mixed with water from f) a water storage module;
Water from a salt water intake is provided to, and/or reclaimed from, and/or mixed with water from g) irrigation;
Water from a salt water intake is provided to, and/or reclaimed from, and/or mixed with water from h) firefighting;
Water from a salt water intake is provided to, and/or reclaimed from, and/or mixed with water from i) fountains;
Water from a salt water intake is provided to, and/or reclaimed from, and/or mixed with water from j) lakes;
Water from a salt water intake is provided to, and/or reclaimed from, and/or mixed with water from k) cleaning;

TABLE 2-continued

Any combination herein is optionally collocated:

Water from a salt water intake is provided to, and/or reclaimed from, and/or mixed with water from l) a BGM;
Water from a salt water intake is provided to, and/or reclaimed from, and/or mixed with water from m) a traditional WWTP module;
Water from a salt water intake is provided to, and/or reclaimed from, and/or mixed with water from n) a refinery module;
Water from a salt water intake is provided to, and/or reclaimed from, and/or mixed with water from o) a BPP module;
Water from a salt water intake is provided to, and/or reclaimed from, and/or mixed with water from p) heating and/or cooling to the Plan;
Water from a salt water intake is provided to, and/or reclaimed from, and/or mixed with water from q) a recycling module;
Water from a salt water intake is provided to, and/or reclaimed from, and/or mixed with water from r) a waste receiving module;
Water from a salt water intake is provided to, and/or reclaimed from, and/or mixed with water from s) a BBPP module;
Water from a salt water intake is provided to, and/or reclaimed from, and/or mixed with water from t) a desalination module;
Water from a salt water intake is provided to, and/or reclaimed from, and/or mixed with water from u) water for discharge/export;
Water from a salt water intake is provided to, and/or reclaimed from, and/or mixed with water from v) a processing and/or treatment module; and/or
Water from a salt water intake is provided to, and/or reclaimed from, and/or mixed with water from w) a thermal plant module.
Water from a salt water pretreatment module is provided to, and/or reclaimed from, and/or mixed with water from a) a fresh water source;
Water from a salt water pretreatment module is provided to, and/or reclaimed from, and/or mixed with water from b) a fresh water pretreatment module;
Water from a salt water pretreatment module is provided to, and/or reclaimed from, and/or mixed with water from c) a salt water intake;
Water from a salt water pretreatment module is provided to, and/or reclaimed from, and/or mixed with water from d) a salt water pretreatment module;
Water from a salt water pretreatment module is provided to, and/or reclaimed from, and/or mixed with water from e) a preheating/cooling module;
Water from a salt water pretreatment module is provided to, and/or reclaimed from, and/or mixed with water from f) a water storage module;
Water from a salt water pretreatment module is provided to, and/or reclaimed from, and/or mixed with water from g) irrigation;
Water from a salt water pretreatment module is provided to, and/or reclaimed from, and/or mixed with water from h) firefighting;
Water from a salt water pretreatment module is provided to, and/or reclaimed from, and/or mixed with water from i) fountains;
Water from a salt water pretreatment module is provided to, and/or reclaimed from, and/or mixed with water from j) lakes;
Water from a salt water pretreatment module is provided to, and/or reclaimed from, and/or mixed with water from k) cleaning;
Water from a salt water pretreatment module is provided to, and/or reclaimed from, and/or mixed with water from l) a BGM;
Water from a salt water pretreatment module is provided to, and/or reclaimed from, and/or mixed with water from m) a traditional WWTP module;
Water from a salt water pretreatment module is provided to, and/or reclaimed from, and/or mixed with water from n) a refinery module;
Water from a salt water pretreatment module is provided to, and/or reclaimed from, and/or mixed with water from o) a BPP module;
Water from a salt water pretreatment module is provided to, and/or reclaimed from, and/or mixed with water from p) heating and/or cooling to the Plan;
Water from a salt water pretreatment module is provided to, and/or reclaimed from, and/or mixed with water from q) a recycling module;
Water from a salt water pretreatment module is provided to, and/or reclaimed from, and/or mixed with water from r) a waste receiving module;
Water from a salt water pretreatment module is provided to, and/or reclaimed from, and/or mixed with water from s) a BBPP module;
Water from a salt water pretreatment module is provided to, and/or reclaimed from, and/or mixed with water from t) a desalination module;
Water from a salt water pretreatment module is provided to, and/or reclaimed from, and/or mixed with water from u) water for discharge/export;
Water from a salt water pretreatment module is provided to, and/or reclaimed from, and/or mixed with water from v) a processing and/or treatment module; and/or
Water from a salt water pretreatment module is provided to, and/or reclaimed from, and/or mixed with water from w) a thermal plant module.
Water from a preheating/cooling module is provided to, and/or reclaimed from, and/or mixed with water from a) a fresh water source;
Water from a preheating/cooling module is provided to, and/or reclaimed from, and/or mixed with water from b) a fresh water pretreatment module;
Water from a preheating/cooling module is provided to, and/or reclaimed from, and/or mixed with water from c) a salt water intake;
Water from a preheating/cooling module is provided to, and/or reclaimed from, and/or mixed with water from d) a salt water pretreatment module;

TABLE 2-continued

Any combination herein is optionally collocated:

Water from a preheating/cooling module is provided to, and/or reclaimed from, and/or mixed with water from e) a preheating/cooling module;
Water from a preheating/cooling module is provided to, and/or reclaimed from, and/or mixed with water from f) a water storage module;
Water from a preheating/cooling module is provided to, and/or reclaimed from, and/or mixed with water from g) irrigation;
Water from a preheating/cooling module is provided to, and/or reclaimed from, and/or mixed with water from h) firefighting;
Water from a preheating/cooling module is provided to, and/or reclaimed from, and/or mixed with water from i) fountains;
Water from a preheating/cooling module is provided to, and/or reclaimed from, and/or mixed with water from j) lakes;
Water from a preheating/cooling module is provided to, and/or reclaimed from, and/or mixed with water from k) cleaning;
Water from a preheating/cooling module is provided to, and/or reclaimed from, and/or mixed with water from l) a BGM;
Water from a preheating/cooling module is provided to, and/or reclaimed from, and/or mixed with water from m) a traditional WWTP module;
Water from a preheating/cooling module is provided to, and/or reclaimed from, and/or mixed with water from n) a refinery module;
Water from a preheating/cooling module is provided to, and/or reclaimed from, and/or mixed with water from o) a BPP module;
Water from a preheating/cooling module is provided to, and/or reclaimed from, and/or mixed with water from p) heating and/or cooling to the Plan;
Water from a preheating/cooling module is provided to, and/or reclaimed from, and/or mixed with water from q) a recycling module;
Water from a preheating/cooling module is provided to, and/or reclaimed from, and/or mixed with water from r) a waste receiving module;
Water from a preheating/cooling module is provided to, and/or reclaimed from, and/or mixed with water from s) a BBPP module;
Water from a preheating/cooling module is provided to, and/or reclaimed from, and/or mixed with water from t) a desalination module;
Water from a preheating/cooling module is provided to, and/or reclaimed from, and/or mixed with water from u) water for discharge/export;
Water from a preheating/cooling module is provided to, and/or reclaimed from, and/or mixed with water from v) a processing and/or treatment module; and/or
Water from a preheating/cooling module is provided to, and/or reclaimed from, and/or mixed with water from w) a thermal plant module.
Water from a water storage module is provided to, and/or reclaimed from, and/or mixed with water from a) a fresh water source;
Water from a water storage module is provided to, and/or reclaimed from, and/or mixed with water from b) a fresh water pretreatment module;
Water from a water storage module is provided to, and/or reclaimed from, and/or mixed with water from c) a salt water intake;
Water from a water storage module is provided to, and/or reclaimed from, and/or mixed with water from d) a salt water pretreatment module;
Water from a water storage module is provided to, and/or reclaimed from, and/or mixed with water from e) a preheating/cooling module;
Water from a water storage module is provided to, and/or reclaimed from, and/or mixed with water from f) a water storage module;
Water from a water storage module is provided to, and/or reclaimed from, and/or mixed with water from g) irrigation;
Water from a water storage module is provided to, and/or reclaimed from, and/or mixed with water from h) firefighting;
Water from a water storage module is provided to, and/or reclaimed from, and/or mixed with water from i) fountains;
Water from a water storage module is provided to, and/or reclaimed from, and/or mixed with water from j) lakes;
Water from a water storage module is provided to, and/or reclaimed from, and/or mixed with water from k) cleaning;
Water from a water storage module is provided to, and/or reclaimed from, and/or mixed with water from l) a BGM;
Water from a water storage module is provided to, and/or reclaimed from, and/or mixed with water from m) a traditional WWTP module;
Water from a water storage module is provided to, and/or reclaimed from, and/or mixed with water from n) a refinery module;
Water from a water storage module is provided to, and/or reclaimed from, and/or mixed with water from o) a BPP module;
Water from a water storage module is provided to, and/or reclaimed from, and/or mixed with water from p) heating and/or cooling to the Plan;
Water from a water storage module is provided to, and/or reclaimed from, and/or mixed with water from q) a recycling module;
Water from a water storage module is provided to, and/or reclaimed from, and/or mixed with water from r) a waste receiving module;
Water from a water storage module is provided to, and/or reclaimed from, and/or mixed with water from s) a BBPP module;
Water from a water storage module is provided to, and/or reclaimed from, and/or mixed with water from t) a desalination module;

TABLE 2-continued

Any combination herein is optionally collocated:

Water from a water storage module is provided to, and/or reclaimed from, and/or mixed with water from u) water for discharge/export;
Water from a water storage module is provided to, and/or reclaimed from, and/or mixed with water from v) a processing and/or treatment module; and/or
Water from a water storage module is provided to, and/or reclaimed from, and/or mixed with water from w) a thermal plant module.
Water from irrigation is provided to, and/or reclaimed from, and/or mixed with water from a) a fresh water source;
Water from irrigation is provided to, and/or reclaimed from, and/or mixed with water from b) a fresh water pretreatment module;
Water from irrigation is provided to, and/or reclaimed from, and/or mixed with water from c) a salt water intake;
Water from irrigation is provided to, and/or reclaimed from, and/or mixed with water from d) a salt water pretreatment module;
Water from irrigation is provided to, and/or reclaimed from, and/or mixed with water from e) a preheating/cooling module;
Water from irrigation is provided to, and/or reclaimed from, and/or mixed with water from f) a water storage module;
Water from irrigation is provided to, and/or reclaimed from, and/or mixed with water from g) irrigation;
Water from irrigation is provided to, and/or reclaimed from, and/or mixed with water from h) firefighting;
Water from irrigation is provided to, and/or reclaimed from, and/or mixed with water from i) fountains;
Water from irrigation is provided to, and/or reclaimed from, and/or mixed with water from j) lakes;
Water from irrigation is provided to, and/or reclaimed from, and/or mixed with water from k) cleaning;
Water from irrigation is provided to, and/or reclaimed from, and/or mixed with water from l) a BGM;
Water from irrigation is provided to, and/or reclaimed from, and/or mixed with water from m) a traditional WWTP module;
Water from irrigation is provided to, and/or reclaimed from, and/or mixed with water from n) a refinery module;
Water from irrigation is provided to, and/or reclaimed from, and/or mixed with water from o) a BPP module;
Water from irrigation is provided to, and/or reclaimed from, and/or mixed with water from p) heating and/or cooling to the Plan;
Water from irrigation is provided to, and/or reclaimed from, and/or mixed with water from q) a recycling module;
Water from irrigation is provided to, and/or reclaimed from, and/or mixed with water from r) a waste receiving module;
Water from irrigation is provided to, and/or reclaimed from, and/or mixed with water from s) a BBPP module;
Water from irrigation is provided to, and/or reclaimed from, and/or mixed with water from t) a desalination module;
Water from irrigation is provided to, and/or reclaimed from, and/or mixed with water from u) water for discharge/export;
Water from irrigation is provided to, and/or reclaimed from, and/or mixed with water from v) a processing and/or treatment module; and/or
Water from irrigation is provided to, and/or reclaimed from, and/or mixed with water from w) a thermal plant module.
Water from firefighting is provided to, and/or reclaimed from, and/or mixed with water from a) a fresh water source;
Water from firefighting is provided to, and/or reclaimed from, and/or mixed with water from b) a fresh water pretreatment module;
Water from firefighting is provided to, and/or reclaimed from, and/or mixed with water from c) a salt water intake;
Water from firefighting is provided to, and/or reclaimed from, and/or mixed with water from d) a salt water pretreatment module;
Water from firefighting is provided to, and/or reclaimed from, and/or mixed with water from e) a preheating/cooling module;
Water from firefighting is provided to, and/or reclaimed from, and/or mixed with water from f) a water storage module;
Water from firefighting is provided to, and/or reclaimed from, and/or mixed with water from g) irrigation;
Water from firefighting is provided to, and/or reclaimed from, and/or mixed with water from h) firefighting;
Water from firefighting is provided to, and/or reclaimed from, and/or mixed with water from i) fountains;
Water from firefighting is provided to, and/or reclaimed from, and/or mixed with water from j) lakes;
Water from firefighting is provided to, and/or reclaimed from, and/or mixed with water from k) cleaning;
Water from firefighting is provided to, and/or reclaimed from, and/or mixed with water from l) a BGM;
Water from firefighting is provided to, and/or reclaimed from, and/or mixed with water from m) a traditional WWTP module;

TABLE 2-continued

| Any combination herein is optionally collocated: |
|---|

Water from firefighting is provided to, and/or reclaimed from, and/or mixed with water from n) a refinery module;
Water from firefighting is provided to, and/or reclaimed from, and/or mixed with water from o) a BPP module;
Water from firefighting is provided to, and/or reclaimed from, and/or mixed with water from p) heating and/or cooling to the Plan;
Water from firefighting is provided to, and/or reclaimed from, and/or mixed with water from q) a recycling module;
Water from firefighting is provided to, and/or reclaimed from, and/or mixed with water from r) a waste receiving module;
Water from firefighting is provided to, and/or reclaimed from, and/or mixed with water from s) a BBPP module;
Water from firefighting is provided to, and/or reclaimed from, and/or mixed with water from t) a desalination module;
Water from firefighting is provided to, and/or reclaimed from, and/or mixed with water from u) water for discharge/export;
Water from firefighting is provided to, and/or reclaimed from, and/or mixed with water from v) a processing and/or treatment module; and/or
Water from firefighting is provided to, and/or reclaimed from, and/or mixed with water from w) a thermal plant module.
Water from fountains is provided to, and/or reclaimed from, and/or mixed with water from a) a fresh water source;
Water from fountains is provided to, and/or reclaimed from, and/or mixed with water from b) a fresh water pretreatment module;
Water from fountains is provided to, and/or reclaimed from, and/or mixed with water from c) a salt water intake;
Water from fountains is provided to, and/or reclaimed from, and/or mixed with water from d) a salt water pretreatment module;
Water from fountains is provided to, and/or reclaimed from, and/or mixed with water from e) a preheating/cooling module;
Water from fountains is provided to, and/or reclaimed from, and/or mixed with water from f) a water storage module;
Water from fountains is provided to, and/or reclaimed from, and/or mixed with water from g) irrigation;
Water from fountains is provided to, and/or reclaimed from, and/or mixed with water from h) firefighting;
Water from fountains is provided to, and/or reclaimed from, and/or mixed with water from i) fountains;
Water from fountains is provided to, and/or reclaimed from, and/or mixed with water from j) lakes;
Water from fountains is provided to, and/or reclaimed from, and/or mixed with water from k) cleaning;
Water from fountains is provided to, and/or reclaimed from, and/or mixed with water from l) a BGM;
Water from fountains is provided to, and/or reclaimed from, and/or mixed with water from m) a traditional WWTP module;
Water from fountains is provided to, and/or reclaimed from, and/or mixed with water from n) a refinery module;
Water from fountains is provided to, and/or reclaimed from, and/or mixed with water from o) a BPP module;
Water from fountains is provided to, and/or reclaimed from, and/or mixed with water from p) heating and/or cooling to the Plan;
Water from fountains is provided to, and/or reclaimed from, and/or mixed with water from q) a recycling module;
Water from fountains is provided to, and/or reclaimed from, and/or mixed with water from r) a waste receiving module;
Water from fountains is provided to, and/or reclaimed from, and/or mixed with water from s) a BBPP module;
Water from fountains is provided to, and/or reclaimed from, and/or mixed with water from t) a desalination module;
Water from fountains is provided to, and/or reclaimed from, and/or mixed with water from u) water for discharge/export;
Water from fountains is provided to, and/or reclaimed from, and/or mixed with water from v) a processing and/or treatment module; and/or
Water from fountains is provided to, and/or reclaimed from, and/or mixed with water from w) a thermal plant module.
Water from lakes is provided to, and/or reclaimed from, and/or mixed with water from a) a fresh water source;
Water from lakes is provided to, and/or reclaimed from, and/or mixed with water from b) a fresh water pretreatment module;
Water from lakes is provided to, and/or reclaimed from, and/or mixed with water from c) a salt water intake;
Water from lakes is provided to, and/or reclaimed from, and/or mixed with water from d) a salt water pretreatment module;
Water from lakes is provided to, and/or reclaimed from, and/or mixed with water from e) a preheating/cooling module;
Water from lakes is provided to, and/or reclaimed from, and/or mixed with water from f) a water storage module;

TABLE 2-continued

| Any combination herein is optionally collocated: |
| --- |

Water from lakes is provided to, and/or reclaimed from, and/or mixed with water from g) irrigation;
Water from lakes is provided to, and/or reclaimed from, and/or mixed with water from h) firefighting;
Water from lakes is provided to, and/or reclaimed from, and/or mixed with water from i) fountains;
Water from lakes is provided to, and/or reclaimed from, and/or mixed with water from j) lakes;
Water from lakes is provided to, and/or reclaimed from, and/or mixed with water from k) cleaning;
Water from lakes is provided to, and/or reclaimed from, and/or mixed with water from l) a BGM;
Water from lakes is provided to, and/or reclaimed from, and/or mixed with water from m) a traditional WWTP module;
Water from lakes is provided to, and/or reclaimed from, and/or mixed with water from n) a refinery module;
Water from lakes is provided to, and/or reclaimed from, and/or mixed with water from o) a BPP module;
Water from lakes is provided to, and/or reclaimed from, and/or mixed with water from p) heating and/or cooling to the Plan;
Water from lakes is provided to, and/or reclaimed from, and/or mixed with water from q) a recycling module;
Water from lakes is provided to, and/or reclaimed from, and/or mixed with water from r) a waste receiving module;
Water from lakes is provided to, and/or reclaimed from, and/or mixed with water from s) a BBPP module;
Water from lakes is provided to, and/or reclaimed from, and/or mixed with water from t) a desalination module;
Water from lakes is provided to, and/or reclaimed from, and/or mixed with water from u) water for discharge/export;
Water from lakes is provided to, and/or reclaimed from, and/or mixed with water from v) a processing and/or treatment module; and/or
Water from lakes is provided to, and/or reclaimed from, and/or mixed with water from w) a thermal plant module.
Water from cleaning is provided to, and/or reclaimed from, and/or mixed with water from a) a fresh water source;
Water from cleaning is provided to, and/or reclaimed from, and/or mixed with water from b) a fresh water pretreatment module;
Water from cleaning is provided to, and/or reclaimed from, and/or mixed with water from c) a salt water intake;
Water from cleaning is provided to, and/or reclaimed from, and/or mixed with water from d) a salt water pretreatment module;
Water from cleaning is provided to, and/or reclaimed from, and/or mixed with water from e) a preheating/cooling module;
Water from cleaning is provided to, and/or reclaimed from, and/or mixed with water from f) a water storage module;
Water from cleaning is provided to, and/or reclaimed from, and/or mixed with water from g) irrigation;
Water from cleaning is provided to, and/or reclaimed from, and/or mixed with water from h) firefighting;
Water from cleaning is provided to, and/or reclaimed from, and/or mixed with water from i) fountains;
Water from cleaning is provided to, and/or reclaimed from, and/or mixed with water from j) lakes;
Water from cleaning is provided to, and/or reclaimed from, and/or mixed with water from k) cleaning;
Water from cleaning is provided to, and/or reclaimed from, and/or mixed with water from l) a BGM;
Water from cleaning is provided to, and/or reclaimed from, and/or mixed with water from m) a traditional WWTP module;
Water from cleaning is provided to, and/or reclaimed from, and/or mixed with water from n) a refinery module;
Water from cleaning is provided to, and/or reclaimed from, and/or mixed with water from o) a BPP module;
Water from cleaning is provided to, and/or reclaimed from, and/or mixed with water from p) heating and/or cooling to the Plan;
Water from cleaning is provided to, and/or reclaimed from, and/or mixed with water from q) a recycling module;
Water from cleaning is provided to, and/or reclaimed from, and/or mixed with water from r) a waste receiving module;
Water from cleaning is provided to, and/or reclaimed from, and/or mixed with water from s) a BBPP module;
Water from cleaning is provided to, and/or reclaimed from, and/or mixed with water from t) a desalination module;
Water from cleaning is provided to, and/or reclaimed from, and/or mixed with water from u) water for discharge/export;
Water from cleaning is provided to, and/or reclaimed from, and/or mixed with water from v) a processing and/or treatment module; and/or TABLE 2-continued

| Any combination herein is optionally collocated: |
| --- |

Water from cleaning is provided to, and/or reclaimed from, and/or mixed with water from w) a thermal plant module.
Water from a BGM is provided to, and/or reclaimed from, and/or mixed with water from a) a fresh water source;
Water from a BGM is provided to, and/or reclaimed from, and/or mixed with water from b) a fresh water pretreatment module;
Water from a BGM is provided to, and/or reclaimed from, and/or mixed with water from c) a salt water intake;
Water from a BGM is provided to, and/or reclaimed from, and/or mixed with water from d) a salt water pretreatment module;
Water from a BGM is provided to, and/or reclaimed from, and/or mixed with water from e) a preheating/cooling module;
Water from a BGM is provided to, and/or reclaimed from, and/or mixed with water from f) a water storage module;
Water from a BGM is provided to, and/or reclaimed from, and/or mixed with water from g) irrigation;
Water from a BGM is provided to, and/or reclaimed from, and/or mixed with water from h) firefighting;
Water from a BGM is provided to, and/or reclaimed from, and/or mixed with water from i) fountains;
Water from a BGM is provided to, and/or reclaimed from, and/or mixed with water from j) lakes;
Water from a BGM is provided to, and/or reclaimed from, and/or mixed with water from k) cleaning;
Water from a BGM is provided to, and/or reclaimed from, and/or mixed with water from l) a BGM;
Water from a BGM is provided to, and/or reclaimed from, and/or mixed with water from m) a traditional WWTP module;
Water from a BGM is provided to, and/or reclaimed from, and/or mixed with water from n) a refinery module;
Water from a BGM is provided to, and/or reclaimed from, and/or mixed with water from o) a BPP module;
Water from a BGM is provided to, and/or reclaimed from, and/or mixed with water from p) heating and/or cooling to the Plan;
Water from a BGM is provided to, and/or reclaimed from, and/or mixed with water from q) a recycling module;
Water from a BGM is provided to, and/or reclaimed from, and/or mixed with water from r) a waste receiving module;
Water from a BGM is provided to, and/or reclaimed from, and/or mixed with water from s) a BBPP module;
Water from a BGM is provided to, and/or reclaimed from, and/or mixed with water from t) a desalination module;
Water from a BGM is provided to, and/or reclaimed from, and/or mixed with water from u) water for discharge/export;
Water from a BGM is provided to, and/or reclaimed from, and/or mixed with water from v) a processing and/or treatment module; and/or
Water from a BGM is provided to, and/or reclaimed from, and/or mixed with water from w) a thermal plant module.
Water from a traditional WWTP module is provided to, and/or reclaimed from, and/or mixed with water from a) a fresh water source;
Water from a traditional WWTP module is provided to, and/or reclaimed from, and/or mixed with water from b) a fresh water pretreatment module;
Water from a traditional WWTP module is provided to, and/or reclaimed from, and/or mixed with water from c) a salt water intake;
Water from a traditional WWTP module is provided to, and/or reclaimed from, and/or mixed with water from d) a salt water pretreatment module;
Water from a traditional WWTP module is provided to, and/or reclaimed from, and/or mixed with water from e) a preheating/cooling module;
Water from a traditional WWTP module is provided to, and/or reclaimed from, and/or mixed with water from f) a water storage module;
Water from a traditional WWTP module is provided to, and/or reclaimed from, and/or mixed with water from g) irrigation;
Water from a traditional WWTP module is provided to, and/or reclaimed from, and/or mixed with water from h) firefighting;
Water from a traditional WWTP module is provided to, and/or reclaimed from, and/or mixed with water from i) fountains;
Water from a traditional WWTP module is provided to, and/or reclaimed from, and/or mixed with water from j) lakes;
Water from a traditional WWTP module is provided to, and/or reclaimed from, and/or mixed with water from k) cleaning;
Water from a traditional WWTP module is provided to, and/or reclaimed from, and/or mixed with water from l) a BGM;
Water from a traditional WWTP module is provided to, and/or reclaimed from, and/or mixed with water from m) a traditional WWTP module;
Water from a traditional WWTP module is provided to, and/or reclaimed from, and/or mixed with water from n) a refinery module;
Water from a traditional WWTP module is provided to, and/or reclaimed from, and/or mixed with water from o) a BPP module;

TABLE 2-continued

Any combination herein is optionally collocated:

Water from a traditional WWTP module is provided to, and/or reclaimed from, and/or mixed with water from p) heating and/or cooling to the Plan;
Water from a traditional WWTP module is provided to, and/or reclaimed from, and/or mixed with water from q) a recycling module;
Water from a traditional WWTP module is provided to, and/or reclaimed from, and/or mixed with water from r) a waste receiving module;
Water from a traditional WWTP module is provided to, and/or reclaimed from, and/or mixed with water from s) a BBPP module;
Water from a traditional WWTP module is provided to, and/or reclaimed from, and/or mixed with water from t) a desalination module;
Water from a traditional WWTP module is provided to, and/or reclaimed from, and/or mixed with water from u) water for discharge/export;
Water from a traditional WWTP module is provided to, and/or reclaimed from, and/or mixed with water from v) a processing and/or treatment module; and/or
Water from a traditional WWTP module is provided to, and/or reclaimed from, and/or mixed with water from w) a thermal plant module.
Water from a refinery module is provided to, and/or reclaimed from, and/or mixed with water from a) a fresh water source;
Water from a refinery module is provided to, and/or reclaimed from, and/or mixed with water from b) a fresh water pretreatment module;
Water from a refinery module is provided to, and/or reclaimed from, and/or mixed with water from c) a salt water intake;
Water from a refinery module is provided to, and/or reclaimed from, and/or mixed with water from d) a salt water pretreatment module;
Water from a refinery module is provided to, and/or reclaimed from, and/or mixed with water from e) a preheating/cooling module;
Water from a refinery module is provided to, and/or reclaimed from, and/or mixed with water from f) a water storage module;
Water from a refinery module is provided to, and/or reclaimed from, and/or mixed with water from g) irrigation;
Water from a refinery module is provided to, and/or reclaimed from, and/or mixed with water from h) firefighting;
Water from a refinery module is provided to, and/or reclaimed from, and/or mixed with water from i) fountains;
Water from a refinery module is provided to, and/or reclaimed from, and/or mixed with water from j) lakes;
Water from a refinery module is provided to, and/or reclaimed from, and/or mixed with water from k) cleaning;
Water from a refinery module is provided to, and/or reclaimed from, and/or mixed with water from l) a BGM;
Water from a refinery module is provided to, and/or reclaimed from, and/or mixed with water from m) a traditional WWTP module;
Water from a refinery module is provided to, and/or reclaimed from, and/or mixed with water from n) a refinery module;
Water from a refinery module is provided to, and/or reclaimed from, and/or mixed with water from o) a BPP module;
Water from a refinery module is provided to, and/or reclaimed from, and/or mixed with water from p) heating and/or cooling to the Plan;
Water from a refinery module is provided to, and/or reclaimed from, and/or mixed with water from q) a recycling module;
Water from a refinery module is provided to, and/or reclaimed from, and/or mixed with water from r) a waste receiving module;
Water from a refinery module is provided to, and/or reclaimed from, and/or mixed with water from s) a BBPP module;
Water from a refinery module is provided to, and/or reclaimed from, and/or mixed with water from t) a desalination module;
Water from a refinery module is provided to, and/or reclaimed from, and/or mixed with water from u) water for discharge/export;
Water from a refinery module is provided to, and/or reclaimed from, and/or mixed with water from v) a processing and/or treatment module; and/or
Water from a refinery module is provided to, and/or reclaimed from, and/or mixed with water from w) a thermal plant module.
Water from a BPP module is provided to, and/or reclaimed from, and/or mixed with water from a) a fresh water source;
Water from a BPP module is provided to, and/or reclaimed from, and/or mixed with water from b) a fresh water pretreatment module;
Water from a BPP module is provided to, and/or reclaimed from, and/or mixed with water from c) a salt water intake;
Water from a BPP module is provided to, and/or reclaimed from, and/or mixed with water from d) a salt water pretreatment module;
Water from a BPP module is provided to, and/or reclaimed from, and/or mixed with water from e) a preheating/cooling module;
Water from a BPP module is provided to, and/or reclaimed from, and/or mixed with water from f) a water storage module;
Water from a BPP module is provided to, and/or reclaimed from, and/or mixed with water from g) irrigation;
Water from a BPP module is provided to, and/or reclaimed from, and/or mixed with water from h) firefighting;

TABLE 2-continued

| Any combination herein is optionally collocated: |
|---|

Water from a BPP module is provided to, and/or reclaimed from, and/or mixed with water from i) fountains;
Water from a BPP module is provided to, and/or reclaimed from, and/or mixed with water from j) lakes;
Water from a BPP module is provided to, and/or reclaimed from, and/or mixed with water from k) cleaning;
Water from a BPP module is provided to, and/or reclaimed from, and/or mixed with water from l) a BGM;
Water from a BPP module is provided to, and/or reclaimed from, and/or mixed with water from m) a traditional WWTP module;
Water from a BPP module is provided to, and/or reclaimed from, and/or mixed with water from n) a refinery module;
Water from a BPP module is provided to, and/or reclaimed from, and/or mixed with water from o) a BPP module;
Water from a BPP module is provided to, and/or reclaimed from, and/or mixed with water from p) heating and/or cooling to the Plan;
Water from a BPP module is provided to, and/or reclaimed from, and/or mixed with water from q) a recycling module;
Water from a BPP module is provided to, and/or reclaimed from, and/or mixed with water from r) a waste receiving module;
Water from a BPP module is provided to, and/or reclaimed from, and/or mixed with water from s) a BBPP module;
Water from a BPP module is provided to, and/or reclaimed from, and/or mixed with water from t) a desalination module;
Water from a BPP module is provided to, and/or reclaimed from, and/or mixed with water from u) water for discharge/export;
Water from a BPP module is provided to, and/or reclaimed from, and/or mixed with water from v) a processing and/or treatment module; and/or
Water from a BPP module is provided to, and/or reclaimed from, and/or mixed with water from w) a thermal plant module.
Water from heating and/or cooling to the Plan is provided to, and/or reclaimed from, and/or mixed with water from a) a fresh water source;
Water from heating and/or cooling to the Plan is provided to, and/or reclaimed from, and/or mixed with water from b) a fresh water pretreatment module;
Water from heating and/or cooling to the Plan is provided to, and/or reclaimed from, and/or mixed with water from c) a salt water intake;
Water from heating and/or cooling to the Plan is provided to, and/or reclaimed from, and/or mixed with water from d) a salt water pretreatment module;
Water from heating and/or cooling to the Plan is provided to, and/or reclaimed from, and/or mixed with water from e) a preheating/cooling module;
Water from heating and/or cooling to the Plan is provided to, and/or reclaimed from, and/or mixed with water from f) a water storage module;
Water from heating and/or cooling to the Plan is provided to, and/or reclaimed from, and/or mixed with water from g) irrigation;
Water from heating and/or cooling to the Plan is provided to, and/or reclaimed from, and/or mixed with water from h) firefighting;
Water from heating and/or cooling to the Plan is provided to, and/or reclaimed from, and/or mixed with water from i) fountains;
Water from heating and/or cooling to the Plan is provided to, and/or reclaimed from, and/or mixed with water from j) lakes;
Water from heating and/or cooling to the Plan is provided to, and/or reclaimed from, and/or mixed with water from k) cleaning;
Water from heating and/or cooling to the Plan is provided to, and/or reclaimed from, and/or mixed with water from l) a BGM;
Water from heating and/or cooling to the Plan is provided to, and/or reclaimed from, and/or mixed with water from m) a traditional WWTP module;
Water from heating and/or cooling to the Plan is provided to, and/or reclaimed from, and/or mixed with water from n) a refinery module;
Water from heating and/or cooling to the Plan is provided to, and/or reclaimed from, and/or mixed with water from o) a BPP module;
Water from heating and/or cooling to the Plan is provided to, and/or reclaimed from, and/or mixed with water from p) heating and/or cooling to the Plan;
Water from heating and/or cooling to the Plan is provided to, and/or reclaimed from, and/or mixed with water from q) a recycling module;
Water from heating and/or cooling to the Plan is provided to, and/or reclaimed from, and/or mixed with water from r) a waste receiving module;
Water from heating and/or cooling to the Plan is provided to, and/or reclaimed from, and/or mixed with water from s) a BBPP module;
Water from heating and/or cooling to the Plan is provided to, and/or reclaimed from, and/or mixed with water from t) a desalination module;
Water from heating and/or cooling to the Plan is provided to, and/or reclaimed from, and/or mixed with water from u) water for discharge/export;
Water from heating and/or cooling to the Plan is provided to, and/or reclaimed from, and/or mixed with water from v) a processing and/or treatment module; and/or
Water from heating and/or cooling to the Plan is provided to, and/or reclaimed from, and/or mixed with water from w) a thermal plant module.
Water from a recycling module is provided to, and/or reclaimed from, and/or mixed with water from a) a fresh water source;

TABLE 2-continued

Any combination herein is optionally collocated:

Water from a recycling module is provided to, and/or reclaimed from, and/or mixed with water from b) a fresh water pretreatment module;
Water from a recycling module is provided to, and/or reclaimed from, and/or mixed with water from c) a salt water intake;
Water from a recycling module is provided to, and/or reclaimed from, and/or mixed with water from d) a salt water pretreatment module;
Water from a recycling module is provided to, and/or reclaimed from, and/or mixed with water from e) a preheating/cooling module;
Water from a recycling module is provided to, and/or reclaimed from, and/or mixed with water from f) a water storage module;
Water from a recycling module is provided to, and/or reclaimed from, and/or mixed with water from g) irrigation;
Water from a recycling module is provided to, and/or reclaimed from, and/or mixed with water from h) firefighting;
Water from a recycling module is provided to, and/or reclaimed from, and/or mixed with water from i) fountains;
Water from a recycling module is provided to, and/or reclaimed from, and/or mixed with water from j) lakes;
Water from a recycling module is provided to, and/or reclaimed from, and/or mixed with water from k) cleaning;
Water from a recycling module is provided to, and/or reclaimed from, and/or mixed with water from l) a BGM;
Water from a recycling module is provided to, and/or reclaimed from, and/or mixed with water from m) a traditional WWTP module;
Water from a recycling module is provided to, and/or reclaimed from, and/or mixed with water from n) a refinery module;
Water from a recycling module is provided to, and/or reclaimed from, and/or mixed with water from o) a BPP module;
Water from a recycling module is provided to, and/or reclaimed from, and/or mixed with water from p) heating and/or cooling to the Plan;
Water from a recycling module is provided to, and/or reclaimed from, and/or mixed with water from q) a recycling module;
Water from a recycling module is provided to, and/or reclaimed from, and/or mixed with water from r) a waste receiving module;
Water from a recycling module is provided to, and/or reclaimed from, and/or mixed with water from s) a BBPP module;
Water from a recycling module is provided to, and/or reclaimed from, and/or mixed with water from t) a desalination module;
Water from a recycling module is provided to, and/or reclaimed from, and/or mixed with water from u) water for discharge/export;
Water from a recycling module is provided to, and/or reclaimed from, and/or mixed with water from v) a processing and/or treatment module; and/or
Water from a recycling module is provided to, and/or reclaimed from, and/or mixed with water from w) a thermal plant module.
Water from a waste receiving module is provided to, and/or reclaimed from, and/or mixed with water from a) a fresh water source;
Water from a waste receiving module is provided to, and/or reclaimed from, and/or mixed with water from b) a fresh water pretreatment module;
Water from a waste receiving module is provided to, and/or reclaimed from, and/or mixed with water from c) a salt water intake;
Water from a waste receiving module is provided to, and/or reclaimed from, and/or mixed with water from d) a salt water pretreatment module;
Water from a waste receiving module is provided to, and/or reclaimed from, and/or mixed with water from e) a preheating/cooling module;
Water from a waste receiving module is provided to, and/or reclaimed from, and/or mixed with water from f) a water storage module;
Water from a waste receiving module is provided to, and/or reclaimed from, and/or mixed with water from g) irrigation;
Water from a waste receiving module is provided to, and/or reclaimed from, and/or mixed with water from h) firefighting;
Water from a waste receiving module is provided to, and/or reclaimed from, and/or mixed with water from i) fountains;
Water from a waste receiving module is provided to, and/or reclaimed from, and/or mixed with water from j) lakes;
Water from a waste receiving module is provided to, and/or reclaimed from, and/or mixed with water from k) cleaning;
Water from a waste receiving module is provided to, and/or reclaimed from, and/or mixed with water from l) a BGM;
Water from a waste receiving module is provided to, and/or reclaimed from, and/or mixed with water from m) a traditional WWTP module;
Water from a waste receiving module is provided to, and/or reclaimed from, and/or mixed with water from n) a refinery module;
Water from a waste receiving module is provided to, and/or reclaimed from, and/or mixed with water from o) a BPP module;
Water from a waste receiving module is provided to, and/or reclaimed from, and/or mixed with water from p) heating and/or cooling to the Plan;
Water from a waste receiving module is provided to, and/or reclaimed from, and/or mixed with water from q) a recycling module;

TABLE 2-continued

Any combination herein is optionally collocated:

Water from a waste receiving module is provided to, and/or reclaimed from, and/or mixed with water from r) a waste receiving module;
Water from a waste receiving module is provided to, and/or reclaimed from, and/or mixed with water from s) a BBPP module;
Water from a waste receiving module is provided to, and/or reclaimed from, and/or mixed with water from t) a desalination module;
Water from a waste receiving module is provided to, and/or reclaimed from, and/or mixed with water from u) water for discharge/export;
Water from a waste receiving module is provided to, and/or reclaimed from, and/or mixed with water from v) a processing and/or treatment module; and/or
Water from a waste receiving module is provided to, and/or reclaimed from, and/or mixed with water from w) a thermal plant module.
Water from a BBPP module is provided to, and/or reclaimed from, and/or mixed with water from a) a fresh water source;
Water from a BBPP module is provided to, and/or reclaimed from, and/or mixed with water from b) a fresh water pretreatment module;
Water from a BBPP module is provided to, and/or reclaimed from, and/or mixed with water from c) a salt water intake;
Water from a BBPP module is provided to, and/or reclaimed from, and/or mixed with water from d) a salt water pretreatment module;
Water from a BBPP module is provided to, and/or reclaimed from, and/or mixed with water from e) a preheating/cooling module;
Water from a BBPP module is provided to, and/or reclaimed from, and/or mixed with water from f) a water storage module;
Water from a BBPP module is provided to, and/or reclaimed from, and/or mixed with water from g) irrigation;
Water from a BBPP module is provided to, and/or reclaimed from, and/or mixed with water from h) firefighting;
Water from a BBPP module is provided to, and/or reclaimed from, and/or mixed with water from i) fountains;
Water from a BBPP module is provided to, and/or reclaimed from, and/or mixed with water from j) lakes;
Water from a BBPP module is provided to, and/or reclaimed from, and/or mixed with water from k) cleaning;
Water from a BBPP module is provided to, and/or reclaimed from, and/or mixed with water from l) a BGM;
Water from a BBPP module is provided to, and/or reclaimed from, and/or mixed with water from m) a traditional WWTP module;
Water from a BBPP module is provided to, and/or reclaimed from, and/or mixed with water from n) a refinery module;
Water from a BBPP module is provided to, and/or reclaimed from, and/or mixed with water from o) a BPP module;
Water from a BBPP module is provided to, and/or reclaimed from, and/or mixed with water from p) heating and/or cooling to the Plan;
Water from a BBPP module is provided to, and/or reclaimed from, and/or mixed with water from q) a recycling module;
Water from a BBPP module is provided to, and/or reclaimed from, and/or mixed with water from r) a waste receiving module;
Water from a BBPP module is provided to, and/or reclaimed from, and/or mixed with water from s) a BBPP module;
Water from a BBPP module is provided to, and/or reclaimed from, and/or mixed with water from t) a desalination module;
Water from a BBPP module is provided to, and/or reclaimed from, and/or mixed with water from u) water for discharge/export;
Water from a BBPP module is provided to, and/or reclaimed from, and/or mixed with water from v) a processing and/or treatment module; and/or
Water from a BBPP module is provided to, and/or reclaimed from, and/or mixed with water from w) a thermal plant module.
Water from a desalination module is provided to, and/or reclaimed from, and/or mixed with water from a) a fresh water source;
Water from a desalination module is provided to, and/or reclaimed from, and/or mixed with water from b) a fresh water pretreatment module;
Water from a desalination module is provided to, and/or reclaimed from, and/or mixed with water from c) a salt water intake;
Water from a desalination module is provided to, and/or reclaimed from, and/or mixed with water from d) a salt water pretreatment module;
Water from a desalination module is provided to, and/or reclaimed from, and/or mixed with water from e) a preheating/cooling module;
Water from a desalination module is provided to, and/or reclaimed from, and/or mixed with water from f) a water storage module;
Water from a desalination module is provided to, and/or reclaimed from, and/or mixed with water from g) irrigation;
Water from a desalination module is provided to, and/or reclaimed from, and/or mixed with water from h) firefighting;
Water from a desalination module is provided to, and/or reclaimed from, and/or mixed with water from i) fountains;
Water from a desalination module is provided to, and/or reclaimed from, and/or mixed with water from j) lakes;

TABLE 2-continued

Any combination herein is optionally collocated:

Water from a desalination module is provided to, and/or reclaimed from, and/or mixed with water from k) cleaning;
Water from a desalination module is provided to, and/or reclaimed from, and/or mixed with water from l) a BGM;
Water from a desalination module is provided to, and/or reclaimed from, and/or mixed with water from m) a traditional WWTP module;
Water from a desalination module is provided to, and/or reclaimed from, and/or mixed with water from n) a refinery module;
Water from a desalination module is provided to, and/or reclaimed from, and/or mixed with water from o) a BPP module;
Water from a desalination module is provided to, and/or reclaimed from, and/or mixed with water from p) heating and/or cooling to the Plan;
Water from a desalination module is provided to, and/or reclaimed from, and/or mixed with water from q) a recycling module;
Water from a desalination module is provided to, and/or reclaimed from, and/or mixed with water from r) a waste receiving module;
Water from a desalination module is provided to, and/or reclaimed from, and/or mixed with water from s) a BBPP module;
Water from a desalination module is provided to, and/or reclaimed from, and/or mixed with water from t) a desalination module;
Water from a desalination module is provided to, and/or reclaimed from, and/or mixed with water from u) water for discharge/export;
Water from a desalination module is provided to, and/or reclaimed from, and/or mixed with water from v) a processing and/or treatment module; and/or
Water from a desalination module is provided to, and/or reclaimed from, and/or mixed with water from w) a thermal plant module.
Water from water for discharge/export is provided to, and/or reclaimed from, and/or mixed with water from a) a fresh water source;
Water from water for discharge/export is provided to, and/or reclaimed from, and/or mixed with water from b) a fresh water pretreatment module;
Water from water for discharge/export is provided to, and/or reclaimed from, and/or mixed with water from c) a salt water intake;
Water from water for discharge/export is provided to, and/or reclaimed from, and/or mixed with water from d) a salt water pretreatment module;
Water from water for discharge/export is provided to, and/or reclaimed from, and/or mixed with water from e) a preheating/cooling module;
Water from water for discharge/export is provided to, and/or reclaimed from, and/or mixed with water from f) a water storage module;
Water from water for discharge/export is provided to, and/or reclaimed from, and/or mixed with water from g) irrigation;
Water from water for discharge/export is provided to, and/or reclaimed from, and/or mixed with water from h) firefighting;
Water from water for discharge/export is provided to, and/or reclaimed from, and/or mixed with water from i) fountains;
Water from water for discharge/export is provided to, and/or reclaimed from, and/or mixed with water from j) lakes;
Water from water for discharge/export is provided to, and/or reclaimed from, and/or mixed with water from k) cleaning;
Water from water for discharge/export is provided to, and/or reclaimed from, and/or mixed with water from l) a BGM;
Water from water for discharge/export is provided to, and/or reclaimed from, and/or mixed with water from m) a traditional WWTP module;
Water from water for discharge/export is provided to, and/or reclaimed from, and/or mixed with water from n) a refinery module;
Water from water for discharge/export is provided to, and/or reclaimed from, and/or mixed with water from o) a BPP module;
Water from water for discharge/export is provided to, and/or reclaimed from, and/or mixed with water from p) heating and/or cooling to the Plan;
Water from water for discharge/export is provided to, and/or reclaimed from, and/or mixed with water from q) a recycling module;
Water from water for discharge/export is provided to, and/or reclaimed from, and/or mixed with water from r) a waste receiving module;
Water from water for discharge/export is provided to, and/or reclaimed from, and/or mixed with water from s) a BBPP module;
Water from water for discharge/export is provided to, and/or reclaimed from, and/or mixed with water from t) a desalination module;
Water from water for discharge/export is provided to, and/or reclaimed from, and/or mixed with water from u) water for discharge/export;
Water from water for discharge/export is provided to, and/or reclaimed from, and/or mixed with water from v) a processing and/or treatment module; and/or
Water from water for discharge/export is provided to, and/or reclaimed from, and/or mixed with water from w) a thermal plant module.
Water from a processing and/or treatment module is provided to, and/or reclaimed from, and/or mixed with water from a) a fresh water source;
Water from a processing and/or treatment module is provided to, and/or reclaimed from, and/or mixed with water from b) a fresh water pretreatment module;
Water from a processing and/or treatment module is provided to, and/or reclaimed from, and/or mixed with water from c) a salt water intake;

TABLE 2-continued

Any combination herein is optionally collocated:

Water from a processing and/or treatment module is provided to, and/or reclaimed from, and/or mixed with water from d) a salt water pretreatment module;
Water from a processing and/or treatment module is provided to, and/or reclaimed from, and/or mixed with water from e) a preheating/cooling module;
Water from a processing and/or treatment module is provided to, and/or reclaimed from, and/or mixed with water from f) a water storage module;
Water from a processing and/or treatment module is provided to, and/or reclaimed from, and/or mixed with water from g) irrigation;
Water from a processing and/or treatment module is provided to, and/or reclaimed from, and/or mixed with water from h) firefighting;
Water from a processing and/or treatment module is provided to, and/or reclaimed from, and/or mixed with water from i) fountains;
Water from a processing and/or treatment module is provided to, and/or reclaimed from, and/or mixed with water from j) lakes;
Water from a processing and/or treatment module is provided to, and/or reclaimed from, and/or mixed with water from k) cleaning;
Water from a processing and/or treatment module is provided to, and/or reclaimed from, and/or mixed with water from l) a BGM;
Water from a processing and/or treatment module is provided to, and/or reclaimed from, and/or mixed with water from m) a traditional WWTP module;
Water from a processing and/or treatment module is provided to, and/or reclaimed from, and/or mixed with water from n) a refinery module;
Water from a processing and/or treatment module is provided to, and/or reclaimed from, and/or mixed with water from o) a BPP module;
Water from a processing and/or treatment module is provided to, and/or reclaimed from, and/or mixed with water from p) heating and/or cooling to the Plan;
Water from a processing and/or treatment module is provided to, and/or reclaimed from, and/or mixed with water from q) a recycling module;
Water from a processing and/or treatment module is provided to, and/or reclaimed from, and/or mixed with water from r) a waste receiving module;
Water from a processing and/or treatment module is provided to, and/or reclaimed from, and/or mixed with water from s) a BBPP module;
Water from a processing and/or treatment module is provided to, and/or reclaimed from, and/or mixed with water from t) a desalination module;
Water from a processing and/or treatment module is provided to, and/or reclaimed from, and/or mixed with water from u) water for discharge/export;
Water from a processing and/or treatment module is provided to, and/or reclaimed from, and/or mixed with water from v) a processing and/or treatment module; and/or
Water from a processing and/or treatment module is provided to, and/or reclaimed from, and/or mixed with water from w) a thermal plant module.
Water from a thermal plant module module is provided to, and/or reclaimed from, and/or mixed with water from a) a fresh water source;
Water from a thermal plant module module is provided to, and/or reclaimed from, and/or mixed with water from b) a fresh water pretreatment module;
Water from a thermal plant module module is provided to, and/or reclaimed from, and/or mixed with water from c) a salt water intake;
Water from a thermal plant module module is provided to, and/or reclaimed from, and/or mixed with water from d) a salt water pretreatment module;
Water from a thermal plant module module is provided to, and/or reclaimed from, and/or mixed with water from e) a preheating/cooling module;
Water from a thermal plant module module is provided to, and/or reclaimed from, and/or mixed with water from f) a water storage module;
Water from a thermal plant module module is provided to, and/or reclaimed from, and/or mixed with water from g) irrigation;
Water from a thermal plant module module is provided to, and/or reclaimed from, and/or mixed with water from h) firefighting;
Water from a thermal plant module module is provided to, and/or reclaimed from, and/or mixed with water from i) fountains;
Water from a thermal plant module module is provided to, and/or reclaimed from, and/or mixed with water from j) lakes;
Water from a thermal plant module module is provided to, and/or reclaimed from, and/or mixed with water from k) cleaning;
Water from a thermal plant module module is provided to, and/or reclaimed from, and/or mixed with water from l) a BGM;
Water from a thermal plant module module is provided to, and/or reclaimed from, and/or mixed with water from m) a traditional WWTP module;
Water from a thermal plant module module is provided to, and/or reclaimed from, and/or mixed with water from n) a refinery module;
Water from a thermal plant module module is provided to, and/or reclaimed from, and/or mixed with water from o) a BPP module;
Water from a thermal plant module module is provided to, and/or reclaimed from, and/or mixed with water from p) heating and/or cooling to the Plan;
Water from a thermal plant module module is provided to, and/or reclaimed from, and/or mixed with water from q) a recycling module;
Water from a thermal plant module module is provided to, and/or reclaimed from, and/or mixed with water from r) a waste receiving module;
Water from a thermal plant module module is provided to, and/or reclaimed from, and/or mixed with water from s) a BBPP module;

TABLE 2-continued

Any combination herein is optionally collocated:

Water from a thermal plant module module is provided to, and/or reclaimed from, and/or mixed with water from t) a desalination module;
Water from a thermal plant module module is provided to, and/or reclaimed from, and/or mixed with water from u) water for discharge/export;
Water from a thermal plant module module is provided to, and/or reclaimed from, and/or mixed with water from v) a processing and/or treatment module; and/or
Water from a thermal plant module module is provided to, and/or reclaimed from, and/or mixed with water from w) a thermal plant module.

TABLE 3

Any combination herein is optionally collocated:

A thermal plant module provides carbon dioxide to a) a BGM;
A thermal plant module provides carbon dioxide to b) a refinery module;
A thermal plant module provides carbon dioxide to c) a BPP module;
A thermal plant module provides carbon dioxide to d) a purification/processing module;
A thermal plant module provides carbon dioxide to e) a carbon dioxide storage module;
A thermal plant module provides carbon dioxide to f) a BBPP module;
A thermal plant module provides carbon dioxide to g) a desalination module; and/or
A thermal plant module provides carbon dioxide to h) a discharge and/or export module.
A sludge processing module provides carbon dioxide to a) a BGM;
A sludge processing module provides carbon dioxide to b) a refinery module;
A sludge processing module provides carbon dioxide to c) a BPP module;
A sludge processing module provides carbon dioxide to d) a purification/processing module;
A sludge processing module provides carbon dioxide to e) a carbon dioxide storage module;
A sludge processing module provides carbon dioxide to f) a BBPP module;
A sludge processing module provides carbon dioxide to g) a desalination module; and/or
A sludge processing module provides carbon dioxide to h) a discharge and/or export module.
A traditional WWTP module provides carbon dioxide to a) a BGM;
A traditional WWTP module provides carbon dioxide to b) a refinery module;
A traditional WWTP module provides carbon dioxide to c) a BPP module;
A traditional WWTP module provides carbon dioxide to d) a purification/processing module;
A traditional WWTP module provides carbon dioxide to e) a carbon dioxide storage module;
A traditional WWTP module provides carbon dioxide to f) a BBPP module;
A traditional WWTP module provides carbon dioxide to g) a desalination module; and/or
A traditional WWTP module provides carbon dioxide to h) a discharge and/or export module.
A carbon dioxide storage module provides carbon dioxide to a) a BGM;
A carbon dioxide storage module provides carbon dioxide to b) a refinery module;
A carbon dioxide storage module provides carbon dioxide to c) a BPP module;
A carbon dioxide storage module provides carbon dioxide to d) a purification/processing module;
A carbon dioxide storage module provides carbon dioxide to e) a carbon dioxide storage module;
A carbon dioxide storage module provides carbon dioxide to f) a BBPP module;
A carbon dioxide storage module provides carbon dioxide to g) a desalination module; and/or
A carbon dioxide storage module provides carbon dioxide to h) a discharge and/or export module.
An ambient carbon dioxide source(s) provides carbon dioxide to a) a BGM;
An ambient carbon dioxide source(s) provides carbon dioxide to b) a refinery module;
An ambient carbon dioxide source(s) provides carbon dioxide to c) a BPP module;
An ambient carbon dioxide source(s) provides carbon dioxide to d) a purification/processing module;
An ambient carbon dioxide source(s) provides carbon dioxide to e) a carbon dioxide storage module;
An ambient carbon dioxide source(s) provides carbon dioxide to f) a BBPP module;
An ambient carbon dioxide source(s) provides carbon dioxide to g) a desalination module; and/or
An ambient carbon dioxide source(s) provides carbon dioxide to h) a discharge and/or export module.
A purification module provides carbon dioxide to a) a BGM;
A purification module provides carbon dioxide to b) a refinery module;
A purification module provides carbon dioxide to c) a BPP module;
A purification module provides carbon dioxide to d) a purification/processing module;
A purification module provides carbon dioxide to e) a carbon dioxide storage module;
A purification module provides carbon dioxide to f) a BBPP module;
A purification module provides carbon dioxide to g) a desalination module; and/or
A purification module provides carbon dioxide to h) a discharge and/or export module.
A refinery module provides carbon dioxide to a) a BGM;
A refinery module provides carbon dioxide to b) a refinery module;
A refinery module provides carbon dioxide to c) a BPP module;
A refinery module provides carbon dioxide to d) a purification/processing module;
A refinery module provides carbon dioxide to e) a carbon dioxide storage module;
A refinery module provides carbon dioxide to f) a BBPP module;
A refinery module provides carbon dioxide to g) a desalination module; and/or
A refinery module provides carbon dioxide to h) a discharge and/or export module.
A BPP module provides carbon dioxide to a) a BGM;
A BPP module provides carbon dioxide to b) a refinery module;
A BPP module provides carbon dioxide to c) a BPP module;
A BPP module provides carbon dioxide to d) a purification/processing module;
A BPP module provides carbon dioxide to e) a carbon dioxide storage module;
A BPP module provides carbon dioxide to f) a BBPP module;
A BPP module provides carbon dioxide to g) a desalination module; and/or
A BPP module provides carbon dioxide to h) a discharge and/or export module.
A supercritical fluids extraction module provides carbon dioxide to a) a BGM;
A supercritical fluids extraction module provides carbon dioxide to b) a refinery module;
A supercritical fluids extraction module provides carbon dioxide to c) a BPP module;
A supercritical fluids extraction module provides carbon dioxide to d) a purification/processing module;
A supercritical fluids extraction module provides carbon dioxide to e) a carbon dioxide storage module;
A supercritical fluids extraction module provides carbon dioxide to f) a BBPP module;
A supercritical fluids extraction module provides carbon dioxide to g) a desalination module; and/or
A supercritical fluids extraction module provides carbon dioxide to h) a discharge and/or export module.

TABLE 3-continued

Any combination herein is optionally collocated:

A gasification module provides carbon dioxide to a) a BGM;
A gasification module provides carbon dioxide to b) a refinery module;
A gasification module provides carbon dioxide to c) a BPP module;
A gasification module provides carbon dioxide to d) a purification/processing module;
A gasification module provides carbon dioxide to e) a carbon dioxide storage module;
A gasification module provides carbon dioxide to f) a BBPP module;
A gasification module provides carbon dioxide to g) a desalination module; and/or
A gasification module provides carbon dioxide to h) a discharge and/or export module.
A BGM provides carbon dioxide to a) a BGM;
A BGM provides carbon dioxide to b) a refinery module;
A BGM provides carbon dioxide to c) a BPP module;
A BGM provides carbon dioxide to d) a purification/processing module;
A BGM provides carbon dioxide to e) a carbon dioxide storage module;
A BGM provides carbon dioxide to f) a BBPP module;
A BGM provides carbon dioxide to g) a desalination module; and/or
A BGM provides carbon dioxide to h) a discharge and/or export module.
A cellulosic ethanol/butanol/isobutanol module provides carbon dioxide to a) a BGM;
A cellulosic ethanol/butanol/isobutanol module provides carbon dioxide to b) a refinery module;
A cellulosic ethanol/butanol/isobutanol module provides carbon dioxide to c) a BPP module;
A cellulosic ethanol/butanol/isobutanol module provides carbon dioxide to d) a purification/processing module;
A cellulosic ethanol/butanol/isobutanol module provides carbon dioxide to e) acarbon dioxide storage module;
A cellulosic ethanol/butanol/isobutanol module provides carbon dioxide to f) a BBPP module;
A cellulosic ethanol/butanol/isobutanol module provides carbon dioxide to g) a desalination module; and/or
A cellulosic ethanol/butanol/isobutanol module provides carbon dioxide to h) a discharge and/or export module.
A landfill module provides carbon dioxide to a) a BGM;
A landfill module provides carbon dioxide to b) a refinery module;
A landfill module provides carbon dioxide to c) a BPP module;
A landfill module provides carbon dioxide to d) a purification/processing module;
A landfill module provides carbon dioxide to e) a carbon dioxide storage module;
A landfill module provides carbon dioxide to f) a BBPP module;
A landfill module provides carbon dioxide to g) a desalination module; and/or
A landfill module provides carbon dioxide to h) a discharge and/or export module.
Offsite source(s) provides carbon dioxide to a) a BGM;
Offsite source(s) provides carbon dioxide to b) a refinery module;
Offsite source(s) provides carbon dioxide to c) a BPP module;
Offsite source(s) provides carbon dioxide to d) a purification/processing module;
Offsite source(s) provides carbon dioxide to e) a carbon dioxide storage module;
Offsite source(s) provides carbon dioxide to f) a BBPP module;
Offsite source(s) provides carbon dioxide to g) a desalination module; and/or
Offsite source(s) provides carbon dioxide to h) a discharge and/or export module.

TABLE 4

Any combination herein is optionally collocated:

A desalination module supplies pressure to a) a desalination module;
A desalination module supplies pressure to b) a thermal plant heat and/or pressure-intensive processes module;
A desalination module supplies pressure to c) a BBPP module;
A desalination module supplies pressure to d) an HTP module(s) or processes;
A desalination module supplies pressure to e) a pressure generated to create movement of substances of any kind in the Plan module by turning a turbine, creating a vacuum, pressurizing a pump, and/or directing a pressurized substance into a conveyance;
A desalination module supplies pressure to f) a refinery module;
A desalination module supplies pressure to g) a BPP module; and/or
A desalination module supplies pressure to h) a power generation module - the system and/or method comprising: capturing fluid pressure from a module a-h and directing a portion of that fluid pressure to another module a-h.
A a thermal plant heat and/or pressure-intensive processes module supplies pressure to a) a desalination module;
A a thermal plant heat and/or pressure-intensive processes module supplies pressure to b) a thermal plant heat and/or pressure-intensive processes module;
A a thermal plant heat and/or pressure-intensive processes module supplies pressure to c) a BBPP module;
A a thermal plant heat and/or pressure-intensive processes module supplies pressure to d) an HTP module(s) or processes;
A a thermal plant heat and/or pressure-intensive processes module supplies pressure to e) a pressure generated to create movement of substances of any kind in the Plan module by turning a turbine, creating a vacuum, pressurizing a pump, and/or directing a pressurized substance into a conveyance;
A a thermal plant heat and/or pressure-intensive processes module supplies pressure to f) a refinery module;
A a thermal plant heat and/or pressure-intensive processes module supplies pressure to g) a BPP module; and/or
A a thermal plant heat and/or pressure-intensive processes module supplies pressure to h) a power generation module - the system and/or method comprising: capturing fluid pressure from a module a-h and directing a portion of that fluid pressure to another module a-h.
A a BBPP module supplies pressure to a) a desalination module;
A a BBPP module supplies pressure to b) a thermal plant heat and/or pressure-intensive processes module;
A a BBPP module supplies pressure to c) a BBPP module;
A a BBPP module supplies pressure to d) an HTP module(s) or processes;
A a BBPP module supplies pressure to e) a pressure generated to create movement of substances of any kind in the Plan module by turning a turbine, creating a vacuum, pressurizing a pump, and/or directing a pressurized substance into a conveyance;
A a BBPP module supplies pressure to f) a refinery module;
A a BBPP module supplies pressure to g) a BPP module; and/or
A a BBPP module supplies pressure to h) a power generation module - the system and/or method comprising: capturing fluid pressure from a module a-h and directing a portion of that fluid pressure to another module a-h.
An HTP module(s) or processes supplies pressure to a) a desalination module;
An HTP module(s) or processes supplies pressure to b) a thermal plant heat and/or pressure-intensive processes module;
An HTP module(s) or processes supplies pressure to c) a BBPP module;
An HTP module(s) or processes supplies pressure to d) an HTP module(s) or processes;
An HTP module(s) or processes supplies pressure to e) a pressure generated to create movement of substances of any kind in the Plan module by turning a turbine, creating a vacuum, pressurizing a pump, and/or directing a pressurized substance into a conveyance;
An HTP module(s) or processes supplies pressure to f) a refinery module;
An HTP module(s) or processes supplies pressure to g) a BPP module; and/or
An HTP module(s) or processes supplies pressure to h) a power generation module - the system and/or method comprising: capturing fluid pressure from a module a-h and directing a portion of that fluid pressure to another module a-h.
A pressure generated to create movement of substances of any kind in the Plan module by turning a turbine, creating a vacuum, pressurizing a pump, and/or directing a pressurized substance into a conveyance supplies pressure to a) a desalination module;
A pressure generated to create movement of substances of any kind in the Plan module by turning a turbine, creating a vacuum, pressurizing a pump, and/or directing a pressurized substance into a conveyance supplies pressure to b) a thermal plant heat and/or pressure-intensive processes module;
A pressure generated to create movement of substances of any kind in the Plan module by turning a turbine, creating a vacuum, pressurizing a pump, and/or directing a pressurized substance into a conveyance supplies pressure to c) a BBPP module;

TABLE 4-continued

Any combination herein is optionally collocated:

A pressure generated to create movement of substances of any kind in the Plan module by turning a turbine, creating a vacuum, pressurizing a pump, and/or directing a pressurized substance into a conveyance supplies pressure to d) an HTP module(s) or processes;
A pressure generated to create movement of substances of any kind in the Plan module by turning a turbine, creating a vacuum, pressurizing a pump, and/or directing a pressurized substance into a conveyance supplies pressure to e) a pressure generated to create movement of substances of any kind in the Plan module by turning a turbine, creating a vacuum, pressurizing a pump, and/or directing a pressurized substance into a conveyance;
A pressure generated to create movement of substances of any kind in the Plan module by turning a turbine, creating a vacuum, pressurizing a pump, and/or directing a pressurized substance into a conveyance supplies pressure to f) a refinery module;
A pressure generated to create movement of substances of any kind in the Plan module by turning a turbine, creating a vacuum, pressurizing a pump, and/or directing a pressurized substance into a conveyance supplies pressure to g) a BPP module; and/or
A pressure generated to create movement of substances of any kind in the Plan module by turning a turbine, creating a vacuum, pressurizing a pump, and/or directing a pressurized substance into a conveyance supplies pressure to h) a power generation module - the system and/or method comprising: capturing fluid pressure from a module a-h and directing a portion of that fluid pressure to another module a-h.
A refinery module supplies pressure to a) a desalination module;
A refinery module supplies pressure to b) a thermal plant heat and/or pressure-intensive processes module;
A refinery module supplies pressure to c) a BBPP module;
A refinery module supplies pressure to d) an HTP module(s) or processes;
A refinery module supplies pressure to e) a pressure generated to create movement of substances of any kind in the Plan module by turning a turbine, creating a vacuum, pressurizing a pump, and/or directing a pressurized substance into a conveyance;
A refinery module supplies pressure to f) a refinery module;
A refinery module supplies pressure to g) a BPP module; and/or
A refinery module supplies pressure to h) a power generation module - the system and/or method comprising: capturing fluid pressure from a module a-h and directing a portion of that fluid pressure to another module a-h.
A BPP module supplies pressure to a) a desalination module;
A BPP module supplies pressure to b) a thermal plant heat and/or pressure-intensive processes module;
A BPP module supplies pressure to c) a BBPP module;
A BPP module supplies pressure to d) an HTP module(s) or processes;
A BPP module supplies pressure to e) a pressure generated to create movement of substances of any kind in the Plan module by turning a turbine, creating a vacuum, pressurizing a pump, and/or directing a pressurized substance into a conveyance;
A BPP module supplies pressure to f) a refinery module;
A BPP module supplies pressure to g) a BPP module; and/or
A BPP module supplies pressure to h) a power generation module - the system and/or method comprising: capturing fluid pressure from a module a-h and directing a portion of that fluid pressure to another module a-h.
A power generation module - the system and/or method comprising: capturing fluid pressure from a module a-h and directing a portion of that fluid pressure to another module a-h supplies pressure to a) a desalination module;
A power generation module - the system and/or method comprising: capturing fluid pressure from a module a-h and directing a portion of that fluid pressure to another module a-h supplies pressure to b) a thermal plant heat and/or pressure-intensive processes module;
A power generation module - the system and/or method comprising: capturing fluid pressure from a module a-h and directing a portion of that fluid pressure to another module a-h supplies pressure to c) a BBPP module;
A power generation module - the system and/or method comprising: capturing fluid pressure from a module a-h and directing a portion of that fluid pressure to another module a-h supplies pressure to d) an HTP module(s) or processes;
A power generation module - the system and/or method comprising: capturing fluid pressure from a module a-h and directing a portion of that fluid pressure to another module a-h supplies pressure to e) a pressure generated to create movement of substances of any kind in the Plan module by turning a turbine, creating a vacuum, pressurizing a pump, and/or directing a pressurized substance into a conveyance;
A power generation module - the system and/or method comprising: capturing fluid pressure from a module a-h and directing a portion of that fluid pressure to another module a-h supplies pressure to f) a refinery module;
A power generation module - the system and/or method comprising: capturing fluid pressure from a module a-h and directing a portion of that fluid pressure to another module a-h supplies pressure to g) a BPP module; and/or
A power generation module - the system and/or method comprising: capturing fluid pressure from a module a-h and directing a portion of that fluid pressure to another module a-h supplies pressure to h) a power generation module - the system and/or method comprising: capturing fluid pressure from a module a-h and directing a portion of that fluid pressure to another module a-h.

We claim:

1. A method of using and reclaiming heat and/or cooling from a thermal plant module, the thermal plant module either a) being: a fossil fuel-fired plant, a nuclear plant, a solar thermal plant, a steel plant, a cement plant, a paper mill, a textile mill, a metal manufacturing plant, an incinerator, and/or a rotary kiln incinerator, and/or b) comprising: a cellulosic ethanol/isobutanol/butanol module, a hydrothermal processing module, a gasification module, a waste-to-energy module, a plasma gasification unit, and/or a desorber/condenser module, the method comprising:
   generating heat and/or cooling at the thermal plant module;
   transmitting the heat and/or the cooling to a biomass growth module (BGM); and
   using all or a portion of the heat and/or cooling in the thermal plant module and/or in the BGM,
   wherein the BGM does not include, nor is operatively connected to, an anaerobic bioreactor.

2. The method according to claim 1 wherein the method further comprises growing biomass in the BGM.

3. The method according to claim 1 wherein heat and/or cooling is further provided to and/or reclaimed from:
   a. a refinery module;
   b. a BPP module;
   c. an air conditioning/heating module;
   d. a recycling module;
   e. a BBPP module;
   f. a products storage module;
   g. a desalination module;
   h. a waste to energy module;
   i. a biogas storage module;
   j. a heat/cooling storage module;
   k. a heat/cooling recovery module;
   l. heating/cooling external to or apart from the method;
   m. heating/cooling for discharge;
   n. biomass products;
   o. a gasification module;
   p. processing of biofuel; and/or
   q. systems optionally comprised by the thermal plant module selected from:
      i. a pyrolysis processes module;
      ii. a hydrothermal processing module;
      iii. a cellulosic ethanol/butanol/isobutanol module; and/or
      iv. a desorber/condenser module.

4. The method of claim 3 wherein heat and/or cooling reclaimed from any one or more of components a.-q. is provided to any one or more of components a.-q.

5. The method of claim 1 wherein the thermal plant module and the BGM are collocated.

6. The method of claim 3 wherein any two or more of components a.-q. are collocated.

7. The method of claim 1 wherein the step of transmitting includes transmitting heat from the thermal plant module as a heated fluid.

8. The method of claim 7 wherein the heated fluid is fed directly or in part as a water source and/or gas source to the BGM, a BGU, and/or any subunit of a BGU.

9. The method of claim 7 wherein the heated fluid is configured to provide heat transfer to the BGM, a BGU, and/or any subunit of a BGU without direct interaction with the BGM.

10. The method of claim 1 wherein heat is reclaimed from exhaust gases generated by the thermal plant module and/or from cooling fluid output from the thermal plant module.

11. The method of claim 10 wherein heat is reclaimed from cooling fluid output from the thermal plant module and the cooling fluid is cooling a power cycle comprising one or more of:
  a. a Rankine cycle;
  b. a Simple cycle;
  c. a Combined cycle; and/or
  d. an Open Rankine cycle.

12. The method of claim 1 wherein the method is performed in a system comprising the thermal plant module and the biomass growth module (BGM) that grows biomass.

13. A system configured to use and reclaim heat and/or cooling from a thermal plant module, the thermal plant module either a) being: a fossil fuel-fired plant, a nuclear plant, a solar thermal plant, a steel plant, a cement plant, a paper mill, a textile mill, a metal manufacturing plant, an incinerator, and/or a rotary kiln incinerator, and/or b) comprising: a cellulosic ethanol/isobutanol/butanol module, a hydrothermal processing module, a gasification module, a waste-to-energy module, a plasma gasification unit, and/or a desorber/condenser module, using the method of claim 1, wherein the reclaimed heat and/or cooling is provided in whole or in part to a biomass growth module (BGM) that grows biomass,
  wherein the BGM does not include, nor is operatively connected to, an anaerobic bioreactor.

14. The system according to claim 13 wherein the system is further configured to provide heat and/or cooling to and/or to reclaim heat and/or cooling from:
  a. a refinery module;
  b. a BPP module;
  c. an air conditioning/heating module;
  d. a recycling module;
  e. a BBPP module;
  f. a products storage module;
  g. a desalination module;
  h. a waste to energy module;
  i. a biogas storage module;
  j. a heat/cooling storage module;
  k. a heat/cooling recovery module;
  l. offsite heating/cooling;
  m. heating/cooling for discharge;
  n. biomass products;
  o. a gasification module;
  p. processing of biofuel; and/or
  q. systems optionally comprised by the thermal plant module selected from:
    i. a pyrolysis processes module;
    ii. a hydrothermal processing module;
    iii. a cellulosic ethanol/butanol/isobutanol module; and/or
    iv. a desorber/condenser module.

15. The system of claim 14 wherein heat and/or cooling reclaimed from any one or more of components a.-q. as described is provided to any one or more of components a.-q.

16. The system of claim 14 wherein any two or more of components a.-q. are collocated.

17. The system of claim 14, wherein outputs of heat and/or cooling from any one of components a.-q. share heating and/or cooling transmission modules and/or technologies, and/or heat and/or cooling storage module(s) and/or unit(s).

18. The system of claim 14 wherein the thermal plant module is configured to discharge waste heat as a heated fluid to heat the BGM.

19. The system of claim 18 wherein the heated fluid is fed directly or in part as a water source and/or gas source to the BGM, a BGU, and/or any subunit of a BGU and/or any of the other components a.-q.

20. The system of claim 18 wherein the heated fluid is configured to provide heat transfer to the BGM, a BGU, and/or any subunit of a BGU without direct interaction with the BGM and/or any of the other components a.-q.

21. The system of claim 14 in which cooling is provided to the BGM, wherein the cooling is provided by a cogenerated cooling module which uses heat from the thermal plant module to provide cooling to the BGM and/or the other components a.-q.

22. The system of claim 13 wherein the thermal plant module and the BGM are collocated.

23. The system of claim 13 wherein the thermal plant module is configured to supply waste heat to heat the BGM.

24. The system of claim 23 wherein the thermal plant module is configured to discharge waste heat as a heated fluid.

25. The system of claim 24 wherein the heated fluid is fed directly or in part as a water source and/or gas source to the BGM, a BGU, and/or any subunit of a BGU.

26. The system of claim 24 wherein the heated fluid is configured to provide heat transfer to the BGM, a BGU, and/or any subunit of a BGU without direct interaction with the BGM.

27. The system of claim 13 in which cooling is provided to the BGM, wherein the cooling is provided by a cogenerated cooling module which uses heat from the thermal plant module to provide cooling to the BGM.

28. The system of claim 13 wherein heat is reclaimed from either exhaust gases generated by the thermal plant module and/or from cooling fluid output from the thermal plant module.

29. The system of claim 28 wherein heat is reclaimed from cooling fluid output from the thermal plant module and the cooling fluid is cooling a power cycle comprising one or more of:
  a. a Rankine cycle;
  b. a Simple cycle;
  c. a Combined cycle; and/or
  d. an Open Rankine cycle.

30. A method of using and reclaiming heat and/or cooling from a thermal plant module, the method comprising: generating heat and/or cooling at the thermal plant module; transmitting heat and/or cooling to a biomass growth module (BGM);

and
using all or a portion of the heat and/or cooling in the thermal plant module and/or in the BGM,
wherein heat and/or cooling is further provided to and/or reclaimed from:
  a. a refinery module;
  b. a BPP module;
  c. an air conditioning/heating module;
  d. a recycling module;
  e. a BBPP module;
  f. a products storage module;
  g. a desalination module;
  h. a waste to energy module;
  i. a biogas storage module;
  j. a heat/cooling storage module;
  k. a heat/cooling recovery module;
  l. heating/cooling external to or apart from the method;
  m. heating/cooling for discharge;
  n. biomass products;
  o. a gasification module;
  p. processing of biofuel; and/or
  q. systems optionally comprised by the thermal plant module selected from:
    i. a pyrolysis processes module;
    ii. a hydrothermal processing module;
    iii. a cellulosic ethanol/butanol/isobutanol module; and/or
    a desorber/condenser module,
wherein any two or more of components a.-q. are collocated and wherein outputs of heat and/or cooling from any one of components a.-q. share heating and/or cooling transmission modules and/or technologies, and/or heat and/or cooling storage module(s) and/or unit(s).

31. A method of using and reclaiming heat and/or cooling from a thermal plant module, the method comprising: generating cooling at the thermal plant module by cogenerating cooling using heat from the thermal plant module; transmitting the cogenerated cooling to a biomass growth module (BGM); and using all or a portion of the cogenerated cooling in the BGM.

* * * * *